US006913916B1

(12) United States Patent
Mukerji et al.

(10) Patent No.: US 6,913,916 B1
(45) Date of Patent: Jul. 5, 2005

(54) ELONGASE GENES AND USES THEREOF

(75) Inventors: Pradip Mukerji, Gahanna, OH (US); Tapas Das, Worthington, OH (US); Yung-Sheng Huang, Upper Arlington, OH (US); Jennifer M. Parker-Barnes, New Albany, OH (US); Amanda Eun-Yeong Leonard, Gahanna, OH (US); Jennifer Thurmond, Columbus, OH (US)

(73) Assignee: Abbott Laboratories, Abbott Park, IL (US)

( * ) Notice: Subject to any disclaimer, the term of this patent is extended or adjusted under 35 U.S.C. 154(b) by 517 days.

(21) Appl. No.: 09/624,670

(22) Filed: Jul. 24, 2000

Related U.S. Application Data

(63) Continuation-in-part of application No. 09/379,095, filed on Aug. 23, 1999, now abandoned, which is a continuation-in-part of application No. 09/145,828, filed on Sep. 2, 1998, now Pat. No. 6,403,349.

(51) Int. Cl.$^7$ ............................ C12N 9/00; C12N 5/00; C12N 1/20; C12N 15/00; C12P 21/06

(52) U.S. Cl. ........................ 435/183; 435/4; 435/69.1; 435/325; 435/410; 435/252.3; 435/252.31; 435/252.33; 435/254.2; 435/254.21; 435/320.1; 435/419; 435/254.11; 435/254.22; 435/254.3; 435/254.5; 435/254.4; 435/254.7; 435/254.23; 435/348; 800/295; 536/23.2

(58) Field of Search .......................... 435/183, 4, 69.1, 435/325, 410, 252.3, 252.31, 252.33, 254.2, 254.21, 320.1, 419, 254.11, 254.22, 254.3, 254.5, 254.4, 254.7, 254.23, 348; 800/295; 536/23.2

(56) References Cited

U.S. PATENT DOCUMENTS

| | | | |
|---|---|---|---|
| 5,443,974 A | 8/1995 | Hitz et al. | ............... 435/173.3 |
| 5,484,724 A | 1/1996 | El-Sherbeini et al. | ....... 435/193 |
| 5,552,306 A | 9/1996 | Thomas et al. | ............. 435/134 |

FOREIGN PATENT DOCUMENTS

| | | | |
|---|---|---|---|
| EP | 0285405 | * | 10/1988 |
| EP | 0296751 | A | 12/1988 |
| FR | 2648347 | A | 12/1990 |
| WO | 8807577 | | 10/1988 |
| WO | 8807577 | A | 10/1988 |
| WO | 9311245 | | 6/1993 |
| WO | 9411516 | | 5/1994 |
| WO | 9613591 | | 5/1996 |
| WO | 9846765 | A | 10/1998 |
| WO | 0012720 | | 3/2000 |
| WO | 0159128 | A | 8/2000 |
| WO | 0070945 | A | 11/2000 |

OTHER PUBLICATIONS

Witkowski et al., Biochemistry 38:11643–11650, 1999.*
Bork, Genome Research, 10:398–400, 2000.*
Broun et al., Science 282:1315–1317, 1998.*
Van de Loo et al., Proc. Natl. Acad. Sci. 92:6743–6747, 1995.*
Seffernick et al., J. Bacteriol. 183(8):2405–2410, 2001.*
Tvrdik et al., J. Cell Biol. 149(3):707–717, May 2000.*
GenEMBL accession No. I05465, 1994.*
GenBank accession No. AF170908, May 2000.*
Tvrdik, P., et al., "Role of a New Mammalian Gene Family in the Biosynthesis of Very Long Chain Fatty Acids and Sphingolipids," The Journal of Cell Biology, vol. 149, No. 3 (May 1, 2000), pp. 707–717.
Database EMBL [online] Oct. 19, 1999, Hashimo, K., et al.: "Mus Musculus Brain cDNA, Clone:MNCb–4912, 5' end." Database Accession No. AU079897 XP002223157.
Das, T., et al, ".Gamma.–Linolenic Acid Metabolism: Identification and Characterization of .Gamma.–Linolenic Acid Elongation Enzyme" International Symposium on .Gamma.–Linolenic Acid, 2$^{nd}$, San Diego, CA, Apr. 25–28, 2000, XP008011237, In: .Gamma.–Linolenic Acid: Recent Advances in Biotechnology and Clinical Applications (2001), AOCS Press, Champaign, Il.
Kendrick, A., et al., "Lipids of Selected Molds Grown for Production of N–3 and N–6 Polyunsaturated Fatty Acids," vol. 27, No. 1, 1992, pp. 15–20, XP002047887, ISSN: 0024–4201.
Salem, N. et al., "Arachidonic and Docosahexaenoic Acids are Biosynthesized from their 18–Carbon Precursors in Human Infants," Proceedings of the National Academy of Sciences of USA, National Academy of Science, vol. 93, (Jan., 1996), pp. 49–54, XP002131822, ISSN: 0027–8424.

(Continued)

*Primary Examiner*—Rebecca E. Prouty
*Assistant Examiner*—Delia M. Ramirez
(74) *Attorney, Agent, or Firm*—Cheryl L. Becker

(57) ABSTRACT

The subject invention relates to the identification of several genes involved in the elongation of polyunsaturated acids (i.e., "elongases") and to uses thereof. At least two of these genes are also involved in the elongation of monounsaturated fatty acids. In particular, elongase is utilized in the conversion of gamma linolenic acid (GLA) to dihomogama linolenic acid (DGLA) and in the conversion of DGLA or 20:4n-3 to eicosapentaenoic acid (EPA). DGLA may be utilized in the production of polyunsaturated fatty acids, such as arachiodonic acid (AA), docosahexaenoic acid (DHA), EPA, adrenic acid, ω6-docosapentaenoic acid or ω3-docosapentaenoic acid which may be added to pharmaceutical compositions, nutritional compositions, animal feeds, as well as other products such as cosmetics.

24 Claims, 82 Drawing Sheets

OTHER PUBLICATIONS

Bowles, R.D., et al., "Long–Chain N–3 Polyunsaturated Fatty Acid Production by Members of the Marine Protistan Group the Thraustochytrids: Screening of Isolates and Optimisation of Docosahexaenoic Acid Production," Journal of Biotechnology, Elsevier Science Publishers, Amsterdam, NL, vol. 70, No. 1–3, (Apr. 30, 1999) pp. 193–2002, XP004173399 ISSN: 0168–1656.

Lassner et al., *The Plant Cell* 8:281–292 (1996).

Oh et al., *The Journal of Biological Chemistry* 272 (28):17376–17384 (1997).

Arita et al., Effect of n–3 and n–6 polyunsaturated fatty acids and their ethylesters on stimuli–dependent superoxide generation in neutrophils. Physicol Chem Phys Med NMR. 2001;33(2):121–32.

Haban et al., Supplementation with long–chain n–3 fatty acids in non–insulin dependent diabetes mellitus (NIDDM) patients leads to the lowering of oleic acid content in serum phospholipids. Eur J Nutr. Oct. 2000;39(5):201–6.

Pirich et al., Effects of fish oil supplementation on platelet survival and ex vivo platelet function in hypercholesterolemic patients. Thromb Res. Nov. 1, 1999;96(3):219–27.

Calviello et al., Dietary supplementation with eicosapentaenoic and docosahexaenoic acid inhibits growth of Morris hepatocarcinoma 3924A in rats: effects on proliferation and apoptosis. Int J Cancer. Mar. 2, 1998;75(5):699–705.

Tardy et al., Priming effect of adrenic acid (22:4(n–6)) on tissue factor activity expressed by thrombin–stimulated endothelial cells. Atherosclerosis. Jul. 1992;95(1):51–8.

\* cited by examiner

```
jojobakcs   24  ATLPNFKSSINLHHVKL.GYHYLISNALFLVFIPLLGLASAHLSSFSAHD  72
                .||   . ::|: — :|:|.             — || —
ELO2        66  STLPPVLYAITAYYVIIFGGRFLLSKS..KPF.KLNGLFQLHNLVLTSLS 112 jojobakcs   73  LSLLFDLLRRNLLPVVVCSFLFVLLATLHFLTRP 106
                |:.|| |: |.|:|:| |: .: :.|  .|
ELO2       113  LTLLL.LMVEQLVPIIVQHGLYFAICNIGAWTQP 145
```

FIG.2

| S | T | L | P | P | V | L | Y | A | I | T | A | Y | Y | V | I | I | F | G | G | R | F | L |
|---|---|---|---|---|---|---|---|---|---|---|---|---|---|---|---|---|---|---|---|---|---|---|
| TCC | ACC | CTC | CCC | CCC | GTC | CTC | TAC | GCC | ATC | ACC | GCC | TAC | TAC | GTC | ATC | ATC | TTC | GGT | GGT | CGC | TTC | CTC |
| 66 | 67 | 68 | 69 | 70 | 71 | 72 | 73 | 74 | 75 | 76 | 77 | 78 | 79 | 80 | 81 | 82 | 83 | 84 | 85 | 86 | 87 | 88 |

<-- R0339

| L | S | K | S | K | P | F | K | L | N | G | L | F | Q | L | H | N | L | V | L | T | S | L |
|---|---|---|---|---|---|---|---|---|---|---|---|---|---|---|---|---|---|---|---|---|---|---|
| CTC | TCC | AAG | TCC | AAG | CCC | TTC | AAG | CTC | AAC | GGT | CTC | TTC | CAG | CTC | CAC | AAC | CTC | GTC | CTC | ACC | TCC | CTC |
| 89 | 90 | 91 | 92 | 93 | 94 | 95 | 96 | 97 | 98 | 99 | 100 | 101 | 102 | 103 | 104 | 105 | 106 | 107 | 108 | 109 | 110 | 111 |

| S | L | T | L | L | L | L | M | V | E | Q | L | V | P | I | I | V | Q | H | G | L | Y | F |
|---|---|---|---|---|---|---|---|---|---|---|---|---|---|---|---|---|---|---|---|---|---|---|
| TCC | CTC | ACC | CTC | CTC | CTC | CTC | ATG | GTC | GAG | CAG | CTC | GTC | CCC | ATC | ATC | GTC | CAG | CAC | GGT | CTC | TAC | TTC |
| 112 | 113 | 114 | 115 | 116 | 117 | 118 | 119 | 120 | 121 | 122 | 123 | 124 | 125 | 126 | 127 | 128 | 129 | 130 | 131 | 132 | 133 | 134 |

| A | I | C | N | I | G | A | W | T | Q | P |
|---|---|---|---|---|---|---|---|---|---|---|
| GCC | ATC | TGC | AAC | ATC | GGT | GCC | TGG | ACC | CAG | CCC |
| 135 | 136 | 137 | 138 | 139 | 140 | 141 | 142 | 143 | 144 | 145 |

FIG.3 pRAE-5  GAATTCAGG * * * * * * *CATGGCCCGCCGCAATCTTGGACAA
pRAE-6  GAATTCAGGCATCTCATGGATCCGCCATGGCCCGCCGCAATCTTGGACAA
        EcoRI                BamHI    NcoI

FIG.5

```
  1 ATGGCCGCCG CAATCTCTTGGA CAAGGTCAAC TTCGGCATTG ATCAGCCCTT
 51 CGGAATCAAG CTCGACACCT ACTTTGCTCA GGCCTATGAA CTCGTCACCG
101 GAAAGTCCAT CGACTCCTTC GTCTTCCAGG AGGGCGTCAC GCCTCTCTCG
151 ACCCAGAGAG AGGTCGCCAT GTGGACTATC ACTTACTTCG TCGTCATCTT
201 TGGTGGTCGC CAGATCATGA AGAGCCAGGA CGCCTTCAAG CTCAAGCCCC
251 TCTTCATCCT CCACAACTTC CTCCTGACGA TCGCGTCCGG ATCGCTGTTG
301 CTCCTGTTCA TCGAGAACCT GGTCCCCATC CTCGCCAGAA ACGGACTTTT
351 CTACGCCATC TGCGACGACG GTGCCTGGAC CCAGCGCCTC GAGCTCCTCT
401 ACTACCTCAA CTACCTGGTC AAGTACTGGG AGTTGGCCGA CACCGTCTTT
451 TTGGTCCTCA AGAAGAAGCC TCTTGAGTTC CTGCACTACT TCCACCACTC
501 GATGACCATG GTTCTCTGCT TTGTCCAGCT TGGAGGATAC ACTTCAGTGT
551 CCTGGGTCCC TATTACCCTC AACTTGACTG TCCACGTCTT CATGTACTAC
601 TACTACATGC GCTCCGCTGC CGGTGTTCGC ATCTGGTGGA AGCAGTACTT
651 GACCACTCTC CAGATCGTCC AGTTCGTTCT TGACCTCGGA TTCATCTACT
701 TCTGGGCCTA CACCTACTTC GCCTTCACCT ACTTCCCCTG GGCTCCCAAC
751 GTCGGCAAGT GCGCCGGTAC CGAGGGTGCT GCTCTCTTTG GCTGCGGACT
801 CCTCTCCAGC TATCTCTTGC TCTTTATCAA CTTCTACCGC ATTACCTACA
851 ATGCCAAGGC CAAGGCAGCC AAGGAGCGTG GAAGCAACTT TACCCCAAG
901 ACTGTCAAGT CCGGCGGATC GCCCAAGAAG CCCTCCAAGA GCAAGCACAT
951 CTAA
```

FIG.6

```
  1  MAAAILDKVN FGIDQPFGIK LDTYFAQAYE LVTGKSIDSF VFQEGVTPLS
 51  TQREVAMWTI TYFVVIFGGR QIMKSQDAFK LKPLFILHNF LLTIASGSLL
101  LLFIENLVPI LARNGLFYAI CDDGAWTQRL ELLYYLNYLV KYWELADTVF
151  LVLKKPLEF LHYFHHSMTM VLCFVQLGGY TSVSWVPITL NLTVHVFMYY
201  YYMRSAAGVR IWWKQYLTTL QIVQFVLDLG FIYFCAYTYF AFTYFPWAPN
251  VGKCAGTEGA ALFGCGLLSS YLLLFINFYR ITYNAKAKAA KERGSNFTPK
301  TVKSGGSPKK PSKSKHI*
```

```
      251
GNS1  F V L D G F I Y F A V Q K A V H L Y F P I L . P H C G D V S T T A T F A G C A I I S S Y L V  300
SUR4    L I D L V F V Y F A T T F Y A H K L D G I L P A K G T C Y T Q A A A Y Y L I T G L L S S Y L
MAELO F V L D L G F I Y F C A Y T Y F A F T Y F P W A . P N V G K C A G T E G A A L F G C G L L S Y L L

301
GNS1  L F I S F I N V Y K R K G T K T S R V V K R A H G G V A A K V N E Y V N V D L K N V P T P S P  350
SUR4  L F Y I Q S Y K K G G K T V K K E S E V S G . S V A S G S T G V K T S N T K V S S R K A - - -
MAELO L F I N F Y R I T Y N A K A K A A K E R G S N F T P K T V K S G G S P K . K P S K S K H I * - -

351
GNS1  K P Q H R R R K R
SUR4  - - - - - - - - -
MAELO - - - - - - - - -
```

FIG. 8B

```
              150        160        170        180        190        200
MAELO    TCTCGACCCAGAGAGGTCGCCATGTGGACTATCACTTACTTGTCGTCATCTTTGGTG
              ||||||     ||       |||||||  ||   ||   ||
S78624   CATTAAGCACTTTGCCCCCTGTGCTATACGCCATCACTGCCTATTACGTTATTTTG
              5990       6000       6010       6020       6030       6040

210        220        230        240        250        260
MAELO    GTCGCCAGATCATGAAGAGCCAG--GACGCC-TTCAAGTCAACCCCCTCTTCATCCTCC
              |  |    ||   |    |||    ||| ||   ||   ||     ||  ||
S78624   GTGGCAGTTTTTGTTAAGTAAGTCGAAACCATTAAATTAAAATGGCCTTTTCCAATTGC
              6050       6060       6070       6080       6090       6100

270        280        290        300        310        320
MAELO    ACAACTTCCTCCTGACGATGCGTCC--GGATCGCTGTGTTGTCCTCGTTCATCGAGAACCT
              |||  |  |  |     ||||||    ||   |  ||  ||   |||
S78624   ATAATTGGTTTTAAC-TTCACTTTCATTGA-CGCTTTTATTGCTTATGGTTGAACAATT
              6110       6120       6130       6140       6150       6160

330        340        350        360        370        380
MAELO    GGTCCCCATCCTCGCCAGAAACGGACTTTTCTACGCCATCTGGACGACGGTGCCTGAC
              ||||   ||  |  ||   |  |||  |||   ||||   |||| |  |||||||||
S78624   AGTGCCAATTATTGTTCAGCACGGGTTATACTTCGTATCTGTAATATTGGTGCTTGAC
              6170       6180       6190       6200       6210       6220
```

FIG.9A

```
MAE10   CCAGGGCCTCGAGCTCCTCTACTACCTCAACTACCTGGTCAAGTACTGGGAGTTGGCCGA
                                    390       400       410       420       430       440
             || | ||||    ||   |||   |||  ||| |  |||||      ||   ||  ||  ||
S78624  TCAACCGCTCGTTACATTATATTACATGAATTACATTGTCAAGTTTATTGAATTTATAGA
                                    6230      6240      6250      6260      6270      6280

MAE10   CACCGTCTCTTTTTGGTCCTCAAGAAGAAGCCTCTTGAGTTCCTGCACTACTTCCACCACTC
                                    450       460       470       480       490       500
             ||| ||||||    ||  ||||    || |||     |   ||||||    |||  |||| | |
S78624  CACCTTTTTCTTGGTGCTAAAACATAAAAAATTGACATTTTTGCA-TACTT--ATCA--C
                                    6290      6300      6310      6320      6330      6340

MAE10   GATGACCATGGTTCTCTGCTTTGT-----CCAGCTTGGAGGATA-CACTTCAGTGTCCTGG
                                    510       520       530       540       550
             ||| |  ||    || ||   | |     || |||  |  | |  ||  ||| |||| |||
S78624  CATGGGCTACTGCCTTATTATGTTACACCAATTGATGGGCCACCACCACATCTATTCTTGG
                                    6350      6360      6370      6380      6390      6400

MAE10   GTCCCTATTACCCTCAACTTGACTGTCCAGTCTTCATGTACTACTACTACATGGCGCTCC
                                    560       570       580       590       600       610
             |||||||| |  ||   |||  | ||  ||| |||  ||||     | ||||||||||
S78624  GTCCCTATTTCATTGAACCTTGGTGTTCAGGTGTTATGTTATTGGTACTATTT----CTTG
                                    6410      6420      6430      6440      6450
```

FIG.9B

```
MAELO        GCTGCC----GGTGTTCGCATCTGGTGGAAGCAGTACTTGACCACTCTCCAGATCGTCCAG
             ||||      ||||| ||  ||| ||||||||||||| ||||  ||||    |||  |||
S78624       GCTGCCAGAGGCATCAGGGTCTCGGTGGAAGGAATGGGTTACCAGATTTCAAATTATCCAA
             6460         6470       6480        6490       6500       6510

MAELO        TTCGTTCTTGACCTCGGGATTCATTCTACTTCTCTGCGCCTACACCTACTTCGCCTTCACCTAC
             || ||| ||||  ||| |||  |||  |||||||||||  ||||| |||| ||||||||||||
S78624       TTTGTTTTGGATATCGGTTTCATATATTTGCTGTCTACCAAAAGCAGTTCACTTGTAT
             6520       6530       6540       6550       6560       6570
```

FIG.9C

| Host(plasmid) | 334(pCGN7875) | | 334(pYES2) | | 334(pYX242) | | 334(pRAE-5) | | 334(pRAE-6) | | 334(pYX242) | | 334(pRAE-5) | |
|---|---|---|---|---|---|---|---|---|---|---|---|---|---|---|
| Added substrate | 25 µM OA | | 25 µM OA | | 25 µM GLA | | 25 µM GLA | | 25 µM GLA | | no substrate | | no substrate | |
| Fatty acid | lipid (µg) | | lipid (µg) | | lipid (µg) | | lipid (µg) | | lipid (µg) | | lipid (µg) | | lipid (µg) | |
| C16:0 | | 11.948 | | 23.601 | | 35.123 | | 92.011 | | 85.160 | | 16.294 | | 25.34 |
| C16:1 | | 30.665 | | 71.217 | | 32.789 | | 315.464 | | 115.456 | | 56.183 | | 113.913 |
| C18:0 | | 6.185 | | 9.704 | | 10.515 | | 22.628 | | 18.879 | | 5.535 | | 11.092 |
| C18:1n-9 | | 35.340 | | 57.429 | | 33.989 | | 154.386 | | 106.881 | | 28.388 | | 51.538 |
| C18:3n-6 | | | | | | 48.856 | | 58.084 | | 12.434 | | | | |
| C20:0 | | | | | | 0.474 | | 0.710 | | 0.244 | | | | |
| C20:1n-9 | (0.375%)* | 0.352 | (0.309%)* | 0.527 | | | | 1.405 | | 0.867 | | | | 0.516 |
| C20:3n-6 | | ND | | ND | (0.092%)* | 0.226 | (0.324%)* | 2.504 | (0.269%)* | 1.006 | | ND | | ND |
| C22:0 | | | | | | | | 0.460 | | | | | | |
| C22:1n-9 | | | | | | | | 0.321 | | 0.315 | | | | |
| C24:0 | | | | | | | | | | 1.825 | | | | 0.999 |
| Total Lipid | | 93.760 | | 170.490 | | 245.090 | | 771.690 | | 374.420 | | 112.99 | | 256.52 |

ND = Not Detected
*% total fatty acid

FIG.10A

| Host(plasmid) | 334(pYX242) | | 334(pYX242) | | 334(pRAE-5) | | 334(pRAE-5) | | 334(pRAE-6) | |
|---|---|---|---|---|---|---|---|---|---|---|
| Added substrate | 25 µM GLA | | 25 µM GLA | | 25 µM GLA | | 25 µM GLA | | 25 µM GLA | |
| Fatty acid | lipid (µg) | | lipid (µg) | | lipid (µg) | | lipid (µg) | | lipid (µg) | |
| C16:0 | | 60.683 | | 61.487 | | 100.998 | | 96.193 | | 66.761 |
| C16:1 | | 79.838 | | 79.586 | | 359.754 | | 220.440 | | 87.359 |
| C18:0 | | 9.784 | | 10.106 | | 15.317 | | 15.165 | | 16.744 |
| C18:1n-9 | | 38.536 | | 39.936 | | 108.472 | | 89.637 | | 71.631 |
| C18:3n-6 | | 17.974 | | 17.833 | | 82.866 | | 56.596 | | 17.766 |
| C20:0 | | | | | | 0.510 | | 0.570 | | |
| C20:1n-9 | | | | | | | | | | |
| C20:3n-6 | (0.136%)* | 0.389 | (0.130%)* | 0.374 | (0.336%)* | 3.035 | (0.401%)* | 2.689 | (0.353%)* | 1.185 |
| C22:0 | | | | | | 0.414 | | | | |
| C22:1n-9 | | | | | | | | 0.383 | | |
| C24:0 | | | | | | 1.513 | | 1.626 | | |
| Total Lipid | | 285.560 | | 288.045 | | 902.560 | | 671.113 | | 335.496 |
| *% total fatty acid | | | | | | | | | | |

FIG. 10B

| Host(plasmid) | 334(pRAE-5/pCGR4) | | 334(pYX242/pYES2) | | Host(plasmid) | 334(pRAE-5/pCGR4) | | 334(pYX242/pYES2) | |
|---|---|---|---|---|---|---|---|---|---|
| Added substrate | 25 μM GLA | | 25 μM GLA | | Added substrate | 25 μM GLA | | 25 μM GLA | |
| Fatty Acid | lipid (μg) | | lipid (μg) | | | lipid (μg) | | lipid (μg) | |
| C16:0 | 41.050 | | 37.169 | | C16:0 | 96.986 | | 32.221 | |
| C16:1 | 99.393 | | 100.552 | | C16:1n-7 | 209.667 | | 62.757 | |
| C18:0 | 34.432 | | 27.852 | | C18:0 | 80.418 | | 14.027 | |
| C18:1 | 110.631 | | 92.786 | | C18:1n-9 | 207.104 | | 28.701 | |
| C18:3n-6 | 15.004 | | 7.924 | | C18:3n-6 | 25.264 | | 10.543 | |
| C20:0 | 0.643 | | 0.574 | | C20:0 | 2.038 | | | |
| C20:1 | 1.996 | | 1.684 | | C20:1n-9 | 3.591 | | | |
| C20:3n-6 | 0.542 | | 0.607 | | C20:3n-6 | 1.284 | | 0.326 | |
| C20:4n-6 | 0.579 | | | | C20:4n-6 | 1.392 | | | |
| C22:0 | 1.242 | | 2.604 | | C22:0 | 1.124 | | | |
| C24:0 | 4.754 | | 4.563 | | C24:0 | 3.952 | | | |
| Total Lipid | 334 | | 300 | | Total Lipid | 756 | | 197 | |

FIG.11

| Host(plasmid) | 334(pYX242) | | 334(pRAE-5) | | 334(pRELO-1) | | 334(pRELO-2) | |
|---|---|---|---|---|---|---|---|---|
| Added substrate | 25 μM GLA | | 25 μM GLA | | 25 μM GLA | | 25 μM GLA | |
| | 25°C/48hrs | | 25°C/48hrs | | 25°C/48hrs | | 25°C/48hrs | |
| Fatty acid | lipid (μg) | | lipid (μg) | | lipid (μg) | | lipid (μg) | |
| C16:0 | 28.7 | | 76.707 | | 84.424 | | 77.445 | |
| C16:1 | 0.729 | | 2.513 | | 1.532 | | 1.056 | |
| C18:0 | 7.432 | | 15.761 | | 27.17 | | 21.32 | |
| C18:1n-9 | 28.9 | | 77.323 | | 109.419 | | 82.844 | |
| C18:3n-6 | 9.729 | | 29.236 | | 19.085 | | 18.804 | |
| C20:0 | | | 0.643 | | 0.522 | | 0.537 | |
| C20:1n-9 | | | 0.77 | | 0.426 | | 0.299 | |
| C20:3n-6 | (0.185%)* | 0.374 | (0.279%)* | 1.472 | (0.153%)* | 0.748 | (0.200%)* | 0.832 |
| C22:0 | | | 0.451 | | | | | |
| C22:1n-9 | | | | | 0.224 | | | |
| C24:0 | | | 0.918 | | | | | |
| Total Lipid | 202 | | 527 | | 490 | | 416 | |
| *%total fatty acid | | | | | | | | |

FIG. 12

```
U61954           10        20        30        40        50        60
        RTFKMMDQILGTNFTYEGAKEVARGLEGFSAKLAVGYIATIFGLKYYMKDRKAFDLSTPL
                     | :: |:::|| . | |::: ||  ||::  :||    ||
MAELO   AQAYELVTGKSIDSFVFQEGVTPLSTQREVAMWTITYFVVIFGGRQIMKSQDAFKLK-PL
               30        40        50        60        70        80

U61954       70        80        90       100       110   119  120
        NIWNGILSTFSLLGFLFTF-PTLLSVIRKDGFSHTYSHVSELYTDSTSGYWI------F
        | :::|  ::: |||  |   |:.  :|: :: ::  ::|              |
MAELO   FILHNFLLTIASGSLLLLFIENLVPILARNGL------FYAICDDGAWTQRLELLYY
           90       100       110              120       130

U61954          130       140       150       160       170
        LWVISKIPELLDTVFIVLRKRPLIFMHWYHHALTGYYALVCYHE--DAVHMVWV-VWMNY
        |  | ||  :|  || ||:::||:|: ||| |:|::| |: |      ::|   : :|
MAELO   LNYLVKYWELADTVFLVLKKKPLEFLHYFHHSMT---MVLCFVQLGGYTSVSWVPITLNL
           140       150       160       170       180       190
```

FIG. 13A

```
             180       190       200       210       220       230
U61954   IIHAFMYGYYLLKSLKVPIPPSVAQAITTSQMVQFA------VAIFAQVHVSYKHYVEGVE
          :|:|||.||.:  |      |    :.||.|||    :   |::  ::  ::  ::
MAELO    TVHVFMYYYMRSAAGVRI--WWKQYLTTLQIVQFVLDLGFIYFCAYTYFAFTYFPWAPN
             200       210       220       230       240       250

240       260       270       280
U61954   -GLAYSFRGTAI-GFFMLTTYFYLWIQFYKEHYLKNGGKKYNLAKDQAKTQTKKKAN
          |   :|:.|: .|: ||  . :|.:::  |:.|:    ||::.:..|.::::::
MAELO    VGKCAGTEGAALFGCGLLSSYLLFINFYRITY----NAKAKAAKERGSNFTPKTVKSGG
             260       270       280       290       300

MAELO    SPKKPSKSKHIX
             310
```

FIG.13B

```
Z68749  SLLTNQDEVFPHIRARRFIQEHFGLFVQMAIAYVILVFSIKRFMRDREPFQLTTALRLWN
                :|: :::|::::|:::::|:|    | ||
MAELO   ELVTGKSIDSFVFQEGVTPLSTQREVAMWTITYFVVIFGGRQIMKSQDAFKLKPLFILHN

Z68749  FFLSVFSIYGSWTMFPF--MVQQIRLYGLYGCGCEALSNLPSQAEYWLFLTILSKAVEFV
        |:|: ||  |     |  ::|    |:  :     |:  |::|
MAELO   FLLTIAS--GSLLLLFIENLVPILARNGLFYAICDD-GAWTQRLELLYYLNYLVKYWELA

Z68749  DTFFLVLRKKPLIFLHWYHHMATFVFFCSNYPTPSSQSRVGVIVNLFVHAFMYPYYFTRS
        ||  ||||:||| |||| ||||  :|| ||| :|  || |||:|||||| :|||||  :
MAELO   DTVFLVLKKKPLEFLHYFHHSMTMVLCFVQLGGYTSVSWVPITLNLTVHVFMYYYYMRSA
```

FIG. 14A

```
Z68749    MNIKVPAKISMAVTVLQLTQF---MCFIYGCTLMYYSLATNQARYPSNTPATLQCLSYTL
                 :  |   : :|:||| :: ||    :  |||:|  |::::
MAELO     AGVRIWWK--QYLTTLQIVQFVLDLGFIYFCAYTYFAFTYFPWAPNVGKCAGTEGAALFG
                210       220       230       240       250       260

Z68749    HLL
MAELO     CGLLSSYLLLFINFYRITYNAKAKAAKERGSNFTPKTVKSGGSPKKPSKSKHIX
                270       280       290       300       310
```

FIG. 14B

```
AF003134                MLYSITRRCYTFFVTSLHFYQLYVTECLENVIFNVLVNGQSINSRWKD
                         |:|:  |:|  :  : ::|:  :|:  ::|:: :|
MAELO    MAAAILDKVNFGIDQPFGIKLDTYFAQA---YELVTGKSIDSFVFQEGVT---PLSTQREV
                  10        20           30            40         50

AF003134 AEKTITSFPFHF--------PQTFFQQPHILTLHFLFFVSVTLVTVFKKPKCEFPHSLA
         | |||           |     |  :: ||     ::|:|  :| |  |  :|  :
MAELO    AMWTITYFVVIFGGRQIMKSQDAFKLKPLFILHNFLLTIASGSLLLLFIENLVPILARNG
              60         70        80        90        100       110
```

FIG. 15

Mouse

U97107      MDTSMNFSRGLKMD---LMQPYDEETFQDLRPFLEEYWVSSF------LIVV
                 |:|:|  :||   |::  |:::   |: |:::        ::
MAELO       MAAAILDKVNEGIDQPFGIKLDTYFAQAYELVTGKSIDSFVQEGVTPLSTQREVAMWTI

U97107      VYLLLIVGQTYMRTRKSFSLQRPLIIWSFFLAIFSILGTLRMWKFMATVMFTVGLKQTV
            :|:::|   |: |:::  :||   :||  |: |:   |:|   :  :: ::    :
MAELO       TYFVVIFGGRQIMKSQDAFKLKPLFILHNFLLTIAS---GSL-LLLFIENLV-PILARNGL

U97107      CFAIYTDDAVVRFWSFLFLISKVV----ELGDTAFIILRKRPLIEVHWYHST---VLLFTS
            :||   |||       ||  ::  :       |:|:|  |:|:|::|   ::    ||
MAELO       FYAICDDGAWTQRLELLYYLNYLVKYWELADTVFLVLKKKPLEFLYFHHSMTMVLCFVQ

FIG. 16A

```
Mouse         160                170           180            190            200             210
U97107        FGYKNKVPSGGWF-MTMNFGVHSVMYTYTMKAAKLKHPNLLPMVITSLQILQMVLG---
              :|  ::|      :|    :|::|  ||    ||        ::   ||::|| |::||:||
MAELO         LGGYTSV----SWVPITLNLTVHVEMYYYMRSAAGVR---IWWKQYLTTLQIVQFVLDLGF
              180            190            200            210             220            230

220              230           240             250            260
U97107        -----TIEGILNYIWRQEKG--CHTTTEHFFWSFMLYGTYFILFAHFFHRAYLRPKGKVA
                   |:|::|       |::|   | ::|:||   |  ::|::||  |:: |
MAELO         IYFCAYTYFAFTYFPWAPNVGKCAGTEGAALFGCGLLSSYLLLFINFYRITY-NAKAKAA
              240              250           260             270            280             290

270
U97107        SKSQX
              ::
MAELO         KERGSNFTPKTVKSGGSPKKPSKSKHIX
              300           310
```

FIG. 16B

```
Human
MAELO      NLVPILARNGLEFYAICDDGAWTQRLELLYYINYLVKYWELADTVFLVLKKKPLEFLHYFH
              |:||:       :||:|||:|: |||::::|
AC004050                  SLIVVKDLTYLLPLCLPGDTIFIILRKQKLIFLHWYH
                          10        20        30

MAELO      HSMTMVLCFVQLGGYTSVSWVPITLNLTVHVEMYYYMRSAAGVRIWWK--QYLTTLQIV
           |::::    :  :    :|:|  :|:| ||  ||  |||   ||  |  ::: ||  ||
AC004050   HITVLLYSWYSYKDMVAGGWEMTMNYGVHAVMYSYYAIRAAGFRVSRKFAMFITLSQIT
               40        50        60        70        80        90

MAELO      QFVLDLGFIYFCAYTYFAFTYFPWAPNVGKCAGTEGAALFGCGLISSYLLFINFYRITY
           |:::        |: :|::||  : |   |   :  ::    |||:||:|||::   :|
AC004050   QMLMG-----CVVNYLVFC---WMQH-DQCHSHFQNIFWSSLMYLSYLVLFCHFFFEAY
           100            110           120       130        140
```

FIG. 16C

```
                  40          50          60          70          80          90
MAELO             SFVFQEGVTPLSTQREVAMTITYFVVIFGGRQIMKSQDAFKLKPLFILHNFLLTIASGS
                       :|   |     :|:   |  ||  |: :|:  ||  |
I05465            PRYKSQRMVPPGQLHPYVCLFCYLLTHCMAGTKIHEEPAAVLLPSILQLYNLGLTLLS--
                  20          30          40          50          60          70

100         110         120         130         140         150
MAELO             LLLLFIENLVPILARNGLFYAICDDGAWTQRLELLYYL--NYLVKYWELADTVFLVLKKK
                  |  :|   ::    :|   :|        :|       | |: |  |   ::    :|:
I05465            -LYMFYELVTGVWEGKYNFFCQGTRSAGESDMKIIRVLWWYFSKLIEFMDTFFFILRKN
                  80          90          100         110         120

160         170         180         190         200         210
MAELO             ---PLEFLHYFHH-SMTMVLCFVQLGGYTSVSWVPITLNLTVHVFMYYY--MRSAAGVR--
                  :  || :| |:|| |  | |   :|: |   | || ||   ::|  |   | ::
I05465            NHQITVLHVYHHATMLNIWWFVMNWPCGHSYFGATLNSFIHVLMYSYYGLSSIPSMRPY
                  130         140         150         160         170         180

FIG.17A
```

```
              220       230       240       250       260       270
MAELO   IWWKQYLTTLQIVQFVLDLGFIYFCAYTYFAFTYFPWAPNVGKCAGTEGAALFGCGLLSS
         :|||:|:| |:|||||  : :|||||  : ::|||   |: ||||  :| |:|||
I05465  LWWKKYITQGQLVQFVLTI-IQTTCG-----VFWP--------CSFPLGWLFFQIGYMIS
        190       200       210        220          230

280       290       300       310
MAELO   YLLLFINFYRITYNAKAAKERGSNFTPKTVKSGGSPKKPSKSKHIX
         : ||  ||| |||   :   |::
I05465  LIALFTNFYIQTYNKKGASRRKEHLKGHQNGSVAAVNGHTNSFPSLENSVKPRKQRKDXQ
        240       250       260       270       280       290
```

FIG. 17B

```
  1  MGTDQGKTFT WEELAAHNTK DDLLLAIRGR VYDVTKFLSR HPGGVDTLLL
 51  GAGRDVTPVF EMYHAFGAAD AIMKKYYVGT LVSNELPIFP EPTVFHKTIK
101  TRVEGYFTDR NIDPKNRPEI WGRYALIFGS LIASYYAQLF VPFVVERTWL
151  QVVFAIIMGF ACAQVGLNPL HDASHFSVTH NPTVWKILGA THDFFNGASY
201  LVWMYQHMLG HHPYTNIAGA DPDVSTSEPD VRRIKPNQKW FVNHINQHMF
251  VPFLYGLLAF KVRIQDINIL YFVKTNDAIR VNPISTWHTV MFWGGKAFFV
301  WYRLIVPLQY LPLGKVLLLF TVADMVSSYW LALTFQANHV VEEVQWPLPD
351  ENGIIQKDWA AMQVETTQDY AHDSHLWTSI TGSLNYQAVH HLFPNVSQHH
401  YPDILAIIKN TCSEYKVPYL VKDTFWQAFA SHLEHLRVLG LRPKEE*
```

FIG.18

| Host(plasmid) | 334(MAD708-2) | 334 (MAD708-10) | 334(MAD708-18) | 334 (MAD708-19) | 334(MAD708-30) | 334 (pRAE5) |
|---|---|---|---|---|---|---|
| Added substrate | 25µM GLA | 25µM GLA | 25µM GLA | 25µM GLA | 25µM GLA | 25µM GLA |
| Fatty Acid | | | % total lipid | | | |
| C16:0 | 14.1 | 14.68 | 14.38 | 15.45 | 14.13 | 13.59 |
| C16:1 | 42.84 | 43.42 | 42.57 | 38.03 | 43.58 | 43.98 |
| C18:0 | 3.19 | 3.28 | 3.63 | 4.08 | 3.37 | 2.04 |
| C18:1n-9 | 17.66 | 19.39 | 19.6 | 20.8 | 20.06 | 10.88 |
| C18:3n-6 | 6.65 | 5.58 | 10.24 | 9.46 | 3.56 | 11.14 |
| C20:0 | 0.26 | 0.3 | 0.32 | 0.4 | 0.46 | 0.57 |
| C20:3n-6 | 6.03 (47.5%) | 3.92 (41.2%) | 0.91 (8.0%) | 2.59 (21.5%) | 3.43 (49%) | 0.24 (3.4%) |
| Total Lipid (µg) | 238.47 | 307.86 | 188.51 | 167.31 | 207.47 | 466.65 |

(% conversion) = product/(substrate+product)

FIG. 20

```
  1  ATGGAGTCGA TTGCGCCATT CCTCCCATCA AAGATGCCGC AAGATCTGTT
 51  TATGGACCTT GCCACGCTA  TCGGTGTCCG GGCCGGCGCC TATGTCGATC
101  CTCTCGAGGC CGCGCTGGTG GCCCAGGCCG AGAAGTACAT CCCCACGATT
151  GTCCATCACA CGCGTGGGTT CCTGGTCGCG GTGGAGTCGC CTTTGGCCCG
201  TGAGCTGCCG TTGATGAACC CGTTCCACGT GCTGTTGATC GTGCTGCTT
251  ATTTGGTCAC GGTCTTTGTG GGCATGCAGA TCATGAAGAA CTTTGAGCGG
301  TTCGAGGTCA AGACGTTTTC GCTCCTGCAC AACTTTGTC  TGGTCTCGAT
351  CAGCGCCTAC ATGTGCGGTG GGATCCTGTA CGAGGCTTAT CAGGCCAACT
401  ATGGACTGTT TGAGAACGCT GCTGATCATA CCTTCAAGGG TCTTCCTATG
451  GCCAAGATGA TCTGGCTCTT CTACTTCTCC AAGATCATGG AGTTGTCGA
501  CACCATGATC ATGGTCCTCA AGAAGAACAA CCGCCAGATC TCCTTCTTGC
551  ACGTTTACCA CCACAGCTCC ATCTTCACCA TCTGGTGGTT GGTCACCTTT
601  GTTGCACCCA ACGGTGAAGC CTACTTCTCT GCTCGCGTGA ACTCGTTCAT
651  CCATGTGATC ATGTACGGCT ACTACTTCTT GTCGGCCTTG GGCTTCAAGC
701  AGGTGTCGTT CATCAAGTTC TACATCACGC GTCGCGAGAT GACACAGTTC
751  TGCATGATGT CGGTCCCAGT TTCCTGGGAC ATGTACGCCA TGAAGGTCCT
801  TGGCCGCCCC GGATACCCCT TCTTCATCAC GGCTCTGCTT TGGTTCTACA
851  TGTGGACCAT GCTCGGTCTC TTCTACAACT TTTACAGAAA GAACGCCAAG
901  TTGCCAAGGC AGGCCAAGGC CGACGCTGCC AAGGAGAAGG CAAGGAAGTT
951  GCAGTAA
```

FIG.22

```
  1  MESIAPFLPS KMPQDLFMDL ATAIGVRAAP YVDPLEAALV AQAEKYIPTI
 51  VHHTRGFLVA VESPLARELP LMNPFHVLLI VLAYLVTVFV GMQIMKNFER
101  FEVKTFSLLH NFCLVSISAY MCGGILYEAY QANYGLFENA ADETFKGLPM
151  AKMIWLFYFS KIMEFVDTMI MVLKKNNRQI SFLHVYHHSS IFTIWWLVTF
201  VAPNGEAYFS AALNSFIHVI MYGYYFLSAL GFKQVSFIKF YITRSQMTQF
251  CMMSVQSSWD MYAMKVLGRP GYPFFITALL WFYMWTMLGL FYNFYRKNAK
301  LAKQAKADAA KEKARKLQ*
```

FIG.23

| Host(plasmid) | 334(pRPB2) | 334 (pYES2) |
|---|---|---|
| Added substrate | 25μM GLA | 25μM GLA |
| | (n=4) | |
| Fatty Acid | % total lipid | |
| C16:0 | 15.65 | 15.23 |
| C16:1 | 35.2 | 38.59 |
| C18:0 | 5.68 | 5.55 |
| C18:1n-9 | 25.55 | 25.27 |
| C18:3n-6 | 3.1 | 6.75 |
| C20:0 | 0.36 | 0.14 |
| C20:3n-6 | (62.0%) 5.06 | (2.6%) 0.18 |
| Total Lipid (μg) | 314 | 247 |

(% conversion) = product/(substrate+product)

FIG. 24

| Host(plasmid) | 334(pRPB2) | 334(pRPB2) | 334(pRPB2) | 334(pRPB2) | 334(pRPB2) | 334(pRPB2) |
|---|---|---|---|---|---|---|
| Added substrate | 25μM SA | 25μM OA | 25μM LA | 25μM DGLA | 25μM AA | 25μM Adrenic |
| | C18:0 | C18:1n-9 | C18:2n-6 | C20:3n-6 | C20:4n-6 | C22:4n-6 |
| Fatty Acid | | | % total lipid | | | |
| C16:0 | 15.07 | 14.52 | 15.74 | 15.69 | 16.06 | 15.15 |
| C16:1 | 33.7 | 32.37 | 32.23 | 25.65 | 33.65 | 33.39 |
| C18:0 | *9.78 | 5.83 | 5.61 | 8.33 | 4.52 | 5.35 |
| C18:1n-9 | 31.2 | *37.25 | 26.05 | 20.15 | 24.54 | 28.54 |
| C18:2n-6 | | | *10.4 | | | |
| C18:3n-6 | | | | | | |
| C20:2n-6 | | | 0.29 | | | |
| C20:3n-6 | | | | *16.5 | | |
| C20:4n-6 | | | | 0.27 | *11.7 | |
| C22:4n-6 | | | | | | *7.46 |
| Total Lipid (μg) | 132 | 130 | 171 | 55 | 225 | 163 |

*indicates substrate added
(% conversion) = product/(substrate+product)

FIG.25A

| Host(plasmid) | 334(pRPB2) | 334(pRPB2) | 334(pRPB2) |
|---|---|---|---|
| Added substrate | 25μM ALA<br>C18:3n-3 | 25μM STA<br>C18:4n-3 | 25μM EPA<br>C20:5n-3 |
| Fatty Acid | % total lipid | | |
| C16:0 | 17.32 | 16.01 | 20.67 |
| C16:1 | 27.68 | 34.31 | 50.7 |
| C18:0 | 6.75 | 5.39 | 6.14 |
| C18:1n-9 | 28.4 | 28.54 | |
| C18:3n-3 | *8.39 | | |
| C18:4n-3 | | *1.95 | |
| C20:4n-3 | | (73.2%) 5.33 | |
| C20:5n-3 | | | *10.33 |
| C22:5n-3 | | | 0.25 |
| Total Lipid (μg) | 114 | 199 | 201 |

*indicates substrate added
(% conversion) = product/(substrate+product)

FIG. 25B

| Host(plasmid) | 334(pRPB2+PRPE31) | 334(pYES2+pYX242) |
|---|---|---|
| Added substrate | 25µM GLA | 25µM GLA |
| | | |
| Fatty Acid | % total lipid | |
| C16:0 | 15.54 | 18.26 |
| C16:1 | 30.16 | 33.51 |
| C18:0 | 8.76 | 5.58 |
| C18:1n-9 | 27 | 27.37 |
| C18:3n-6 | *2.6 | *5.6 |
| C20:0 | 0.4 | 0.32 |
| C20:3n-6 | (57.4%) 3.55 | (2.9%) 0.17 |
| C20:4n-6 | (27.6%) 1.32 | ND |
| | | |
| Total Lipid (µg) | 254 | 258 |

* indicates substrate added (% conversion) = product/(substrate+product)

FIG. 26A

| Host(plasmid) | 334(pRPB2+PRPE31) | 334(pYES2+pYX242) |
|---|---|---|
| Added substrate | 25µM STA | 25µM STA |
| | | |
| Fatty Acid | % total lipid | |
| C16:0 | 18 | 16.4 |
| C16:1 | 28.37 | 34.78 |
| C18:0 | 7.42 | 5.71 |
| C18:1n-9 | 26.44 | 30.15 |
| C18:4n-3 | *2.93 | *4.57 |
| C20:0 | 0.25 | 0.17 |
| C20:4n-3 | 4.13 | 0.32 |
| C20:5n-3 | (39%) 1.87 | (2.1%) .10 |
| | | |
| Total Lipid (µg) | 257 | 304 |

* indicates substrate added (% conversion) = product/(substrate+product)

FIG. 26B

```
GLELO       VAQAEKYIPTIVHHTRGFLVAVESPLARELPLMNPFHVLLIVLAYLVTVFVGMQIMKNFE
                40        50        60        70        80        90        99
            ||  |:  :  ::|:||||    :|  ::  :::|:|::  |||||:  ||||
MAELO       GIKLDTYFAQAYELVTGKSIDSFVFQEGVTPLSTQREVAMTITYFVVIFGGRQIMKSQD
                20        30        40        50        60        70

GLELO       RFEVKTFSLLHNFCLVSISAYMCGGILYE--AYQANYGLFENAADHTFKGLPMAKMIWLF
                100       110       120       130       140       150
            |::|  |:::|||  |:  |:  :::    :  ||:
MAELO       AFKLKPLFILHNFLLTIASGSLLLLFIENLVPILARNGLFYAICDDGAWTQRLELLYYLN
                80        90        100       110       120       130

GLELO       YFSKIMEFVDTMIMVLKKNNRQISFLHVYHHSSIFTIWWLVTFVAPNGEAYFSAALNSFI
                160       170       180       190       200       210
            |::|    :|::|||||   :  ::|||  :|:   :|  ::  :: ::  |
MAELO       YLVKYWELADTVFLVLKK---KPLEFLHYFHHS-MTMVLCFVQLGGYTSVSWVPITLNLTV
                140       150       160       170       180       190

FIG.27A
```

```
              220        230        240        250        260
GLELO    HVIMYGYYFLSALGFKQVSFIKFYITRSQMTQF--------CMMSVQS----SWDMYAM
         ||:||   ||::  |:    |:::||       |        |  |  :       ::
MAELO    HVFMYYYMRSAAGVRI--WWKQYLTTLQIVQFVLDLGFIYFCAYTYFAFTYFPWAPNVG
              200        210        220        230        240        250

270        280        290        300        310
GLELO    KVLGRPGYPFFITALLWFYMWTMLGLFYNFYRKNAKLAKQAKADAAKEKARKLQ
         |   :|  ||   :|  |:     ||||||      :: :||  ||||::
MAELO    KCAGTEGAALFGCGLLSSYLL----LFINFYR----ITYNAKAKAAKERGSNFTPKTVKS
              260        270        280        290        300

MAELO    GGSPKKPSKSKHIX
              310
```

```
GLELO  211  AALNSFIHVIMYGYYFLSALGFKQVSFIKFYITRSDMTQFCMM  253
MAELO  188  ITLNLTVHVFMYYYYMRSAAGVR---IWWKQYLTLDIVDFVLD  228
GNS1   204  SLNLGVHVIMYWYYYFLAARGIR---VWWKENVTRFQIIQFVLD  244
SUR4   211  LLNLGVHVIMYWYYFLSSCGIR---VWWKQWVTRFQIIQFLID  251

GLELO  254  SMQSSWDMYAMKVLGRPGYPFFITALLWFYMWTMLGLFYNFYR  296
MAELO  229  -GFIYFCAYTYFAFT/FPW-APNVGKCAGTEGAALFGCGLSS  270
GNS1   245  IGFIYFAVYQKAHLYFP-ILPHCCDVGSTTATFAGCAIIS  286
SUR4   252  LVFVYFATVTFYAHKYLDGILPNKGTYGTQAAAYGYLILTS  294

GLELO  297  KNAKLAKQAKADAAEKARKLQ   AKAAKERGSNFTPKTVKSGGSPKPSK  318
MAELO  271  YRITNAKAKAAKERGSVVKRAHGGVAAKVNEYMNVDL  313
GNS1   287  NVYKRKTSRVVKRAHGGSVASGSSTGVKTSN  329
SUR4   295  IQSYKKGGKKTIVKKESEVSGSVASGSSTGVKTSN  337

MAELO  314  SKHI
GNS1   330  KNVPTPSPSPKPQHRRKR
SUR4   338  TKVSSRKA
```

FIG.28B

```
          30         40         50         60         70         80
MAELO  YELVTGKSIDSFVFQEGVTPLSTQREVAMWTITYFVVIFGGRQIMKSQDAFKLKPLFILH
         ::   |::  |:::::   |:  |: ::::|: :::::
HS1    STYFKALLGPRDTRVKGWFLLDNYIPTFICSVIYLLIVWLGPKYMRNKQPFSCRGILVVY
          10         20         30         40         50         60

90        100        110        120        130        140
MAELO  NFLLTIASGSLLLLFIENLVPILARNGLFYAICDDGAWTQRLELLYYL--NYLVKYWELA
       |: ||:  :  :|:        |: ::       ||:            |: :  |
HS1    NLGLTLLS---LYMFCELVTGVWEGKYNFFCQGTRTAGESDMKIIRVLWWYFSKLIEFM
          70         80         90        100        110        120

150        160        170        180        190        200
MAELO  DTVFLVLKK--KPLEFLHYFHH-SMTMVLCFVQLGGYTSVSWVPITLNLTVHVFMYYYY-
       ||  ::|::  ||: :|| ||  |: |  |:|  |:  : ||   |||  ::||:||
HS1    DTFFFILRKNNHQITVLHVYHHASMLNIWFVMNWVPCGHSYFGATLNSFIHVLMYSYYG
         130        140        150        160        170        180

FIG. 29A
```

```
              210       220       230        240       250       260
MAELO  MRSAAGVR--IWWKQYLTTLQIVQFVLDLGFIYFCAYTYFAFTYFPWAPNVGKCAGTEGA
           : |: ::|  :|||||:|:  |::||||   |:  |    |:        |—
HS1    LSSVPSMRPYLWWKKYITQGQLLQFVLTI-IQTSCGVI--------W-P----CTFPLGW
            190       200       210       220                  230

270       280       290       300       310
MAELO  ALFGCGLLSSYLLLFINFYRITYNAKAKAAKERGSNFTPKTVKSGGSPKKPSKSKHI
        |  :|  |||   |::|| |||   |::  ||
HS1    LYFQIGYMISLIALFTNFYIQTYNKKGASRRKDHLKDHQNGSMAAVNGHTNSFSPLENNV
            240       250       260       270       280       290

HS1    KPRKLRKDX
            300
```

FIG. 29B

```
MAELO   QAYELVTGKSIDSFVFQEGVTPLSTQREVAMTITYFVVIFGGRQIMKSQDAFKLKPLFI
             :  :|||  ||   |   :|:|:|: |:|:::
HS2     VNLYQEVMKHADPRIQGYPLMGSPLLMTSILLITVYFVLSLGPR--IMANRKPFQLRGFMI
                  10        20        30        40        50        60

MAELO   LHNFLLTTIASGSLLLLFIEN---LVPILAR-NGLFYAICDDGAWTQRLELLYYLNYLVKYW
        ::||||||  :: ::     ::  :       :   :  :
HS2     VYNFSLVALSLYIVYEFLMSGWLSTYTWRCDPVDYSNSPEALRMVRVAWLFLFS---KFI
                  70        80        90       100       110       120

MAELO   ELADTVFLVLKKK---PLEFLHYFHHSMT----MVLCFVQLGGYTSVSWVPITLNLTVHVF
        || |||  |::|:|   |||  |||             :  |        : :|| :| :
HS2     ELMDTVIFILRKKDGQVTFLHVFHHSVLPWSWWWGVKIAPGGMGSFHAM---INSSVHVI
                 140       150       160       170            170
```

FIG. 30A

```
              200         210         220         230         240
MAELO  MYYYYMRSAAGV----RIWMKQYLTTLQIVQFVL----DLGFIYF---CAYTYFAFTYFPW
       ||  |||  ||       : |||| :|:|||||        ||||       |  || ::
HS2    MYLYYGLSAFGPVAQPYLMWKKHMTAIQLIQFVLVSLHISQYYFMSSCNYQYPVIIHLIW
           180         190         200         210         220         230

250         260         270         280         290         300
MAELO  APNVGKCAGTEGAALFGCGLLSSYLLLFINFYRITYNAKAKAAKERGSNFTPKTVKSGGS
              ::   :   :  ::: || : :: ||  ::  :  ::     :|   :|
HS2    ----MYG----TIFFMLFSNFWYHSYIKGKRLPRALQQNGAPGIAKVKAN
           240         250         260         270

310
MAELO  PKKPSKSKHI
HS2    x
       280
```

FIG. 30B

```
MAELO      LLLLFIENLVPILARNGLFYAICDDGAWTQRLELLYYLNLVKYWELADTVFLVLKKP-
                                   :| : :|| |:  |   ||  |  |:::|:||
MM2        IVYEFLMSGWLSTYTWRCDPIDFSNSPEALRMVRVAWLFMLSKVIELMDTVIFILRKKDG
                                                                    70

MAELO      -LEFLHYFHHSMTMVLCF----VQLGGYTSVSWVPITLNLTVHVFMYYYMRSAAGV---
            : |||  ||||        :|| :| ||  |  : :||||||||    || |
MM2        QVTFLHVFHHSVLPWSWWGIKLAPGGMGSFHAM---INSSVHVVMYLYYGLSALGPVAQ
                                                                    130

MAELO      -RIWWKQYLTTLQIVQFVL----DLGFIYF---CAYTYFAFTYFPWAPNVGKCAGTEGAAL
            :||| : ::|:||||    ||  :|    ||||| ||||:  ::      ::
MM2        PYLWKKHMTAIQLIQFVLVSLHISQYYFMPSCNYQYPVIIHLIW-----------M
                                                                    260

MAELO      FGCGLLSSYLLLFINFYRITYNAKAKERGSNFTPKTVKSGGSPKKPSKSKHI
           :|  :  :::||| |:  :|  :  :: ::|
MM2        YG

```
            30         40         50         60         70         80
MAELO       YELVTGKSIDSFVFQEGVTPLSTQREVAMTITYFVVIFGGRQIMKSQDAFKLKPLFILH
            |||:: :|: ::||:: :|  ||| ::  ||
AI225632                       NAFLDNMFGPRDSRVRGWFLLDSYLPTFILTTYLLSIWLGNKYMKNRPALSLRGILTLY
                               20         30         40         50         60         70

90        100        110        120        130        140
MAELO       NFLLTIASGSLLLLFTENLVPILARNGLFYAICDD----GAWTQRLELLYYLNYLVKYWE
            |: ||:||:|:  |  :|:|   ::|   |:  ::|
AI225632    NLAITLLSAYMLVELI----LSSWEGGYNLQCQNLDSAGEGDVRVAKVLVWYFSKLVE
            80         90        100        110        120

150        160        170        180        190        200
MAELO       LADTVFLVLKKK---PLEFLHYFHHSMTMVLCFVQLGGYTSVSWVPITLNLTVHVFMYYYY
            : ||:||:|| :||  |||:||:  ||:
AI225632    FLDTIFFVLRKKANQITFLHVYHHASMFNI
            130        140        150
```

FIG. 32

```
GLELO     LIVLAYLVTVFVGMQIMKNFERFEVKTFSLLHNFCLVSISAYMCGGILYEAYQANYGL-F
              : | :  :: : ||||  : ::   ::::: |::|
AI815960                        LYNLGITLLSAYMLAELILSTWEGGYNLQC
                                10        20        30

GLELO     ENAADHTFKGLPMAKMIWLFYFSKIMEFVDTMIMVLKNNRQISFLHVYHHSSIFTIWL
          :: ::    :|||: :|||||  :|::::| :|:|:::   |: |||||||::|:|||
AI815960  QDLTSAGEADIRVAKVLWWYFSKSVEFLDTIFFVLRKKTSQITPLHVYHHASMFNIWWC
                    40        50        60        70        80        90

GLELO     VTFVAPNGEAYFSAALNSFIHVIMYGYYFLSAL-GFKQVSFIKFYITRSQMTQFCMMSVQ
           |   | :: :: :|||||: :|||::||| :::  ::: ::|:|
AI815960  VLNWIPCGQSFFGPTLNSFIHILMYSYYGLSVFPSMHKYLWKKYLTQAQLVQF
                   100       110       120       130       140

GLELO     SSWDMYAMKVLGRPGYPFFITALLWFYMWTMLGLFYNFYRKNAKLAKQAKADAAKEKARK
                   270       280       290       300       310
```

FIG.33

```
GLELO        AQAEKYIPTIVHHTRGFLVAVESPLARELPLMNPFHVLLIVLAYLVTFVFVGMQIMKNFER
                   50        60        70        80        90       100
                                     |  | :::  | |:  :  :||: |:: | |:|  :
HS1          MEHFDASLSTYFKALLGPRDTRVKGWFLLDNYIPTFICSVIYLLIVWLGPKYMRNKQP
                   10        20        30        40        50

GLELO        FEVKTFSLLHNFCLVSISAYMCGGILYEAYQANYGLF-ENAADHTFKGLPMAKMIWLFYF
                  110       120       130       140       150      159
                |  : :::| |: :|  |    ::    :::::|::|: |   ::  :|:||
HS1          FSCRGILVVYNLGLTLLSLYMFCELVTGVWEGKYNFFCQGTRTAGESDMKIIRVLWYYF
                   60        70        80        90       100       110

GLELO        SKIMEFVDTMIMVLKKNNRQISFLHVYHHSSIFTIWLVTFVAPNGEAYFSAALNSFIHV
                  160       170       180       190       200       210   219
             ||:||::||  ||| |::|  |::   ||||||||||:|  :|  |  |||||||||||
HS1          SKLIEFMDTFFFILRKNNHQITVLHVYHHASMLNIWWFVMNWVPCGHSYFGATLNSFIHV
                  120       130       140       150       160       170

GLELO        IMYGYYFLSAL-GFKQVSFIKFYITRSQMTQFCMMSVQSSWDMYAMKVLGRPGYPFFITA
                  220       230       240       250       260       270
             :|||| ||  :  ::  :  | ||:|:|| || :|  :|       |: :  |  :
HS1          LMYSYYGLSSVPSMRPYLWKKYITQGQLLQFVLTIQTS----CGVIWPCTFPLGWLY
                  180       190       200       210       220       230

GLELO        LLWFYMWTMLGLFYNFYRK--NAKLAKQAKADAAKEKARKLQ
                  280       290       300       310
             :  ::| | ||  |||:| |||   ||| |:|
HS1          FQIGYMISLIALFTNFYIQTYNKKGASRRKDHLKDHQNGSMAAVNGHTNSFSPLENNVKP
                  240       250       260       270       280       290
```

FIG.34

```
GLELO      FENAADHTFKGLPMAKMIWLFYFSKIMEFVDTMIMVLKKNNRQISFLHVYHHSSIFTIWW
                                   |::::|:|  ::: ||| ||| :::         |
AC004050                           DTIFIILRK--QKLIFLHWYHHITVLLYSW
           140       150       160       170       180       190
                                                    10        20

GLELO      LVTFVAPNGEAYFSAALNSFIHVIMYGYYFLSALGFKQVSFIKFYITRSQMTQFCMMSVQ
            ::  |   ::|| ::||::|||:||: :| ||::| ||:||:|:  ||:|: :||:|
AC004050   YSYKDMVAGGGWF-MTMNYGVHAVMYSYYALRAAGFRVSRKFAMFITLSQITQMLGCVV
           200       210       220       230       240       250
           30        40        50        60        70        80

GLELO      SSWDMYAMKVLGRPGYPFFITALLW--FYMWTMLGLFYNFYRKN--AKLAKQAKADAAKE
           ::      |:     |  ::|||||  |: || :::|:|:|:|    |:||:       
AC004050   NYLVFCWMQ--HDQCHSHF-QNIFWSSLMYLSYLVLFCHFFFEAYIGKMRKTTKAEX
           260       270       280       290       300       310
                     90        100       110       120       130       140

GLELO      KARKLQ
```

FIG.35

```
GLELO    LLIVLAYLVTVFVGMQIMKNFERFEVKTFSLLHNFCLVSISAYMCGGILYEAYQANYGLF
              80        90       100       110       120       130
                                           :::||  ||  |:  |:    :|:::  :| :: ::|
MM2                                        IVYNFSLVILSLYIVYEFLMSGWLSTYTWR
                                            10        20        30

GLELO    ENAAD--HTFKGLPMAKMIWLFYFSKIMEFVDTMIMVLKKNNRQISFLHVYHHSSIFTIW
             140       150       160       170       180       190
         :  | :: :|::: |::|  ||||||:||:|:|::|: |:::|:|||:||||| ||  |
MM2      CDPIDFSNSPEALRMVRVAWLFMLSKVIELMDTVIFILRKKDGQVTFLHVFHHSVLPWSW
             40        50        60        70        80        90

GLELO    WLVTFVAPNGEAYFSAALNSFIHVTMYGYYFLSALGFKQVSFI---KFYITRSQMTQFCMM
             200       210       220       230       240       250
         |   :||| |  || | ||::  ||||  :|:||||||      ::         ||   ||
MM2      WWGIKIAPGGMGSFHAMINSSVHVVMYLYYGLSALGPVAQPYLMWKKHMTAIQLIQFVLV
             100       110       120       130       140       150

GLELO    SVQSSWDMYAMKVLGRPGYPFFITALLWFYMWTMLGLFYNF----YRKNAKLAKQAKADA
             260       270       280       290       300       309
         |::: ||||    |:||| ||  |||| |:|   |  |     ::         ::
MM2      SLHIS-QYYFMPSCNYQ-YPVIIH-LIWMYGTIFFILFSNFWYHSYTKGKRLPRAVQQNG
             160       170       180       190       200

GLELO    AKEKARKLQ
         310
         |
MM2      APATTKVKAN
             210
```

FIG. 36

```
GLELO      PTIVHHTRGFLVAVESPLARELPLMNPFHVLLIVLAYLVTFVGMQIMKNFERFEVKTFS
                      :::::|| |:::: | ||| : ::
AI225632   NEVNAFLDNMFGPRDSRVRGWFLLDSYLPTFILTITYLLSIWLGNKYMKNRPALSLRGIL
                 10        20        30        40        50        60

GLELO      LLHNFCLVSISAYMCGGILYEAYQANYGLFENAADHTFKG--LPMAK-MIWLFYFSKIMEF
           |:|: ::: ||||          :: :||:||  :  | |  :: || ||||| ::|||
AI225632   TLYNLAITLLSAYMLVELILSSWEGGYNLQCQNLDSAGEGDVRVAKVLVW-YYFSKLVEF
                 80        90       100       110       120

GLELO      VDTMIMVLKKNNRQISFLHVYHHSSIFTIWWLVTFVAPNGEAYFSAALNSFIHVIMYGYY
           :||:|| :|:: ||||:||:||||||||||||:|:|
AI225632   LDTIFFVLRKKANQITFLHVYHHASMFNI
                140       150
```

FIG.37

```
GLELO   FMDLATAIGVRAAPYVDPLEAALVAQAEKYIPTIVHHTRGFLVAVESPLAREL----PL
             : | :: :||: :: :| — | — |:|
U97107                              MDTSMNFSRGLKMDLMQPYDFETFQDLRPF
                                         10        20        30

GLELO   MNPFHV--LLIVLAYLVTVFVGMQIMKNFERFEVKTFSLLHNFCLVSISAYMCGGILYEA
        :: | ||| :|: || :: |:: | :| |:|| :|: ||| :
U97107  LEEYWVSSFLIVVVYLLLIIVGQTYMRTRKSFSLQRPLILWSFFLAIFS--ILGTLRMWK
                    40        50        60        70        80

GLELO   YQAN----YGLFENAADHTFKGLPMAKMIW--LFYFSKIMEFVDTMIMVLKKNNRQISFL
        ::|: || :: ::: || ||:: || |:|:|
U97107  FMATVMFTVGLKQTVCFAIYTDDAVVRF-WSFLFLLSKVVELGDTAFIILRK--RPLIFV
              90       100       110       120       130       140
```

FIG.38A

```
            190           200           210           220           230           240
GLELO   HVYHHSSI--FTIWLVTFVAPNGEAYFSAALNSFIHVIMYGYYFLSALGFKQVSFIKFY
         |||||::  ||  ::  :  |:|   :|: :||:  ::||  ::  :|::  :|::
U97107  HWYHHSTVLLFTSFGYKNKV-PSGGWFMT--MNFGVHSVMYTYYTMKAAKLKHPNLLPMV
            150           160           170           180           190           200

250           260           270           280           290
GLELO   ITRSQMTQFCMMSVQSSWDMYAMKVLG--RPGYPFFITALLWFYMWIMLGLFYN--FYRK
         | |:  | |:  ::    :  :  |     | | ||:|| | | ::|| |::    |
U97107  ITSLQILQMVLGTIFGILNYIWRQEKGCHTTEHFFWSFMLYGTYFILFAHFFHRAYLRP
            210           220           230           240           250           260

300           310
GLELO   NAKLAKQAKADAAKEKARKLQ
         ::  ::|:  :::::
U97107  KGKVASKSQ
            270
```

FIG.38B

```
GLELO              TRGFLVAVESPLARELPLMNPFHVLLIVLAYLVTFVGMQIMKNFERFEVKTFSLLHNFC
                       60        70        80        90       100       110
                      : |:||             :|:|:::    :|:|::   ||
U68749             ATHGPKNFPDAEGRKFFADHFDVTIQASILYMVVVFGTKWFMRNRQPFQLTIPLNIWNFI
(F56H11.4)              30        40        50        60        70        80

GLELO              LVSISAYMCGGILYEAYQ--ANYGL---FENAADHTFKGLPMAKMIWLFYFSKIMEFVDT
                      120       130       140       150       160
                   |::::|         ::  |:  ::: |||||| :|||: ||::|::|:|||
U68749             LAAFSIAGAVKMTPEFFGTIANKGIVASYCKVFDFT-KG-ENGYWVLFMASKLFELVDT
(F56H11.4)              90       100       110       120       130       140

GLELO              MIMVLKKNNRQISFLHVYHHSSIFTIWLVTFVAPNGEAYFSAALNSFIHVIMYGYYFLS
                      170       180       190       200       210       220
                   :::||:|       |||    ::  ||        ||   :|:::||::||||:
U68749             IFLVLRK--RPLMFLHWYHHILTMIYAWYSHPLTP-GFNRYGIYLNFVVHAFMYSYYFLR
(F56H11.4)              150       160       170       180       190

GLELO              ALGFKQVSFIKFYITRSQMTQFCMMSVQSSWDMYAMKVLGRP-GYPFFITALLWFYMWTM
                      230       240       250       260       270       280
                   ::  ::  ||:|       |      :|| ||:  ||:|   ||||:    ||| ::
U68749             SMKIRVPGFIAQAITSLQIVQFIISCAVLAHLGYLMHFTNANCDFEPSVFKLAVFMDTTY
(F56H11.4)              200       210       220       230       240       250

GLELO              LGLFYNFYRKNAKLAKQAKADAAKEKARKLQ
                      290       300       310
                   |::|  :||
U68749             LALFVNFFLQSYVLRGGKDKYKAVPKKKNN
(F56H11.4)              260       270       280
```

FIG. 39

```
MAELO             MAAAILDKVNFGIDQPFGIKLDTYFAQAYELVTGKSIDSFVFQEGVTPLSTQREVAMW-T
                  ::    :|:||               :|       ||  :|:::   |:|::
U68749            MAQHPLVQRLLDVKFDT---KRFVAIATHGPKNFPDAEGRKFFADHFDVTIQAS
(F56H11.4)                 10          20         30         40         50

MAELO             ITYFVVIFGGRQIMKSQDAFKLK-PLFILHNFLLTIASGSLLLLFIENLVPILARNGLFY
                  |  |:||:||  :  |::|::::  |:|:  ||  | :: |  ::      :|  :|:|
U68749            ILYMVVFGTKWFMRNRQPFQLTIPLNIW-NFILAAFSIAGAVKMTPEFFGTIANKGIVA
(F56H11.4)              60         70         80         90        100        110

MAELO             AICDDGAWTQRLELLYYLNYLV-KYWELADTVFLVLKKKPLEFLHYFHHSMTMVLCFVQL
                  ::  |:     |  :   :::   :|||  ||||||||   |||:|:||  ::|  ::
U68749            SYCKVFDFTKGENGYWWLFMASKLFELVDTIFLVLRKKRPLMFLHWYHHILTMIYAWYSH
(F56H11.4)             120        130        140        150        160        170
```

FIG. 40A

```
                      180       190       200       210       220       230
MAELO           GGYTSVSWVPITLNLTVHVFMY-YYYMRSAAGVRI--WWKQYLTTLQIVQFVLDLGFIYF
                   :: ||::||: |||  ||::||   :|:  : | :|:|||||::: :
U68749          PLTPGFNRYGIYLNFVVHAFMYSYYFLRSMK-IRVPGFIAQAITSLQIVQFIISCAVLAH
(F56H11.4)          180       190       200       210       220

240       250       260       270       280
MAELO           CAYT-YFAFTYFPWAPNVGKCAGTEGAALFGCGLLSSYLLFINFYRITY-----NAKAK
                 :| :|: :::||| ||   :|     |  :| |  ::||:|| :|   |     ||
U68749          LGYLMHFTNANCDFEPSVFKLA------VF----MDTTYLALFVNFFLQSYVLRGGKDKYK
(F56H11.4)  230       240       250       260       270       280

290       300       310
MAELO           AAKERGSNFTPKTVKSGGSPKKPSKSKHI
                |: :: :|
U68749          AVPKKKNN
(F56H11.4)
```

FIG. 40B

```
GLELO                          AALVAQAEKYIPTIVHHTRGFLVAVESPLARELPLMNPFHVLLIVLAYLVTVFVGMQIMK
                                        :  |    :  |  |   :|   |  ::::|   |:: |::
DM1    PTKMINMDISVTPNYSYIFDFENDFIHQRTRKWMLENWTWVFYYCGIYMLVIFGGQHFMQ
              10        20        30        40        50        60

40        50        60        70        80        90

GLELO  NFERFEVKTFSLLHNFCLVSISAYMCGGILYEAYQA--NYGLFENAADHTF--KGLPMAK
       |  ||   ::  |   ::    :  ::      ::  ||| |:||||:::  :       :
DM1    NRPRFQLRGPLIIWNTLLAMFSIMGAARTAPELIHVLRHYGLFHSVCVPSYIEQDRVCGF
              80        90       100       110       120

100       110       120       130       140       150

GLELO  MIWLFYFSKIMEFVDTMIMVLKKNNRQISFLHVYHHSSIFTIWWLVTFVAPNGEAYFSAA
       ||| | |:  :  ||| ||::|:|:|   :: |||  :|||   |: ::: ::   :
DM1    WTWLFVLSKLPELGDTIFIVLRK--QPLIFLHWYHHITVLIYSWF--SYTEYTSSARWFIV
          130       140       150       160       170       180

160       170       180       190       200       210

GLELO  LNSFIHVIMYGYYFLSALGFKQVSFIKFYITRSQMTQFCMMSVQSSWDMYAMKVLGRPGY
       :|  :| ::|:|| |::|  ||:|| ||:   ||:|   :|: |    |:|       :|:
DM1    MNYCVHSVMYSYYALKAARFNPPRFISMIITSLQLAQMIIGCAINVWANGFLKTHGTXSC
             190       200       210       220       230       240

220       230       240       250       260       270

GLELO  PFFITALLWFYMWTMLGLFYNFYRKNAKLAKQAKADAAKEKARKLQ
DM1    HISQRNINLSIAMYSSYFVLFARFFYKAYLAPGGHKSRRMA
             250       260       270       280

```
MAELO       VTGKSIDSFVFQEGVTPLSTQREVAMWTITYFVVIFGGRQIMKSQDAFKLKPLFILHNFL
                          :::|||||:|:::      |:|:   :|:    :|
DM1         IFDFENDFIHQRTRKWMLENWTWVFYYCGIYMLVIFGGQHFMQNRPRFQLRGPLIIWNTL
            30        40        50        60        70        80

MAELO       LTIASGSLLLLFIENLVPILARNGLFYAICDDGAWTQ-RLELLY--YLNYLVKYWELADTV
            |::  |         :|:|||::|:  : |     | :  :    :|  ||:||:|
DM1         LAMFSIMGAARTAPELIHVLRHYGLFHSVCVPSYIEQDRVCGFWTWLFVLSKLPELGDTI
            90       100       110       120       130       140

MAELO       FLVLKKKPLEFLHYFHHSMTMVLCFVQLGGYTS-VSWVPITLNLTVHVFMYYYMRSAAG
            |:|||:||    |||   |||   :    :      |:|      |::|
DM1         FIVLRKQPLIFLHWYHHITVLIYSWFSYTEYTSSARWF-IVMNYCVHSVMYSYYALKAAR
            150      160       170       180       190       200

MAELO       VRI--WWKQYLTTLQIVQFVLDLGFIYFCAYTYFAFTYFPWAPNVGKCAGTEGAALFGCG
              ::  |||:||  |: ||::|::|                    ||     :    :
DM1         FNPPRFISMIITSLQLAQMIIG------CAINVWANGFLK-THGTXSCHISQRNINLSIA
            210       220       230       240       250       260

MAELO       LLSSYLLLFINFYRITYNAKAKAAKERGSNFTPKTVKSGGSPKKPSKSKHI
            :  ||::||  :    :|  :|  ||::
DM1         MYSSYFVLFARFFYKAYLAPGGHKSRRMA
            260       270       280
```

FIG. 42

```
  1  ATGGAACATT TTGATGCATC ACTTAGTACC TATTTCAAGG CATTGCTAGG
 51  CCCTCGAGAT ACTAGAGTAA AAGGATGGTT TCTTCTGGAC AATTATATAC
101  CCACATTTAT CTGCTCTGTC ATATATTTAC TAATTGTATG GCTGGGACCA
151  AAATACATGA GGAATAAACA GCCATTCTCT TGCCGGGGGA TTTTAGTGGT
201  GTATAACCTT GGACTCACAC TGCTGTCTCT GTATATGTTC TGTGAGTTAG
251  TAACAGGAGT ATGGGAAGGC AAATACAACT TCTTCTGTCA GGGCACACGC
301  ACCGCAGGAG AATCAGATAT GAAGATTATC CGTCCTCCT GGTGGTACTA
351  CTTCTCCAAA CTCATAGAAT TTATGGACAC TTTCTTCTTC ATCCTGCGCA
401  AGAACAACCA CCAGATCACG GTCCTGCACG TCTACCACCA TGCCTCGATG
451  CTGAACATCT GGTGGTTTGT GATGAACTGG GTCCCCTGCG GCCACTCTTA
501  TTTTGGTGCC ACACTTAATA GCTTCATCCA CGTCCTCATG TACTCTTACT
551  ATGGTTGTC GTCAGTCCCT TCCATGCGTC CGTCCTCTG GTGGAAGAAG
601  TACATCACTC AGGGGCAGCT GCTTCAGTTT GTGCTGACAA TCATCCAGAC
651  CAGCTGCGGG GTCATCTGGC CGTGCACATT CCCTCTTGGT TGGTTGTATT
701  TCCAGATTGG ATACATGATT TCCCTGATTG CTCTCTTCAC AAACTTCTAC
751  ATTCAGACCT ACAACAAGAA AGGGCCTCC CGAAGGAAAG ACCACCTGAA
801  GGACCACCAG AATGGGTCCA TGGCTGCTGT GAATGGACAC ACCAACAGCT
851  TTTCACCCCT GGAAACAAT GTGAAGCCAA GGAAGCTGCG GAAGGATTGA
901  AGTCAAAGAA TTGA
```

FIG.43

```
  1  MEHFDASLST YFKALLGPRD TRVKGWFLLD NYIPTFICSV IYLLIVWLGP
 51  KYMRNKQPFS CRGILVVYNL GLTLLSLYMF CELVTGVWEG KYNFFCQGTR
101  TAGESDMKII RVLWWYYFSK LIEFMDTFFF ILRKNNHQIT VLHVYHHASM
151  LNIWWFVMNW VPCGHSYFGA TLNSFIHVLM YSYYGLSSVP SMRPYLWWKK
201  YITQGQLLQF VLTIIQTSCG VIWPCTFPLG WLYFQIGYMI SLIALFTNFY
251  IQTYNKKGAS RRKDHLKDHQ NGSMAAVNGH TNSFSPLENN VKPRKLRKD*
```

FIG. 44

| Host (plasmid) | 334(pYX242) | 334(pRAE-58-A1) | 334(pYX242) | 334(pRAE-58-A1) |
|---|---|---|---|---|
| Added substrate | 25 µM GLA | 25 µM GLA | 25 µM AA | 25 µM AA |
| Fatty acid | %total fatty acid | %total fatty acid | %total fatty acid | %total fatty acid |
| C18:3n-6 | 4.40 | 2.71 | 0.03 | 0.04 |
| C20:3n-6 | 0.09 | (50.34%)* 2.75 | 0.02 | 0.02 |
| C20:4n-6 | | | 7.84 | 3.97 |
| C22:4n-6 | | | ND | (23.37%)* 1.21 |
| C16:1n-7 | 41.11 | 34.72 | 41.49 | 35.07 |
| C18:1n-7 | 1.85 | 11.33 | 2.01 | 11.57 |
| C20:1n-7 | 0.04 | 1.48 | 0.04 | 1.62 |
| C18:1n-9 | 15.60 | 15.66 | 15.16 | 14.57 |
| C20:1n-9 | 0.06 | 0.22 | 0.06 | 0.23 |
| C18:1n-5 | 0.11 | 0.62 | 0.12 | 0.58 |
| Total Lipid | 370 | 969 | 359 | 514 |

*% conversion=product/(substrate+product)

FIG. 45

```
  1  ATGGCTCAGC ATCCGCTCGT TCAACGGCTT CTCGATGTCA AATTCGACAC
 51  GAAACGATTT GTGGCTATTG CTACTCATGG GCCAAAGAAT TTCCCTGACG
101  CAGAAGGTCG CAAGTTCTTT GCTGATCACT TTGATGTTAC TATTCAGGCT
151  TCAATCCTGT ACATGGTCGT TGTGTTCGGA ACAAAATGGT TCATGCGTAA
201  TCGTCAACCA TTCCAATTGA CTATTCCACT CAACATCTGG AATTCATCC
251  TCGCCGCATT TTCCATCGCA GGAGCTGTCA AAATGACCCC AGAGTTCTTT
301  GGAACCATTG CCAACAAAGG AATTGTCGCA TCCTACTGCA AAGTGTTGA
351  TTTCACGAAA GGAGAGAATG GATACTGGGT GTGGCTCTTC ATGGCTTCCA
401  AACTTTTCGA ACTTGTTGAC ACCATCTTCT TGGTTCTCCG TAAACGTCCA
451  CTCATGTTCC TTCACTGGTA TCACCATGA TCTACGCCTG
501  GTACTCTCAT CCATTGACCC CAGGATTCAA CAGATACGGA ATTTATCTTA
551  ACTTTGTCGT CCACGCCTTC ATGTACTCCT ACTACTTCCT TCGCTCGATG
601  AAGATTCGCG TGCCAGGATT CATCGCCCAA GCTATCACAT CTCTTCAAAT
651  CGTTCAATTC ATCATCTCTT CCACGCCGTT CT TGCTCATCTT GGTTATCTCA
701  TGCACTTCAC CAATGCCAAC TGTGATTTCG AGCCATCAGT ATTCAAGCTC
751  GCAGTTTTCA TGGACACAAC ATACTTGGCT CTTTTCGTCA ACTTCTTCCT
801  CCAATCATAT GTTCTCCGCG GAGGAAAAGA CAAGTACAAG GCAGTGCCAA
851  AGAAGAAGAA CAACTAA
```

FIG. 46

1   MAQHPLVQRL LDVKFDTKRF VAIATHGPKN FPDAEGRKFF ADHFDVTIQA
51  SILYMVVFG TKWFMRNRQP FQLTIPLNIW NFILAAFSIA GAVKMTPEFF
101 GTIANKGIVA SYCKVFDFTK GENGYWVWLF MASKLFELVD TIFLVLRKRP
151 LMFLHWYHHI LTMIYAWYSH PLTPGFNRYG IYLNFVVHAF MYSYYFLRSM
201 KIRVPGFIAQ AITSLQIVQF IISCAVLAHL GYLMHFTNAN CDFEPSVFKL
251 AVFMDTTYLA LFVNFFLQSY VLRGGKDKYK AVPKKKNN

FIG. 47

| Host (plasmid) | 334(pYX242) | 334(pRET-21) | 334(pRET-22) |
|---|---|---|---|
| Added Substrates | 50 µM GLA + 50 µM AA | 50 µM GLA + 50 µM AA | 50 µM GLA + 50 µM AA |
| Fatty Acid | %total fatty acid | %total fatty acid | %total fatty acid |
| C16:0 | 9.22 | 12.46 | 9.9 |
| C16:1 | 0.09 | 0.18 | 0.13 |
| C18:0 | 1.46 | 2.41 | 1.49 |
| C18:1n-9 | 4.03 | 4.92 | 3.91 |
| C18:3n-6 | 10.02 | 11.89 | 8.69 |
| C20:3n-6 | (1.28%)* 0.13 | (11.1%)* 1.48 | (19.4%)* 2.09 |
| C20:4n-6 | 46.98 | 28.87 | 35.25 |
| C22:4n-6 | 0 | 0 | 0 |
| Total lipid (mg) | 212 | 174 | 187 |

*% conversion=product/(substrate+product)

FIG. 48

```
  1 ATGAACATGT CAGTGTTGAC TTTACAAGAA TATGAATTCG AAAAGCAGTT
 51 CAACGAGAAT GAAGCCATCC AATGGATGCA GGAAAACTGG AAGAAATCTT
101 TCCTGTTTTC TGCTCTGTAT GCTGCCTTTA TATTCGGTGG TCGGCACCTA
151 ATGAATAAAC GAGCAAAGTT TGAACTGAGG AAGCCATTAG TGCTCTGGTC
201 TCTGACCCTT GCAGTCTTCA GTATATTCGA TGCTCTTCGA ACTGGTGCTT
251 ATATGGTGTA CATTTTGATG ACCAAAGGCC TGAAGCAGTC AGTTTGTGAC
301 CAGGGTTTTT ACAATGGACC TGTCAGCAAA TTCTGGGCTT ATGCATTTGT
351 GCTAAGCAAA GCACCCGAAC TAGGAGATAC AATATTCATT ATTCTGAGGA
401 AGCAGAAGCT GATCTTCCTG CACTGGTATC ACCACATCAC TGTGCTCCTG
451 TACTCTTGGT ACTCCTACAA AGACATGGTT GCCGGGGAG GTTGGTTCAT
501 GACTATGAAC TATGGCGTGC ACGCCGTGAT ACGCCGTGAT GTACTCTTAC TATGCCTTGC
551 GGGCGGCAGG TTTCCGAGTC TCCCGGAAGT GATGGGCTGT TTGGTTAACT CATCACCTTG
601 TCCCAGATCA CTCAGATGCT AGTGTCACTC GTGGTTAACT TCACTTTCAG ACCTGGTCTT
651 CTGCTGGATG CAGCATGACC CATGTACCTC AGCTACCTTC TCACTTTCAG AACATCTTCT
701 GGTCCCTCACT CATGTACCTC AGCTACGACC TGCTCTTCTG CCATTCTTTC
751 TTTGAGGCCT ACATCGGCAA AATGAGGAAA ACAACGAAAG CTGAATAG
```

FIG.49

```
  1  MNMSVLTLQE YEFEKQFNEN EAIQWMQENW KKSFLFSALY AAFIFGGRHL
 51  MNKRAKFELR KPLVLWSLTL AVFSIFGALR TGAYMVYILM TKGLKQSVCD
101  QGFYNGPVSK FWAYAFVLSK APELGDTIFI ILRKQKLIFL HWYHHITVLL
151  YSWYSYKDMV AGGGWFMTMN YGVHAVMYSY YALRAAGFRV SRKFAMFITL
201  SQITQMLMGC VVNYLVFCWM QHDQCHSHFQ NIFWSSLMYL SYLVLFCHFF
251  FEAYIGKMRK TTKAE*
```

FIG.50

| Host | 334 | 334 | 334 | 334 | 334 | 334 | 334 | 334 | 334 | 334 | 334 | 334 |
|---|---|---|---|---|---|---|---|---|---|---|---|---|
| Plasmid | pYX242 | pRAE-58 | pYX242 | pRAE-58 | pYX242 | pRAE-58 | pYX242 | pRAE-58 | pYX242 | pRAE-58 | pYX242 | pRAE-58 |
| Substrate | GLA | GLA | AA | AA | STA | STA | EPA | EPA | OA | OA | ALA | ALA |
| Concentration | 25μM | 25μM | 25μM | 25μM | 25μM | 25μM | 25μM | 25μM | 25μM | 25μM | 25μM | 25μM |
| | | | | | % total lipid | | | | | | | |
| C18:1n-9 | 18.75 | 12.96 | 16.95 | 12.76 | 16.06 | 14.18 | 19.55 | 13.78 | 29.42 | 23.06 | ND | 14.58 |
| C18:1n-7 | 2.00 | 18.49 | 2.30 | 18.70 | 1.45 | 13.26 | 2.75 | 13.62 | 2.50 | 16.42 | 1.87 | 13.76 |
| C18:1n-5 | 0.29 | 1.63 | 0.24 | 1.61 | 0.33 | 0.97 | 0.32 | 1.10 | 0.30 | 1.64 | 0.28 | 1.18 |
| C18:3n-6 | 4.61 | 2.02 | 0.04 | 0.04 | 0.02 | 0.09 | 0.06 | 0.05 | 0.02 | 0.05 | 0.01 | 0.01 |
| C18:3n-3 | 0.02 | 0.08 | 0.02 | 0.07 | 0.01 | 0.03 | 0.04 | 0.05 | 0.02 | 0.08 | 14.74 | 14.08 |
| C18:4n-3 | ND | ND | ND | ND | 7.01 | 2.65 | ND | ND | ND | ND | ND | ND |
| C20:1n-9 | 0.10 | 0.77 | 0.11 | 0.70 | 0.15 | 0.55 | 0.15 | 0.46 | 0.27 | 2.25 | 0.10 | 0.57 |
| C20:1n-7 | 0.08 | 8.45 | 0.10 | 8.06 | 0.04 | 3.95 | 0.14 | 4.48 | 0.10 | (8.9%)9.35 | 0.06 | 3.53 |
| C20:3n-6 | 0.17 | (78.3%)7.29 | 0.01 | 8.40 | ND | 0.04 | ND | ND | ND | ND | ND | ND |
| C20:3n-3 | ND | ND | ND | ND | ND | 0.07 | ND | ND | ND | ND | ND | (30.4%)6.15 |
| C20:4n-6 | ND | ND | 22.07 | (42.7%)6.26 | ND | 0.08 | ND | ND | ND | ND | ND | ND |
| C20:4n-3 | ND | ND | ND | ND | 0.25 | (79.2%)10.07 | ND | ND | ND | ND | ND | ND |
| C20:5n-3 | 0.01 | ND | 0.01 | ND | 0.18 | 0.08 | 8.21 | 2.63 | ND | 0.02 | ND | ND |
| C22:4n-6 | ND | ND | ND | ND | ND | ND | ND | ND | ND | ND | ND | ND |
| C22:5n-3 | ND | ND | ND | ND | ND | 0.18 | ND | (71.7%)6.66 | ND | ND | ND | ND |
| Total Lipid | 158 | 104 | 144 | 112 | 324 | 209 | 178 | 94 | 148 | 87 | 243 | 315 |

(% conversion) = product/(substrate + product)
ND = not detected

FIG.51

| Host | 334 | 334 | 334 | 334 | 334 | 334 | 334 | 334 | 334 | 334 | 334 | 334 |
|---|---|---|---|---|---|---|---|---|---|---|---|---|
| Plasmid | pYX242 | pRAE-58 | pYX242 | pRAE-58 | pYX242 | pRAE-58 | pYX242 | pRAE-58 | pYX242 | pRAE-58 | pYX242 | pRAE-58 |
| Substrate | GLA | GLA | GLA | GLA | AA | AA | AA | AA | EPA | EPA | EPA | EPA |
| Concentration | 25μM | 25μM | 100μM | 100μM | 25μM | 25μM | 100μM | 100μM | 25μM | 25μM | 100μM | 100μM |
|  | | | | | | % total lipid | | | | | | |
| C18:1n-9 | 23.82 | 21.49 | 18.49 | 17.41 | 22.09 | 19.23 | 17.45 | 18.44 | 24.78 | 21.28 | 19.42 | 18.85 |
| C18:1n-7 | 2.52 | 18.35 | 1.71 | 11.82 | 2.54 | 18.77 | 1.78 | 12.67 | 2.64 | 19.48 | 1.79 | 12.40 |
| C18:1n-5 | 0.15 | 1.13 | 0.10 | 0.54 | 0.15 | 1.23 | 0.10 | 0.63 | 0.15 | 1.18 | 0.09 | 0.62 |
| C18:3n-6 | 6.10 | 2.38 | 23.30 | 14.46 | 0.04 | 0.02 | 0.04 | 0.02 | 0.04 | 0.02 | 0.01 | 0.01 |
| C20:1n-9 | 0.08 | 0.83 | 0.05 | 0.48 | 0.10 | 1.18 | 0.04 | 0.56 | 0.10 | 1.30 | 0.06 | 0.63 |
| C20:1n-7 | 0.10 | 5.75 | 0.07 | 3.09 | 0.11 | 9.49 | 0.05 | 3.62 | 0.10 | 9.94 | 0.08 | 4.07 |
| C20:3n-6 | 0.15 | (62.4%)3.95 | 0.31 | (39.8%)9.56 | 0.02 | ND | ND | 0.04 | 0.02 | 0.02 | 0.01 | 0.01 |
| C20:4n-6 | ND | ND | 0.01 | ND | 11.76 | 7.68 | 28.39 | 21.02 | 4.79 | 2.04 | 26.47 | 13.69 |
| C20:5n-3 | ND | ND | ND | ND | 0.03 | 0.02 | 0.10 | 0.07 | ND | ND | 0.00 | ND |
| C22:4n-6 | ND | ND | ND | ND | ND | (27.5%)2.91 | 0.01 | (15.7%)3.90 | ND | (70.3%)4.82 | 0.04 | (45.7%)11.50 |
| C22:5n-3 | ND | ND | ND | ND | ND | ND | ND | 0.03 | 0.02 | ND | ND | ND |
| Total Lipid | 230 | 419 | 590 | 576 | 249 | 332 | 1014 | 961 | 372 | 390 | 1323 | 1065 |

(% conversion) = product/(substrate + product)
ND = not detected

FIG.52

| Host | 334 | 334 | 334 | 334 | 334 | 334 | 334 | 334 | 334 | 334 | 334 | 334 | 334 | 334 | 334 | 334 |
|---|---|---|---|---|---|---|---|---|---|---|---|---|---|---|---|---|
| Plasmid | pYX242 | pRAE-58 | pYX242 | pRAE-58 | pYX242 | pRAE-58 | pYX242 | pRAE-58 | pYX242 | pRAE-58 | pYX242 | pRAE-58 | pYX242 | pRAE-58 | pYX242 | pRAE-58 |
| Substrate | PA | PA | SA | SA | ARA | ARA | BA | BA | PTA | PTA | OA | OA | EA | EA |
| Concentration | 25μM | 25μM | 25μM | 25μM | 25μM | 25μM | 25μM | 25μM | 25μM | 25μM | 25μM | 25μM | 25μM | 25μM |
| | | | | | | | % total lipid | | | | | | | | | |
| C16:0 | 24.17 | 17.23 | 11.22 | 7.90 | 7.74 | 7.98 | 7.62 | 7.11 | 17.28 | 11.04 | 16.06 | 12.76 | 14.37 | 11.98 |
| C16:1n-7 | 39.83 | 33.83 | 30.62 | 20.56 | 21.61 | 19.81 | 21.34 | 22.89 | 50.06 | 39.43 | 40.95 | 30.06 | 43.34 | 29.51 |
| C16:1n-5 | 0.30 | 0.74 | 0.29 | 0.58 | 0.17 | 0.47 | 0.18 | 0.59 | 0.38 | 0.80 | 0.34 | 0.68 | 0.37 | 0.71 |
| C18:0 | 1.90 | 1.50 | 35.82 | 38.10 | 1.12 | 0.89 | 1.03 | 0.88 | 1.90 | 1.44 | 1.82 | 1.43 | 1.51 | 1.23 |
| C18:1n-9 | 15.36 | 14.11 | 11.52 | 10.88 | 8.29 | 10.03 | 8.09 | 10.25 | 14.55 | 13.86 | 20.12 | 21.37 | 14.12 | 15.15 |
| C18:1n-7 | 1.36 | 11.44 | 0.90 | 8.72 | 0.69 | 8.51 | 0.69 | 8.58 | 1.30 | 12.76 | 1.30 | 13.79 | 1.21 | 12.66 |
| C18:1n-5 | 0.11 | 0.78 | 0.08 | 0.69 | 0.08 | 0.54 | 0.06 | 0.61 | 0.19 | 0.76 | 0.10 | 0.90 | 0.15 | 0.84 |
| C20:0 | 0.15 | 0.17 | 0.09 | 0.12 | 52.07 | 41.48 | ND | ND | ND | ND | ND | ND | 0.17 | 0.23 |
| C20:1n-9 | 0.09 | 0.45 | 0.05 | 0.30 | 0.03 | ND | 0.06 | 0.28 | 0.05 | 0.38 | 0.18 | 0.58 | 7.47 | 10.97 |
| C20:1n-7 | 0.20 | 2.84 | ND | 1.52 | 0.05 | 1.43 | 0.14 | 1.60 | 0.07 | 2.76 | 0.12 | 2.08 | ND | 2.30 |
| C22:0 | 0.43 | 0.56 | 0.29 | 0.22 | 0.31 | 0.19 | 52.91 | 38.43 | ND | ND | ND | ND | ND | 0.32 |
| C24:0 | 0.59 | 1.39 | 0.36 | 0.85 | 0.45 | 0.71 | 0.53 | 1.14 | 0.45 | 1.63 | 0.66 | 1.02 | 0.56 | 0.79 |
| | | | | | | | | | | | | | | | | |
| Total Lipid | 297 | 272 | 573 | 542 | 558 | 846 | 585 | 519 | 464 | 295 | 306 | 448 | 309 | 648 |

ND = not detected

FIG. 53A

| Host | 334 | 334 | 334 | 334 | 334 | 334 | 334 | 334 | 334 | 334 |
|---|---|---|---|---|---|---|---|---|---|---|
| Plasmid | pYX242 | pRAE-58 | pYX242 | pRAE-58 | pYX242 | pRAE-58 | pYX242 | pRAE-58 | pYX242 | pRAE-58 |
| Substrate | LA | LA | GLA | GLA | DGLA | DGLA | AA | AA | ADA | ADA |
| Concentration | 25μM | 25μM | 25μM | 25μM | 25μM | 25μM | 25μM | 25μM | 25μM | 25μM |
| | | | | % total lipid | | | | | | |
| C18:1n-9 | 15.27 | 16.83 | 14.85 | 15.58 | 13.62 | 16.24 | 15.08 | 15.64 | 16.18 | 13.98 |
| C18:1n-7 | 1.21 | 13.53 | 1.22 | 11.80 | 1.16 | 12.63 | 1.18 | 11.70 | 1.30 | 10.67 |
| C18:1n-5 | 0.13 | 0.95 | 0.20 | 0.73 | 0.12 | 0.72 | 0.14 | 0.59 | 0.12 | 0.70 |
| C18:2n-6 | 4.09 | 4.85 | 0.09 | 0.07 | 0.07 | 0.04 | 0.04 | 0.04 | 0.03 | 0.07 |
| C18:3n-6 | ND | ND | 4.66 | 2.33 | ND | ND | ND | ND | ND | ND |
| C20:1n-9 | 0.07 | 2.60 | 0.07 | 0.33 | 0.07 | 0.33 | 0.04 | 0.27 | 0.08 | 0.33 |
| C20:1n-7 | 0.10 | 0.18 | 0.14 | 1.65 | 0.08 | 1.68 | 0.12 | 1.58 | 0.12 | 1.85 |
| C20:2n-6 | ND | (13.2%)0.74 | ND | ND | ND | ND | ND | ND | ND | ND |
| C20:3n-6 | ND | ND | ND | (51.4%)2.46 | 6.37 | 7.86 | ND | 0.03 | ND | ND |
| C20:4n-6 | ND | ND | ND | ND | ND | 0.09 | 6.49 | 5.77 | ND | ND |
| C22:4n-6 | ND | ND | ND | ND | ND | ND | ND | (27.1%)2.14 | 10.91 | 15.57 |
| C24:0 | 0.59 | 1.61 | 0.64 | 1.12 | 0.69 | 0.79 | 0.52 | 0.77 | 0.54 | 1.26 |
| | | | | | | | | | | |
| Total Lipid | 333 | 373 | 260 | 392 | 260 | 672 | 553 | 690 | 706 | 440 |

(% conversion) = product/(substrate + product)
ND = not detected

FIG.53B

| Host | 334 | 334 | 334 | 334 | 334 | 334 | 334 | 334 | 334 | 334 |
|---|---|---|---|---|---|---|---|---|---|---|
| Plasmid | pYX242 | pRAE-58 | pYX242 | pRAE-58 | pYX242 | pRAE-58 | pYX242 | pRAE-58 | pYX242 | pRAE-58 |
| Substrate | ALA | ALA | STA | STA | EPA | EPA | DPA | DPA | | |
| Concentration | 25μM | 25μM | 25μM | 25μM | 25μM | 25μM | 25μM | 25μM | | |
| | | | | | % total lipid | | | | | |
| C18:1n-9 | 17.21 | 17.36 | 16.85 | 17.71 | 16.45 | 16.93 | 17.08 | 16.68 | 18.36 | 18.77 |
| C18:1n-7 | 1.29 | 12.20 | 1.15 | 11.38 | 1.23 | 11.48 | 1.33 | 11.61 | 1.46 | 13.72 |
| C18:1n-5 | 0.14 | 0.68 | 0.12 | 0.57 | 0.12 | 0.54 | 0.12 | 0.63 | 0.13 | 0.79 |
| C18:3n-3 | 4.42 | 3.61 | ND | 0.03 | ND | 0.03 | ND | 0.03 | ND | 0.03 |
| C18:4n-3 | ND | 0.13 | 3.04 | 1.38 | ND | 0.13 | ND | 0.13 | ND | 0.17 |
| C20:1n-9 | 0.09 | 0.33 | 0.11 | 0.34 | 0.05 | 0.31 | 0.09 | 0.30 | 0.13 | 0.34 |
| C20:1n-7 | 0.13 | 1.55 | 0.05 | 1.38 | 0.23 | 1.89 | 0.18 | 1.73 | 0.15 | 1.76 |
| C20:3n-3 | 0.06 | (22.2%)1.03 | ND | ND | ND | 0.11 | ND | ND | ND | ND |
| C20:4n-3 | ND | ND | 0.06 | (61.9%)2.24 | ND | ND | ND | ND | ND | ND |
| C20:5n-3 | ND | ND | 0.05 | 0.05 | 7.43 | 4.88 | ND | ND | 0.07 | ND |
| C22:4n-3 | ND | ND | ND | 0.39 | ND | ND | 0.28 | 0.41 | ND | ND |
| C22:5n-6 | ND | ND | ND | ND | ND | ND | 3.99 | 5.94 | ND | ND |
| C22:5n-3 | ND | ND | ND | ND | ND | (39.5%)3.19 | 0.64 | 1.07 | ND | ND |
| C24:0 | 0.43 | 0.73 | 0.33 | 0.73 | 0.45 | 0.84 | ND | 0.06 | 0.68 | 0.77 |
| C24:5n-3 | ND | ND | ND | ND | ND | 0.08 | ND | 0.06 | ND | ND |
| Total Lipid | 696 | 729 | 911 | 710 | 719 | 703 | 602 | 642 | 397 | 684 |

(% conversion) = product/(substrate + product)
ND = not detected

FIG.53C

```
  1 ATGGAGCAGC TGAAGGCCTT TGATAATGAA GTCAATGCTT TCTTGGACAA
 51 CATGTTTGGA CCACGAGATT CTCGAGTTCG CGGGTGGTTC CTGCTGGACT
101 CTTACCTTCC CACCTTCATC CTCACCATCA CGTACCTGCT CTCGATATGG
151 CTGGGTAACA AGTACATGAA GAACAGGCCT GCTCTGTCTC TCAGGGGCAT
201 CCTCACCTTG TATAACCTCG CAATCACACT TCTTTCTGCG TATATGCTGG
251 TGGAGCTCAT CCTCTCCAGC TGGGAAGGAG GTTACAACTT GCAGTGTCAG
301 AATCTCGACA GTGCAGGAGA AGGTGATGTC CGGGTAGCCA AGGTCTTGTG
351 GTGGTACTAC TTCTCCAAAC TAGTGGAGTT CCTGGACACG ATTTTCTTTG
401 TTCTACGAAA AAAGACCAAT CAGATCACCT TCCTTCATGT CTATCACCAC
451 GCGTCCATGT TCAACATCTG GTGGTGTGTT TTGAACTGGA TACCTTGTGG
501 TCAAAGCTTC TTTGGACCCA CCCTGAACAG CTTTATCCAC ATTCTCATGT
551 ACTCCTACTA CGGCCTGTCT GTGTTCCCGT CCATGCACAA GTACCTTTGG
601 TGGAAGAAGT ACCTCACACA GGCTCAGCTG GTGCAGTTCG TACTCACCAT
651 CACGCACACG CTGAGTGCCG TGGTGAAGCC CTGTGGCTTC CCCTTTGGCT
701 GTCTCATCTT CCAGTCTTCC TATATGATGA CGCTGGTCAT CCTGTTCTTA
751 AACTTCTATA TTCAGACATA CCGGAAAAAG CCAGTGAAGA AAGAGCTGCA
801 AGAGAAAGAA GTGAAGAATG GTTTCCCCAA AGCCCACTTA ATTGTGGCTA
851 ATGGCATGAC GGACAAGAAG GCTCAATAA
```

FIG. 54

```
  1 MEQLKAFDNE VNAFLDNMFG PRDSRVRGWF LLDSYLPTFI LTITYLLSIW
 51 LGNKYMKNRP ALSLRGILTL YNLAITLLSA YMLVELILSS WEGGYNLQCQ
101 NLDSAGEGDV RVAKVLWWYY FSKLVEFLDT IFFVLRKKTN QITFLHVYHH
151 ASMFNIWWCV LNWIPCGQSF FGPTLNSFIH ILMYSYYGLS VFPSMHKYLW
201 WKKYLTQAQL VQFVLTITHT LSAVVKPCGF PFGCLIFQSS YMMTLVILFL
251 NFYIQTYRKK PVKKELQEKE VKNGFPKAHL IVANGMTDKK AQ*
```

| Host | 334 | 334 | 334 | 334 | 334 | 334 | 334 | 334 | 334 | 334 | 334 | 334 |
|---|---|---|---|---|---|---|---|---|---|---|---|---|
| Plasmid | pYX242 | pRAE-84 | pYX242 | pRAE-84 | pYX242 | pRAE-84 | pYX242 | pRAE-84 | pYX242 | Prae-84 | pYX242 | pRAE-84 |
| Substrate | GLA | GLA | AA | AA | ADA | ADA | STA | STA | EPA | EPA | DPA | DPA |
| Concentration | 25μM | 25μM | 25μM | 25μM | 25μM | 25μM | 25μM | 25μM | 25μM | 25μM | 25μM | 25μM |
| % total lipid | | | | | | | | | | | | |
| C18:1N-9 | 15.94 | 14.16 | 12.30 | 15.67 | 11.77 | 11.41 | 14.81 | 17.92 | 15.91 | 16.33 | 15.04 | 14.63 |
| C18:1N-7 | 1.25 | 1.21 | 1.10 | 1.50 | 1.13 | 1.18 | 1.19 | 1.38 | 1.33 | 1.49 | 1.37 | 1.38 |
| C18:3N-6 | 4.53 | 4.21 | ND | ND | ND | ND | ND | ND | ND | ND | ND | ND |
| C18:4N-3 | ND | ND | ND | ND | ND | ND | 2.78 | 2.70 | ND | ND | ND | ND |
| C20:1N-7 | ND | ND | ND | ND | ND | ND | ND | 0.03 | ND | 0.05 | ND | ND |
| C20:3N-6 | 0.10 | 0.37 | ND | ND | ND | 0.32 | ND | ND | ND | ND | ND | ND |
| C20:4N-6 | ND | ND | 11.44 | 5.55 | ND | ND | ND | ND | ND | ND | ND | ND |
| C20:4N-3 | ND | ND | ND | ND | ND | ND | ND | (14%)0.44 | ND | ND | ND | ND |
| C20:5N-3 | ND | ND | ND | ND | ND | ND | ND | ND | 9.68 | 3.02 | 0.57 | 0.57 |
| C22:4N-6 | ND | ND | ND | (10.4%)0.64 | 20.41 | 23.61 | ND | ND | ND | ND | ND | ND |
| C22:4N-3 | ND | ND | ND | ND | ND | ND | ND | (42.3%)0.33 | ND | ND | ND | ND |
| C22:5N-3 | ND | ND | ND | ND | ND | ND | ND | ND | ND | (32.7%)1.47 | 7.87 | 4.88 |
| C24:4N-6 | ND | ND | ND | (62.6%)1.07 | ND | (9.2%)2.4 | ND | ND | ND | ND | ND | ND |
| C24:5N-3 | ND | ND | ND | ND | ND | ND | ND | ND | ND | (82.8%)7.06 | ND | (43.9%)3.82 |
| Total Lipid | 208 | 126 | 115 | 189 | 158 | 149 | 124 | 433 | 221 | 271 | 127 | 126 |

(% conversion) = product/(substrate + product)
ND = not detected

| Host | 334 | 334 | 334 | 334 | 334 | 334 | 334 | 334 | 334 | 334 | 334 | 334 | 334 | 334 |
|---|---|---|---|---|---|---|---|---|---|---|---|---|---|---|
| Plasmid | pYX242 | pRAE-84 | pYX242 | pRAE-84 | pYX242 | pRAE-84 | pYX242 | pRAE-84 | pYX242 | pRAE-84 | pYX242 | pRAE-84 | pYX242 | pRAE-84 |
| Substrate | PA | PA | SA | SA | ARA | ARA | BA | BA | PTA | PTA | OA | OA | EA | EA |
| Concentration | 25µM | 25µM | 25µM | 25µM | 25µM | 25µM | 25µM | 25µM | 25µM | 25µM | 25µM | 25µM | 25µM | 25µM |
| | | | | | | | % total lipid | | | | | | | |
| C16:0 | 36.30 | 39.95 | 7.12 | 8.31 | 5.78 | 4.42 | 4.17 | 5.76 | 18.69 | 18.85 | 14.69 | 18.91 | 15.25 | 18.88 |
| C16:1n-7 | 26.22 | 23.52 | 11.77 | 15.25 | 10.23 | 6.29 | 7.01 | 10.10 | 38.48 | 41.23 | 20.55 | 31.48 | 25.89 | 40.32 |
| C16:1n-5 | 0.23 | 0.28 | 0.16 | 0.20 | 0.13 | 0.07 | 0.09 | 0.13 | 0.38 | 0.38 | 0.26 | 0.43 | 0.35 | 0.41 |
| C18:0 | 2.26 | 2.14 | 64.90 | 58.73 | 0.94 | 1.01 | 0.64 | 0.85 | 2.17 | 2.29 | 3.02 | 2.73 | 2.71 | 2.15 |
| C18:1n-9 | 14.83 | 11.27 | 6.35 | 7.22 | 5.20 | 4.33 | 3.84 | 5.12 | 14.25 | 14.27 | 18.44 | 22.20 | 14.62 | 16.91 |
| C18:1n-7 | 1.44 | 1.36 | 0.57 | 0.73 | 0.54 | 0.51 | 0.41 | 0.56 | 1.57 | 1.68 | 1.53 | 1.67 | 1.65 | 1.84 |
| C18:1n-5 | 0.10 | ND | ND | 0.06 | ND | ND | ND | 0.06 | 0.17 | 0.15 | ND | 0.18 | ND | 0.16 |
| C20:0 | 0.59 | 0.24 | 0.09 | 0.08 | 66.40 | 74.78 | 0.10 | 0.05 | 0.17 | 0.17 | 0.24 | 0.20 | 0.33 | 0.04 |
| C20:1n-9 | 0.06 | 0.10 | ND | 0.04 | 0.05 | 0.06 | ND | ND | ND | ND | 0.25 | 0.16 | 13.15 | 7.07 |
| C20:1n-7 | 0.07 | ND | ND | ND | ND | 0.12 | ND | ND | ND | ND | 0.40 | ND | ND | 0.04 |
| C22:0 | 0.45 | 0.75 | 0.29 | 0.30 | 0.43 | 0.31 | 77.35 | 70.71 | 0.74 | 0.80 | 0.98 | 0.74 | 0.83 | 0.44 |
| C24:0 | 0.55 | 1.09 | 0.38 | 0.41 | 0.69 | 0.62 | 0.50 | 0.45 | 0.94 | 0.92 | 1.67 | 0.96 | ND | 0.53 |
| Total Lipid | 158 | 104 | 144 | 112 | 324 | 209 | 178 | 94 | 148 | 87 | 243 | 315 | 70 | 529 |

ND = not detected

FIG.57A

| Host | 334 | 334 | 334 | 334 | 334 | 334 | 334 | 334 | 334 | 334 |
|---|---|---|---|---|---|---|---|---|---|---|
| Plasmid | pYX242 | pRAE-84 | pYX242 | pRAE-84 | pYX242 | pRAE-84 | pYX242 | pRAE-84 | pYX242 | pRAE-84 |
| Substrate | LA | LA | GLA | GLA | DGLA | DGLA | AA | AA | ADA | ADA |
| Concentration | 25μM | 25μM | 25μM | 25μM | 25μM | 25μM | 25μM | 25μM | 25μM | 25μM |
| % total lipid | | | | | | | | | | |
| C18:1n-9 | 12.30 | 16.12 | 15.63 | 16.28 | 14.28 | 13.77 | 16.21 | 15.04 | 15.38 | 12.94 |
| C18:1n-7 | 1.34 | 1.87 | 1.69 | 1.90 | 1.41 | 1.61 | 1.61 | 1.62 | 1.51 | 1.47 |
| C18:2n-6 | 2.67 | 3.61 | 0.17 | 0.20 | 0.24 | 0.21 | 0.09 | 0.09 | 0.06 | 0.14 |
| C18:3n-6 | ND | ND | 2.03 | 2.49 | ND | ND | ND | ND | ND | ND |
| C20:3n-6 | ND | ND | ND | (14.7%)0.43 | 10.59 | 10.73 | ND | 5.27 | ND | ND |
| C20:4n-6 | ND | ND | ND | ND | ND | ND | 14.03 | (8.7%)0.5 | 11.44 | 16.60 |
| C22:4n-6 | 0.79 | 1.00 | 1.08 | 1.16 | 1.30 | 0.87 | 0.87 | 0.72 | 0.77 | 1.18 |
| C24:0 | ND | ND | ND | ND | ND | ND | ND | (43.8%)0.39 | ND | (7.3%)1.3 |
| C24:4n-6 | ND | ND | ND | ND | ND | ND | ND | 0.38 | ND | ND |
| C24:5n-6 | | | | | | | | | | |
| Total Lipid | 85 | 87 | 88 | 79 | 107 | 98 | 208 | 212 | 304 | 122 |

*% Conversion=product/(substrate + product)
ND=not detected

FIG.57B

| Host | 334 | 334 | 334 | 334 | 334 | 334 | 334 | 334 | 334 | 334 |
|---|---|---|---|---|---|---|---|---|---|---|
| Plasmid | pXY242 | pRAE-84 | pYX242 | pRAE-84 | pYX242 | pRAE-84 | pYX242 | pRAE-84 | pYX242 | pRAE-84 |
| Substrate | ALA | ALA | STA | STA | EPA | EPA | DPA | DPA | | |
| Concentration | 25μM | 25μM | 25μM | 25μM | 25μM | 25μM | 25μM | 25μM | | |
| | | | | | % total lipid | | | | | |
| C18:1n-9 | 16.69 | 16.38 | 18.24 | 15.95 | 14.07 | 15.16 | 16.05 | 15.06 | 17.47 | 17.15 |
| C18:1n-7 | 1.37 | 1.43 | 1.71 | 1.40 | 1.37 | 1.47 | 1.67 | 1.51 | 1.75 | 1.73 |
| C18:2n-6 | 0.08 | 0.08 | 0.12 | 0.04 | 0.13 | 0.06 | 0.11 | 0.18 | 0.13 | 0.15 |
| C18:3n-3 | 4.47 | 4.28 | ND | 2.39 | ND | ND | ND | ND | ND | ND |
| C18:4n-3 | ND | ND | 2.28 | ND | ND | 0.26 | ND | ND | ND | 0.12 |
| C20:3n-3 | (1.3%)0.06 | (3.6%)0.16 | ND | (11.1%)0.3 | ND | ND | ND | ND | ND | ND |
| C20:4n-3 | ND | ND | ND | (43.4%)0.23 | ND | 3.84 | ND | ND | ND | ND |
| C20:5n-3 | ND | 0.07 | ND | ND | 9.97 | ND | ND | ND | ND | ND |
| C22:4n-3 | ND | ND | ND | ND | ND | ND | ND | ND | ND | ND |
| C22:5n-6 | ND | ND | ND | ND | ND | (24.0%)1.21 | 0.64 | 0.55 | ND | ND |
| C22:5n-3 | ND | ND | ND | ND | 1.38 | (73.6%)3.38 | 8.79 | 3.57 | ND | ND |
| C24:0 | 0.65 | 0.43 | 1.41 | 0.58 | 1.38 | 0.78 | 1.45 | 1.35 | 0.89 | 0.67 |
| C24:5n-3 | ND | ND | ND | ND | ND | ND | ND | (46.4%)3.09 | ND | ND |
| Total Lipid | 362 | 384 | 173 | 393 | 124 | 280 | 137 | 151 | 190 | 200 |

*% conversion = product/(substrate + product)
ND = not detected

FIG.57C

```
  1 ATGGAACATT TCGATGCGTC ACTCAGTACC TATTTCAAGG CCTTCCTGGG
 51 CCCCCGAGAT ACAAGAGTCA AAGGATGGTT CCTCCTGGAC AATTACATCC
101 CTACGTTTGT CTGTTCTGTT ATTTACTTAC TCATTGTATG GCTGGGACCA
151 AAATACATGA AGAACCGGCA GCCGTTCTCT TGCCGAGGCA TCCTGCAGTT
201 GTATAACCTT GGACTCACCC TGCTGTCTCT CTACATGTTC TATGAGTTGG
251 TGACAGGTGT GTGGGAGGGC AAATACAACT TTTTCTGCCA GGGAACACGC
301 AGCGCGGGAG AATCCGATAT GAAGATCATC CGCGTCCTCT GGTGGTACTA
351 CTTCTCCAAA CTCATCGAAT TCATGGACAC CTTTTTCTTC ATCCTTCGCA
401 AGAACAACCA CCAGATCACC GTGCTCCATG TCTACCACCA CGCTACCATG
451 CTCAACATCT GGTGGTTTGT GATGAACTGG GTTCCCTGCG GCCATTCATA
501 TTTTGGTGCG ACACTCAACA GCTTCATCCA TGTCCTCATG TACTCGTACT
551 ATGGTCTGTC CTCCATCCCG TCCATGCGTC CCTACCTCTG GTGGAAAAAG
601 TACATCACTC AAGGGCAGCT GGTCCAGTTT GTGCTGACAA TCATCCAGAC
651 GACCTGCGGG GTCTTCTGGC CATGCTCCTT CCCTCTCGGG TGGCTGTTCT
701 TCCAGATTGG ATACATGATT TCCCTGATTG CTCTCTTCAC AAACTTCTAC
751 ATTCAGACTT ACAACAAGAA AGGGGCCTCT CGGAGGAAAG ACCACCTGAA
801 GGGCCACCAG AACGGGTCTG TGGCCGCCGT CAACGGACAC ACCAACAGCT
851 TCCCTTCCCT GGAAAACAGC GTGAAGCCCA GGAAGCAGCG AAAGGATTGA
```

FIG.58

```
  1 MEHFDASLST YFKAFLGPRD TRVKGWFLLD NYIPTFVCSV IYLLIVWLGP
 51 KYMKNRQPFS CRGILQLYNL GLTLLSLYMF YELVTGVWEG KYNFFCQGTR
101 SAGESDMKII RVLWWYYFSK LIEFMDTFFF ILRKNNHQIT VLHVYHHATM
151 LNIWWFVMNW VPCGHSYFGA TLNSFIHVLM YSYYGLSSIP SMRPYLWWKK
201 YITQGQLVQF VLTIIQTTCG VFWPCSFPLG WLFFQIGYMI SLIALFTNFY
251 IQTYNKKGAS RRKDHLKGHQ NGSVAAVNGH TNSFPSLENS VKPRKQRKD*
```

FIG.59

| Host | 334 | 334 | 334 | 334 | 334 | 334 | 334 | 334 | 334 | 334 | 334 | 334 |
|---|---|---|---|---|---|---|---|---|---|---|---|---|
| Plasmid | pYX242 | pRAE-87 | pYX242 | pRAE-87 | pYX242 | pRAE-87 | pYX242 | pRAE-87 | pYX242 | pRAE-87 | pYX242 | pRAE-87 |
| Substrate | GLA | GLA | AA | AA | ADA | ADA | STA | STA | EPA | EPA | DPA | DPA |
| Concentration | 25mM | 25mM | 25mM | 25mM | 25mM | 25mM | 25mM | 25mM | 25mM | 25mM | 25mM | 25mM |
| | | | | | % total lipid | | | | | | | |
| C18:1n-9 | 15.94 | 12.05 | 12.30 | 12.61 | 11.77 | 10.91 | 14.81 | 15.52 | 15.91 | 16.66 | 15.04 | 8.07 |
| C18:1n-7 | 1.25 | 8.00 | 1.10 | 9.60 | 1.13 | 8.87 | 1.19 | 8.94 | 1.33 | 11.60 | 1.37 | 6.90 |
| C18:3n-6 | 4.53 | 1.11 | ND | ND | ND | ND | ND | ND | ND | ND | ND | ND |
| C18:4n-3 | ND | ND | ND | 0.09 | ND | 0.14 | 2.78 | 0.80 | ND | ND | ND | ND |
| C20:1n-7 | 0.10 | 0.98 | ND | 0.91 | ND | 0.63 | ND | 0.62 | ND | 0.94 | ND | 1.34 |
| C20:3n-6 | ND | (78.7%)4.1 | ND | ND | ND | ND | ND | ND | ND | ND | ND | ND |
| C20:4n-6 | ND | ND | 11.44 | 11.28 | ND | ND | ND | ND | ND | ND | ND | ND |
| C20:4n-3 | ND | ND | ND | ND | ND | ND | ND | (81.0%)3.4 | ND | ND | ND | ND |
| C20:5n-3 | ND | ND | ND | ND | ND | ND | ND | ND | 9.68 | 4.58 | ND | ND |
| C22:4n-6 | ND | ND | ND | (36.0%)6.33 | 20.41 | 21.15 | ND | ND | ND | ND | ND | ND |
| C22:4n-3 | ND | ND | ND | ND | ND | ND | ND | ND | ND | ND | ND | ND |
| C22:5n-3 | ND | ND | ND | ND | ND | ND | ND | ND | ND | (57.4%)6.18 | 7.87 | 17.24 |
| C24:4n-6 | ND | ND | ND | ND | ND | ND | ND | ND | ND | ND | ND | ND |
| C24:5n-3 | ND | ND | ND | ND | ND | ND | ND | ND | ND | (4.2%)0.27 | ND | (1.4%)0.25 |
| Total Lipid | 208 | 102 | 115 | 177 | 158 | 117 | 124 | 200 | 221 | 199 | 127 | 91 |

(% conversion) = product/(substrate + product)
ND = not detected

FIG.60

| Host(plasmid) | 334(pYX242) | 334(pRET-22) | 334(pYX242) | 334(pRET-22) | 334(pYX242) | 334(pRET-22) |
|---|---|---|---|---|---|---|
| Added Substrates | 50 mM GLA | 50 mM GLA | 50 mM AA | 50 mM AA | no substrate | no substrate |
| | | | % total lipid | | | |
| Fatty Acid | | | | | | |
| C16:0 | 19.8 | 18.59 | 13.8 | 6.23 | 13.62 | 13.63 |
| C16:1n-7 | 20.92 | 17.74 | 26.62 | 13.01 | 40.1 | 47.67 |
| C18:0 | 5.79 | 4.94 | 3.62 | 2 | 4.86 | 5.031 |
| C18:1n-7 | (3.9%) 0.85 | (9.12%) 1.78 | (3.5%) 0.97 | (12.54%) 1.18 | (3.6%) 1.5 | (7.53%) 3.88 |
| C18:1n-9 | 8.46 | 7.45 | 10.27 | 5.36 | 13.7 | 16.93 |
| C18:3n-6 | *26.62 | *22.03 | 0.03 | 0.01 | | |
| C20:3n-6 | (1.1%)0.3 | (38.2%)13.61 | | | | |
| C20:4n-6 | | | *27.36 | *65.38 | | |
| C22:4n-6 | | | | | | |
| Total Lipid (μg) | 36 | 42 | 85 | 280 | 55 | 79 |
| (% conversion) = product/(substrate + product) | | | | | | |
| *indicates substrate added | | | | | | |

FIG.61

| Host(plasmid) | 334(pRET22) | 334(pRET22) | 334(pRET22) | 334(pRET22) | 334(pRET22) | 334(pRET22) |
|---|---|---|---|---|---|---|
| Added Substrate | 50µM SA | 50µM OA | 50µM LA | 50µM DGLA | 25µM AA | 50µM Adrenic |
|  | C18:0 | C18:1n-9 | C18:2n-6 | C20:3n-6 | C20:4n-6 | C22:4n-6 |
| Fatty Acid | %total lipid | | | | | |
| C16:0 | 12.9 | 12.54 | 15.23 | 9.1 | 10.2 | 3.42 |
| C16:1 | 37.71 | 23.83 | 24.87 | 16.61 | 18.375 | 7.66 |
| C18:0 | 11.44 | 4.7 | 4.49 | 2.7 | 2.9 | 1.23 |
| C18:1n-9 | 14.03 | *16.87 | 9.54 | 6.74 | 6.39 | 2.99 |
| C18:2n-6 |  |  | 16.87 |  | 0.15 | 0.28 |
| C18:3n-6 |  |  |  |  |  |  |
| C20:2n-6 |  |  |  |  |  |  |
| C20:3n-6 |  |  |  | *44.34 |  | 0.05 |
| C20:4n-6 |  |  |  | 0.34 | *25.78 | 0.26 |
| C22:4n-6 |  |  |  |  |  | *75.72 |
| Total Lipid (µg) | 63 | 103 | 71 | 110 | 97 | 277 |

*indicates substrate added
(% conversion) = product/(substrate + product)

FIG.62A

| Host(plasmid) | 334(pRET22) | 334(pRET22) | 334(pRET22) | 334(pRET22) |
|---|---|---|---|---|
| Added Substrate | 50µM ALA<br>C18:3n-3 | 50µM PA<br>C18:0 | 50µM EPA<br>C20:5n-3 | 50µM STA<br>C18:4n-3 |
| Fatty Acid | % total lipid | | | |
| C16:0 | 13.91 | 15.06 | 16.92 | 20.08 |
| C16:1 | 14.74 | 31.77 | 23.57 | 20.17 |
| C18:0 | 4.06 | *4.85 | 4.94 | 6.02 |
| C18:1n-9 | 6.65 | 13.59 | 10.46 | 9.29 |
| C18:3n-3 | *38.66 | | | |
| C18:4n-3 | | | | *20.45 |
| C20:4n-3 | | | | (12.57%)2.94 |
| C20:5n-3 | | | *15.48 | |
| C22:5n-3 | | | | |
| Total Lipid (µg) | 80 | 84 | 81 | 60 |

* indicates substrate added
(% conversion) = product/(substrate + product)

FIG. 62B

| Host(plasmid) | 334(pRET-22+pCGR-4) | 334(pYX242+pYES2) |
|---|---|---|
| Added Substrate | 50μM GLA | 50μM GLA |
| | | |
| Fatty Acid | % total lipid | |
| C16:0 | 15.92 | 15.07 |
| C16:1n-7 | 24.97 | 19.48 |
| C18:0 | 8.25 | 6.48 |
| C18:1n-7 | 3.9 | 1.61 |
| C18:1n-9 | 18.48 | 12.71 |
| C18:3n-6 | *7.0 | *10.54 |
| C20:0 | 0 | 0 |
| C20:3n-6 | (27.81%) 4.36 | (1.58%) 0.17 |
| C20:4n-6 | (27.55%) 4.32 | 0 |
| | | |
| Total Lipid(μg) | 508 | 168 |

*indicates substrate added
(% conversion) = product/(substrate + product)

FIG.63A

| Host(plasmid) | 334(pRET-22+pCGR-4) | 334(pYX242+pYES2) |
|---|---|---|
| Added Substrate | 50μM STA | 50μM STA |
| | | |
| Fatty Acid | % total lipid | |
| C16:0 | 18.74 | 16.21 |
| C16:1n-7 | 21.35 | 26.09 |
| C18:0 | 6.78 | 7.57 |
| C18:1n-7 | 1.97 | 1.7 |
| C18:1n-9 | 20.73 | 22.41 |
| C18:4n-3 | *6.05 | *13.43 |
| C20:0 | 0 | 0.45 |
| C20:4n-3 | (15.88%) 1.68 | (4.73%) 0.69 |
| C20:5n-3 | (26.93%) 2.85 | (3.22%) 0.47 |
| | | |
| Total Lipid(μg) | 335 | 161 |

*indicates substrate added
(% conversion) = product/(substrate + product)

FIG.63B

ELONGASE GENES AND USES THEREOF

The subject application is a continuation-in-part of U.S. patent application Ser. No. 09/379,095 filed on Aug. 23, 1999, now abandoned, which is a continuation-in-part of U.S. patent application Ser. No. 09/145,828 filed on Sep. 2, 1998, now U.S. Pat No. 6,403,349, both of which are herein incorporated in their entirety by reference.

BACKGROUND OF THE INVENTION

1. Technical Field

The subject invention relates to the identification of several genes involved in the elongation of long-chain polyunsaturated fatty acids (i.e., "elongases") and to uses thereof. In particular, the elongase enzyme is utilized in the conversion of one fatty acid to another. For example, elongase catalyzes the conversion of gamma linolenic acid (GLA; to dihomo-γ-linolenic acid (DGLA, 20:3n-6) and the conversion of stearidonic acid (STA, 18:4n-3) to (n-3)-eicosatetraenoic acid (20:4n-3). Elongase also catalyzes the conversion of arachidonic acid (AA, 20:4n-6) to adrenic acid (ADA, 22:4n-6), the conversion of eicosapentaenoic acid (EPA, 20:5n-3) to ω3-docosapentaenoic acid (22:5n-3), and the conversation of α-linolenic acid (ALA, 18:3n-3) to 20:3n-3. DGLA, for example, may be utilized in the production of other polyunsaturated fatty acids (PUFAs), such as arachidonic acid (AA) which may be added to pharmaceutical compositions, nutritional compositions, animal feeds, as well as other products such as cosmetics.

2. Background Information

The elongases which have been identified in the past differ in terms of the substrates upon which they act. Furthermore, they are present in both animals and plants. Those found in mammals have the ability to act on saturated, monounsaturated and polyunsaturated fatty acids. In contrast, those found in plants are specific for saturated or monounsaturated fatty acids. Thus, in order to generate polyunsaturated fatty acids in plants, there is a need for a PUFA-specific elongase.

In both plants and animals, the elongation process is believed to be the result of a four-step mechanism (Lassner et al., *The Plant Cell* 8:281–292 (1996)). CoA is the acyl carrier. Step one involves condensation of malonyl-CoA with a long-chain acyl-CoA to yield carbon dioxide and a β-ketoacyl-CoA in which the acyl moiety has been elongated by two carbon atoms. Subsequent reactions include reduction to β-hydroxyacyl-CoA, dehydration to an enoyl-CoA, and a second reduction to yield the elongated acyl-CoA. The initial condensation reaction is not only the substrate-specific step but also the rate-limiting step.

As noted previously, elongases, more specifically, those which utilize PUFAs as substrates, are critical in the production of long-chain polyunsaturated fatty acids which have many important functions. For example, PUFAs are important components of the plasma membrane of a cell where they are found in the form of phospholipids. They also serve as precursors to mammalian prostacyclins, eicosanoids, leukotrienes and prostaglandins. Additionally, PUFAs are necessary for the proper development of the developing infant brain as well as for tissue formation and repair. In view of the biological significance of PUFAs, attempts are being made to produce them, as well as intermediates leading to their production, efficiently.

A number of enzymes are involved in PUFA biosynthesis including elongases (elo) (see FIG. 1). For example, linoleic acid (LA, 18:2–Δ9,12 or 18:2n-6) is produced from oleic acid (OA, 18:1–Δ9 or 18:1n-9) by a Δ12 desaturase. GLA (18:3–Δ6, 9,12) is produced from linoleic acid by a Δ6-desaturase. AA (20:4–Δ5,8,11,14) is produced from dihomo-γ-linolenic acid (DGLA, 20:3–Δ8,11,14) by a Δ5-desaturase. As noted above, DGLA is produced from GLA by an elongase.

In must be noted that animals cannot desaturate beyond the Δ9 position and therefore cannot convert oleic acid into linoleic acid. Likewise, α-linolenic acid (ALA, 18:3–Δ9,12, 15 or 18:3n-3) cannot be synthesized by mammals, since they lack Δ15 desaturase activity. However, α-linolenic acid can be converted to stearidonic acid (STA, 18:4–Δ5,9,12,15) by a Δ6-desaturase (see PCT publication WO 96/13591; see also U.S. Pat. No. 5,552,306), followed by elongation to (n-3)-eicosatetraenoic acid (20:4–Δ8, 11,14,17 or 20:4n-3) in mammals and algae. This polyunsaturated fatty acid (i.e., 20:4–Δ8,11,14,17) can then be converted to eicosapentaenoic acid (EPA, 20:5–Δ5,8,11,14,17) by a Δ5-desaturase. Other eukaryotes, including fungi and plants, have enzymes which desaturate at carbons 12 (see PCT publication WO 94/11516 and U.S. Pat. No. 5,443,974) and 15 (see PCT publication WO 93/11245). The major polyunsaturated fatty acids of animals therefore are either derived from diet and/or from desaturation and elongation of linoleic acid or α-linolenic acid. In view of the inability of mammals to produce these essential long chain fatty acids, it is of significant interest to isolate genes involved in PUFA biosynthesis from species that naturally produce these fatty acids and to express these genes in a microbial, plant or animals system which can be altered to provide production of commercial quantities of one or more PUFAs. Consequently, there is a definite need for the elongase enzyme, the gene encoding the enzyme, as well as recombinant methods of producing this enzyme. Additionally, a need exists for oils containing levels of PUFA beyond those naturally present as well as those enriched in novel PUFAs. Such oils can only be made by isolation and expression of the elongase gene.

One of the most important long chain PUFAs, noted above, is arachidonic acid (AA). AA is found in filamentous fungi and can also be purified from mammalian tissues including the liver and the adrenal glands. As noted above, AA production from DGLA is catalyzed by a Δ5-desaturase, and DGLA production from γ-linolenic acid (GLA) is catalyzed by an elongase. However, until the present invention, no elongase had been identified which was active on substrate fatty acids in the pathways for the production of long chain PUFAs and, in particular, AA, eicosapentaenoic acid (EPA), adrenic acid, docosahexaenoic acid (DHA, 22:6n-3), ω3-docosapentaenoic acid (22:5n-3) or ω6-docosapentaenoic acid (22:5n-6).

Two genes appeared to be of interest in the present search for the elongase gene. In particular, the jojoba β-ketoacyl-coenzyme A synthase (KCS), or jojoba KCS (GenBank Accession #U37088), catalyzes the initial reaction of the fatty acyl-CoA elongation pathway (i.e., the condensation of malonyl-CoA with long-chain acyl-CoA (Lassner et al., *The Plant Cell* 8:281–292 (1996)). Jojoba KCS substrate preference is 18:0, 20:0, 30:1, 18:1, 22:1, 22:0 and 16:0. *Saccharomcyes cerevisiae* elongase (ELO2) also catalyzes the conversion of long chain saturated and monounsaturated fatty acids, producing high levels of 22:0, 24:0, and also 18:0, 18:1, 20:0, 20:1, 22:0, 22:1, and 24:1 (Oh et al., *The Journal of Biological Chemistry* 272 (28):17376–17384 (1997); see also U.S. Pat. No. 5,484,724 for a nucleotide sequence which includes the sequence of ELO2; see PCT publication WO 88/07577 for a discussion of the sequence of a glycosylation inhibiting factor which is described in Example V). The search for a long chain PUFA-specific elongase in *Mortierella alpina* began based upon a review of the homologies shared between these two genes and by expression screening for PUFA-elongase activity.

SUMMARY OF THE INVENTION

The present invention relates to an isolated nucleotide sequence corresponding to or complementary to at least about 50% of the nucleotide sequence shown in SEQ ID NO:1 (FIG. 6). This isolated sequence may be represented by SEQ ID NO:1. The sequence encodes a functionally active elongase which utilizes a polyunsaturated fatty acid or a monounsaturated fatty acid as a substrate. In particular, the sequence may be derived from a fungus of the genus *Mortierella* and may specifically be isolated from *Mortierella alpina*.

The present invention also includes a purified protein encoded by the above nucleotide sequence as well as a purified polypeptide which elongates polyunsaturated fatty acids or monounsaturated fatty acids and has at least about 50% amino acid similarity to the amino acid sequence of the purified protein encoded by the above nucleotide sequence.

Additionally, the present invention encompasses a method of producing an elongase enzyme comprising the steps of: a) isolating the nucleotide sequence represented by SEQ ID NO:1 (FIG. 6); b) constructing a vector comprising: i) the isolated nucleotide sequence operably linked to ii) a promoter; and c) introducing the vector into a host cell under time and conditions sufficient for expression of the elongase enzyme. The host cell may be a eukaryotic cell or a prokaryotic cell.

The prokaryotic cell may be, for example an *E. coli* cell, a cyanobacterial cell, or a *B. subtilis* cell. The eukaryotic cell may be, for example, a mammalian cell, an insect cell, a plant cell or a fungal cell. The fungal cell may be, for example, *Saccharomyces* spp., *Candida* spp., *Lipomyces* spp., *Yarrowia* spp., *Kluyveromyces* spp., *Hansenula* spp., *Aspergillus* spp., *Penicillium* sp., *Neurospora* spp., *Trichoderma* spp. or *Pichia* spp. In particular, the fungal cell may be a yeast cell such as *Saccharomyces* spp., in particular, *Saccharomyces cerevisiae, Candida* spp., *Hansenula* spp. or *Pichia* spp.

The invention also includes a vector comprising: a) a nucleotide sequence as represented by SEQ ID NO:1 (FIG. 6) operably linked to b) a promoter, as well as a host cell comprising this vector. The host may be a prokaryotic cell or a eukaryotic cell. Suitable examples of prokaryotic cells include *E. coli*, Cyanobacteria, and *B. subtilis* cells. Suitable examples of eukaryotic cells include a mammalian cell, an insect cell, a plant cell and a fungal cell. The fungal cell may be, for example, *Saccharomyces* spp., *Candida* spp., *Lipomyces* spp., *Yarrowia* spp., *Kluyveromyces* spp., *Hansenula* spp., *Aspergillus* spp., *Penicillium* spp., *Neurospora* spp., *Trichoderma* spp. and *Pichia* spp. In particular, the fungal cell may be, for example, a yeast cell such as, for example, *Saccharomyces* spp., in particular, *Saccharomyces cerevisiae, Candida* spp., *Hansenula* spp. and *Pichia* spp.

The present invention includes a plant cell, plant or plant tissue comprising the above-described vector, wherein expression of the nucleotide sequence of the vector results in production of at least one fatty acid selected from the group consisting of a monounsaturated fatty acid and a polyunsaturated fatty acid by the plant cell, plant or plant tissue. The polyunsaturated fatty acid may be, for example, dihomo-γ-linolenic acid (DGLA), 20:4n-3, and adrenic acid (ADA). The invention also includes one or more plant oils or fatty acids expressed by the plant cell, plant or plant tissue. Additionally, the present invention encompasses a transgenic plant comprising the above-described vector, wherein expression of the nucleotide sequence of the vector results in production of a polyunsaturated fatty acid in seeds of the transgenic plant.

Furthermore, the present invention includes a transgenic, non-human mammal whose genome comprises a DNA sequence encoding an elongase operably linked to a promoter. The DNA sequence may be represented by SEQ ID NO:1 (FIG. 6). The present invention also includes a fluid (e.g., milk) produced by the transgenic, non-human wherein the fluid comprises a detectable level of at least one elongase or products thereof such as, for example, DGLA, ω6-docosapentaenoic acid, ADA and/or 20:4n-3 (see FIG. 1).

Additionally, the present invention includes a method for producing a polyunsaturated fatty acid comprising the steps of: a) isolating said nucleotide sequence represented by SEQ ID NO:1 (FIG. 6); b) constructing a vector comprising the isolated nucleotide sequence; c) introducing the vector into a host cell under time and conditions sufficient for expression of elongase enzyme encoded by the isolated nucleotide sequence; and d) exposing the expressed elongase enzyme to a "substrate" polyunsaturated fatty acid in order to convert the substrate to a "product" polyunsaturated fatty acid. The substrate polyunsaturated fatty acid may be selected from the group consisting of, for example, γ-linolenic acid (GLA), stearidonic acid (STA) and arachidonic acid (AA), and the product polyunsaturated fatty acid may be selected from the group consisting of, for example, DGLA, 20:4n-3, and ADA, respectively. The method may further comprise the step of exposing the product polyunsaturated fatty acid to at least one desaturase in order to convert the product polyunsaturated fatty acid to "another" polyunsaturated fatty acid. The product polyunsaturated fatty acid may be selected from the group consisting of, for example, DGLA, 20:4n-3, and ADA. The another polyunsaturated fatty acid may be selected from the group consisting of, for example, AA, eicosapentaenoic acid (EPA), ω6-docosapentaenoic acid, respectively, and the at least one desaturase is Δ5-desaturase, with respect to production of AA or EPA, and Δ4-desaturase, with respect to production of ω6-docosapentaenoic acid. The method may further comprise the step of exposing the another polyunsaturated fatty acid to one or more enzymes selected from the group consisting of at least one elongase and at least one additional desaturase in order to convert the another polyunsaturated fatty acid to a "final" polyunsaturated fatty acid. The final polyunsaturated fatty acid may be, for example, docosahexaenoic acid (DHA), AA, ω6-docosapentaenoic acid, or ω3-docosapentaenoic acid.

Also, the present invention includes a nutritional composition comprising at least one polyunsaturated fatty acid selected from the group consisting of the product polyunsaturated fatty acid produced according to the above-described method, the another polyunsaturated fatty acid produced according to the above-described method, and the final polyunsaturated fatty acid produced according to the above-described method. The product polyunsaturated fatty acid may be selected from the group consisting of, for example, DGLA, 20:4n-3 and ADA. The another polyunsaturated fatty acid may be, for example, AA, EPA, or ω6-docosapentaenoic acid. The final polyunsaturated fatty acid may be, for example, DHA, adrenic acid, ω6-docosapentaenoic acid or ω3-docosapentaenoic acid. The nutritional composition may be, for example, an infant formula, a dietary supplement or a dietary substitute and may be administered to a human or an animal and may be administered enterally or parenterally. The nutritional composition may further comprise at least one macronutrient selected from the group consisting of coconut oil, soy oil, canola oil, monoglycerides, diglycerides, triglycerides, glucose, edible lactose, electrodialysed whey, electrodialysed skim milk, milk whey, soy protein, protein hydrolysates, sunflower oil, safflower oil, corn oil, and flax oil. It may also comprise at least one vitamin selected from the group consisting of Vitamins A, C, D, E, and B complex and at least one mineral selected from the group consisting of calcium magnesium, zinc, manganese, sodium, potassium, phosphorus, copper, chloride, iodine, selenium and iron.

Additionally, the present invention encompasses a pharmaceutical composition comprising 1) at least one polyunsaturated fatty acid selected from the group consisting of the product polyunsaturated fatty acid produced according to the above-described method, the another polyunsaturated fatty acid produced according to the above-described method of claim 32, and the final polyunsaturated fatty acid produced according to the above-described method and 2) a pharmaceutically acceptable carrier. The composition may be administered to a human or an animal. It may also further comprise at least one element selected from the group consisting of a vitamin, a mineral, a salt, a carbohydrate, an amino acid, a free fatty acid, a preservative, an excipient, an anti-histamine, a growth factor, an antibiotic, a diluent, a phospholipid, and antioxidant, and a phenolic compound. It may be administered enterally, parenterally, topically, rectally, intramuscularly, subcutaneously, intradermally, or by any other appropriate means.

The present invention also includes an animal feed comprising at least one polyunsaturated fatty acid selected from the group consisting of the product polyunsaturated fatty acid produced according to the above-described method, the another polyunsaturated fatty acid produced according to the above-described method, and the final polyunsaturated fatty acid produced according to the above-described method. The product polyunsaturated fatty acid may be, for example, DGLA, 20:4n-3, and ADA. The another polyunsaturated fatty acid may be, for example, AA, EPA, or ω6-docosapentaenoic acid. The final polyunsaturated fatty acid may be, for example, DHA, adrenic acid, ω6-docosapentaenoic acid or ω3-docosapentaenoic acid.

Moreover, the present invention also includes a cosmetic comprising a polyunsaturated fatty acid selected from the group consisting of the product polyunsaturated fatty acid produced according to the above described method, the another polyunsaturated fatty acid produced according to the above-described method, and the final polyunsaturated fatty acid produced according to the above-described method.

Additionally, the present invention includes a method of preventing or treating a condition caused by insufficient intake or production of polyunsaturated fatty acids comprising administering to the patient the above nutritional composition in an amount sufficient to effect prevention or treatment.

The present invention also includes an isolated nucleotide sequence corresponding to or complementary to at least about 35% of the nucleotide sequence shown in SEQ ID NO:2 (FIG. 22). This sequence may be represented by SEQ ID NO:2. The sequence encodes a functionally active elongase which utilizes a polyunsaturated fatty acid as a substrate. This sequence may also be derived, for example, from a fungus of the genus *Mortierella*. In particular, it may be derived from *M. alpina*.

Additionally, the present invention includes a purified protein encoded by the above nucleotide sequence as well as a purified polypeptide which elongates polyunsaturated fatty acids and has at least about 30% amino acid similarity to the amino acid sequence of the purified protein.

The present invention also includes a method of producing an elongase enzyme as described above. The sequence inserted in the vector is represented by SEQ ID NO:2 (FIG. 22). The host cell may be prokaryotic or eukaryotic. Suitable examples are described above.

The present invention also includes a vector comprising: a) a nucleotide sequence as represented by SEQ ID NO:2 (FIG. 22) operably linked to b) a promoter, as well as a host cell comprising this vector. Again, the host cell may be eukaryotic or prokaryotic. Suitable examples are described above.

The invention also includes a plant cell, plant or plant tissue comprising the above vector, wherein expression of the nucleotide sequence of the vector results in production of a polyunsaturated fatty acid by the plant cell, plant or plant tissue. The polyunsaturated fatty acid may be, for example, DGLA, 20:4n-3, or ADA. Additionally, the invention includes one or more plant oils or fatty acids expressed by the plant cell, plant or plant tissue.

Furthermore, the present invention also includes a transgenic plant comprising the above vector, wherein expression of the nucleotide sequence (SEQ ID NO:2) of the vector results in production of a polyunsaturated fatty acid in seeds of the transgenic plant.

The invention also includes a transgenic, non-human mammal whose genome comprises a DNA sequence (SEQ ID NO:2) encoding an elongase operably linked to a promoter. The invention also includes a fluid produced by this transgenic, non-human mammal wherein the fluid comprises a detectable level of at least one elongase or products thereof.

The present invention also includes a method for producing a polyunsaturated fatty acid comprising the steps of: a) isolating the nucleotide sequence represented by SEQ ID NO:2 (FIG. 22); b) constructing a vector comprising the isolated nucleotide sequence; c) introducing the vector into a host cell under time and conditions sufficient for expression of an elongase enzyme encoded by the isolated nucleotide sequence; and d) exposing the expressed elongase enzyme to a substrate polyunsaturated fatty acid in order to convert the substrate to a product polyunsaturated fatty acid. The substrate polyunsaturated fatty acid may be, for example, GLA, STA, or AA, the product polyunsaturated fatty acid may be, for example, DGLA, 20:4n-3, or ω6-decosapentaenoic acid, respectively. The method may further comprise the step of exposing the expressed elongase enzyme to at least one desaturase in order to convert the product polyunsaturated fatty acid to another polyunsaturated fatty acid. The product polyunsaturated fatty acid may be, for example, DGLA, 20:4n-3, or ADA, the another polyunsaturated fatty acid may be, for example, AA, EPA, or ω6-docosapentaenoic acid, respectively, and the at least one desaturase is Δ5 desaturase with respect to production of AA or EPA, and Δ4-desaturase with respect to production of ω6-docosapentaenoic acid. The method may further comprise the step of exposing the another polyunsaturated fatty acid to one or more enzymes selected from the group consisting of at least one elongase and at least one additional desaturase in order to convert the another polyunsaturated fatty acid to a final polyunsaturated fatty acid. The final polyunsaturated fatty acid may be, for example, docosahexaenoic acid, AA, ω6-docosapentaenoic acid, or ω3-docosapentaenoic acid.

The invention also includes a nutritional composition comprising at least one polyunsaturated fatty acid selected from the product polyunsaturated fatty acid produced according to the method described with respect to SEQ ID NO:2, the another polyunsaturated fatty acid produced according to the method described with respect to SEQ ID NO:2, and the final polyunsaturated fatty acid produced according to the method described with respect to SEQ ID NO:2. The product polyunsaturated fatty acid may be selected from the group consisting of, for example, DGLA, 20:4n-3 and ADA. The another polyunsaturated fatty acid may be selected from the group consisting of, for example, AA, EPA, and ω6-docosapentaneoic acid. The final polyunsaturated fatty acid may be selected from the group consisting of, for example, DHA, AA, ω6-docosapentaenoic acid, and ω3-docosapentaenoic acid. The other attributes of the composition are the same as those described above with respect to the administration, characterization, components, etc.

The present invention also includes a pharmaceutical composition comprising 1) at least one polyunsaturated fatty acid selected from the group consisting of the product polyunsaturated fatty acid produced according to the method of noted above with respect to SEQ ID NO:2, the another polyunsaturated fatty acid produced according to the method described above with respect to SEQ ID NO:2, and the final polyunsaturated fatty acid produced according to the method described above with respect to SEQ ID NO:2, and 2) a pharmaceutically acceptable carrier. The characteristics of the above-described pharmaceutical composition (e.g., administration, components, etc.) also apply to this composition.

The present invention also includes an animal feed comprising at least one polyunsaturated fatty acid selected from the group consisting of: the product polyunsaturated fatty acid produced according to the method described with respect to SEQ ID NO:2, the another polyunsaturated fatty acid produced according to the method described above with respect to SEQ ID NO:2, and the final polyunsaturated fatty acid produced according to the method described with respect to SEQ ID NO:2. The product polyunsaturated fatty acid may be, for example, DGLA, 20:4n-3 or ADA. The another polyunsaturated fatty acid may be, for example, AA, EPA or ω6-docosapentaenoic acid. The final polyunsaturated fatty acid may be, for example, DEA, adrenic acid, ω6-docosapentaenoic acid or ω3-docosapentaenoic acid.

The invention also includes a cosmetic comprising a polyunsaturated fatty acid selected from the group consisting of: the product polyunsaturated fatty acid produced according to the method described above with respect to SEQ ID NO:2, the another polyunsaturated fatty acid produced according to the method described above with respect to SEQ ID NO:2, and the final polyunsaturated fatty acid produced according to the method described above with respect to SEQ ID NO:2.

Additionally, the present invention includes a method of preventing or treating a condition caused by insufficient intake or production of polyunsaturated fatty acids comprising administering to the patient the nutritional composition described directly above in an amount sufficient to effect the prevention or treatment.

Furthermore, the present invention includes an isolated nucleotide sequence corresponding to or complementary to at least about 35% of the nucleotide sequence shown in SEQ ID NO:3 (FIG. 43). This sequence may be that represented by SEQ ID NO:3. This sequence encodes a functionally active elongase which utilizes a polyunsaturated fatty acid or a monounsaturated fatty acid as a substrate. The sequence is derived from a mammal such as, for example, a human.

The invention also includes a purified protein encoded by this nucleotide sequence. Also, the invention includes a purified polypeptide which elongates polyunsaturated fatty acids or monounsaturated fatty acids and has at least about 30% amino acid similarity to the amino acid sequence of this purified protein.

Additionally, the invention includes method of producing an elongase enzyme comprising the steps of: a) isolating the nucleotide sequence represented by SEQ ID NO:3 (FIG. 43); b) constructing a vector comprising: i) the isolated nucleotide sequence operably linked to ii) a promoter; and c) introducing said vector into a host cell under time and conditions sufficient for expression of the elongase enzyme. The host cell may be the same as that described above with respect to the corresponding methods utilizing SEQ ID NO:1 or 2.

The invention also includes a vector comprising: a) a nucleotide sequence as represented by SEQ ID NO:3 (FIG. 43) operably linked to b) a promoter, as well as a host cell comprising this vector. The host cell may be the same as that described above.

The invention also includes a plant cell, plant or plant tissue comprising the above-described vector comprising SEQ ID NO:3, wherein expression of the nucleotide sequence of the vector results in production of at least one fatty acid selected from the group consisting of a monounsaturated fatty acid and a polyunsaturated fatty acid by said plant cell, plant or plant tissue. The polyunsaturated fatty acid may be, for example, DGLA, 20:4n-3 or ADA. The invention also includes one or more plant oils or acids expressed by the plant cell, plant or plant tissue.

The invention also includes a transgenic plant comprising the vector comprising SEQ ID NO:3, wherein expression of the nucleotide sequence of the vector results in production of a polyunsaturated fatty acid in seeds of the transgenic plant.

Additionally, the present invention includes a transgenic non-human mammal whose genome comprises a human DNA sequence encoding an elongase operably linked to a promoter. The DNA sequence is represented by SEQ ID NO:3 (FIG. 43). The invention also includes a fluid produced by said transgenic, non-human mammal wherein said fluid comprises a detectable level of at least one elongase or products thereof.

The invention also encompasses a method for producing a polyunsaturated fatty acid comprising the steps of: a) isolating the nucleotide sequence represented by SEQ ID NO:3 (FIG. 43); b) constructing a vector comprising said nucleotide sequence; c) introducing the vector into a host cell under time and conditions sufficient for expression of elongase enzyme encoded by the isolated nucleotide sequence; and d) exposing the expressed elongase enzyme to a substrate polyunsaturated fatty acid in order to convert the substrate to a product polyunsaturated fatty acid. The substrate polyunsaturated fatty acid may be, for example, GLA, STA or AA, and the product polyunsaturated fatty acid may be, for example, DGLA, 20:4n-3, or ADA, respectively. The method may further comprise the step of exposing the product polyunsaturated fatty acid to at least one desaturase in order to convert the product polyunsaturated fatty acid to another polyunsaturated fatty acid. The product polyunsaturated fatty acid may be, for example, DGLA, 20:4n-3 and ADA, the another polyunsaturated fatty acid may be, for example, AA, EPA, and ω6-docosapentaenoic acid, respectively, and the at least one desaturase is Δ5-desaturase with respect to production of AA or EPA and Δ4-desaturate with respect to production of ω6-docosapentaenoic acid. The method may further comprise the step of exposing the another polyunsaturated fatty acid to one or more enzymes selected from the group consisting of at least one elongase and at least one additional desaturase in order to convert the another polyunsaturated fatty acid to a final polyunsaturated fatty acid. The final polyunsaturated fatty acid may be, for example, DHA, ADA, ω6-docosapentaenoic acid, and ω3-docosapentaenoic acid.

The nutritional composition comprising at least one polyunsaturated fatty acid which may be, for example, product polyunsaturated fatty acid produced according to the method recited above in connection with SEQ ID NO:3, another polyunsaturated fatty acid produced according to the method recited above in connection with SEQ ID NO:3, and the final polyunsaturated fatty acid produced according to the method recited above in connection with SEQ ID NO:3. The product polyunsaturated fatty acid may be, for example, DGLA, 20:4n-3, or ADA. The another polyunsaturated fatty acid may be selected from the group consisting of AA, EPA, or ω6-docosapentaenoic acid. The final polyunsaturated fatty acid may be, for example, DHA, ADA, ω6-docosapentaenoic acid, or ω3-docosapentaenoic acid. The other properties or characteristic of the nutritional composition (e.g., administration, components, etc.) as the same as those recited above with respect to the other nutritional compositions.

Moreover, the present invention also includes a pharmaceutical composition comprising 1) at least one polyunsaturated fatty acid selected from the group consisting of: the product polyunsaturated fatty acid produced according to the method described above in connection with SEQ ID NO:3, the another polyunsaturated fatty acid produced according to the method described above in connection with SEQ ID NO:3, and the final polyunsaturated fatty acid produced according to the method described above in connection with SEQ ID NO:3 and 2) a pharmaceutically acceptable carrier. The other properties of the composition (e.g., administration, additional components, etc.) are the same as those recited above with respect to the other pharmaceutical compositions.

The present invention also includes an animal feed comprising at least one polyunsaturated fatty acid selected from the group consisting of: the product polyunsaturated fatty acid produced according to the method recited above with respect to SEQ ID NO:3, the another polyunsaturated fatty acid produced according to the invention recited above with respect to SEQ ID NO:3, and the final polyunsaturated fatty acid produced according to the method recited above with respect to SEQ ID NO:3. The product polyunsaturated fatty acid may be, for example, DGLA, 20:4n-3, or ADA. The polyunsaturated fatty acid may be, for example, AA, EPA, or ω6-docosapentaenoic acid. The final polyunsaturated fatty acid may be, for example, DHA, ADA, ω6-docosapentaenoic acid or ω3-docosapentaenoic acid.

Also, the present invention includes a cosmetic comprising a polyunsaturated fatty acid selected from the group consisting of: the product polyunsaturated fatty acid produced according to the method recited above with respect to SEQ ID NO:3, said another polyunsaturated fatty acid produced according to the method recited above in connection with SEQ ID NO:3, and the final polyunsaturated fatty acid produced according to the method recited above in connection with SEQ ID NO:3.

A method of preventing or treating a conduction caused by insufficient intake of polyunsaturated fatty acids comprising administering to the patient the nutritional composition recited above in connection with SEQ ID NO:3 in an amount sufficient to effect the prevention or treatment.

Additionally, the present invention includes an isolated nucleotide sequence corresponding to or complementary to at least about 35% of the nucleotide sequence shown in SEQ ID NO:4 (FIG. 46). The sequence may be represented by SEQ ID NO:4. It encodes a functionally active elongate which utilizes a polyunsaturated fatty acid as a substrate. The sequence may be derived or isolated from a nematode of the genus *Caenorhabditis* and, in particular, may be isolated from *C. elegans*.

The present invention includes a purified protein encoded by the nucleotide sequence above. The invention also includes a purified polypeptide which elongates polyunsaturated fatty acids and has at least about 30% amino acid similarity of the amino acid sequence of the purified protein.

Additionally, the present invention includes a method of producing an elongase enzyme comprising the steps of: a) isolating the nucleotide sequence represented by SEQ ID NO:4 (FIG. 46); b) constructing a vector comprising: i) the isolated nucleotide sequence operably linked to ii) a promoter; and c) introducing the vector into a host cell under time and conditions sufficient for expression of the elongase enzyme. The properties of the host cell are the same as those described above in connection with SEQ ID NO:1, SEQ ID NO:2 and SEQ ID NO:3.

The present include also encompasses a vector comprising: a) a nucleotide sequence as represented by SEQ ID NO:4 (FIG. 46) operably linked to b) a promoter, as well as a host cell comprising this vector. The host cell has the same properties as those recited above in connection with the host cell recited above for SEQ ID NO:1, SEQ ID NO:2, and SEQ ID NO:3.

Moreover, the present invention includes a plant cell, plant or plant tissue comprising the above vector comprising SEQ ID NO:4, wherein expression of said nucleotide sequence of the vector results in production of a polyunsaturated fatty acid by the plant cell, plant or plant tissue. The polysaturated fatty acid may be, for example, DGLA, 20:4n-3, or ADA. The invention also includes one or more plant oils or fatty acids expressed by this plant cell, plant or plant tissue.

The invention also includes transgenic plant comprising the above vector including the nucleotide sequence corresponding to SEQ ID NO:4, wherein expression of the nucleotide sequence of the vector results in production of a polyunsaturated fatty acid in seeds of the transgenic plant.

Additionally, the present invention includes a transgenic, non-human mammal whose genome comprises a *C. elegans* DNA sequence encoding an elongase operably linked to a promoter. The DNA sequence may be represented by SEQ ID NO:4 (FIG. 46). The invention also includes a fluid produced by the transgenic, non-human mammal of claim 187 wherein the fluid comprises a detectable level of at least one elongase or products thereof.

The invention also includes a method for producing a polyunsaturated fatty acid comprising the steps of: a) isolating the nucleotide sequence represented by SEQ ID NO:4 (FIG. 46); b) constructing a vector comprising the isolated nucleotide sequence; c) introducing the vector into a host cell under time and conditions sufficient for expression of an elongase enzyme encoded by the isolated nucleotide sequence; and d) exposing the expressed elongase enzyme to a substrate polyunsaturated fatty acid in order to convert the substrate to a product polyunsaturated fatty acid. The substrate polyunsaturated fatty acid may be, for example, GLA, STA, or AA, and the product polyunsaturated fatty acid may be, for example, DGLA, 20:4n-3, or ADA, respectively. The method may further comprise the step of exposing the expressed elongase enzyme to at least one desaturase in order to convert said product polyunsaturated fatty acid to another polyunsaturated fatty acid. The product polyunsaturated fatty acid may be, for example, DGLA, 20:4n-3 or ADA, the another polyunsaturated fatty acid may be, for example, AA, EPA or ω6-docosapentaenoic acid, respectively, and the at least one desaturase is Δ5-desaturase with respect to production of AA or EPA, and Δ4-desaturase with respect to production of ω6-docosapentaenoic acid. The method may further comprise the step of exposing the another polyunsaturated fatty acid to one or more enzymes selected from the group consisting of at least one elongase and at least one additional desaturase in order to convert the another polyunsaturated fatty acid to a final polyunsaturated fatty acid. The final polyunsaturated fatty acid may be, for example, DHA, ADA, ω6-docosapentaenoic acid, or ω3-docosapentaenoic acid.

The invention also includes a nutritional composition comprising at least one polyunsaturated fatty acid selected from the group consisting of said the polyunsaturated fatty acid produced according to the method described above in connection with SEQ ID NO:4, the another polyunsaturated fatty acid produced according to the method described above in connection with SEQ ID NO:4, and the final polyunsaturated fatty acid produced according to the method recited above in connection with SEQ ID NO:4. The product polyunsaturated fatty acid may be, for example, DGLA, 20:4n-3, or ADA. The another polyunsaturated fatty acid may be, for example, AA, EPA, or ω6-docosapentaenoic acid. The final polyunsaturated fatty acid may be, for example, DHA, ADA, ω6-docosapentaenoic acid, or ω3-docosapentaenoic acid. The other characteristics of the composition are the same as those recited for the nutritional compositions present above.

Additionally, the present invention includes a pharmaceutical composition comprising 1) at least one polyunsaturated fatty acid selected from the group consisting of: the product polyunsaturated fatty acid produced according to the method recited above in connection with SEQ ID NO:4, the another polyunsaturated fatty acid produced according to the method recited above in connection with SEQ ID NO:4, and the final polyunsaturated fatty acid produced according to the method recited above in connection with SEQ ID NO:4 and 2) a pharmaceutically acceptable carrier. The composition has the same properties (e.g., administration, added elements, etc.) as those described above with respect to the other pharmaceutical compositions.

The present invention also includes an animal feed comprising at least one polyunsaturated fatty acid selected from the group consisting of the product polyunsaturated fatty acid produced according to the method described above in connection with SEQ ID NO:4, the another polyunsaturated fatty acid produced according to the method recited above in connection with SEQ ID NO:4, and the final polyunsaturated fatty acid produced according to the method described above in connection with SEQ ID NO:4. The product polyunsaturated fatty acid may be, for example, DGLA, 20:4n-3 or ADA. The another polyunsaturated fatty acid may be, for example, AA, EPA or ω6-docosapentaenoic acid. The polyunsaturated fatty acid may be, for example, DHA, ADA, ω6-docosapentaenoic acid or ω3-docosapentaenoic acid.

Additionally, the present invention includes a cosmetic comprising a polyunsaturated fatty acid selected from the group consisting of the product polyunsaturated fatty acid produced according to the method recited above in connection with SEQ ID NO:4, the another polyunsaturated fatty acid produced according to the method recited above in connection with SEQ ID NO:4 and the final polyunsaturated fatty acid produced according to the method described above in connection with SEQ ID NO:4.

Furthermore, the present invention encompasses a method of preventing or treating a condition caused by insufficient intake or production of polyunsaturated fatty acids comprising administering to the patient the nutritional composition recited with respect to SEQ ID NO:4 in an amount sufficient to effect the treatment or prevention.

The present invention also includes an isolated nucleotide sequence corresponding to or complementary to at least about 35% of the nucleotide sequence comprising SEQ ID NO:5 (FIG. 54). Thus, the sequence may be that represented by SEQ ID NO:5. The sequence may encode a functionally active elongase which utilizes a polyunsaturated fatty acid as a substrate. It may also be derived from a mammal such as, for example, a mouse. The present invention also includes a purified protein encoded by the nucleotide sequence as well as a purified polypeptide which elongates polyunsaturated fatty acids and has at least about 30% amino acid similarity to the amino acid sequence of the protein.

Additionally, the invention also includes a method of producing an elongase enzyme, as described above, in which the nucleotide sequence isolated comprises either SEQ ID NO:5 or SEQ ID NO:6. The host cell utilized may be as described above.

The present invention also encompasses a vector comprising: a) a nucleotide sequence comprising SEQ ID NO:5 (FIG. 54) (or a nucleotide sequence comprising SEQ ID NO:6 (FIG. 58)) operably linked to b) a promoter, as well as a host cell comprising this vector. Again, the host cell may be as described above for the related methods using the other nucleotide sequences of the present invention.

Additionally, the invention includes a plant cell, plant or plant tissue comprising the vector comprising SEQ ID NO:5 or 6, wherein expression of the nucleotide sequence of the vector results in production of a polyunsaturated fatty acid by the plant cell, plant or plant tissue. When the nucleotide sequence of the vector comprises SEQ ID NO:5, the polyunsaturated fatty acid is selected from the group consisting of AA, ADA, GLA and STA. The invention also includes one or more plant oils or acids expressed by the plant cell, plant or plant tissue.

The present invention also includes a transgenic plant comprising the vector described above, wherein expression of the nucleotide sequence of the vector results in production of a polyunsaturated fatty acid in seeds of the transgenic plant.

Additionally, the present invention encompasses a transgenic, non-human mammal whose genome comprises a DNA sequence encoding an elongase, operably linked to a promoter, wherein the DNA sequence comprises SEQ ID NO:5 (FIG. 54) (or SEQ ID NO:6 (FIG. 58)). Also, the invention includes a fluid produced by this transgenic, non-human mammal, wherewith fluid comprises a detectable level of at least one elongase or products thereof.

The invention also includes method for producing a polyunsaturated fatty acid, similar to the methods described above, except that the isolated nucleotide sequence comprises SEQ ID NO:5 (FIG. 54). The substrate polyunsaturated fatty acid may be selected from the group consisting of GLA, STA, AA, ADA and ALA, and the product polyunsaturated fatty acid may be selected from the group consisting of DGLA, 20:4n-3, ADA, ω6-docosapentaenoic acid and STA, respectively. The method may further comprise the step of exposing the expressed elongase enzyme to at least one desaturase in order to convert the product polyunsaturated fatty acid to another polyunsaturated fatty acid. The product polyunsaturated fatty acid may be selected from the group consisting of of DGLA, 20:4n-3, ADA and ω6-docosapentaenoic acid, the another polyunsaturated fatty acid is selected from the group consisting of AA, EPA, ω6-docosapentaenoic acid and docosahexaenoic acid respectively, and the at least one desaturase is Δ5-desaturase with respect to production of AA or EPA, and Δ4-desaturase with respect to production of ω6-docosapentaenoic acid, and Δ19-desaturase with respect to production of docosahexaenoic acid. The method may further comprises the step of exposing the another polyunsaturated fatty acid to one or more enzymes selected from the group consisting of at least one elongase and at least one additional desaturase in order to convert the another polyunsaturated fatty acid to a final polyunsaturated fatty acid. The final polyunsaturated fatty acid may selected from the group consisting of ADA, ω3-docosapentaenoic acid and docosahexaenoic acid.

The present invention also includes a nutritional composition comprising at least one polyunsaturated fatty acid selected from the group consisting of the product polyunsaturated fatty acid produced according to the method above, the another polyunsaturated fatty acid is produced according to the method above, and the final polyunsaturated fatty acid produced according to the method above. The product polyunsaturated fatty acid may be selected from the group consisting of DGLA, 20:4n-3, ADA, and ω6-docosapentaenoic acid and STA. The another polyunsaturated fatty acid is selected from the group consisting of AA, EPA, ω6-docosapentaenoic acid and docosahexaenoic acid. The final polyunsaturated fatty acid is selected from the group consisting of ADA, ω3-docosapentaenoic acid and docosahexaenoic acid. The nutritional composition may be selected from the group consisting of an infant formula, a dietary supplement and a dietary substitute.

The present invention also includes a pharmaceutical composition comprising 1) at least one polyunsaturated fatty acid selected from the group consisting of the product polyunsaturated fatty acid produced according to the method above, the another polyunsaturated fatty acid produced according to the method above, and the final polyunsaturated fatty acid produced according to the method above and 2) a pharmaceutically acceptable carrier.

Additionally, the present invention includes an animal feed comprising at least one polyunsaturated fatty acid selected from the group consisting of the product polyunsaturated fatty acid produced according to the method above, the another polyunsaturated fatty acid produced according to the method above and the final polyunsaturated fatty acid produced according to the method above. The product polyunsaturated fatty acid may be selected from the group consisting of DGLA, 20:4n-3, ADA, ω6 docosapentaenoic acid and STA. The another polyunsaturated fatty acid may be selected from the group consisting of AA, EPA, ω6-docosapentaenoic acid and docosahexaenoic acid. The final polyunsaturated fatty acid may be selected from the group consisting of ADA, ω3-docosapentaenoic acid and docosahexaenoic acid.

The invention includes a cosmetic comprising a polyunsaturated fatty acid selected from the group consisting of the product polyunsaturated fatty acid produced according to the method above, the another polyunsaturated fatty acid produced according to the method above and the final polyunsaturated fatty acid produced according to the method above.

Additionally, a method of preventing or treating a condition caused by insufficient intake of polyunsaturated fatty acids comprising administering to the patient the nutritional composition in an amount sufficient to effect the prevention or treatment.

The present invention includes an isolated nucleotide sequence corresponding to or complementary to at least about 35% of the nucleotide sequence comprising SEQ ID NO:6 (FIG. 58). The isolated nucleotide sequence may comprise SEQ ID NO:6. The invention also includes a purified protein encoded by the nucleotide sequence.

All U.S. patents and publications referred to herein are hereby incorporated in their entirety by reference.

BRIEF DESCRIPTION OF THE DRAWINGS

FIG. 2 represents the percent similarity and percent identity between the amino acid sequences of jojoba ECS (SEQ ID NO:7) and ELO2 (SEQ ID NO:8).

FIG. 3 represents the S. cerevisiae ELO2 sequence (SEQ ID NO:9) homologous to the jojoba KCS sequence (primer sequence underlined) of FIG. 2.

FIG. 5 represents a comparison of the nucleotide sequences of clones pRAE-5 (SEQ ID NO:10) and pRAE-6 (SEQ ID NO:11).

FIG. 6 illustrates the complete nucleotide sequence of Mortierella alpina elongase (MAELO) (SEQ ID NO:1).

FIG. 7 represents the amino acid sequence of the Mortierella alpina elongase (SEQ ID NO:12) translated from MAELO (see FIG. 6).

Figure 8A:
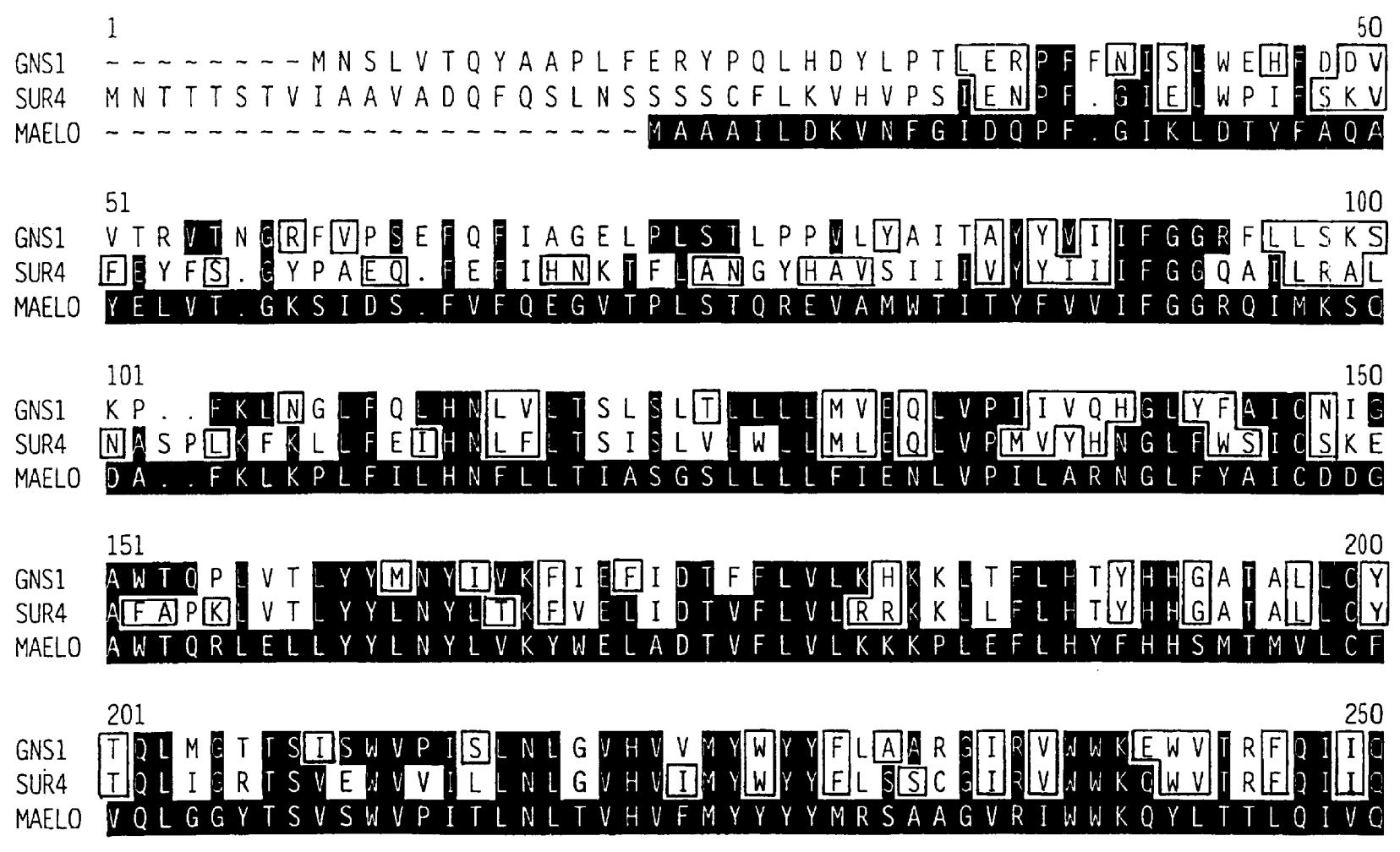

FIG. 8 represents an amino acid sequence alignment among 3 elongases: S. cerevisiae ELO2 (SNS1) (SEQ ID NO:13), S. cerevisiae ELO3 (SUR4) (SEQ ID NO:14) and the translated MAELO sequence as shown in FIG. 7.

FIG. 9 represents a comparison between the nucleotide sequence MAELO (SEQ ID NO:15) and the nucleotide sequence of ELO2 from S. cerevisiae (SEQ ID NO:16).

FIGS. 10A and 10B represents the PUFA elongase activity of MAELO expressed in baker's yeast.

FIG. 11 illustrates the PUFA elongase activity of MAELO when co-expressed with the Δ5-desaturase cDNA from M. alpina to produce AA.

FIG. 12 compares the PUFA elongase activity of MAELO to the overexpression of ELO2 from S. cerevisiae in baker's yeast.

FIGS. 13 (SEQ ID NO:17 and SEQ ID NO:18), 14 (SEQ ID NO:19 and SEQ ID NO:20) and 15 (SEQ ID NO:21 and SEQ ID NO:22) represent three separate comparisons of amino acid sequences (SEQ ID NO:17, SEQ ID NO:19 and SEQ ID NO:21) derived from C. elegans nucleotide sequences in the GenEMBL database with the translated MAELO (SEQ ID NO:18, SEQ ID NO:20 and SEQ ID NO:22).

FIG. 16 shows the comparison between amino acid translations of two different mammalian sequences in the GenEMBL database (SEQ ID NO:23 and SEQ ID NO:26) and the translated MAELO (SEQ ID NO:24 and SEQ ID NO:25).

FIG. 17 shows the comparison of a translated DNA sequence (see published PCT application WO 88/07577) (SEQ ID NO:28) with the amino acid sequence derived from MAELO (SEQ ID NO:27), which was detected during a database search.

FIG. 18 shows the complete amino acid sequence of the Δ5-desaturase from M. alpina (SEQ ID NO:29).

FIG. 20 represents the PUFA elongase activity of the five MAD708 clones in yeast with GLA as substrate. All clones have apparent elongase activity.

FIG. 22 shows the complete nucleotide sequence of the M. alpina cDNA (SEQ ID NO:2), contained in the plasmid pRPB2, which is designated GLELO for its GLA elongase activity.

FIG. 23 represents the amino acid sequence of the M. alpina elongase (SEQ ID NO:30) translated from GLELO (see FIG. 22).

FIG. 24 illustrates the n-6 PUFA elongase activity in an induced culture of 334(pRPB2) when supplemented with GLA.

FIG. 25 represents the n-3 and n-6 PUFA elongase activity in an induced culture of 334(pRPB2) when supplemented with 25 μm of other fatty acid substrates.

FIG. 26A illustrates the elongase activity of GLELO with GLA as a substrate when co-expressed with the M. alpina Δ5-desaturase cDNA to produce AA. FIG. 26B illustrates the elongase activity of GLELO with STA as a substrate when co-expressed with the M. alpina Δ5-desaturase cDNA to produce EPA.

FIG. 27 illustrates the comparison between the translated GLELO sequence (SEQ ID NO:31) (see FIG. 23) and the translated MAELO sequence (SEQ ID NO:32) (see FIG. 7).

FIG. 28 represents a comparison of the amino acid sequence of 4 elongases: the translated amino acid sequence of GLELO (see FIG. 23), MAELO (see FIG. 7), S. cerevisiae ELO2 (GNS1), and S. cerevisiae ELO3 (SUR4). The histidine box is underlined.

FIG. 29 represents an alignment between translated MAELO sequence (SEQ ID NO:33)) and translated putative human homologue HS1 sequence (SEQ ID NO:34).

FIG. 30 represents an alignment between the translated MAELO sequence (SEQ ID NO:35) and the translated putative human homologue HS2 sequence (SEQ ID NO:36).

FIG. 31 shows an alignment between the translated MAELO sequence (SEQ ID NO:35) and the translated putative mouse homologue MM2 sequence (SEQ ID NO:36).

FIG. 32 represents an alignment between the translated MAELO sequence (SEQ ID NO:39) and the translated putative mouse homologue AI225632 sequence (SEQ ID NO:40).

FIG. 33 illustrates an alignment between the translated GLELO sequence (SEQ ID NO:41) and the translated human homologue AI815960 sequence (SEQ ID NO:42).

FIG. 34 shows an alignment between the translated GLEO sequence (SEQ ID NO:43) and the translated putative human homologue HS1 sequence (SEQ ID NO:44).

FIG. 35 represents an alignment between the translated GLELO sequence (SEQ ID NO:45) and the translated putative human homologue sequence from AC004050 (SEQ ID NO:46).

FIG. 36 illustrates an alignment between the translated GLELO sequence (SEQ ID NO:47) and the translated putative mouse homologue MM2 sequence (SEQ ID NO:48).

FIG. 37 represents an alignment of the translated GLELO sequence (SEQ ID NO:49) and a translated putative mouse homologue AI225632 sequence (SEQ ID NO:50).

FIG. 38 illustrates an alignment of the translated GLELO sequence (SEQ ID NO:51) and a translated putative mouse homologue U97107 (SEQ ID NO:52).

FIG. 39 represents an alignment of the translated GLELO sequence (SEQ ID NO:53) and a translated putative C. elegans U68749 (F56H11.4) homologue sequence (SEQ ID NO:54).

FIG. 40 shows an alignment between the translated MAELO sequence and a translated putative C. elegans U68749 (F56H11.4) homologue sequence (SEQ ID NO:55).

FIG. 41 represents an alignment between the translated GELO sequence (SEQ ID NO:55) and a translated putative Drosophila melanogaster homologue sequence, DM1 (SEQ ID NO:57).

FIG. 42 illustrates an alignment between the translated MAELO (SEQ ID NO:58) sequence and a translated putative Drosophila melanogaster homologue sequence, DM1 (SEQ ID NO:59).

FIG. 43 illustrates the complete nucleotide sequence of a human elongase HSELO1 (SEQ ID NO:3).

FIG. 44 represents the deduced amino acid sequence of the human elongase HSELO1 (SEQ ID NO:60).

FIG. 45 illustrates the elongase activity (PUFA and others) of an induced culture of 334(pRAE-58-A1) when supplemented with GLA or AA.

FIG. 46 shows the complete nucleotide sequence of the C. elegans elongate CEELO (SEQ ID NO:4).

FIG. 47 represents the deduced amino acid of C. elegans elongase CEELO (SEQ ID NO:55).

FIG. 48 illustrates the PUFA elongase activity of an induced culture of 334(Prêt-21) and 834(Prêt-22) when supplemented with GLA and AA.

FIG. 49 represents the complete nucleotide sequence of the putative human elongase gene HS3 (SEQ ID NO:61).

FIG. 50 illustrates the deduced amino acid sequence of the putative human elongase enzyme HS3 (SEQ ID NO:62).

FIG. 51 represents the elongase activity (PUFA and others) of HSELO1 expressed in baker's yeast when supplemented with GLA, AA, STA, EPA, OA, or ALA.

FIG. 52 represents the elongase activity (PUFA and others) of HSELO1 expressed in baker's yeast when supplemented with 25 MM or 100 mM of GLA, AA, or EPA.

FIGS. 53A, 53B, and 53C represent the elongase activity (PUFA and others) of HSELO1 expressed in baker's yeast when supplemented with PA, SA, ARA, BA, PTA, OA, EA, LA, GLA, DGLA, AA, ADA, ALA, STA, EPA, or DPA, or when no substrate is present.

FIG. 54 represents the complete nucleotide sequence of mouse elongase MELO4 (SEQ ID NO:5).

FIG. 55 represents the deduced amino acid sequence of the mouse elongase MELO4 (SEQ ID NO:63).

FIG. 56 represents the PUFA elongase activity of MELO4 expressed in baker's yeast when supplemented with GLA, AA, ADA, STA, EPA, or DPA.

FIGS. 57A, 57B, and 57C represent the PUFA elongase activity of MELO4 expressed in baker's yeast when supplemented with PA, SA, AFA, BA, PTA, OA, EA, LA, GLA, DGLA, AA, ADA, ALA, STA, EPA, or DPA, or when no substrate is present.

FIG. 58 represents the complete nucleotide sequence of mouse elongase MELO7 (SEQ ID NO:6).

FIG. 59 represents the deduced amino acid sequence of the mouse elongase MELO7 (SEQ ID NO:64).

FIG. 60 represents the elongase activity (PUFA and others) of MELO7 expressed in baker's yeast when supplemented with GLA, AA, ADA, STA, EPA, or DPA.

FIG. 61 shows the activity of the *C. elegans* elongase when expressed in yeast when no substrate is present and with addition of AA or GLA.

FIG. 62 illustrates the PUFA elongase activity of an induced culture of 334(pRET22) when supplemented with 50 mM of various substrates.

FIG. 63 represents the PUFA elongase activity with GLA (FIG. 63A) or STA (FIG. 63B) as a substrate when co-expressed with the *M. alpina* Δ5-desaturase cDNA to produce AA or EPA, respectively.

DETAILED DESCRIPTION OF THE INVENTION

Figure 1:
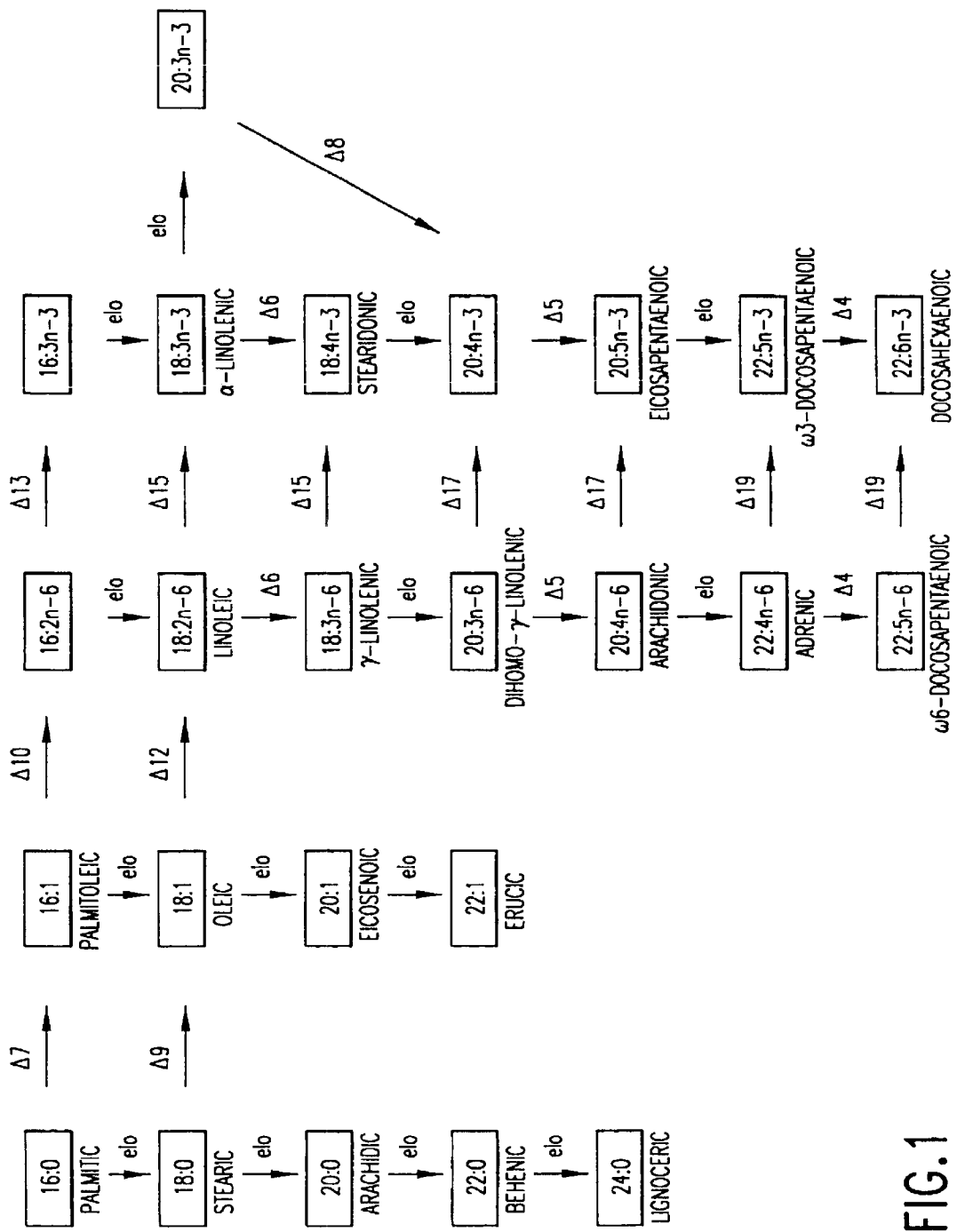
FIG. 1 represents various fatty acid biosynthesis pathways. The role of the elongase enzyme (elo) should be noted.

The subject invention relates to nucleotide and corresponding amino acid sequences of two elongase cDNAs derived from *Mortierella alpina*, as well as to nucleotide and corresponding amino acid sequences of an elongase cDNA derived from a human, an elongase cDNA derived for *C. elegans*, and two elongase cDNAs derived from a mouse. Furthermore, the subject invention also includes uses of the cDNAs and of the proteins encoded by the genes. For example, the genes and corresponding enzymes may be used in the production of polyunsaturated fatty acids and/or monounsaturated fatty acids such as, for example, DGLA, AA, ADA, EPA and/or DHA which may be added to pharmaceutical compositions, nutritional compositions, animal feeds, cosmetics, and to other valuable products.

The Elongase Cones and Enzymes Encoded Thereby

As noted above, an elongase enzyme encoded by an elongase cDNA is essential in the production of various polyunsaturated fatty acids, in particular, 20–24 carbon PUFAs. With respect to the present invention, the nucleotide sequence of the isolated *M. aplina* elongase cDNA (MAELO) is shown in FIG. 6, and the amino acid sequence of the corresponding purified protein or enzyme encoded by this nucleotide sequence is shown in FIG. 7. Additionally, the nucleotide sequence of the isolated GLA elongase cDNA (GLELO) is shown in FIG. 22, and the amino acid sequence of the corresponding purified protein or enzyme encoded by this nucleotide sequence is shown in FIG. 23. The nucleotide sequence of the isolated human sequence 1 (HSELO1) elongase is shown in FIG. 43, and the amino acid sequence of the corresponding purified protein or enzyme encoded by this sequence is shown in FIG. 44. Furthermore, the nucleotide sequence of the isolated *C. elegans* elongase cDNA (CEELO1) is shown in FIG. 46, and the amino acid sequence of the corresponding purified protein or enzyme encoded thereby is shown in FIG. 47. Additionally, the nucleotide sequence of the isolated mouse PUFA elongation enzyme (MELO4) is shown in FIG. 54, and the amino acid sequence of the corresponding purified protein or enzyme encoded thereby is shown in FIG. 55. Moreover, the nucleotide sequence of the second isolated mouse PUFA elongation enzyme (MELO7) is shown in FIG. 58, and the amino acid sequence of the corresponding purified protein or enzyme encoded thereby is shown in FIG. 59.

As an example, several of the isolated elongases encoded by the cDNAs of the present invention elongate GLA to DGLA or elongate STA to 20:4n-3 or elongate AA to ADA. The production of arachidonic acid from DGLA, or EPA from 20:4n-3, is then catalyzed by, for example, a Δ5-desaturase. Thus, neither AA (or EPA), nor DGLA (or 20:4n-3) nor ADA (or ω3-docosapentaenoic acid), can be synthesized without at least one elongase cDNA and enzyme encoded thereby.

It should be noted that the present invention also encompasses nucleotide sequences (and the corresponding encoded proteins) having sequences corresponding to (i.e., having identity to) or complementary to at least about 50%, preferably at least about 60%, and more preferably at least about 70% of the nucleotides in SEQ ID NO:1 (i.e., the nucleotide sequence of the MAELO cDNA described herein (see FIG. 6)). Furthermore, the present invention also includes nucleotide sequences (and the corresponding encoded proteins) having sequences corresponding to (i.e., having identity to) or complementary to at least about 35%, preferably at least about 45%, and more preferably at least about 55% of the nucleotides in SEQ ID NO:2 (i.e., the nucleotide sequence of the GLELO cDNA described herein (see FIG. 22). Additionally, the present invention also includes nucleotide sequences (and the corresponding encoded proteins) having sequences corresponding to (i.e., having identity to) or complementary to at least about 35%, preferably at least about 45%, and more preferably at least about 55% of the nucleotides in SEQ ID NO:3 (i.e., the nucleotide sequence of the human sequence 1 (HSELO1) cDNA described herein (see FIG. 43). In addition, the present invention also includes nucleotide sequences (and the corresponding encoded proteins) having sequences corresponding to (i.e., having identity to) or complementary to at least about 35%, preferably at least about 45%, and more preferably at least about 55% of the nucleotides in SEQ ID NO:4 (i.e., the nucleotide sequence of the *C. elegans* cDNA, CEELO1, described herein (see FIG. 46)). Further, the present invention also includes nucleotide sequences (and the corresponding encoded proteins) having sequences corresponding to (i.e., having identity to) or complementary to at least about 35%, preferably at least about 45%, and more preferably at least about 55% of the nucleotides in SEQ ID NO:5 or SEQ ID NO:6 (i.e., the nucleotide sequence of the mouse FUFA elongases MELO4 and MELO7, described herein (see FIGS. 54 and 58, respectively)). It should be noted that the "most preferable" range, referred to in each instance, may be increased by increments of ten percent. For example, if "at least 55%" is the most preferable range recited above, with respect to a particular sequence, such a range also naturally includes "at least 65% identity", "at least 75% identity", "at least 85% identity", and "at least 95% identity".

The corresponding or complementary sequences may be derived from non-Mortierella sources (e.g., a eukaryote (e.g., *Thraustochytrium* spp. (e.g., *Thraustochytrium aureum* and *Thraustochytrium roseum*), *Schizochytrium* spp. (e.g., *Schizochytrium aggregatum*), *Conidiobolus* spp. (e.g., *Conidiobolus nanodes*), *Entomorphthora* spp. (e.g., *Ento-*

*morphthora exitalis*), *Saprolegnia* spp. (e.g., *Saprolegnia parasitica* and *Saprolegnia diclina*), *Leptomitus* spp. (e.g., *Leptomitus lacteus*), *Entomophthora* spp., *Pythium* spp., *Porphyridium* spp. (e.g., *Porphyridium cruentum*), *Conidiobolus* spp., *Phytophathora* spp., *Penicillium* spp., *Coidosporium* spp., *Mucor* spp. (e.g., *Mucor circinelloides* and *Mucor javanicus*), *Fusarium* spp., *Aspergillus* spp. and *Rhodotorula* spp.), at yeast (e.g., *Dipodascopsis uninucleata*), a non-mammalian organism such as a fly (e.g., *Drosophila melanogaster*) or *Caenorhabditis* spp. (e.g., *Caenorhabditis elegans*), or a mammal (e.g., a human or a mouse). Such sequences may be derived from species within the genus *Mortierella*, other than the species *alpina*, for example, *Mortierella elongata, Mortierella exigua, Mortierella isabellina, Mortierella hygrophila,* and *Mortierella ramanniana,* va. *angulispora.*

Furthermore, the present invention also encompasses fragments and derivaties of the nucleotide sequences of the present invention (i.e., SEQ ID NO:1 (MAELO), SEQ ID NO:2 (GLELO), SEQ ID NO:3 (HSELO1), SEQ ID NO:4 (CEELO1)), SEQ ID NO:5 (MELO4) and SEQ ID NO:6 (MELO7)) as well as of the corresponding sequences derived from non-Mortierella or non-mammalian sources, etc., as described above, and having the above-described complementarity or correspondence/identity to the 6 sequences. Functional equivalents of the above-sequences (i.e., sequences having elongase activity) are also encompassed by the present invention.

For purposes of the present invention, "complementarity" is defined as the degree of relatedness between two DNA segments. It is determined by measuring the ability of the sense strand of one DNA segment to hybridize with the antisense strand of the other DNA segment, under appropriate conditions, to form a double helix. In the double helix, wherever adenine appears in one strand, thymine appears in the other strand. Similarly, wherever guanine is found in one strand, cytosine is found in the other. The greater the relatedness between the nucleotide sequences of two DNA segments, the greater the ability to form hybrid duplexes between the strands of two DNA segments.

"Identity" between two nucleotide sequences is defined as the degree of sameness, correspondence or equivalence between the same strands (either sense or antisense) of two DNA segments. The greater the percent identity, the higher the correspondence, sameness or equivalence between the strands.

"Similarity" between two amino acid sequences is defined as the presence of a series of identical as well as conserved amino acid residues in both sequences. The higher the degree of similarity between two amino acid sequences, the higher the correspondence, sameness or equivalence of the two sequences. ("Identity" between two amino sequences is defined as the presence of a series of exactly alike or invariant amino acid residues in both sequences.)

The definitions of "complementarity", "identity", and "similarity" are well known to those of ordinary skill in the art.

The invention also includes a purified polypeptide which elongates polyunsaturated and monounsaturated fatty acids and has at least about 50%, preferably at least about 70%, and more preferably at least about 90% amino acid similarity to the amino acid sequences of the above-noted proteins (see, e.g., FIG. 7 (MAELO)) and which are, in turn, encoded by the above-described nucleotide sequences. Additionally, the present invention includes a purified polypeptide which elongates polyunsaturated fatty acids and has at least about 30%, preferably at least about 60%, and more preferably at least about 90% amino acid similarity to the amino acid sequences of the above-noted proteins (see, e.g., FIG. 23 (CLELO)) and which are, in turn, encoded by the above-described nucleotide sequences. Furthermore, the invention also includes a purified polypeptide which elongates polyunsaturated and monounsaturated fatty acids and has at least about 30%, preferably at least about 60%, and more preferably at least about 90% amino acid similarity to the amino acid sequences of the above-noted proteins (see, e.g., FIG. 44 (HSELO1)) and which are, in turn, encoded by the above-described nucleotide sequences. Also, the present invention includes a purified polypeptide which elongates polyunsaturated fatty acids and has at least about 30%, preferably at least about 60%, and more preferably at least about 90% amino acid similarity to the amino acid sequences of the above-noted proteins (see, e.g., FIG. 47 (CEELO1)) and which are, in turn, encoded by the above-described nucleotide sequences. The present invention also includes a purified polypeptide which elongates polyunsaturated fatty acids and has at least about 30%, preferably at least about 60%, and more preferably at least about 90% amino acid similarity to the amino acid sequences of the above noted proteins (see, e.g., FIG. 55 (MELO4) and FIG. 58 (MELO7)) and which are, in turn, encoded by the above-described nucleotide sequences.

The present invention also encompasses an isolated nucleotide sequence which encodes PUFA elongase activity and that is hybridizable, under moderately stringent conditions, to a nucleic acid having a nucleotide sequence corresponding or complementary to the nucleotide sequence represented by SEQ ID NO:1 shown in FIG. 6 (MAELO) and/or SEQ ID NO:2 shown in FIG. 22 (GLELO) and/or SEQ ID NO:3 (HSELO1) shown in FIG. 43 and/or SEQ ID NO:4 (CEELO1) shown in FIG. 46 and/or SEQ ID NO:5 (MELO4) shown in FIG. 54 and/or SEQ ID NO:6 (MELO7) shown in FIG. 58. A nucleic acid molecule is "hybridizable" to another nucleic acid molecule when a single-stranded form of the nucleic acid molecule can anneal to the other nucleic acid molecule under the appropriate conditions of temperature and ionic strength (see Sambrook et al., "Molecular Cloning: A Laboratory Manual, Second Edition (1989), Cold Spring Harbor Laboratory Press, Cold Spring Harbor, N.Y.)). The conditions of temperature and ionic strength determine the "stringency" of the hybridization. "Hybridization" requires that two nucleic acids contain complementary sequences. However, depending on the stringency of the hybridization, mismatches between bases may occur. The appropriate stringency for hybridizating nucleic acids depends on the length of the nucleic acids and the degree of complementarity. Such variables are well known in the art. More specifically, the greater the degree of similarity or homology between two nucleotide sequences, the greater the value of Tm, melting temperature, for hybrids of nucleic acids having those sequences. For hybrids of greater than 100 nucleotides in length, equations for calculating Tm have been derived (see Sambrook et al., supra). For hybridization with shorter nucleic acids, the position of mismatches becomes more important, and the length of the oligonucleotide determines its specificity (see Sambrook et al., supra).

Production of the Elongase Enzyme

Once the gene encoding the elongase has been isolated, it may then be introduced into either a prokaryotic or eukaryotic host cell through the use of a vector, plasmid or construct.

The vector, for example, a bacteriophage, cosmid or plasmid, may comprise the nucleotide sequence encoding the elongase as well as any promoter which is functional in the host cell and is able to elicit expression of the elongase encoded by the nucleotide sequence. The promoter is in operable association with or operably linked to the nucleotide sequence. (A promoter is said to be "operably linked" with a coding sequence if the promoter affects transcription or expression of the coding sequence.) Suitable promoters include, for example, those from genes encoding alcohol dehydrogenase, glyceraldehyde-3-phosphate dehydrogenase, phosphoglucoisomerase, phosphoglycerate kinase, acid phosphatase, T7, TP1, lactase, metallothionein, cytomegalovirus immediate early, whey acidic protein, glucoamylase, and promoters activated in the presence of galactose, for example, GAL1 and GAL10. Additionally, nucleotide sequences which encode other proteins, oligosaccharides, lipids, etc. may also be included within the vector as well as other regulatory sequences such as a polyadenylation signal (e.g., the poly-A signal of SV-40T-antigen, ovalbumin or bovine growth hormone). The choice of sequences present in the construct is dependent upon the desired expression products as well as the nature of the host cell.

As noted above, once the vector has been constructed, it may then be introduced into the host cell of choice by methods known to those of ordinary skill in the art including, for example, transfection, transformation and electroporation (see *Molecule Cloning: A Laboratory Manual*, $2^{nd}$ ed., Vol. 1–3, ed. Sambrook et al., Cold Spring Harbor Laboratory Press (1989)). The host cell is then cultured under suitable conditions permitting expression of the PUFA which is then recovered and purified.

It should also be noted that one may design a unique triglyceride or oil if one utilizes one construct or vector comprising the nucleotide sequences of two or more cDNAs (e.g., MAELO, GLELO, HSELO1 and/or CEELO1). This vector may then be introduced into one host cell. Alternatively, each of the sequences may be introduced into a separate vector. These vectors may then be introduced into two host cells, respectively, or into one host cell.

Examples of suitable prokaryotic host cells include, for example, bacteria such as *Escherichia coli, Bacillus subtilis* as well as cyanobacteria such as *Spirulina* spp. (i.e., blue-green algae). Examples of suitable eukaryotic host cells include, for example, mammalian cells, plant cells, yeast cells such as *Saccharomyces* spp., *Lipomyces* spp., *Candida* spp. such as *Yarrowia (Candida)* spp., *Kluyveromyces* spp., *Pichia* spp., *Trichoderma* spp. or *Hansenula* spp., or fungal cells such as filamentous fungal cells, for example, *Aspergillus, Neurospora* and *Penicillium*. Preferably, *Saccharomyces cerevisiae* (baker's yeast) cells are utilized.

Expression in a host cell can be accomplished in a transient or stable fashion. Transient expression can occur from introduced constructs which contain expression signals functional in the host cell, but which constructs do not replicate and rarely integrate in the host cell, or where the host cell is not proliferating. Transient expression also can be accomplished by inducing the activity of a regulatable promoter optionally linked to the gene of interest, although such inducible systems frequently exhibit a low basal level of expression. Stable expression can be achieved by introduction of a construct that can integrate into the host genome or that autonomously replicates in the host cell. Stable expression of the gene of interest can be selected for through the use of a selectable marker located on or transfected with the expression construct, followed by selection for cells expressing the marker. When stable expression results from integration, the site of the construct's integration can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus.

A transgenic mammal may also be used in order to express the enzyme of interest (i.e., the elongase) encoded by one or both of the above-described nucleotide sequences. More specifically, once the above-described construct is created, it may be inserted into the pronucleus of an embryo. The embryo may then be implanted into a recipient female. Alternatively, a nuclear transfer method could also be utilized (Schnieke et al., *Science* 278:2130–2133 (1997)). Gestation and birth are then permitted to occur(see, e.g., U.S. Pat. No. 5,750,176 and U.S. Pat. No. 6,700,671). Milk, tissue or other fluid samples from the offspring should then contain altered levels of PUFAs, as compared to the levels normally found in the non-transgenic animal. Subsequent generations may be monitored for production of the altered or enhanced levels of PUFAs and thus incorporation of the gene or genes encoding the elongase enzyme into their genomes. The mammal utilized as the host may be selected from the group consisting of, for example, a mouse, a rat, a rabbit, a pig, a goat, a sheep, a horse and a cow. However, any mammal may be used provided it has the ability to incorporate DNA encoding the enzyme of interest into its genome.

For expression of an elongase polypeptide, functional transcriptional and translational initiation and termination regions are operably linked to the DNA encoding the elongase polypeptide. Transcriptional and translational initiation and termination regions are derived from a variety of nonexclusive sources, including the DNA to be expressed, genes known or suspected to be capable of expression in the desired system, expression vectors, chemical synthesis, or from an endogenous locus in a host cell. Expression in a plant tissue and/or plant part presents certain efficiencies, particularly where the tissue or part is one which is harvested early, such as seed, leaves, fruits, flowers, roots, etc. Expression can be targeted to that location with the plant by utilizing specific regulatory sequence such as those of U.S. Pat. Nos. 5,463,174, 4,943,674, 5,106,739, 5,175,095, 5,420,034, 5,186,958, and 5,589,379. Alternatively, the expressed protein can be an enzyme which produces a product which may be incorporated, either directly or upon further modifications, into a fluid fraction from the host plant. Expression of an elongase gene or genes, or antisense elongase transcripts, can alter the levels of specific PUFAs, or derivatives thereof, found in plant parts and/or plant tissues. The elongase polypeptide coding region may be expressed either by itself or with other genes, in order to produce tissues and/or plant parts containing higher proportions of desired PUFAs or in which the PUFA composition more closely resembles that of human breast milk (Prieto et al., PCT publication WO 95/24494). The termination region may be derived from the 3' region of the gene from which the initiation region was obtained or from a difference gene. A large number of termination regions are known to and have been found to be satisfactory in a variety of hosts from the same and different genera and species. The termination region usually is selected as a matter of convenience rather than because of any particular property.

As noted above, a plant (e.g., *Glycine max* (soybean) or *Brassica napus* (canola)), plant cell, plant tissue, corn, potatoe, sunflower, safflower or flax may also be utilized as a host or host cell, respectively, for expression of the elongase enzyme(s) which may, in turn be utilized in the production of polyunsaturated fatty acids. More specifically, desired PUFAs can be expressed in seed. Methods of isolating seed oils are known in the art. Thus, in addition to providing a source for PUFAs, seed oil components may be maintained through the expression of the elongase genes, as well as perhaps desaturase genes, in order to provide seed oils that can be added to nutritional compositions, pharmaceutical compositions, animal feeds and cosmetics. Once again, a vector which comprises a DNA sequence encoding the elongase operably linked to a promoter, will be introduced into the plant tissue or plant for a time and under conditions sufficient for expression of the elongase gene. The vector may also comprise one or more genus which encode other enzymes, for example, Δ4-desaturase, Δ5-desaturase, Δ6-desaturase, Δ8-desaturase, Δ9-desaturase, Δ10-desaturase, Δ12-desaturase, Δ13-desaturase, Δ15-desaturase, Δ17-desaturase and/or Δ19-desaturase. The plant tissue or plant may produce the relevant substrate (e.g., DGLA, GLA, STA, AA, ADA, EPA, 20:4n-3, etc.) upon which the enzymes act or a vector encoding enzymes which produce such substrates may be introduced into the plant tissue, plant cell, plant, or host cell of interest. In addition, substrate may be sprayed on plant tissues expressing the appropriate enzymes. Using these various techniques, one may produce PUFAs (e.g., n-6-unsaturated fatty acids such as DGLA, AA or ADA, or n-3 fatty acids such as EPA or DHA) by use of a plant cell, plant tissue, plant, or host cell of interest. It should also be noted that the invention also encompasses a transgenic plant comprising the above-described vector, wherein expression of the nucleotide sequence of the vector results in production of a polyunsaturated fatty acid in, for example, the seeds of the transgenic plant.

The substrates which may be produced by the host cell either naturally or transgenically, as well as the enzymes which may be encoded by DNA sequences present in the vector, which is subsequently introduced into the host cell, are shown in FIG. 1.

In view of the above, the present invention also encompasses a method of producing one of the elongase enzymes described above comprising the steps of: 1) isolating the desired nucleotide sequence of the elongase cDNA; 2) constructing a vector comprising said nucleotide sequence; and 3) introducing said vector into a host cell under time and conditions sufficient for the production of the elongase enzyme.

The present invention also encompasses a method of producing polyunsaturated fatty acids comprising exposing an acid to the elongase(s) produced as above such that the elongase converts the acid to a polyunsaturated fatty acid. For example, when GLA is exposed to elongase, it is converted to DGLA. DGLA may then be exposed to Δ5-desaturase which converts to DGLA to AA. The AA may then be converted to EPA by use of Δ17-desaturase which may be, in turn, converted to DHA by use of elongase and a Δ4-desaturase. Alternatively, elongase may be utilized to convert 18:4n-3 to 20:4n-3 which may be exposed to Δ5-desaturase and converted to EPA. Elongase may also be used to convert 18:3n-3 to 20:3n-3, which may be, in turn, converted to 20:4n-3 by a Δ8-desaturase. Thus, elongase may be used in the production of polyunsaturated fatty acids which may be used, in turn, for particular beneficial purposes. (see FIG. 1 for an illustration of the many critical roles the elongase enzyme plays in several biosynthetic pathways.)

Uses of the Elongase Gene and Enzyme Encoded Thereby

As noted above, the isolated elongase cDNAs and the corresponding elongase enzyme (or purified polypeptides) encoded thereby have many uses. For example, each cDNA and corresponding enzyme may be used indirectly or directly in the production of polyunsaturated fatty acids, for example, DGLA, AA, ADA, 20:4n-3 or EPA. ("Directly" is meant to encompass the situation where the enzyme directly converts the acid to another acid, the latter of which is utilized in a composition (e.g., the conversion of GLA to DGLA)). "Indirectly" is meant to encompass the situation where a fatty acid is converted to another fatty acid (i.e., a pathway intermediate) by elongase (e.g., GLA to DGLA) and then the latter fatty acid is converted to another fatty acid by use of a non-elongase enzyme (e.g., DGLA to AA by Δ5-desaturase)). These polyunsaturated fatty acids (i.e., those produced either directly or indirectly by activity of the elongase enzyme) may be added to, for example, nutritional compositions, pharmaceutical compositions, cosmetics, and animal feeds, all of which are encompassed by the present invention. These uses are described, in detail, below.

Nutritional Compositions

The present invention includes nutritional compositions. Such compositions, for purposes of the present invention, include any food or preparation for human consumption including for enteral or parenteral consumption, which when taken into the body (a) serve to nourish or build up tissues or supply energy and/or (b) maintain, restore or support adequate nutritional status or metabolic function.

The nutritional composition of the present invention comprises at least one oil acid produced by use of at least one elongase enzyme, produced using the respective elongase gene, and may either be in a solid or liquid form. Additionally, the composition may include edible macronutrients, vitamins and minerals in amounts desired for a particular use. The amount of such ingredients will vary depending on whether the composition is intended for use with normal, healthy infants, children or adults having specialized needs such as those which accompany certain metabolic conditions (e.g., metabolic disorders).

Examples of macronutrients which may be added to the composition include but are not limited to edible fats, carbohydrates and proteins. Examples of such edible fats include but are not limited to coconut oil, soy oil, and mono- and diglycerides. Examples of such carbohydrates include but are not limited to glucose, edible lactose and hydrolyzed starch. Additionally, examples of proteins which may be utilized in the nutritional composition of the invention include but are not limited to soy proteins, electrodialysed whey, electrodialysed skim milk, milk whey, or the hydrolysates of these proteins.

With respect to vitamins and minerals, the following may be added to the nutritional compositions of the present invention: calcium, phosphorus, potassium, sodium, chloride, magnesium, manganese, iron, copper, zinc, selenium, iodine, and Vitamins A, E, D, C, and the B complex. Other such vitamins and minerals may also be added.

The components utilized in the nutritional compositions of the present invention will be of sem-purified or purified origin. By semi-purified or purified is meant a material which has been prepared by purification of a natural material or by synthesis.

Examples of nutritional compositions of the present invention include but are not limited to infant formulas, dietary supplements, dietary substitutes, and rehydration compositions. Nutritional compositions of particular interest include but are not limited to those utilized for enteral and parenteral supplementation for infants, specialist infant formulae, supplements for the elderly, and supplements for those with gastrointestinal difficulties and/or malabsorption.

The nutritional composition of the present invention may also be added to food even when supplementation of the diet is not required. For example, the composition may be added to food of any type including but not limited to margarines, modified butters, cheeses, milk, yogurt, chocolate, candy, snacks, salad oils, cooking oils, cooking fats, meats, fish and beverages.

In a preferred embodiment of the present invention, the nutritional composition is an enteral nutritional product, more preferably, an adult or pediatric enteral nutritional product. This composition may be administered to adults or children experiencing stress or having specialized needs due to chronic or acute disease states. The composition may comprise, in addition to polyunsaturated fatty acids produced in accordance with the present invention, macronutrients, vitamins and minerals as described above. The macronutrients may be present in amounts equivalent to those present in human milk or on an energy basis, i.e., or a per calorie basis.

Methods for formulating liquid or solid enteral and parenteral nutritional formulas are well known in the art. (See also the Examples below.)

The enteral formula, for example, may be sterilized and subsequently utilized on a ready-to-feed (RTF) basis or stored in a concentrated liquid or powder. The powder can be prepared by spray drying the formula prepared as indicated above, and reconstituting it by rehydrating the concentrate. Adult and pediatric nutritional formulas are well known in the art and are commercially available (e.g., Similac®, Ensure®, Jevity® and Alimentum® from Ross Products Division, Abbott Laboratories, Columbus, Ohio). An oil or fatty acid produced in accordance with the present invention may be added to any of these formulas.

The energy density of the nutritional compositions of the present invention, when in liquid form, may range from about 0.6 Kcal to about 3 Kcal per ml. When in solid or powdered form, the nutritional supplements may contain from about 1.2 to more than 9 Kcals per gram, preferably about 3 to 7 Kcals per gm. In general, the osmolality of a liquid product should be less than 700 mOsm and, more preferably, less than 1600 mOsm.

The nutritional formula may include macronutrients, vitamins, and minerals, as noted above, in addition to the PUFAs produced in accordance with the present invention. The presence of these additional components helps the individual ingest the minimum daily requirements of these elements. In addition to the provision of PUFAs, it may also be desirable to add zinc, copper, folic acid and antioxidants to the composition. It is believed that these substance boost a stressed immune system and will therefore provide further benefits to the individual receiving the composition. A pharmaceutical composition may also be supplemented with these elements.

In a more preferred embodiment, the nutritional composition comprises, in addition to antioxidants and at least one PUFA, a source of carbohydrate wherein at least 5 weight % of the carbohydrate is indigestible oligosaccharide. In a more preferred embodiment, the nutritional composition additionally comprises protein, taurine, and carnitine.

As noted above, the PUFAs produced in accordance with the present invention, or derivatives thereof, may be added to a dietary substitute or supplement, particularly an infant formula, for patients undergoing intravenous feeding or for preventing or treating malnutrition or other conditions or disease states. As background, it should be noted that human breast milk has a fatty acid profile comprising from about 0.15% to about 0.36% as DHA, from about 0.3% to about 0.13% as EPA, from about 0.30% to about 0.98% as AA, from about 0.22% to about 0.67% as DGLA, and from about 0.27% to about 1.04% as GLA. Thus, fatty acids such as DGLA, AA, EPA and/or docosahexaenoic acid (DHA), produced in accordance with the present invention, can be used to alter, for example, the composition of infant formulas in order to better replicate the PUFA content of human breast, milk or to alter the presence of PUFAs normally found in a non-human mammal's milk. In particular, a composition for use in a pharmacologic or food supplement, particularly a breast milk substitute or supplement, will preferably comprise one or more of AA, DGLA and GLA. More preferably, the oil blend will comprise from about 0.3 to 30% AA, from about 0.2 to 30% DGLA, and/or from about 0.2 to about 30% GLA.

Parenteral nutritional compositions comprising from about 2 to about 30 weight percent fatty acids calculated as triglycerides are encompassed by the present invention. The preferred composition has about 1 to about 25 weight percent of the total PJFA composition as GLA (U.S. Pat. No. 5,196,198). Other vitamins, particularly fat-soluble vitamins such as vitamin A, D, E and L-carnitine can optionally be included. When desired, a preservative such as alpha-tocopherol may be added in amount of about 0.1% by weight.

In addition, the ratios of AA, DGLA and GLA can be adapted for a particular given end use. When formulated as a breast milk supplement or substitute, a composition which comprises one or more of AA, DGLA and GLA will be provided in a ratio of about 1:19:30 to about 6:1:0.2, respectively. For example, the breast milk of animals can vary in ratios of AA:DGLA:CLA ranging from 1:19:30 to 6:1:0.2, which includes intermediate rations which are preferably about 1:1:1, 1:2:1, 1:1:4. When produced together in a host cell, adjusting the rate and percent of conversion of a precursor substrate such as GLA and DGLA to AA can be used to precisely control the PUFA ratios. For example, a 5% to 10% conversions rate of DGLA to AA can be used to produce an AA to DGLA ratio of about 1:19, whereas a conversion rate of about 75% to 80% can be used to produce an AA to DGLA ratio of about 6:1. Therefore, whether in a cell culture system or in a host animal, regulating the timing, extent and specificity of elongase expression, as well as the expression of other desaturases, can be used to modulate PUFA levels and ratios. The PUFAs/acids produced in accordance with the present invention (e.g., AA and DGLA) may then be combined with other PUFAs/acids (e.g., GLA) in the desired concentrations and ratios.

Additionally, PUFA produced in accordance with the present invention or host cells containing them may also be used as animal food supplements to alter an animal's tissue or milk fatty acid composition to one more desirable for human or animal consumption.

Pharmaceutical Compositions

The present invention also encompasses a pharmaceutical composition comprising one or more of the fatty acids and/or resulting oils produced using at least one of the elongase cDNAs (i.e., MAELO, GLELO, HSELO1, CEELO, MELO4 and MELO7), in accordance with the methods described herein. More specifically, such a pharmaceutical composition may comprise one or more of the acids and/or oils as well as a standard, well-known, non-toxic pharmaceutically acceptable carrier, adjuvant or vehicle such as, for example, phosphate buffered saline, water, ethanol, polyols, vegetable oils, a wetting agent or an emulsion such as a water/oil emulsion. the composition may be in either a liquid or solid form. For example, the composition may be in the form of a tablet, capsule, ingestible liquid or powder, injectible, or topical ointment or cream. Proper fluidity can be maintained, for example, by the maintenance of the required particle size in the case of dispersions and by the use of surfactants. It may also be desirable to include isotonic agents, for example, sugars, sodium chloride and the like. Besides such inert diluents, the composition can also include adjuvants, such as wetting agents, emulsifying and suspending agents, sweetening agents, flavoring agents and perfuming agents.

Suspensions, in addition to the active compounds, may comprise suspending agents such as, for example, ethoxylated isostearyl alcohols, polyoxyethylene sorbitol and sorbitan esters, microcrystalline cellulose, aluminum metahydroxide, bentionate, agar-agar and tragacanth or mixtures of these substances.

Solid dosage forms such as tablets and capsules can be prepared using techniques well known in the art. For example, PUFAs produced in accordance with the present invention can be tableted with conventional tablet bases such as lactose, sucrose, and cornstarch in combination with binders such as acacia, cornstarch or gelatin, disintegrating agents such as potato starch or alginic acid, and a lubricant such as stearic acid or magnesium stearate. Capsules can be prepared by incorporating these excipients into a gelatin capsule along with antioxidants and the relevant PUFA(s). The antioxidant and PUFA components should fit within the guidelines presented above.

For intravenous administration, the PUFAs produced in accordance with the present invention or derivatives thereof may be incorporated into commercial formulations such as Intralipids™. The typical normal adult plasma fatty acid profile comprises 6.64 to 9.46% of AA, 1.45 to 3.11% of DGLA, and 0.02 to 0.06% of GLA. These PUFAs or their metabolic precursors can be administered alone or in combination with other PUFAs in order to achieve a normal fatty acid profile in a patient. Where desired, the individual components of the formulations may be provided individually, in kit form, for single or multiple use. A typical dosage of a particular fatty acid is from 0.1 mg to 20 g (up to 100 g) daily and is preferably from 10 mg to 1, 2, 5 or 10 g daily.

Possible routes of administration of the pharmaceutical compositions of the present invention include, for example, enteral (e.g., oral and rectal) and parenteral. For example, a liquid preparation may be administered, for example, orally or rectally. Additionally, a homogenous mixture can be completely dispersed in water, admixed under sterile conditions with physiologically acceptable diluents, preservatives, buffers or propellants in order to form a spray or inhalant.

The route of administration will, of course, depend upon the desired effect. For example, if the composition is being utilized to treat roughly, dry, or aging skin, to treat injured or burned skin, or to treat skin or hair affected by a disease or condition, it may perhaps be applied topically.

The dosage of the composition to be administered to the patient may be determined by one of ordinary skill in the art and depends upon various factors such as eight of the patient, age of the patient, immune status of the patient, etc.

With respect to form, the composition may be, for example, a solution, a dispersion, a suspension, an emulsion or a sterile powder which is then reconstituted.

The present invention also includes the treatment of various disorders by use of the pharmaceutical and/or nutritional compositions described herein. In particular, the compositions of the present invention may be used to treat restenosis after angioplasty. Furthermore, symptoms of inflammation, rheumatoid arthritis, asthma and psoriasis may also be treated with the compositions of the invention. Evidence also indicates that PUFAs may be involved in calcium metabolism; thus, the compositions of the present invention may, perhaps, be utilized in the treatment or prevention of osteoporosis and of kidney or urinary tract stones.

Additionally, the compositions of the present invention may also be used in the treatment of cancer. Malignant cells have been shown to have altered fatty acid compositions. Addition of fatty acids has been shown to slow their growth, cause cell death and increase their susceptibility to chemotherapeutic agents. Moreover, the compositions of the present invention may also be useful for treating cachexia associated with cancer.

The compositions of the present invention may also be used to treat diabetes (see U.S. Pat. No. 4,826,877 and Horrobin et al., *Am. J. Clin. Nutr.* Vol. 57 (Suppl.) 732S–737S). Altered fatty acid metabolism and composition have been demonstrated in diabetic animals.

Furthermore, the compositions of the present invention, comprising PUFAs produced either directly or indirectly through the use of the elongase enzyme(s), may also be used in the treatment of eczema, in the reduction of blood pressure, and in the improvement of mathematics examination scores. Additionally, the compositions of the present invention may be used in inhibition of platelet aggregation, induction of vasodilation, reduction in cholesterol levels, inhibition of proliferation of vessel wall smooth muscle and fibrous tissue (Brenner et al., *Adv. Exp. Med. Biol.* Vol. 83, p.85–101, 1976), reduction or prevention of gastrointestinal bleeding and other side effects of non-steroidal anti-inflammatory drugs (see U.S. Pat. No. 4,666,701), prevention or treatment of endometriosis and premenstrual syndrome (see U.S. Pat. No. 4,758,592), and treatment of myalgic encephalomyelitis and chronic fatigue after viral infections (see U.S. Pat. No. 5,116,871).

Further uses of the compositions of the present invention include use in the treatment of AIDS, multiple sclerosis, and inflammatory skin disorders, as well as for the maintenance of general health.

Additionally, the composition of the present invention may be utilized for cosmetic purposes. It may be added to pre-existing cosmetic compositions such that a mixture is formed or may be used as a sole composition.

Veterinary Applications

It should be noted that the above-described pharmaceutical and nutritional compositions may be utilized in connection with animals (i.e., domestic or non-domestic), as well as humans, as animals experience many of the same needs and conditions as humans. For example, the oil or acids of the present invention may be utilized in animal feed supplements, animal feed substitutes, animal vitamins or in animal topical ointments.

The present invention may be illustrated by the use of the following non-limiting examples:

EXAMPLE I

Determination of Codon Usage in *Mortierella alpina*

The 5' end of 1000 random cDNA clones were sequenced from *Mortierella alpina* cDNA library. The sequences were translated in six reading frames using GCG (Genetics Computer Group (Madison, Wis.)) with the FastA algorithm (Pearson and Lipman, *Proc. Natl. Acad. Sci. USA* 85:2444–2448 (1998)) to search for similarity between a query sequence and a group of sequences of the same type (nucleic acid or protein), specifically with the Swissport database (GeneBio, Geneva, Switzerland). Many of the clones were identified as a putative housekeeping gene based on protein sequence homology to known genes. Twenty-one *M. alpina* cDNA sequences which matched with known, housekeeping genes in the database were selected (see Table 1 below). *M. alpina* codon bias table (see Table 2) was generated based on these 21 sequences as well as infull length *M. alpina* Δ5- (see FIG. 18), Δ6-, and Δ12-desaturase sequences. Sine the FastA alignment between the putative protein coded by the *M. alpina* cDNA sequence and the known protein sequence was weak in some areas, only the codons from areas of strong homology were used.

TABLE 1

| Clone # | Match | # of bp | # of aa |
|---|---|---|---|
| 193 | Elongation factor 1-alpha | 426 | 142 |
| 143 | 60S ribosomal protein L17 | 417 | 139 |
| 235 | Actin I | 360 | 120 |
| 299 | 40S ribosomal protein YS11 | 387 | 129 |
| 390 | Ras-related protein rab-1a | 342 | 114 |
| 65 | 40S ribosomal protein RP10 | 366 | 122 |
| 289 | Ubiquitin-conjugating enzyme E2-16 KD | 294 | 98 |
| 151 | Ubiquinol-cytochrome C reductase | 375 | 125 |
| 80 | Initiation factor 5A-2 | 183 | 61 |
| 33 | 60S ribosomal protein L15 | 252 | 84 |
| 132 | 60S ribosomal protein L3-2 | 300 | 100 |
| 198 | Histone H3 | 285 | 95 |
| 286 | 6-phosphogluconate dehydrogenase, decarboxylating | 363 | 121 |
| 283 | 40S ribosomal protein S22 | 261 | 87 |
| 127 | Elongation factor 2 | 231 | 77 |
| 197 | Actin, gamma | 252 | 84 |
| 496 | 40S ribosomal protein S16 | 270 | 90 |
| 336 | Histone H4 | 219 | 73 |
| 262 | Ubiquitin | 228 | 76 |
| 188 | Guanine nucleotide-binding protein beta subunit-like protein | 213 | 71 |
| 81 | Ubiquitin | 228 | 76 |
| 21 | TOTAL | 6252 | 2084 |

TABLE 2

| Amino acid | Codon Bias | % used | Amino acid | Codon Bias | % used |
|---|---|---|---|---|---|
| Ala | GCC | 63% | Lys | AAG | 96% |
| Arg | CGC | 50% | Met | ATG | 100% |
| Asn | AAC | 97% | Phe | TTC | 78% |
| Asp | GAC | 65% | Pro | CCC | 68% |
| Cys | TGC | 87% | Ser | TCC | 46% |
| Gln | CAG | 78% | Thr | ACC | 78% |
| Glu | GAG | 85% | Trp | TGG | 100% |
| Gly | GGT | 47% | Tyr | TAC | 95% |
| His | CAC | 91% | Val | GTC | 72% |
| Ile | ATC | 72% | Stop | TAA | 50% |
| Leu | CTC | 49% | | | |

EXAMPLE II

Cloning of a Full-Length Elongase-like cDNA from *M. alpina*

The β-ketcacyl-coenzyme A synthase (KCS) from jojoba and the *Saccharomyces cerevisiae* elongase (ELO2) were aligned to determine an area of amino acid homology (see FIG. 2). The codon bias was applied to the area of sequence corresponding to the homologous amino acids between the two elongases, and primers were designed based on this biased sequence (see FIG. 3). The cDNA was excised from the M11 *M. alpina* cDNA library (Knutzon et al., *J. Biol. Chem.* 273:29360–29366 (1966)), which contains approximately $6 \times 10^5$ clones with an average insert size of 1.1 Kb. The excised cDNA was amplified with internal primer RO339 (5'-TTG GAG AGG AGG AAG CGA CCA CCG AAG ATG ATG- 3') (SEQ ID NO:65) and a vector forward primer PO317 (5'- CAC ACA GGA AAC AGC TAT GAC CAT GAT TAC G -3') (SEQ ID NO:66). Polymerase Chain Reaction (PCR) was carried out in a 100 ® 1 volume containing 300 ng of excised *M. alpina* cDNA library, 50 pmole each primer, 10 μl of 10× buffer, 1 μl 10 mM PCR Nucleotide Mix (Boehringer Mannheim Corp., Indianapolis, Ind.) and 1.0 U of Taq Polymerase. Thermocycler conditions in Perkin Elmer 9600 (Norwalk, Conn.) were as follows: 94° C. for 2 mins., then 30 cycles of 94° C. for 1 min., 58° C. for 2 mins., and 72° C. for 3 mins. PCR was followed by an additional extension at 72° C. for 7 minutes.

The PCR amplified product was run on gel, an amplified fragment of approximately 360 bp was gel purified, and the isolated fragment was directly sequenced using ABI 373A DNA Sequencer (Perkin Elmer, Foster City, Calif.). The sequence analysis package of GCG was used to compare the obtained sequence with known sequences. The sequence was translated in all six reading frames in the GCG Analysis Program using the FastA algorithm (Pearson and Lipman, supra). The Swissprot database (GeneBio, Geneva, Switzerland) of proteins was searched. This translated cDNA fragment was identified as a part of a putative elongase based on the homology of the putative protein sequence to the *S. cerevisiae* ELO2 (GNS1), having 41.3% identity in 63 amino acids.

Figure 4A:
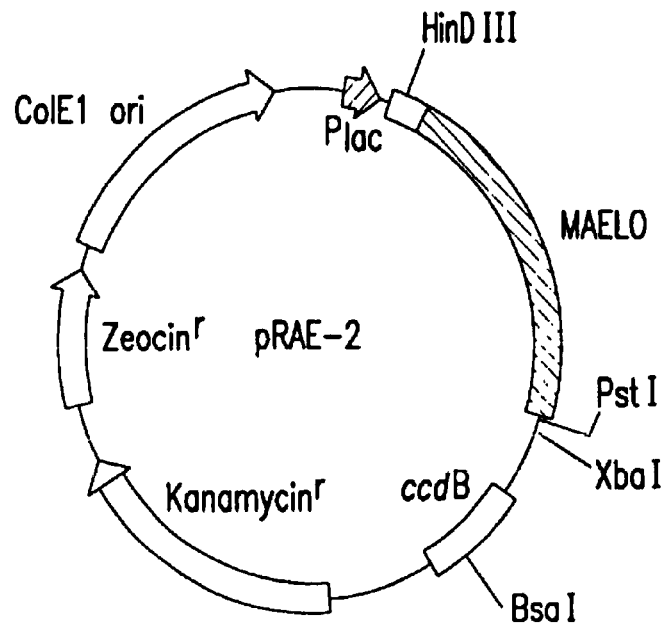
FIG. 4A shows the physical map of pRAE-2 containing the MAELO cDNA.
Figure 4B:
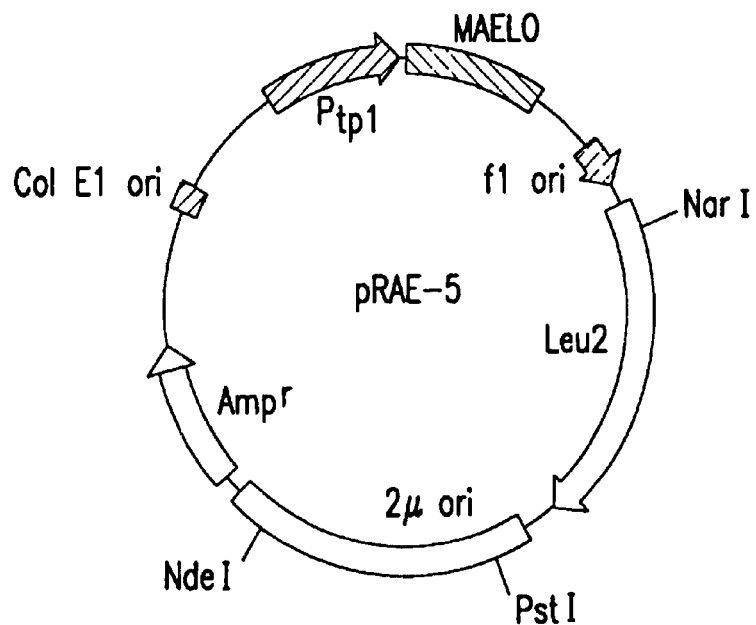
FIG. 4B represents the physical map of the constitutive expression vector, pRAE-5, used for elongase enzyme production in yeast.

New primers were designed based on the putative elongase sequence and the vector, PZL1 (Life Technologies, Inc., Gaithersburg, (Md.) sequence used to construct *M. alpina* cDNA library. The *M. alpina* excised cDNA library was PCR amplified again using primers RO350 (5'- CAT CTC ATG GAT CCG CCA TGG CCG CCG CAA TCT TG- 3') (SEQ ID NO:67), which has an added BamHI restriction site (underlined), and the vector reverse primer PO352 (5'-ACG CGT ACG TAA AGC TTG- 3') (SEQ ID NO:68) to isolate the full length *M. alpina* elongase cDNA, using previously described conditions. The terminal of the approximately 1.5 Kb PCR amplified fragment was filled-in with T4 DNA polymerase (Boehringer Mannheim Corp., Indianapolis, Ind.) to create blunt ends and cloned into the pCR-blunt vector (Invitrogen Corp., Carlsbad, Calif.). This resulted in two clones, pRAE-1 and pRAE-2 (see FIG. 4A). (Plasmid DNA pRAE-2 was deposited with the American Type Culture Collection, 10801 University Boulevard Manassas, Va. 20110-2209, on Aug. 28, 1998, under the terms of the Budapest Treaty, and was accorded deposit number ATCC 103166.) The elongase cDNAs from these vectors were cut out as an EcoRI fragment and cloned into the EcoRI digested pYX242 (Novagen, Madison, Wis.) vector. The clones pFAE-5 and pFAE-6 (see FIG. 4B) have the elongase cDNAs from pRAE-1 and pRAE-2, respectively, (Plasmid DNA pRAE-5 was deposited with the American Type

EXAMPLE III

Expression of *M. alpina* Elongase cDNA in Baker's Yeast

The constructs pRAE-5, and pRAE-6 were transformed into *S. cerevisiae* 334 (Hoveland et al., *Gene* 83:57–64

(1989)) and screened for elongase activity. The plasmid pCGN7875 (Calgene LLC, Davis, Calif.) containing jojoba KCS gene in pYES2 vector (Invitrogen Corp., Carlsbad, Calif.) was used as a positive control. The substrate used to detect elongase activity in *M. alpina* elongase (MAELO) was GLA and that in jojoba KCS was oleic acid (OA). The negative control strain was *S. cerevisiae* 334 containing pYX242 vector. The cultures were grown for 40–48 hours at 25° C., in selective media (Ausubel et al., *Short Protocols in Molecular Biology*, Ch. 13, p. 3–5 (1992)), in the presence of a particular substrate. The expression of the jojoba KCs gene cloned in pYES2 was under the control of GAL1 promoter, while the promoter in pYX242 is TP1, which is constitutive. Hence, the 334(pCGN7875) and 334 (pYES2) cultures were induced with galactose. The GC-FAME analysis of the lipid fraction of cash cell pellet was performed as previously described (Knutzon et al., supra).

The elongase activity results from different experiments are provided in FIGS. 10A and 10B. The jojoba KCS elongates long chain monounsaturated fatty acids 18:1n–9 to 20:1n–9. The amino acid homology between the *M. alpina* elongase (MAELO) and the *S. cerevisiae* ELO2 and ELO3 suggested that the proteins encoded by these genes may have similar substrate specificity. The activity of the *M. alpina* elongase, elongation (MAELO) of long chain monounsaturated and saturated fatty acids, is seen in the conversion of 18:1n–9 to 20:1n–9 and also in the synthesis of 24:0. The control strain 334(pYX242) has very little or no detectable amount of 20:1 and 24:0 (see FIG. 10A). *M. alpina* elongase (MAELO) also acts on at least one PUFA, converting 18:3n–6 (GLA) to 20:3n–6 (DGLA). The percentage of the 20:3n–6 in total lipid is higher in the strain 334 (pRAE-5) and 334 (pRAE-6) with the *M. alpina* elongase (MAELO) cDNA when compared to that in the control 334 (pYX242). The percentage of 20:3n–6 produced were 0.092% for 334 (pYX242) vs. 0.324% for 334 (pRAE-5) and 0.269% for 334 (pRAE-6) (shown in parenthesis in FIGS. 10A and 10B). This difference in the fatty acid profile is also seen in the total amount of 20:3n–6 produced. Only 0.226 μg of 20:3n–6 was produced by 334 (pYX242) while 334 (pRAE-5) and 334 (pRAE-6) produced 2.504 μg of 20:3n–6 and 1.006 μg of 20:3n–6, respectively. Also, when no substrate is added, the level of 20:3n–6 is not detectable.

Once 20:3n–6 is generated by the *M. alpina* elongase (MAELO), the Δ5-desaturase can convert it to AA in the desired expression system. To test this hypothesis, the constructs pRAE-5 and pCGR-4 (a Δ5-desaturase containing plasmid) were co-transformed into *S. cerevisiae* 334 and screened for AA production. The substrate used was 25 μM GLA (18:3n–6). If the *M. alpina* elongase (MAELO) is active in yeast, then the substrate will be converted to DGLA (20:3n–6), which the Δ5-desaturase will convert to AA (20:4n–6). The results in FIG. 11 confirm the production of AA and therefore, the activity of the *M. alpina* elongase (MAELO).

The expression of Δ5-, Δ6-, and Δ12-desaturases, in yeast, along with the elongase, should result in the production of AA (see FIG. 1) without the need for an exogenous supply of fatty acids.

EXAMPLE IV

A Comparison of the Expression of *M. alpina* Elongase cDNA MAELO and *S. cerevisiae* Elongase ELO2 in Baker's Yeast The ELO2 gene encoding for the yeast elongate was cloned form an *S. cerevisiae* genomic library (Origene, Rockville, Md.) using the primers RO514 (5'-GGC TAT GGA TCC ATG AAT TCA CTC GTT ACT CAA TAT G-3') (SEQ ID NO:69) and RO515 (5'-CCT GCC AAG CTT TTA CCT TTT TCT TCT GTG TTG AG-3') (SEQ ID NO:70) incorporating the restriction sites (underlined) BamHI and HindIII (respectively). The ELO2 gene was cloned into the vector pYX242 at the BamHI and HindIII sites, designated pRELO, transformed into the *S. cerevisiae* host 334 (Hoveland et al., supra) and screened for PUFA elongase activity. The vector plasmid was used as a negative control and 334(pRAE-6) was grown to compare the PUFA elongase activity. The cultures were grown as previously described with no galactose in the media and 25 μM GLA added as a substrate. FIG. 12 shows that amount of 20:3n–6 or DGLA produced (elongated from 18:3n–6 or GLA) by 334(pRAE-5) was approximately 4 times the negative control containing the unaltered vector pYX242, while the two individual clones 334(pRELO-1) and 334(pRELO-2) were twice the negative control. Additionally, when DGLA produced is expressed as a percent of the total lipids (shown in parenthesis, FIG. 12), the clones 334(pRELO-1) and 334 (pRELO-2) produced 0.1531 and 0.2% DGLA respectively, while 334 (pYX242) produced 0.1851 DGLA. Hence all these strains produced comparable percentages of DGLA. The strain 334 (pRAE-5), however, produced 0.279% DGLA, an increase of 50.8% over 334 (pYX242) negative control). These data show that the *S. cerevisiae* elongate gene ELO1, even when overexpressed in yeast, does not elongate GLA to DGLA effectively. The *M. alpina* PUFA elongase activity is specific for this conversion as evidenced by the higher amount of DGLA produced compared to the control, 334(pYX242).

EXAMPLE V

Identification of Elongases from Other Sources Using MAELO

The TFastA algorithm (Pearson and Lipman, supra) is used to search for similarity between a query peptide sequence and the database DNA sequence translated in each of the six reading frames. Translated MAELO was used as the query for a TFastA search in GCG with the GenEMBL database (6/98) from GCG to identify other potential elongase sequences based on their amino acid similarity comparisons to translated MAELO. For example, in FIGS. 13 and 14, two alignments are shown between translations of two different *C. elegans* sequences from chromosome III and MAELO. *C. elegans* DNA sequence (GenBank accession #Z268749) was annotated denoting similarity with GNS1 (ELO2), while the additional *C. elegans* DNA sequence (GenBank accession #U61954) was noted as similar to both GNS1 and SUR4 (ELO3). These are applied DNA fragments in which the introns have been removed from the genomic sequence, and the exons assembled and translated. The amount of amino acid identity between the putative PUFA elongates from *C. elegans* and translated MAELO are around 30%. This would point towards a common function in the fatty acid metabolism, e. g., a PUFA elongase. FIG. 15 is another example of a translated *C. elogans* sequence (GenBank accession #AF003134) from chromsome III. The DNA sequence was identified that had DNA homology to the *S. cerevisiae* ELO2. Further inspection of this DNA sequence and its amino acid translation determined that there was homology to translated MAELO. *C. elegans*, therefore, may contain a PUFA elongase.

FIG. 16 shows the alignment of translated DNA sequences from mouse and human, respectively, with translated MAELO. The mouse sequence CIG30, GenBank accession #U97107, was isolated from brown adipose tissue and reported as being "similar to yeast SUR4 protein". As shown in FIG. 16, amino acids numbered 130 to 152 in the U97107 translation contain a high degree of similarity to the translated MAELO. The human sequence, GenBank accession #AC004050, from chromosome 4 was from an HTGS (High Throughput Genome Sequence). There were no annotations contained with this sequence. However, translated AC004050 had 28.7% identity in 150 amino acids with translated MAELO. This gene fragment could be a fragment of a human PUFA elongase based on its amino acid similarity to translated MAELO.

FIG. 17 shows the amino acid alignment of translated MAELO and a mammalian sequence (GenBank accession #I05465, PCT#WO 88/07577) which claims that the protein derived from expression of this sequence is a glycoslylation inhibition factor. The amino acid identifies between the two proteins, signifying that there could be related function, such as PUFA elongase activity.

These examples of other translated DNA sequences and their homology to the translated MAELO illustrate that any of the above examples could potentially be a PUFA elongase. These examples are not inclusive of all the possible elongases. However, use of MAELO or its amino acid translation as a query for database searches can identify other genes which have PUFA elongase activities.

EXAMPLE VI

M. alpina cDNA Library Screening Using A Plaque Hybridization Method

In an effect to isolate additional PUFA elongase genes from M. alpina, a conventional plaque hybridization method was used to screen an M. alpina cDNA library made in a lambda vector. The DNA probe was generated based on MAELO nucleotide sequence and was used to screen the M7+8 M. alpina cDNA library made in a ΔZiplox vector (Knutzon et al., J. Biol. Chem. 273:29360–29366 (1998)).

To make the DNA probe for screening the library, the MAELO cDNA was digested with NspI and PvuI restriction endonucleases. Three small DNA fragments, with an average size of approximately 300 bp, were produced and used as probes. The rationale for using a mixture of fragmented MAELO cDNA was based on the assumption that there might be a common region or domain in the amino acid sequence which is conserved among various PUFA elongase present in M. alpina. Using MAELO DNA probes, the cDNA library was screened by a plaque hybridization technique according to standard protocol (Sambrook et al., Molecular Cloning, $2^{nd}$ Ed., Cold Spring Harbor, 1989).

Briefly, 50,000 primary clones were placed and transferred to nylon membranes. The membranes were denatured and hybridized with alpha $^{32}$p-dCTP-labelled MAELO DNA probes overnight in the hybridization buffer which contained 20% formamide, 0.2% PVP, BSA, Ficoll, 0.1% SDS and 0.5 M NaCl. The filters were washed with 0.5× SSC at 37° C. and exposed to X-ray film for autoradiography. This procedure was repeated three times. Four clones (designated as F1, F2, F3, and F4) which hybridized repeatedly were picked and suspended in SM buffer (Sambrook et al., supra) containing 7% DMSO.

The largest open reading frame each candidate was subcloned into yeast expression vector pYX242 (Novagen, Inc., Madison, Wis.). The cDNA clones F1 and F3 were subcloned into pYX242 at the EcoRI site while F2 and F4 were subcloned at NcoI/HindIII sites. The recombinant pYX242 containing each candidate was transformed into SC334 (Hoveland et al., supra) for expression in yeast. To determine the elongase activity, as well as substrate specifically, SC334 containing each cDNA clone was grown in minimal media lacking leucine in the presence of 26 μM of GLA substrate as described in Example III. The fatty acid analysis was performed as described in Knutzon et al. (J. Biol. Chem. 273:29360–29366 (1998)). The results indicated that none of these four cDNA clones showed any significant activity in converting GLA to DGLA. Thus, the hybridization approach appeared to be unsuccessful in identifying additional PUFA elongases.

EXAMPLE VII

Construction of Direct cDNA Expression Library of M. alpina in Yeast

To identify PUFA elongase genes other than MAELO, a different approach was taken to screen the M. alpina cDNA library. In particular, since Baker's yeast is incapable of producing long chain PUFAs due to the absence of respective desaturases and elongases, an attempt was made to construct an expression cDNA library of M. alpina in Saccharomyces cerevisiae. The vector pYES2 (Novagen, Inc., Madison, Wis.), containing the GAL1 promoter, was chosen for the expression of cDNA library in S. cerevisiae.

The conventional way by which the cDNA library is made (i.e. transformation of cDNA/vector ligated DNA mixture into host cells) is difficult in yeast because the transformation efficiency by direct electroporation of ligated DNA mix is very low compared to the efficiency of purified supercoiled plasmid DNA. However, the major advantage of this method is to avoid amplification of primary clones which happens when the library is made in E. coli as an intermediate. Due to the limitation in the number of colonies to be screened, it was decided to first optimize the efficiency of transformation in different S. cerevisiae strains using cDNA/vector ligated mix. The best results were obtained with a yield of 4–5×10$^3$ transformants per μg of ligated DNA in S. cerevisiae strain SC334 (Hoveland et al., supra).

To make a direct M. alpina cDNA expression library in yeast total RNA was isolated from the fungus. M. alpina fungus (ATCC #32221) was plated onto cornmeal agar (Difco Laboratories, Detroit, Mich.) and grown at room temperature for 3–4 days. Once fungus growth was visible, it was inoculated into 50 ml of potato dextrose broth and shaken at room temperature very slowly to formulate spores. Once spores were visable, the 50 ml culture was inoculated into a 1 liter culture of potato dextrose, and spores were grown for 72 hours. After filtering through sterile gauze, the cells were immediately frozen into liquid nitrogen for future RNA extraction. Total RNA was prepared from 36 g of cell pellet using the hot phenol/LiCl extraction method (Sambrook et al., supra). The cell pellets were homogenized in a 10 mM EDTA, 1% SDS and 200 mM sodium acetate, pH 4.8 solution. Phenol and chloroform were added to the homogenates, and the aqueous layer was extracted. The aqueous layer was back extracted one more time with phenol and chloroform. Then an equal volume of 4 M lithium chloride was added. The samples were ethanol precipitated on ice for 3 hours, and pellets were obtained by centrifugation. The RNA pellets were washed with 70% ethanol and resuspended in DEPC treated water. Total RNA was quantitated by spectrophotometry and visualization by agarose gel electrophoresis to confirm the presence of 28S and 18S ribosomal bands. Approximately, 15 mg of total RNA were obtained from 36 gram of cell pellet.

The library was constructed according to the standard protocol (Sambrook et al., *Molecular Cloning, 2nd Ed., Cold Spring Harbor,* 1989). Messenger RNA was prepared from the total RNA using oligo dT cellulose affinity purification. Messenger RNA was reverse transcribed with oligo dT primer containing a XhoI restriction site using AMV reverse transcriptase. Following first strand cDNA synthesis, the second strand of cDNA was synthesized by adding *E. coli* DNA polymerase, *E. coli* DNA ligase and RNAse H.

The EcorRi adaptor was ligated into the blunt-ended cDNA by T4 DNA ligase. The cDNA sample was kinased using T4 polynucleotide kinase and digested with XhoI, diluted with column buffer and passed through a Sepnacryl S-400 column. The DNA samples were eluted by high salt buffer. Samples containing DNA from 400–5,000 bps were pooled and used for ligation into a pYES2 vector (Invitrogen Corp., Carlsbad, Calif.). The cDNA was ligated into the EcoRI/XhoI digested pYES2 vector using T4 DNA ligase. A large scale ligation reaction was carried out since a large amount of the ligated DNA (2–3 $\mu$g) is required in direct transformation of yeast.

To transform yeast cells directly with the cDNA/pYES2 ligated mixture, competent SC334 cells were prepared using the LiAc TRAFO method (Gietz, et al., *Mol. Cell. Biol,* 5, 255–269, 1995). Briefly, fresh culture of SC334 from the plate was inoculated into 50 ml YPD medium. The culture was grown at 30° C. with shaking until the OD at 600 had reached 1.0. Thirty ml of this starter was inoculated into 300 ml of YPD liquid medium and incubated with shaking until the cell number of the culture reached ~3–5×10$^6$ cell/ml (approximately 3–4 h). The cells were harvested and washed with sterile water. The entire cell pellet was resuspended in 1.5 ml of freshly prepared 1× TE/LiAc (0.1M LiAc). These cells were used immediately for the transformations.

Seven hundred and fifty microliters of competent SC334 cells were aliquoted into 15 ml falcon tubes. Approximately 2 ug of cDNa/pYES2 ligated DNA were added to the cells along with carrier DNA and mixed gently. Three milliliters of sterile 40% PEG/LiAc was added to the cells and mixed gently but thoroughly. The cells were incubated at 30° C. for 30 min with shaking and subsequently given heat shock at 42° C. for 15 min. The cells were cooled, pelleted, and resuspended in 5 ml of 1× TE. A 100 ul aliquot of the above cells was plated onto fifty 150 mm selective agar plates lacking uracil (Ausubel et al., supra) and incubated at 30° C. for 3 days. A total of 8×10$^5$ primary clones were obtained. Five colonies were pooled in 1 ml minimal media lacking uracil (Ausubel et al., supra) and glycerol added to prepare stocks. A total of 5,000 pools were made for screening.

EXAMPLE VIII

MAD (*M. alpina* Direct) Screening in Yeast

The quality of the library was analyzed by determining the average size of the cDNAs in the library. Since the screening of the library was based on the expression of the cDNA, it was important to determine the average size of the cDNA present in the library. The expression library containing the longest cDNAs would be the best appropriate choice to isolate full-length cDNAs of interest. To this end, randomly selected pools were plated onto selective agar plates, as described in Example VII, to obtain individual colonies. Forty different yeast colonies were randomly picked, and each colony was inoculated into 5 ml of selective liquid medium lacking uracil (as described in Example VII) and grown, while shaking, for 24 hours at 30° C. Plasmid DNA was extracted from these colonies by the bead beating method (Hoffman et al., *Gene* 57:267 (1987)) adapted as follows:

Pellets from 5 ml of culture were lysed in 0.5 ml of a 100 mM NaCl, 10 mM Tris, pH 8.0, 1 mM EDTA and 0.1% SDS solution. Sterile 0.5 mm glass beads of equal volume were added and manually vortexed for 3 minutes. Two hundred microliters of the same buffer were added, and the mixture was vortexed for an additional minute. The samples were centrifuged on high for 2 minutes, and cytoplasmic extract was then transferred to a fresh tube. An equal volume of phenol/CHCl$_3$ was added to the sample, vortexed and centrifuged again for 2 minutes. The aqueous layer was re-extracted twice and precipitated with 0.3 M sodium acetate and approximately 2.5 volumes of ethanol for 30 minutes at −20° C. The precipitates were washed with 70% ethanol and resuspended in water. To eliminate RNA and any protein contamination, the plasmid DNAs isolated from 40 different samples were further purified using the QIAprep Spin Miniprep Kit according to the manufacturer's protocol (Qiagen Inc., Valencia, Calif.). The plasmid DNA samples were then restricted with EcoRI and XhoI restriction endonucleases to release the cDNA fragment, and the digest was analyzed on 1% agarose gel. The results indicated that the majority of the cDNAs of the direct library varied in length from 0.8 Kb to 1.5 Kb.

To screen the library, the glycerol stocks were thawed and approximately 0.5 ml was added to 5 ml of liquid selective media lacking uracil (Ausubel et al., supra) and grown at 30° C. for 24 hours. The culture was then transferred into 50 ml of liquid selective medium lacking uracil with 2% galactose and 25 $\mu$M GLA (substrate for the elongase enzyme) for 24 hours at 25° C. with shaking. The GC-FAME analysis of the lipid content in the cell pellet of each induced culture was performed as previously described (Knutzon et al., supra). The MALEO (pRAE-5 in pYX242 grown in selective media lacking leucine) was used as a positive control in each batch run. MAELO had consistency been able to convert 1.5% of GLA to DGLA (see Example III).

EXAMPLE IX

Identification of a cDNA Encoding a Potential PUFA Elongase

Figure 19:
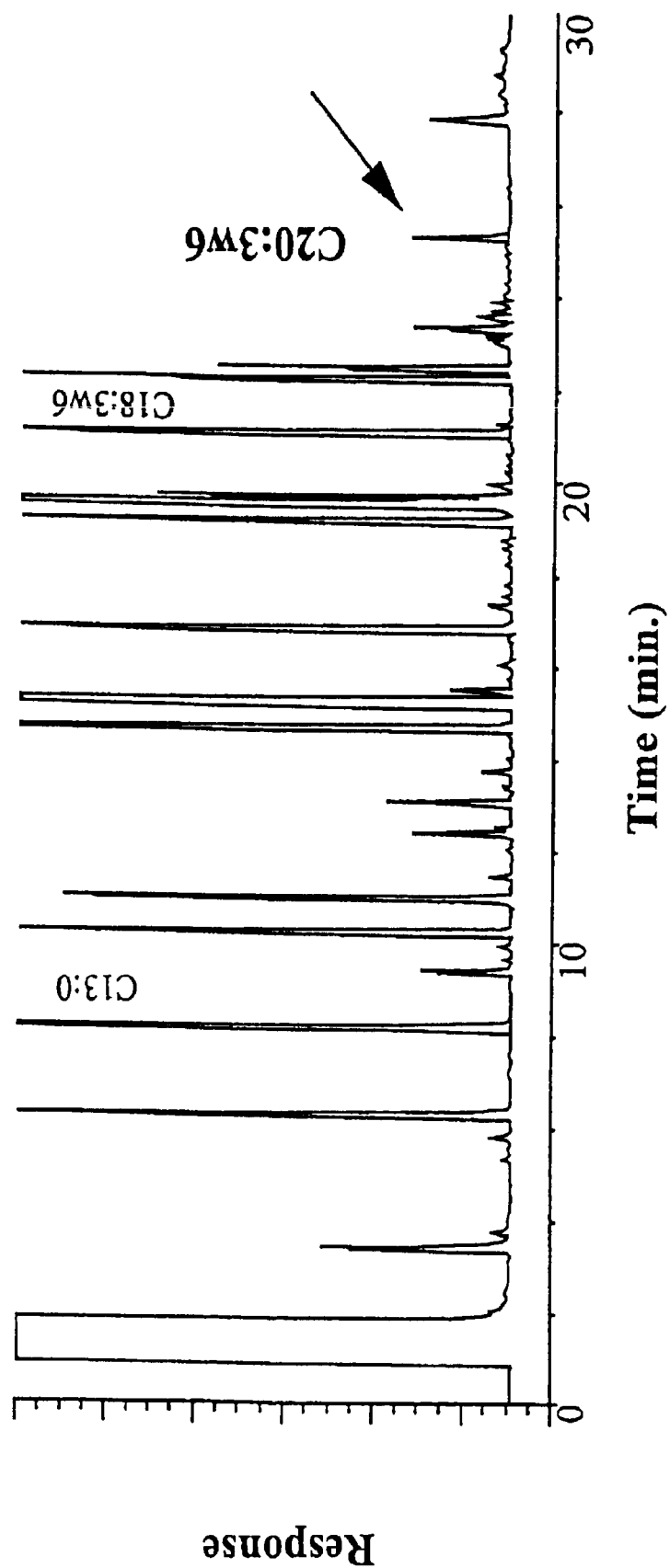
FIG. 19 represents the initial GC-FAME analysis of MAD708 pool. The detection of a DGLA (C20:3n-6) peak should be noted.

After screening and analyzing approximately 750 individual pools by GC-FAME analysis, as described in Example VIII, one pool of five colonies (i.e., MAD708) appeared to have significant enzymatic activity in converting GLA to DGLA. This activity was found to be approximately 5 fold higher than the *M. alpina* elongase activity (MAELO) in terms of DGLA/GLA ratio (FIG. 19). This pool was tested again under identical assay conditions to confirm the initial findings. The repeat experiment showed 9.5% conversion of GLA to DGLA and was again around 5 fold higher than *M. alpina* elongase activity (MAELO). These results strongly indicated that the MAD 708 pool contained an elongase candidate which was specific for GLA as substrate. Since MAD703 was a pool of five different clones, it was necessary to isolate the individual cDNA clone which encoded for elongase activity from this pool. To do this, the original MAD708 glycerol stock was plated onto a selective media agar plate lacking uracil (Ausubel et al., supra). Thirty individual colonies were picked and grown in liquid selective medium, lacking uracil with 2% galactose, as previously described in Example VIII, in the presence of GLA. The cell pellet obtained from each culture was then subjected to fatty GC-FAME analysis (Knutzon et al., supra) along with a positive control of 334 (pRAE-5) (MALEO in pYX242). The fatty acid analysis from the 30 individual clones from the MAD708 expression pool in yeast revealed that 5 of the 30 clones showed elongase activity in converting GLA to DGLA. The fatty acid profiles of the active clones MAD708-2, MAD708-10, MAD708-18, MAD708-19 and MAD708-30, are shown in FIG. 20. As shown in this Figure, MAD708-2, 10, and 30 produced the most DGLA, approximately 25 fold more than MAELO (pRAE-5). These 3 converted in the range of 41% to 49% of GLA to DGLA. Other clones, MAD708-18 and MAD708-19, converted 8% and 21% of GLA to DGLA, respectively. All MAD708 clones converted a higher percentage of GLA to DGLA with respect to MAELO encoded elongase (3.4%).

EXAMPLE X

Characterization of cDNAs Encoding Elongase

Plasmid DNA was extracted from SC334 yeast clones (MAD708 pool) that showed significant GLA specific elongase activity by the bead beating method, as described in Example VIII. To determine the size of the cDNA insert, PCR was performed using each plasmid DNA obtained from positive elongase clones as a template. The forward primer RO541 (5'-GAC TAC TAG CAG CTG TAA TAC-3') and the reverse primer RO540 (5'-GTG AAT GTA AGC GTG ACA TAA-3') are in the multicloning site of the pYES2 vector and were used to amplify the cDNA insert within the EcoRI and XhoI sites. PCR reaction was performed in a 50 µl volume containing 4 µl of plasmid DNA, 50 pmole of each primer, 5 µl of 10× buffer, 1 µl 10 µM PCR Nucleotide Mix (Boehringer Mannheim Corp., Indianapolis, Ind.) and 0.5 µl of High Five Taq polymerase (Boehringer Mannheim, Indianapolis, Ind.). The amplification was carried out as follows: 2 mins. denaturation at 94° C., then 94° C. for 1 min, 55° C. for 2 mins., and 72° C. for 3 mins. for 30 cycles, and 7 mins. extension at 72° C. at the end of the amplification. Analysis of PCR amplified products on a 1% agarose gel showed the sizes of the elongase cDNAs to be around 1.0–1.2 Kb. The plasmid DNAs, containing the potential elongase cDNAs, were designated as pRPB2, pRBP10, pRBP18, pRPB19, and pRPB30. Since the cDNA library was made in the pYES2 vector at the EcoRI and XhoI sites, the size of the cDNA present in each plasmid was further confirmed by digesting the above plasmids with EcoRI and XhoI.

Figure 21:
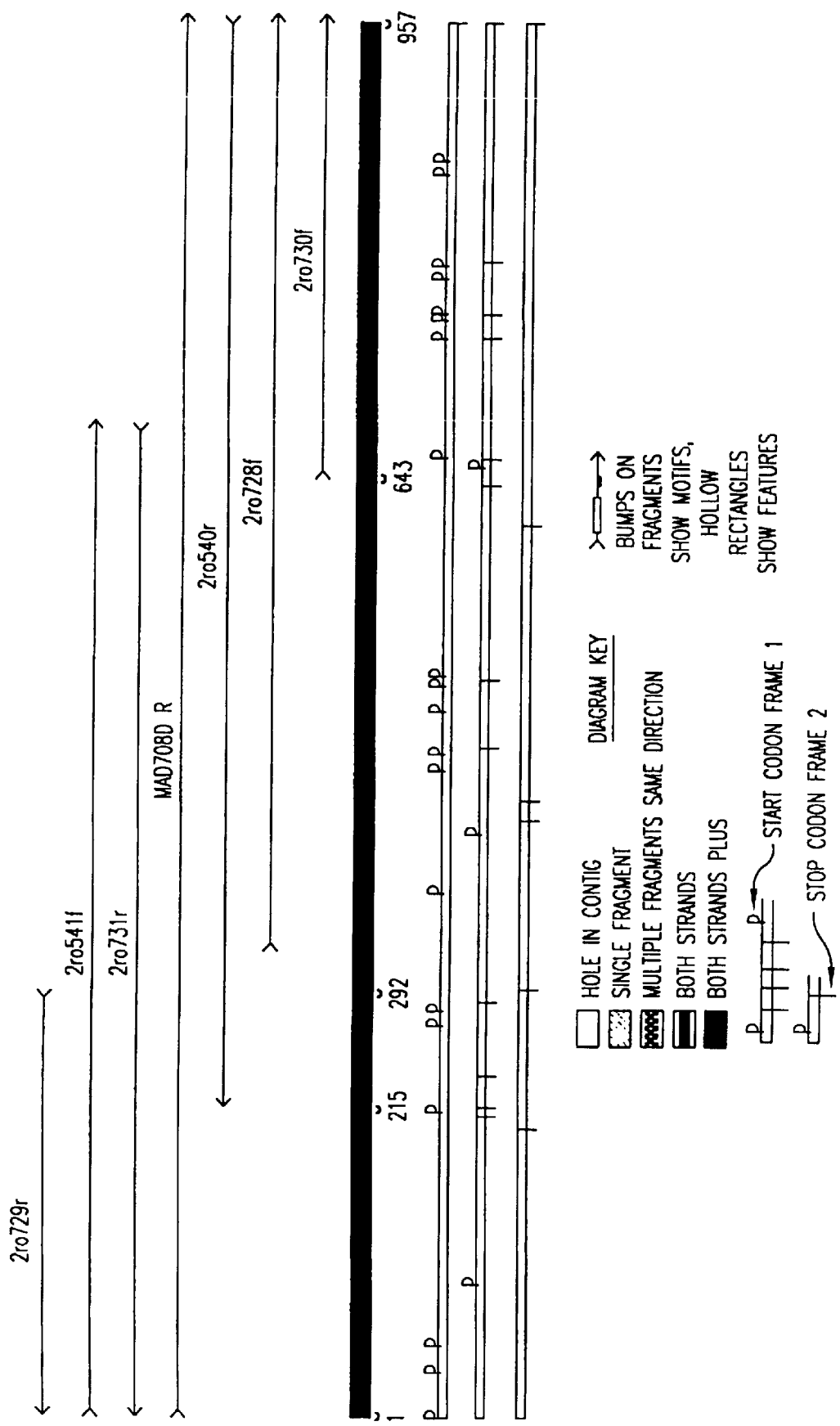
FIG. 21 represents the DNA sequencing analysis of plasmid pRPB2. The analysis reveals an open reading frame of 957 bp in length.

The plasmid DNAs isolated from yeast were re-amplified in E. coli for long-term storage of the cDNA clones as well as for DNA sequencing. E. coli TOP10 (Invitrogen Corp., Carlsbad, Calif.) cells were transformed with the pRPB recombinant plasmids according to the manufacturer's protocol. The transformants obtained from each plasmid DNA were inoculated into LB containing ampicillin (50 µg/ml) and grown overnight at 37° C. with shaking. Plasmid DNAs were isolated from these cultures by using QIAprep Spin Miniprep (Qiagen Inc., Valencia, Calif.) according to the manufacturer's protocol. The purified plasmid DNAs were then used for sequencing from both 5' and 3' ends. The DNA sequencing was performed by using a 373A Stretch ABI automated DNA sequencer (Perkin Elmer, Foster City, Calif.) according to the manufacturer's protocol. Primers used for sequencing were the forward primer RO541 (5'-GAC TAC TAG CAG CTG TAA TAC-3') (SEQ ID NO:71) and the reverse primer RO540 (5'-GTG AAT GTA AGC GTG ACA TAA-3') (SEQ ID NO:72) contained in the multicloning sites of the pYES2 vector. The obtained nucleotide sequences were transferred to Sequencher software problem (Gene Codes Corporation, Ann Arbor, Mich.) for analysis. The DNA sequence analysis revealed that all five elongase cDNAs contained the identical nucleotide sequence with a common overlap of 301 nucleotides. Each DNA sequence contains a putative start site at the beginning of the 5' end and a stop codon with poly A tail at the end of the 3' site. To further confirm the DNA sequence, internal forward primers PO728 (5'- GAG ACT TTG AGC GGT TCG-3') (SEQ ID NO:73) and RO730 (5'-TCT CTG CTG CGT TGA ACT CG-3') (SEQ ID NO:74), along with reverse primers RO729 (5'-AAA GCT CTT GAC CTC GAA C-3') (SEQ ID NO:75) and RO731 (5'-AAC TTG ATG AAC GAC ACG TG-3') (SEQ ID NO:76) were designed within the cDNA, and used for sequencing of pRPB1, since this candidate possessed the highest elongase activity. The entire nucleotide sequence was analyzed by the Sequencher program (FIG. 21), and the longest open reading frame deduced from the entire cDNA sequence in pRPB2 appeared to be 957 bp in length (FIG. 22). The deduced open reading frame was then translated into the corresponding amino acid sequence, and the predicted sequence is shown in FIG. 23. The elongase encoded by the cDNA (pRPB2) identified from M. alpina appears to be a 318 amino acid long protein which is nearly identical in size with translated MAELO. This new elongase cDNA was designated as "GLELO" and its encoded protein has been named "GLA elongase".

Plasmid DNA pRPB2 was deposited with the American Type Culture Collection, 10801 University Boulevard, Manassas, Va. 20110-2209 on Jul. 22, 1999 under the terms of the Budapest Treaty. It was accorded ATCC Deposit #PTA-402.

EXAMPLE XI

Biochemical Characterization of GLA Elongase (GLELO)

A. Confirmation of GLA Elongase Activity

To further confirm the activity of the GLA elongase encoded by the pRPB2 recombinant plasmid, elongase activity screening was repeated on the yeast clone SC334 containing pRPB2 plasmid. This experiment was also conducted to assure consistent lipid extraction and to detect the activity of GLA elongase by averaging four independent experiments. The S. cerevisiae 334 glycerol stock containing pRPB2 was plated onto minimal media agar plate lacking uracil. Individual colonies were randomly picked and grown in minimal medium lacking uracil, as described in Example VIII. The four independent cultures were combined, and a 5 ml aliquot was used as an inoculum for four separate 50 ml cultures. The cultures were then grown in the presence of GLA and were subjected to fatty acid analysis along with a negative control of S. cerevisiae 334 containing pYES2, as described in Example VIII. The average elongase activity from four independent cultures of 334(pRPB2) with 25 µM GLA is shown in FIG. 24. The GLA elongase activity of each of the four independent samples of 334(pRPB2) appeared to be consistent with an average conversion of 62% GLA to DGLA.

B. Determination of GLELO Substrate Specificity for GLA Elongase

To analyze the substrate specificity of the GLA elongase, the culture of 334(pRPB2) was tested with different fatty acid substrates besides GLA (e.g., SA(18:0), OA(18:1), LA(18:2n-6), AA(20:4n-6), ADA(22:4n-6), ALA(18:3n-3), and EPA(20:5n-3)). Under identical assay conditions, the only other substrate utilized by the elongase enzyme with STA, a fatty acid from the n-3 pathway. GLA elongase was able to convert 73% of STA to 20:4-n-3 (FIG. 25). From these experiments, it can be concluded that the GLA elongase has substrate specificity for both GLA and STA, indicating that it possesses elongase activity along both the n-5 and n-3 pathways.

C. Co-expression of Fungal GLELO and Δ5-Desaturase Gene in Yeast

Once DGLA (20:3n-6) is produced by the DGLA elongase, the Δ5-desaturase can convert it to AA (20:4n-6) in a desired co-expression system. This scheme, as depicted in FIG. 1, can be tested by co-transforming *S. cerevisiae* 334 with plasmids pRPB2 and pRPE31 (the recombinant plasmid pYX242 containing a Δ5-desaturase cDNA (FIG. 18) cloned at the EcoRI site. The co-transformed yeast cultures were supplemented with 25 μM GLA and analyzed for AA synthesis. If both elongase and Δ5-desaturase enzymes are expressed, the GLA substrate will be converted to DGLA, which will then be converted to AA. The results in FIG. 26A indicate that the sequential action of GLA elongase and Δ5-desaturase on GLA substrate resulted in an average conversion of 27% GLA to AA. Therefore, the GLA elongase has the ability to work with other enzymes in the n-6 PUFA synthetic pathway to procedure desirable fatty acids.

To determine whether the above conversion is also true in n-3 pathways, the similar co-expression experiments were carried out in the presence of 25 μM STA. Again, if both enzymes are expressed, the STA substrate will be converted to 20:4n-3 which will then be converted to EPA (20:5n-3) by the Δ5-desaturase. FIG. 26B shows the results in which the production of EPA (approx. 40%) is observed. Once again, the GLA elongase demonstrates its ability to work with Δ5-desaturase in the n-3 pathway to produce desirable fatty acids.

EXAMPLE XII

Sequence Comparison Between GLELO AND OTHER FUNGAL ELONGASES

Figure 28A:
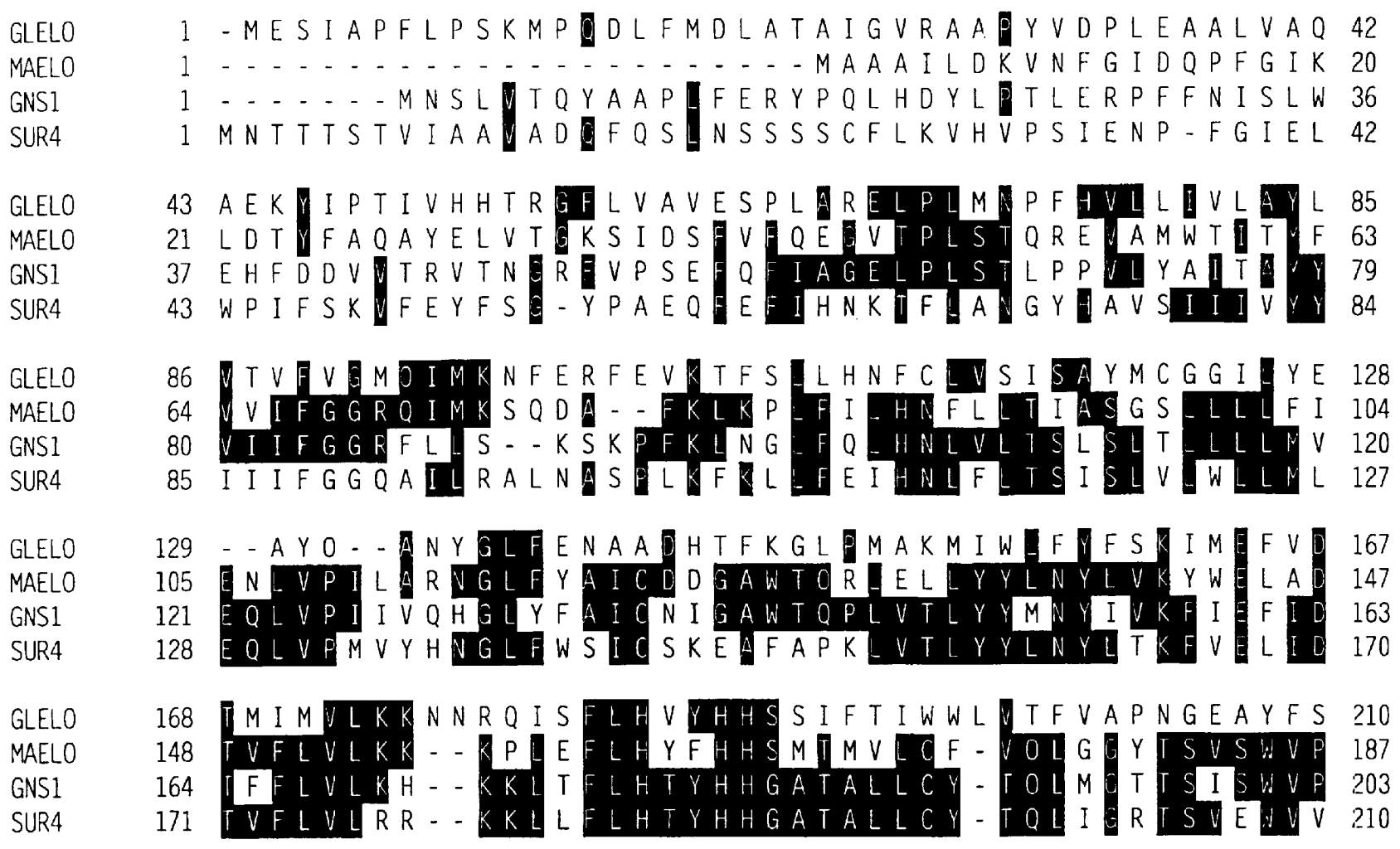

The sequence analysis package of GCG (see Example I) was used to compare the GLELO sequence with known protein sequences. The nucleotide sequence of GLELO open reading frame was first translated into amino acid sequence that was used as a query sequence to search Swissprot database (see Example I) using the FastA algorithm (see Example I). Based on amino acid sequence similarity, the best matches were found with *S. cerevisiae* YUT6 (an EST with unknown annotation) with 33.9% identity in 189 amino acid overlap, *S. cerevisiae* ELO2 (GNS1) with 25.8% identity in 295 amino acid overlap, and *S. cerevisiae* ELO3 (SUR4) with 25.2% identity in 313 amino acid overlap. The FastA alignment of GLELO with MAELO showed 30.9% identity in 275 amino acids (FIG. 27). GCG Pileup program creates a multiple sequence alignment from a group of related sequences using progressive, pairwise alignments (see Example I), and was used with the elongases described above. The Pileup results indicate that there are many conserved regions among the elongases including a putative histidine box, which is underlined (Knutzon et. al., *J. Biol. Chem.* 273: 29360–29366, 1998) (FIG. 28). Thus, although GLELO has similarity with MALEO, the difference in their encoded elongases may presumably be due to their substrate preference. GLA elongase can convert a higher percentage of GLA to DGLA than *M. alpina* elongase. In addition, MAELO expression in *S. cerevisiae* showed elongation of saturated and monosaturated fatty acids in addition to GLA elongation to DGLA (see Example III).

EXAMPLE XIII

Identification of *M. alpina* MAELO Homologues in Mammals

The MAELO translated sequence was used to search the Unified Human Transcript Database of Abbott Laboratories, 100 Abbott Park Rd., Abbott Park, Ill. 60064. This database was searched using Basic Local Alignment Search Tool (BLAST) (Altschul et al., *Nuc. Acids Res.* 25:3389–3402 (1997) which "is a set of similarity search programs designed to explore all of the available sequence databases regardless of whether the query is a protein or DNA." Specifically, the tblastn algorithm was used (i.e., a protein query search to a nucleotide database translated in six reading frames). The contig (CC) sequences in the Unified Human Transcript Database are consensus sequences representing groups of expressed sequence tags (EST) cDNAs derived from the public domain and from the Incyte LIFESEQ™ database of ESTs (Incyte Pharmaceuticals, Inc., 3174 Porter Drive, Palo Alto, Calif. 94304) tha are clustered together on the basis of defined sequence homology, and assembled on the basis of sequence overlap. Two sequences from this database, CC067284R1 and CC1484548T1 had 28% identity in 242 amino acid overlap and 28.6% identity in 266 amino acid overlap, respectively, with the translated MAELO sequence. The two derived and edited sequences were designated as hs1 and hs2, respectively, and copied into the sequence analysis software package of GCG (see Example I). The translated MAELO sequence was aligned with translated HS1 (28.5% identity in 242 amino acids) and HS2 (28.2% identity in 266 amino acids) cDNA sequences using the FastA algorithm, as shown in FIGS. 29 and 30, respectively. HS1 cDNA nucleotide sequence also had 86.9% identity in 844 bp with the 105465 Nucleotide sequence (see Example V). The translated HS2 cDNA sequence had 100% identity with the amino acid sequence from GenBank with accession number W74824 (see published PCT application WO9839448).

The National Center for Biotechnology Information (NCBI at ncbi.nlm.nih.gov/) was used to conduct database searches using tblastn with the 28 amino acid sequence (DTIFIILRKQKLIFL<u>HWYHH</u>ITVLLYSW) (SEQ ID NO:87) translated from AC004050 (a human sequence identified in a TfastA search, see Example V). This amino acid sequence contains a histidine box (underlined), which has a noted motif of desaturases (Knutzon et al., supra), and both PUFA elongase, MAELO and GLELO (see FIG. 28). A translated mouse sequence shown previously in Example V (GenBank Accession #U97107) and a translated *C. elegans* sequence (GenBank Accession #U41011) had the highest matches with this 28 amino acid query. The NCBI mouse EST database was searched again with tblastn, using translated U41011 as a query. An additional mouse sequence was identified (GenBank Accession #AF014033.1), annotated as "putative involvement in fatty acid elongation." Three longer sequences (GenBank Accession #'s AA5591034, AA189549, and AA839346) were identified through a tblastn search of the mouse EST database with translated AF014033.1 and combined into one sequence designated as mm2. The FastA alignment (see Example 1) of translated mm2 and MAELO is shown in FIG. 31. Another related, but not identical mouse sequence (GenBank Accession #AI225632), was also identified in a tblastn search of the mouse EST database with AF014033.1. The FastA alignment with translated AI225632 to MAELO is shown in FIG. 32. The percent identity for both translated MM2 and AI 225632 with translated MAELO is 30.4% in 191 and 115 amino acid overlap, respectively. The level of amino acid identity with translated MAELO with these two translated mouse sequences identifies them as putative homologues of PUFA elongase.

EXAMPLE XIV

Identification of *M. alpina* GLELO Homologues in Mammals

The TFastA algorithm, which compares a protein sequence to the database DNA sequence translated in each of the six reading frames, was used with translated GLELO as the query. The GenEMBL database from GCG was used to identify other potential elongase sequences based on their amino acid similarity to translated GLELO. Three human sequences were found to have matches with the GLELO amino acid sequence. These sequences have GenBank accession numbers 1) AI815960, 2) AL034374, and 3) AC004050. AI815960, a Homo sapien EST sequence, has 40.3% identity in 144 amino acid overlap with translated GLELO (see FIG. 33). A translated region of the human genomic sequence AL034374, derived from chromosome VI has 46.7% identity in a 60 amino acid overlap with translated GLELO. This homologous region in AL034374 appeared to be a part of the HS1 amino acid sequence which was shown to have homology with translated MAELO (See Example XIII). Therefore, HS1 sequence has similarity with both MAELO (see FIG. 29) as well as GLELO (see FIG. 34). A translated region of a human genomic sequence AC004050 from chromosome IV has 34.8% identity in 89 amino acid overlap with translated GLELO (see FIG. 35). The amino acid identities between GLELO and these human sequences indicate that the proteins derived from these human sequences could have related function, such as PUFA elongase activity.

To identify a mouse cDNA similar to GLELO, TFastA searches were performed with the GenEMBL database using translated GLELO as a query. From the TFastA searches, the three mouse sequences with the highest matches to translated GLELO were identified: (GenBank accession numbers 1) AF104033, 2) AI595258, and 3) U97107). AF104033 is annotated as "MUEL protein having putative fatty acid elongase with homology to yeast ELO3 (SUR4)" and is a part of the sequence of MM2. The MM2 sequence was initially derived from AF104033 mouse sequence, but the entire MM2 sequence was finally obtained through further mouse EST database searches and also shown to have homology with translated MAELO (See Example XIII and FIG. 31). When this MM2 amino acid sequence was aligned with translated GLELO sequence using FastA, a 34.6% identity in 211 amino acid overlap was found (see FIG. 36) indicating that MM2 also has homology with GLELO. AI595258 is a mouse cDNA clone having 5' similarity with yeast ELO3 elongase and is part of mouse EST cDNA AI225632. The AI225632 mouse sequence, which is a longer sequence than AI595258, was shown to have similarity with translated MAELO (see FIG. 32). The AI225632 was also aligned with the translated GLELO, and the FastA alignment is shown in FIG. 37. A 35.3% identity in 199 amino acid overlap has been found. The third sequence, U97107, a mouse sequence, was annotated as "similar to yeast ELO3 (SUR4) gene." The FastA alignment of translated GLELO with U97107 is shown in FIG. 38 where a 23.7% identity in 279 amino acid overlap was found. Previously, a region of U97107 was also found to have a high degree of homology with MAELO based on a FastA alignment (see Example V and FIG. 16).

The above searches clearly indicate that the same human and mouse sequences were obtained by using either MAELO or GLELO as a query.

EXAMPLE XV

Identification of M. alpina GLELO and MAELO
Homologues in Other PUFA Producing Organisms
A) Caenorhabditis elegans:
A putative amino acid sequence deduced from a chromosomal sequence of C. elegans (GenBank Accession #U41011) was able to identify a partial sequence contained in the mouse MM2 putative PUFA elongase which has amino acid similarity with both GLA elongase (GLELO) and M. alpina elongase (MAELO). It was therefore conceivable that C. elegans homologues of GLELO or MAELO might be present in the nematode database. The putative amino acid sequences derived from GLELO and MAELO sequences were used as queries independently to search the nematode databases. A BLAST search (see Example XIII) was performed on wormpep16 (blastp compares an amino acid query sequence against a nucleotide sequence database) and wormpep 16cDNAs (tblastn) databases which are predicted proteins and cDNAs obtained from the C. elegans genome sequencing project or EST's and their corresponding cDNA sequences, respectively. These sequence data were produced by the C. elegans Sequencing group, carried out jointly by the Sanger Centre and Genome Sequencing Center, and can be obtained from ftp://ftp.sanger.ac.uk/pub/databases/wormpep/. At least seven putative C. elegans translated sequences were identified by their amino acid sequence homology to the translated amino acid sequence of both GLELO and MAELO. The GenBank Accession #'s of those genomic sequences containing the deduced amino acids were identified as Z19154, U68749 (2 deduced proteins (F56H11.4) and F56H11.3 (wormpep Accession #'s)), U41011, U61954 (2 deduced proteins (F41H10.7 and F41H10.8, (wormpep Accession #'s)), and Z81058. Those underlined were identified in a previous search using translated MAELO as query (see Example V). As an example, the FastA amino acid alignments of translated U68749 (F56H11.4) with translated GLELO and MAELO are shown in FIGS. 39 and 40. Translated U68749 (F56H11.4) has 25–30% identity with both M. alpina elongase and GLA elongase in approximately a 200 amino acid overlap (see FIGS. 39 and 40). For all seven translated putative C. elegans cDNAs, the FastA alignments to translated GLELO was between 35–30% identity in a 200 amino acid overlap, while the identity was 26–34% in at least a 188 amino acid overlap for translated MAELO. The alignment similarities indicate that either translated GLELO or MAELO can be used to identify potential genes from C. elegans with elongase activity.

B) Drosophila melanogaster:

The translated deduced cDNA from the genomic sequence U41011 (C. elegans) had its highest match with a Drosophila melanogaster EST, accession number AI134173 in a blastn search (compares a nucleotide query sequence against a nucleotide database) of the "other ESTs" database through NCBI (see Example XIII) and was assembled with an overlapping DNA EST fragment, accession number AI517255. The translated DNA fragment DM1, derived from the two overlapping sequences was aligned with translated GLELO as well as MAELO (see FIGS. 41 and 42) using FastA in GCG (see Example I). The alignments showed 27.2% identity with GLA elongase in a 206 amino acid overlap and 30% identity with M. alpina elongase in a 237 amino acid overlap. Thus, based on amino acid similarity, the DM1 could be a potential homologue to GLELO or MAELO having PUFA elongase-like activity. Moreover, using DNA sequences of GLELO and MAELO as queries for database searches, homologues with PUFA elongase activity from Drosophila can be identified.

EXAMPLE XVI

Cloning and Expression of A Human PUFA
Elongase Homologue

Many potential PUFA elongase sequences were identified based on their amino acid similarities to translated GLELO and/or MAELO. To determine the potential elongase activities of these sequences, the cDNA encoding the full-length protein is then identified, cloned, and expressed, as demonstrated in the present example.

Primers RO719 (5'-GGT TCT CCC ATG GAA CAT TTT GAT GCA TC-3') (SEQ ID NO:77) and RO720 (5'-GGT TTC AAA GCT TTG ACT TCA ATC CCT CCG-3') (SEQ ID NO:78) were designed based on the putative HS1 sequence, and used to amplify the human liver Marathon-Ready cDNA (Clontech Laboratories, Inc., Palo Alto, Calif.). The polymerase Chain Reaction (PCR) was carried out in a 50 µl volume containing: 5 µl of human liver Marathon-Ready cDNA, 50 pmole each primer, 1 µl 10 mm PCR Nucleotide Mix (Boehringer Mannheim Corp., Indianapolis, Ind.), 5 µl 10× buffer and 1.0 U of Advantage KlenTaq Polymerase Mix (Clontech Laboratories, Inc., Palo Alto, Calif.). Thermocycler conditions in Perkin Elmer 9600 (Norwalk, Conn.) were as follows: 94° C. for 2 mins, then 30 cycles of 94° C. for 1 min., 58° C. for 2 mins, and 72° C. for 3 mins. PCR was followed by an additional extension cycle at 72° C. for 7 minutes.

The PCR amplified product was run on a gel, an amplified fragment of approximately 960 bp was gel purified, the termini of the fragment filled-in with T4 DNA polymerase (Boehringer Mannheim, Corp., Indianapolis, Ind.), and cloned into pCR-Blunt Vector (Invitrogen Corp., Carlsbad, Calif.) following manufacturer's protocol. The new plasmid was designated as pRAE-52, and the putative PUFA elongase cDNA in this clone was sequenced using ABI 373A Stretch DNA Sequencer (Perkin Elmer, Foster City, Calif). The putative PUFA elongase cDNA sequence in plasmid pRAE-52 is shown in FIG. 43, and the translated sequence is shown in FIG. 44.

The putative PUFA elongase cDNA from plasmid pRAE-52 was then digested with NcoI/HindIII, gel purified, and ligated into pXY242 (NcoI/HindIII). The new plasmid was designated as pRAE58-A1. (Plasmid 58-A1 was deposited with the American Type Culture Collection, 10801 University Boulevard, Manassas, Va. 20110-2209 on Aug. 19, 1999, under the terms of the Budapest Treaty and was accorded deposit number PTA-566.)

The construct pRAE-58-A1 was transformed into S. cerevisiae 334 (Hoveland et al., supra) and screened for elongase activity. The negative control strain was S. cerevisiae 334 containing pYX242 vector. The cultures were grown for 24 hours at 30° C., in selective media (Ausubel et al., supra), in the presence of 25 µM of GLA or AA. In this study, DGLA or adrenic acid (ADA, 22:4n-6), respectively, was the predicted product of human elongase activity. When GLA was used as a substrate, the yeast cells containing the human elongase cDNA contained elevated levels of DGLA compared to control cells, 2.75% vs. 0.09% of total fatty acids, respectively (see FIG. 45). When AA was used as a substrate, the yeast cells containing the human elongase cDNA contained elevated levels of ADA compared to control cells, none detected vs. 1.21% of total fatty acids, respectively. Thus, the human elongase converts both 18 and 20 carbon chain long PUFAs to their respective elongated fatty acids.

The yeast cells containing the human elongase cDNA also had elevated levels of monounsaturated fatty acids including 18:1n-7, 20:1n-7, 20:1n-9, and 18:1n-5, compared to the control strain. Therefore, these results indicate that the identified human elongase is capable of utilizing PUFAs as well as monounsaturated fatty acids as substrates. Thus, this human sequence HSELO1, and its encoded protein (HSELO1p), possess elongase activity independent of substrate specificity.

To further confirm the substrate specificity of the human elongation enzyme, described above and referred to herein as HSELO1, the recombinant yeast strain 334 (pRAE-58-A1) was grown in minimal media containing n-6 fatty acids GLA, AA, or n-3 fatty acids ALA, STA, or EPA. The lipid profiles of these yeast cultures, when examined by GC and GC-MS, indicated that there were accumulations of DGLA, ADA, ω3-eicosatrienoic acid (ETrA, C20:3n-3), ETA, and DPA, respectively (FIG. 51). The levels of these fatty acids were 7.29% (DGLA), 6.26% (ADA), 6.15% (ETrA), 10.06% (ETA), and 6.66% (DPA), respectively, of the total fatty acids in the strain containing the pRAE-58-A1 sequence. These represented 78.3%, 42.7%, 30.4%, 79.2%, and 71.7% conversions of the substrate fatty acids, respectively, to the products elongated by two carbon atoms.

The yeast cells expressing the recombinant HSELO1 sequence, compared to the control cells, also contained significantly elevated levels of C18:1n-7, and to a lesser extent, eicosenoic acid (EA, C20:1n-9) (FIG. 45). This finding suggested that the recombinant HSELO1 protein (HSELO1p) might also be involved in the elongation of monounsaturated fatty acids of 16 or 18 carbon lengths. To confirm this hypothesis, 25 µM of exogenous OA was added as a substrate to the recombinant yeast strain 334 (pRAE-58-A1). After incubation, the accumulation of EA at 2.5% of the total fatty acids demonstrated that the expressed HSELO1 enzyme could elongate monounsaturated fatty acids (FIG. 51). However, the conversion of OA to EA by recombinant HSELO1p was only 8.9%, this conversion was significantly lower than the endogenous conversion of C16:1n-7 (to C18:1n-7) or C18:1n-7 (to C20:1n-7), which was 20.4% and 58.1%, respectively.

To determine whether the substrate concentration affects the conversion of 18 and 20 carbon fatty acids to the respective elongated products, two different concentrations of GLA, AA, and EPA were examined (FIG. 52). When 25 µM of the substrates GLA, AA, and EPA were added exogenously, the levels of the fatty acids produced by two carbon elongation were 3.95% (DGLA), 2.91% (ADA), and 4.82% (DPA), respectively, of the total fatty acids in the lysates of 334 (pRAE-58-A1). These represented 62.4%, 27.5%, and 70.3% conversion of the substrate fatty acids, respectively, to the products elongated by two carbon atoms. When 100 µM of the substrates GLA, AA, and EPA were added, the levels of the fatty acids produced by two carbon elongation were 9.56% (DGLA), 3.90% (ADA), and 11.50% (DPA), respectively, of the total fatty acids in the lysates of 334 (pRAE-58-A1). These represented 39.8%, 15.7%, and 45.7% conversions of the substrate fatty acids, respectively, to the products elongated by two carbon atoms. Although the addition of more substrates led to higher percentages of the two carbon elongated products, the overall conversion rate decreased by at least 35%.

To further confirm the substrate specificity of HSELO1p, the recombinant yeast strain 334 (pRAE-58-A1) was grown in minimal media containing 25 µM of saturated, monounsaturated, or PUFAs. The lipid profiles of these various substrates revealed that HSELO1p is not involved in the elongation of saturated fatty acids such as palmitic acid (PA, C16:0), stearic acid (SA, C18:0), arachidic acid (ARA, C20:0), behenic acid (BA, C22:0) (FIG. 53A). HSELO1p is also not involved in the elongation of monounsaturated fatty acids OA and EA. When PTA was added as a substrate, 12.76% of the total fatty acids was OA. However, this is not an increase in the level of OA compared to the samples where PTA was not added, as OA was 25–31% of the total fatty acids in all samples. HSELO1p is involved in the elongation of n-6 PUFAs LA, GLA, and AA, but not DGLA or ADA (FIG. 53B). The lipid profiles of these yeast cultures indicated that there were accumulations of C20:2n-6, DGLA, and ADA, respectively, but not C22:3n-6 or C24:4n-6. The levels of these fatty acids were 0.74% (C20:2n-6), 2.46% (DGLA), and 2.14% (ADA), respectively, of the total fatty acids in the lysates of 334 (pRAE-58-A1). These represented 13.2%, 51.4%, and 27.1% conversions of the substrate fatty acids, respectively, to the products elongated by two carbon atoms. HSELO1p is also involved in the elongation of n-3 PUFAs ALA, STA, and EPA, but not DPA (FIG. 53C). The lipid profiles of these yeast cultures indicated that there were accumulations of ETrA, ETA, and DPA, respectively, but not C24:5n-3. The levels of these fatty acids were 1.03% ETrA, 2.24% (ETA), and 3.19% (DPA), respectively, of the total fatty acids in the strain containing the pRAE-58-A1 sequence. These represented 22.2%, 61.9%, and 39.5% conversions of the substrate fatty acids, respectively, to the products elongated by two carbon atoms. All results confirmed that the expression of HSELO1 from human liver in yeast resulted in the elongation of various long-chain PUFAs in n 6 and n-3 fatty acid pathways.

EXAMPLE XVII

Cloning, Expression and Characterization of a C. elegans PUFA Elongase

Several putative C. elegans elongases were identified with amino acid homology to both translated GLELO and MAELO. As with the human cDNA sequence, cloning of a cDNA and expression in yeast was used to determine if indeed it was a PUFA elongase. Primers RO738 (5'-AAT CAG GAATTC ATG GCT CAG CAT CCG CTC GTT CAA C-3') (SEQ ID NO:79) and RO739 (5'-CCG CTT GTC GAC TTA GTT GTT CTT CTT CTT TGG CAC-3') (SEQ ID NO:80) with restriction sites EcoRI and SalI (underlined), respectively, were based on the putative cDNA sequence contained in the genomic sequence U68749 (wormpep cDNA accession #F56H11.4.). A PCR amplification was performed in a 100 µl volume containing: 250 ng excised C. elegans library cDNA (OriGene Technologies Inc., Rockville, Md.), 50 pmole each primer, 10 µl 10× reaction buffer (Boehringer Mannheim Corp., Indianapolis, Ind.), 1 µl 10 mM PCR Nucleotide mix (Boehringer Mannheim Corp., Indianapolis, Ind.), and 2.5 U Taq polymerase (Boehringer Mannheim Corp., Indianapolis, Ind.). Thermocycler conditions in a Perkin Elmer 9600 (Norwalk, Conn.) were as follows: 95° C. for 5 mins, then 25 cycles of 94° C. for 30 secs, 55° C. for 2 mins, and 72° C. for 2 mins. PCR was followed by an additional cycle of 72° C. for 7 minutes.

The PCR amplified product was purified from an agarose gel, cut with EcoRI and SalI, ligated to pYX242 (Invitrogen Corp., Carlsbad, Calif.) (linearized with EcoRI and SalI) using the Rapid Ligation kit (Boehringer Mannheim Corp., Indianapolis, Ind.), according to the manufacturer's protocol and transformed into E. coli Top10 cells (Invitrogen Corp., Carlsbad, Calif.). The new plasmids, designated pRET-21 and pRET-22 (two individual clones from the ligation), were sequenced with the 373A Stretch DNA sequencer ABI (Perkin Elmer, Foster City, Calif.), and the cDNA sequences were identical. The 867 base cDNA nucleotide sequence of the plasmid pRET-22 containing the putative elongase is shown in FIG. 46 and the translated sequence of 288 amino acids is shown in FIG. 47. (Plasmid pRET-22 was deposited with the American Type Culture Collection, 10801 University Boulevard, Manassas, Va. 20110-2209 on Aug. 19, 1999, under the terms of the Budapest Treaty and was accorded deposit number PTA-565.)

The plasmids pRET-21 and -22 were transformed into S. cerevisiae 334 as previously described (see Example III) and the resulting yeast cultures (334(pRET-21) and 334(pRET-22) grown in 100 ml of selective media without leucine (Ausubel et al, supra) for 48 hours at 20° C. in the presence of 50 µM GLA and AA. The cell pellets were collected and subjected to fatty acid analysis and the results shown in FIG. 48. DGLA, the predicted product from GLA elongation, was found to be an average of 1.79% of the total lipid in the two samples, versus 0.13% for the negative control (334 containing plasmid pYX242) indicating that the enzyme encoded by both pRET-21 and pRET-22 possessed GLA elongase activity. The percent conversion of GLA to DGLA by 334(pRET-21) and 334(pRET-22) was 11.1% and 19.4% respectively with an average of 15.25%. Interestingly, almost no elongation of AA or any endogenous fatty acid was observed (FIG. 48). These results indicate that the elongase encoded by this newly identified C. elegans cDNA, CELLO1, is able to specifically elongate GLA to DGLA, suggesting that it may be a C. elegans homologue of GLA elongase.

To further confirm the GLA elongation activity of CEELO1, the experiment described in the paragraphs above was repeated with the exception that GLA and AA were added to cultures of 334(pRET-22) separately. Again, GLA was elongated to DGLA with a 38.2% conversion rate. No elongation activity of AA was detected as shown in FIG. 61. In this case, the percent conversion appears to be double that described in previous results (see FIG. 48) and may either be due to the absence of the additional substrate (AA) or the subculturing of the yeast. CEELO1 has the additional activity of elongating endogenous 16:1n-7 to 18:1n-7 with a 9.12% conversion rate compared to 3.9% control culture 334(pYX242) under identical conditions. Thus, the C. elegans elongation enzyme possesses a major elongation activity for a C18 polyunsaturated fatty acid and a minor activity for a C16 monounsaturated fatty acid.

Additionally, to further determine the substrate specificity of CCELO1, 50 µM of each substrate besides GLA (e.g., SA (18:0), OA (19:1), LA (18:2n-6), DGLA (20:3n-g), AA (20:2n-6), ADA (22:4n-6), ALA (18:3n-3), PA (18:0), EPA (20:5n-3) and STA (18:4n-2)) was added individually to cultures to 334(pRET-22) and grown for 48 hours at 20° C., as described in Example SVII. STA was the only exogenously added substrate that was elongated. The CEELO1 elongated 13% of STA incorporated to ETA (20:4n-3) (see FIG. 62).

Parallel to Examples III and XI, the C. elegans CEELO1 gene in the plasmid pRET22 and M. alpina N5 desaturase (pCGR-4; see Example III) were co-expressed in yeast to determine if AA or EPA could be produced from exogenously added GLA or STA, respectively. When a yeast culture containing both pRET22 and pCGR4 plasmids was grown in the presence of 50 µM GLA or STA in media lacking leucine and uracil, the percent conversion to the final products of AA and EPA, respectively, appeared identical (27% conversion) (see FIG. 63). Thus, simultaneous heterologous expression of CEELO1 and a Δ5 desaturase results in the biosynthesis of AA and EPA from GLA and STA, respectively in yeast.

EXAMPLE XVIII

Isolation of a Putative Human Elongase cDNA Based on AC004050 Sequence

To isolate the full length putative elongase cDNA based on the AC004050 sequence, primers RP735 (5'-CCT CCT GAA TTC CAA CAC TAT TCA GCT TTC-3') (SEQ ID NO:81) and RO73 (5'-TAA TAC GAC TCA CTA TAG GG-3') (SEQ ID NO:82) were used to PCR amplify the human liver Marathon-Ready cDNA (Clontech Laboratories, Inc., Palo Alto, Calif.). The PCR was carried out using the Advantage™ cDNA PCR Kit (Clontech Laboratories, Inc., Palo Alto, Calif.) with 5 µl of human liver Marathon-Ready cDNA and 50 pmole each primer following manufacturer's instructions. Thermocycler conditions in Perkin Elmer 9600 (Norwalk, Conn.) were as follows: 94° C. for 2 mins, then 30 cycles of 94° C. for 1 min., 58° C. for 2 mins., and 72° C. for 3 mins. PCR was followed by an additional extension at 72° C. for 7 mins.

The PCR amplified product was run on a gel, an amplified fragment of approximately 1 Kb was gel purified, the termini of the fragment were filled in with T4DNA polymerase (Boehringer Mannheim, Corp., Carlsbad, Calif.) following manufacturer's instructions. The new plasmid was designated as pRAE-59, and the putative PUFA elongase cDNA in this plasmid, designated as HS3, was sequenced using the ABI 373A Stretch Sequencer (Perkin Elmer, Foster City, Calif.). The putative PUFA elongase cDNA sequence HS3 is shown in FIG. 49, and the translated sequence is shown in FIG. 50.

EXAMPLE XIX

Cloning and Expression of a Mouse PUFA Elongation Enzyme

The National Center for Biotechnology Information (NCBI at ncbi.nlm.nih.gov) was used to conduct database searches using blastn with the mouse EST sequence AI225632 (see Example XIII). Three mouse EST sequences were identified (GenBank Accession #'s A1428130, AI595258, and AA061089), and assembled to generate a putative full-length elongation enzyme sequence, designated as MELO4. Primers ROS19 (5'-ATG ATG CCA TCG AGC AGC TGA AGG CCT TTG-3') (SEQ ID NO:83) and PO820 (5'-CAG TCT CTG CTT TAA AAC AAG CTC CTC-3') (SEQ ID NO:84) were designed based on the putative full length mouse elongation enzyme sequence, and used to amplify the mouse brain Marathon-Ready cDNA (Clontech Laboratories, Inc., Palo Alto, Calif.). The Polymerase Chain Reaction (PCR) was carried out as previously described (Example XVI). The PCR amplified product was run on a gel, an amplified fragment of approximately 1,000 bp was gel purified, the termini of the fragment were digested with NcoI and DraI (Boehringer Mannheim, Corp., Indianapolis, Ind.), and the fragment was cloned into pYX242 (NcoI/HindIII). The new plasmid was designated as pPAE-84, and the putative PUFA elongation enzyme cDNA in this clone was sequenced using ABI 372A Stretch DNA Sequencer (Perkin Elmer, Foster City, Calif.). The putative PUFA elongation enzyme cDNA sequence in plasmid pFAE-84 is shown in FIG. 54, and the translated sequence is shown in FIG. 55. (Plasmid pRAE-84 was deposited with the American Type Culture Collection, 10802 University Boulevard, Manassas, Va. 20110-2209, on Jul. 25, 2000 and was accorded deposit number PTA-2262.)

The construct pRAE-84 was transformed into *S. cerevisiae* 334 (Hoveland et al., supra) and screened for elongase activity. The negative control strain was *S. cerevisiae* 334 containing pYX242 vector. The cultures were grown for 42–48 hours at 30° C., in selective media (Ausubel et al., supra), in the presence of 25 µM of GLA, AA, ADA, STA, EPA, or DPA. The lipid profiles of these yeast cultures indicated that GLA was not elongated to the expected product of DGLA. However, there were accumulations of ADA, ω6-tetracosatetraenoic acid (TTA, C24:4n-6), ETA, DPA, and ω3-tetracosapentaenoic acid (TPA, C24:5n-3), respectively (FIG. 56). The n-6 fatty acid substrate AA was converted to ADA, which was subsequently converted to TTA, and the n-3 fatty acid EPA was converted to DPA, which was subsequently converted to TPA. The levels of these fatty acids were 0.64% (ADA), 1.07% (TTA), 1.47% (DPA), and 7.06% (TPA), respectively, of the total fatty acids in the strain containing the pRAE-84 sequence. These represented 10.4%, 62.6%, 32.7%, and 82.8% conversions of the substrate fatty acids, respectively, to the products elongated by two carbon atoms. The C22 substrates ADA and EPA were elongated to 2.4% (TTA) and 3.82% (TPA) of the total fatty acids. These represented 9.2% and 43.9% conversions of the substrate fatty acids, respectively. The expression of MELO4 in yeast results in the conversion of C20 and C22 fatty acids to the respective elongated products. The conversion rate of C22 to C24 fatty acids is much greater when the exogenously added substrate is C20 fatty acid.

To further confirm the substrate specificity of MELO4 protein (MELO4), the recombinant yeast strain 334(pRAE-84) was grown in minimal media containing 25 µM of saturated, monounsaturated, or polyunsaturated fatty acids. The lipid profiles of these various substrates revealed that MELO4p is not involved in the elongation of saturated fatty acids such as PA, SA, ARA, or BA (FIG. 57A). MELO4p is also not involved in the elongation of monounsaturated fatty acids PTA, OA, or EA. MELO4p is involved in the elongation of n-6 PUFAs AA and ADA, but not LA or DGLA (FIG. 57B). The lipid profiles of these yeast cultures indicated that there were accumulations of ADA and TTA, but not C20:2n-6 or C22:3n-6. When AA was added exogenously, the levels of product fatty acids were 0.5% (ADA) and 0.39% (TTA), and when ADA was added exogenously, the level of product fatty acid was 1.3% (TTA) of the total fatty acids in the strain containing the pRAE-84 sequence. These represented 8.7%, 43.8%, and 7.3% conversions of the substrate fatty acids, respectively, to the products elongated by two carbon atoms. MELO4p is also involved in the elongation of GLA to DGLA. The lipid profile of the strain containing the pRAE 84 sequence, in presence of GLA, had 0.43% of DGLA, which represented 14.7% conversion of GLA to DGLA. MELO4p is also involved in the elongation of n-3 PUFAs EPA and DPA (FIG. 53C). The lipid profiles of these yeast cultures indicated that there were accumulations of DPA and TPA. When EPA was added, the levels of these fatty acids were 1.21% (DPA) and 3.38% (TPA), and when DPA was added, the level of the product fatty acid was 3.09% (TPA) of the total fatty acids in the strain containing the pRAE-84 sequence. These represented 24.0%, 73.6%, and 46.4% conversions of the substrate fatty acids, respectively, to the products elongated by two carbon atoms. MELO4p is also involved in the elongation of STA to C22:4n-3. When STA was added, the levels of fatty acids produced by two-carbon elongation were 0.3% ETA and 0.23% C22:4n-3. These represented 11.1% and 43.4% conversions of substrate fatty acids to the products elongated by two carbon atoms. MELO4p also appeared to be involved in the elongation of ALA; however, the small amount of the fatty acid produced by two-carbon elongation (0.16% of ETrA) may not be significant. All results confirmed that the expression of MELO4 from mouse brain in yeast resulted in the elongation of C20 and C22 long-chain PUFAs in n-6 and n-3 fatty acid pathways.

EXAMPLE XX

Identification, Cloning, and Expression of HSELO1 Homologue from Mouse

The National Center for Biotechnology Information (NCBI at ncbi.nlm.nih.gov) was used to conduct database searches using blastn with the HSELO1 sequence. Two human EST sequences were identified (GenBank Accession #'s AI787925 and AIU746838) and the respective cDNA clones (I.M.A.G.E. Consortium Clone ID's 2076831 and 206182) were purchased through Research Genetics (Huntsville, Ala.). Primers RO833 (5'-GGT TTT ACC ATG GAA CAT TTC GAT GCG TCA C-3') (SEQ ID NO:85) and RO832 (5'-CGA CCT GCA GCT CGA GCA CA-3') (SEQ ID NO:86) were designed based on 5' sequence of the putative mouse elongation enzyme, and the cDNA clone vector, respectively. Primers RO833 and RO832 were used to amplify the mouse cDNA clone 2076182. The Polymerase Chain Reaction (PCR) was carried out as previously described (Example XVI). The termini of the PCR amplified product were filled-in with T4 DNA polymerase (Boehringer Mannheim, Corp., Indianapolis, Ind.) and the 5' region was digested with NcoI. The modified fragment was run on a gel, an amplified fragment of approximately 2.4 Kp was gel purified, and the fragment was cloned into pYX242 (NcoI/EcoRV). The new plasmid was designated as pRAE-87, and the putative PUFA elongation enzyme cDNA in this clone, MELO7, was sequenced using ABI 373A Stretch DNA Sequencer (Perkin Elmer, Foster City, Calif.). The putative PUFA elongation enzyme cDNA sequence in plasmid pRAE-87 (MELO7) is shown in FIG. 58, and the translated sequence is shown in FIG. 59. (The plasmid pRAE-87 was deposited with the American Type Culture Collection, 10802 University Boulevard, Manassas, Va. 20110-2209, on Jul. 25, 2000 and was accorded deposit number PTA-2261.

The construct pRAE-87 was transformed into *S. cerevisiae* 334 (Hoveland et al., supra) and screened for elongase activity. The negative control strain was *S. cerevisiae* 334 containing pYX242 vector. The cultures were grown for 42–48 hours at 30° C., in selective media (Ausubel et al., supra), in the presence of 25 M of GLA, AA,, STA, EPA, DPA, or ADA. The lipid profiles of the yeast cultures expressing MELO7 indicated that there were accumulations of DGLA, ADA, and ETA, respectively (FIG. 60). The levels of these fatty acids were 4.1% (DGLA), 6.33% (ADA), 3.5% (ETA), and 6.18% (DPA), respectively, of the total fatty acids in the strain containing the pRAE-87 sequence. These represented 78.7%, 36.0%, 81.0%, and 57.4% conversions of the substrate fatty acids, respectively, to the products elongated by two carbon atoms. MELO7 protein (MELO7) was not involved in the elongation of ADA. MELO7p also appeared to be involved in further elongation of the fatty acid DPA produced by two-carbon elongation to TPA when EPA was the added substrate, and when DPA was added. However, the small amounts of the product fatty acids (0.27% and 0.25% of TPA) may not be significant. The yeast cells expressing the recombinant MELO7 sequence, compared to the control cells, also contained significantly elevated levels of C18:1n-7 and C20:1-n7. All results confirmed that the expression of MELO7 from mouse embryo in yeast resulted in the elongation of various long chain PUFAs in n-6 and n-3 fatty acid pathways, and that MELO7 was a homologous of HSELO1.

NUTRITIONAL COMPOSITIONS

The PUFAs described in the Detailed Description may be utilized in various nutritional supplements, infant formulations, nutritional substituents and other nutritional solutions.

I. Infant Formulations

A. Isomil® Soy Formula with Iron:

Usage: As a beverage for infants, children and adults with an allergy or sensitivity to cows milk. A feeding for patients with disorders for which lactose should be avoided: lactase deficiency, lactose intolerance and galactosemia.

Features:
Soy protein isolate to avoid symptoms of cow's milk-protein allergy or sensitivity.
Lactose-free formulation to avoid lactose-associated diarrhea.
Low osmolality (240 mOs/kg water) to reduce risk of osmotic diarrhea.
Dual carbohydrates (corn syrup and sucrose) designed to enhance carbohydrate absorption and reduce the risk of exceeding the absorptive capacity of the damaged gut.
1.8 mg of Iron (as ferrous sulfate) per 100 Calories to help prevent iron deficiency.
Recommended levels of vitamins and minerals.
Vegetable oils to provide recommended levels of essential fatty acids.
Milk-white color, milk-like consistency and pleasant aroma.

Ingredients: (Pareve) 85% water, 4.9% corn syrup, 2.6% sugar (sucrose), 2.1% soy oil, 1.9% soy protein isolate, 1.4% coconut oil, 0.15% calcium citrate, 0.11% calcium phosphate tribasic, potassium citrate, potassium phosphate monobasic, potassium chloride, mono- and disglycerides, soy lecithin, carregeenan, ascorbic acid, L-methionine, magnesium chloride, potassium phosphate dibasic, sodium chloride, choline chloride, taurine, ferrous sulfate, m-inositol, alpha-tocopheryl acetate, zinc sulfate, L-carnitine, niacinamide, calcium pantothenate, cupric sulfate, vitamin A palmitate, thiamine chloride hydrochloride, riboflavin, pyridoxine hydrochloride, folic acid, magnesium sulfate, potassium iodide, phylloquinone, biotin, soidum selenite, vitamin D3 and cyanocabalamin.

B. Isomil® DF Soy Formula For Diarrhea:

Usage: As a short-term feeding for the dietary management of diarrhea in infants and toddlers.

Features:
First infant formula to contain added dietary fiber from soy fiber specifically for diarrhea management.
Clinically shown to reduce the duration of loose, watery stools during mild to severe diarrhea in infants.
Nutritionally complete to meet the nutritional needs of the infant.
Soy protein isolate with added L-methionine meets or exceeds an infant's requirement for all essential amino acids.
Lactose-free formulation to avoid lactose-associated diarrhea.
Low osmolality (240 mOsm/kg water) to reduce the risk of osmotic diarrhea.
Dual carbohydrates (corn syrup and sucrose) designed to enhance carbohydrate absorption and reduce the risk of exceeding the absorptive capacity of the damaged gut.
Meets or exceeds the vitamin and mineral levels recommended by the Committee or Nutrition of the American Academy of Pediatrics and required by the Infant Formula Act.
1.8 mg of iron (as ferrous sulfate) per 100 Calories to help prevent iron deficiency.
Vegetable oils to provide recommended levels of essential fatty acids.

Ingredients: (Pareve) 86% water, 4.8% com syrup, 2.5% sugar (sucrose), 2.1% soy oil, 2.0% soy protein isolate, 1.4% coconut oil, 0.77% soy fiber, 0.12% calcium citrate, 0.11% calcium phosphate tribasic, 0.10% potassium citrate, potassium chloride, potassium phosphate monobasic, mono and diglycerides, soy lecithin, carrageenan, magnesium chloride, ascorbic acid, L-methionine, potassium phosphate dibasic, sodium chloride, choline chloride, taurine, ferrous sulfate, m-inositol, alpha-tocopheryl acetate, zinc sulfate, L-carnitine, niacinamide, calcium pantothenate, cupric sulfate, vitamin A palmitate, thiamine chloride hydrochloride, riboflavin, pyridoxine hydrochloride, folic acid, manganese sulfate, potassium iodide, phylloquinone, biotin, sodium selenite, vitamin D3 and cyanocobalamin.

C. Isomil® SF Sucrose-Free Soy Formula With Iron:

Usage: As a beverage for infants, children and adults with an allergy or sensitivity to cow's-milk protein or an intolerance to sucrose. A feeding for patients with disorders for which lactose and sucrose should be avoided.

Features:

Soy protein isolate to avoid symptoms of cow's-milk-protein allergy or sensitivity.

Lactose-free formulation to avoid lactose-associated diarrhea (carbohydrate source is Polycose® Glucose Polymers).

Sucrose free for the patient who cannot tolerate sucrose.

Low osmolality (180 mOsm/kg water) to reduce risk of osmotic diarrhea.

1.8 mg of iron(as ferrous sulfate) per 100 Calories to help prevent iron deficiency.

Recommended levels of vitamins and minerals.

Vegetable oils to provide recommended levels of essential fatty acids.

Milk-white color, milk-like consistency and pleasant aroma.

Ingredients: (Pareve) 75% water, 11.8% hydrolized cornstarch, 4.1% soy oil, 4.1% soy protein isolate, 2.8% coconut oil, 1.0% modified cornstarch, 0.38% calcium phosphate tribasic, 0.17% potassium citrate, 0.13% potassium chloride, mono- and diglycerides, soy lecithin, magnesium chloride, abscorbic acid, L-methionine, calcium carbonate, sodium chloride, choline chloride, carregeenan, taurine, ferrous sulfate, m-inositol, alpha-tocopheryl acetate, zinc sulfate, L-carnitine, niacinamide, calcium pantothenate, cupric sulfate, vitamin A palmitate, thiamine chloride hydrochloride, riboflavin, pyridoxine hydrochloride, folic acid, manganese sulfate, potassium iodide, phylloquinone, biotin, sodium selenite, vitamin D3 and cyanocobalamin.

D. Isomil® 20 Soy Formula With Iron Ready to Feed, 20 Cal/fl oz.:

Usage: When a soy feeding is desired.

Ingredients: (Pareve) 85% water, 4.9% corn syrup, 2.6% sugar (sucrose), 2.1% soy oil, 1.9% soy protein isolate, 1.4% coconut oil, 0.15% calcium citrate, 0.11% calcium phosphate tribasic, potassium citrate, potassium phosphate monobasic, potassium chloride, mono- and diglycerides, soy lecithin, carrageenan, abscorbic acid, L-methionine, magnesium chloride, potassium phosphate dibasic, choline chloride, taurine, ferrous sulfate, m-inositol, alpha-tocopheryl acetate, zinc sulfate, L-carnitine, niacinamide, calcium pantothenate, cupric sulfate, vitamin A palmitate, thiamine chloride hydrochloride, riboflavin, pyridoxine hydrochloride, folic acid, manganese sulfate, potassium iodide, phylloquinone, biotin, sodium selenite, vitamin D3 and cyanocabalamin.

E. Similac® Infant Formula:

Usage: When an infant formula is needed: if the decision is made to discontinue breastfeading before age 1 year, if a supplement to breastfeeding is needed or as a routine feeding if breastfeeding is not adopted.

Features:

Protein of appropriate quality and quantity for good growth; heat-denatured, which reduces the risk of milk-associated enteric blood loss.

Fat from a blend of vegetable oils (doubly homogenized), providing essential linoleic acid that is easily absorbed.

Carbohydrate as lactose in proportion similar to that of human milk.

Low renal solute load to minimize stress on developing organs.

Powder, Concentrated Liquid and Ready To Feed forms.

Ingredients: (—D) Water, nonfat milk, lactose, soy oil, coconut oil, mono- and diglycerides, soy lecithin, absorbic acid, carrageenan, choline chloride, taurine, m-inositol, alpha-tocopheryl acetate, zinc sulfate, niacinamide, ferrous sulfate, calcium pantothenate, cupric sulfate, vitamin A palmitate, thiamine chloride hydrochloride, riboflavin, pyridoxine hydrochloride, folic acid, manganese sulfate, phylloquinone, biotin, sodium selenite, vitamin D3 and cyanocobalamin.

F. Similac® NeoCare Premature Infant Formula With Iron:

Usage: For premature infants' special nutritional needs after hospital discharge, Similac NeoCare is a nutritionally complete formula developed to provide premature infants with extra calories, protein, vitamins and minerals needed to promote catch-up growth and support development.

Features:

Reduces the need for caloric and vitamin supplementation. More calories (22 Cal/fl oz) than standard term formulas (20 Cal/fl oz).

Highly absorbed fat blend, with medium-chain triglycerides (MCT oil) to help meet the special digestive needs of premature infants.

Higher levels of protein, vitamins and minerals per 100 calories to extend the nutritional support initiated in-hospital.

More calcium and phosphorus for improved bone mineralization.

Ingredients: —D Corn syrup solids, nonfat milk, lactose, whey protein concentrate, soy oil, high-oleic safflower oil, fractionated coconut oil (medium chain triglycerides), coconut oil, potassium citrate, calcium phosphate tribasic, calcium carbonate, ascorbic acid, magnesium chloride, potassium chloride, sodium chloride, taurine, ferrous sulfate, m-inositol, choline chloride, ascorbyl palmitate, L-carnitine, alpha-tocopheryl acetate, zinc sulfate, niacinamide, mixed tocopherols, sodium citrate, calcium pantothenate, cupric sulfate, thiamine chloride hydrochloride, vitamin A palmitate, beta carotene, riboflavin, pyridoxine hydrochloride, folic acid, manganese sulfate, phylloquinone, biotin, sodium selenite, vitamin D3 and cyanocobalamin.

G. Similac Natural Care Low-Iron Human Milk Fortifier Ready To Use, 24 Cal/fl oz.:

Usage: Designed to be mixed with human milk or to be fed alternatively with human milk to low-birth-weight infants.

Ingredients: —D Water, nonfat mil, hydrolyzed cornstarch, lactose, fractionated coconut oil (medium-chain triglycerides), whey protein concentrate, soy oil, coconut oil, calcium phosphate tribasic, potassium citrate, magnesium chloride, sodium citrate, ascorbic acid, calcium carbonate, mono and diglycerides, soy lecithin, carrageenan, choline chloride, m-inositol, taurine, niacinamide, L-carnitine, alpha tocopheryl acetate, zinc sulfate, potassium chloride, calcium pantothenate, ferrous sulfate, cupric sulfate, riboflavin, vitamin A palmitate, thiamine chloride hydrochloride, pyridoxine hydrochloride, biotin, folic acid, manganose sulfate, phylloquinone, vitamin D3, sodium selenite and cyanocobalamin.

Various PUFAs of this invention can be substituted and/or added to the infant formulae described above and to other infant formulae known to those in the art.

II. NUTRITIONAL FORMULATIONS

A. ENSURE®

Usage: ENSURE is a low-residue liquid food designed primarily as an oral nutritional supplement to be used with or between meals or, in appropriate amounts, as a meal replacement. ENSURE is lactose- and gluten free, and is suitable for use in modified diets, including low-cholesterol diets. Although it is primarily an oral supplement, it can be fed by tube.

Patient Conditions:
  For patients on modified diets
  For elderly patients at nutritional risk
  For patients with involuntary weight loss
  For patients recovering from illness or surgery
  For patients who need a low-residue diet Ingredients: —D Water, Sugar (Sucrose), Maltodextrin (Corn), Calcium and Sodium Caseinates, High-Oleic Safflower Oil, Soy Protein Isolate, Soy Oil, Canola Oil, Potassium Citrate, Calcium Phosphate Tribasic, Sodium Citrate, Magnesium Chloride, Magnesium Phosphate Dibasic, Artificial Flavor, Sodium Chloride, Soy Lecithin, Choline Chloride, Ascorbic Acid, Carrageenan, Zinc Sulfate, Ferrous Sulfate, Alpha-Tocopheryl Acetate, Gellan Gum, Niacinamide, Calcium Pantothenate, Manganese Sulfate, Cupric Sulfate, Vitamin A Palmitate, Thiamine Chloride Hydrochloride, Pyridoxine Hydrochloride, Riboflavin, Folic Acid, Sodium Molybdate, Chromium Chloride, Biotin, Potassium Iodide, Sodium Selenate.

B. ENSURE® BARS:

Usage: ENSURE BARS are complete, balanced nutrition for supplemental uses between or with meals. They provide a delicious, nutrient-rich alternative to other snacks. ENSURE BARS contain <1 g lactose/bar, and Chocolate Fudge Brownie flavor is gluten-free, (Honey Graham Crunch flavor contains gluten.)

Patient Conditions:
  For patients who need extra calories, protein, vitamins and minerals.
  Especially useful for people who do not take in enough calories and nutrients.
  For people who have the ability to chew and swallow
  Not to be used by anyone with a peanut allergy or any type of allergy to nuts.

Ingredients: Honey Graham Crunch—High-Fructose Corn Syrup, Soy Protein Isolate, Brown Sugar, Honey, Maltodextrin (Corn), Crisp Rice (Milled Rice, Sugar [Sucrose], Salt [Sodium Chloride] and Malt), Oat Bran, Partially Hydrogenated Cottonseed and Soy Oils, Soy Polysaccharide, Glycerine, Whey Protein Concentrate, Polydextrose, Fructose, Calcium Caseinate, Cocoa Powder, Artificial Flavors, Canola Oil, High-Oleic Safflower Oil, Nonfat Dry Mil, Whey Powder, Soy Lecithin and Corn Oil. Manufactured in a facility that processes nuts.

Vitamins and Minerals: Calcium Phosphate Tribasic, Potassium Phosphate Dibasic, Magnesium Oxide, Salt (Sodium Chloride), Potassium Chloride, Ascorbic Acid, Ferric Orthophosphate, Alpha-Tocopheryl Acetate, Niacinamide, Zinc Oxide, Calcium Pantothenate, Copper Gluconate, Manganese Sulfate, Riboflavin, Beta Carotene, Pyridoxine Hydrochloride, Thiamine Mononitrate, Folic Acid, Biotin, Chromium Chloride, Potassium Iodide, Sodium Selenate, Sodium Molybdate, Phylloquinonone, Vitamin D3 and Cyanocobalamin.

Protein: Honey Graham Crunch—The protein source is a blend of soy protein isolate and milk proteins.

| | |
|---|---|
| Soy protein isolate | 74% |
| Milk proteins | 26% |

Fat: Honey Graham Crunch—The fat source is a blend of partially hydrogenated cottonseed and soybean, canola, high oleic safflower, oils, and soy lecithin.

| | |
|---|---|
| Partially hydrogenated cottonseed and soybean oil | 76% |
| Canola oil | 8% |
| High-oleic safflower oil | 8% |
| Corn oil | 4% |
| Soy lecithin | 4% |

Carbohydrate: Honey Graham Crunch—The carbohydrate source is a combination of high-fructose corn syrup, brown sugar, maltodextrin, honey, crisp rice, glycerine, soy polysaccharide, and oat bran.

| | |
|---|---|
| High-fructose corn syrup | 24% |
| Brown sugar | 21% |
| Maltodextrin | 12% |
| Honey | 11% |
| Crisp rice | 9% |
| Glycerine | 9% |
| Soy Polysaccharide | 7% |
| Oat bran | 7% |

C. ENSURE® HIGH PROTEIN:

Usage: ENSURE HIGH PROTEIN is a concentrated, high-protein liquid food designed for people who require additional calories, protein, vitamins, and minerals in their diets. It can be used as an oral nutritional supplement with or between meals or, in appropriate amounts, as a meal replacement. ENSURE HIGH PROTEIN is lactose- and gluten-free, and is suitable for use by people recovering from general surgery or hip fractures and by patients at risk for pressure ulcers.

Patient Conditions:
  For patients who require additional calories, protein, vitamins, and minerals, such as patients recovering from general surgery or hip fractures, patients at risk for pressure ulcers, and patients on low-cholesterol diets Features:
  Low in saturated fat
  Contains 6 g of total fat and <5 mg of cholesterol per serving
  Rich, creamy taste
  Excellent source of protein, calcium, and other essential vitamins and minerals
  For low-cholesterol diets
  Lactose-free, easily digested Ingredients:
  Vanilla Supreme: —D Water, Sugar (Sucrose), Maltodextrin (Corn), Calcium and Sodium Caseinates, High-Oleic Safflower Oil, Soy Protein Isolate, Soy Oil, Canola Oil, Potassium Citrate, Calcium Phosphate Tribasic, Sodium Citrate, Magnesium Chloride, Magnesium Phosphate Dibasic, Artificial Flavor, Sodium Chloride, Soy Lecithin, Choline Chloride, Ascorbic Acid, Carrageenan, Zinc Sulfate, Ferrous Sulfate, Alpha-Tocopheryl Acetate, Gellan Gum, Niacinamide, Calcium Pantothenate, Manganese Sulfate, Cupric Sulfate, Vitamin A Palmitate, Thiamine Chloride Hydrochloride, Pyridoxine Hydrochloride, Riboflavin, Folic Acid, Sodium Molybdate, Chromium Chloride, Biotin, Potassium Iodide, Sodium Selenate, Phylloquinone, Vitamin D3 and Cyanocobalamin.

Protein:
  The protein source is a blend of two high-biologic-value proteins: casein and soy.

| | |
|---|---|
| Sodium and calcium caseinates | 85% |
| Soy protein isolate | 15% |

Fat:
  The fat source is a blend of three oils: high-oleic safflower, canola, and soy.

| | |
|---|---|
| High-oleic safflower oil | 40% |
| Canola oil | 30% |
| Soy oil | 30% |

The level of fat in ENSURE HIGH PROTEIN meets American Heart Association (AHA) guidelines. The 6 grams of fat in ENSURE HIGH PROTEIN represent 24% of the total calories, with 2.6% of the fat being from saturated fatty acids and 7.9% from polyunsaturated fatty acids. These values are within the AHA guidelines of <30% of total calories from fat, <10% of the calories from saturated fatty acids. and <10% of total calories from polyunsaturated fatty acids.

Carbohydrate:
  ENSURE HIGH PROTEIN contains a combination of maltodextrin and sucrose. The mild sweetness and flavor variety (vanilla supreme, chocolate royal, wild berry, and banana), plus VARI-FLAVORS® Flavor Pacs in pecan, cherry, strawberry, lemon, and orange, help to prevent flavor fatigue and aid in patient compliance.

Vanilla and other nonchocolate flavors:

| | |
|---|---|
| Sucrose | 60% |
| Maltodextrin | 40% |

Chocolate:

| | |
|---|---|
| Sucrose | 70% |
| Maltodextrin | 30% |

D. ENSURE® LIGHT

Usage: ENSURE LIGHT is a low-fat liquid food designed for use as an oral nutritional supplement with or between meals. ENSURE LIGHT is lactose- and gluten-free, and is suitable for use in modified diets, including low-cholesterol diets.

Patient Conditions:
    For normal-weight or overweight patients who need extra nutrition in a supplement that contains 50% less fat and 20% fewer calories than ENSURE.
    For healthy adults who don't eat right and need extra nutrition.

Features:
    Low in fat and saturated fat
    Contains 3 g of total fat per serving and <5 mg cholesterol
    Rich, creamy taste
    Excellent source of calcium and other essential vitamins and minerals
    For low-cholesterol diets
    Lactose-free, easily digested Ingredients:
    French Vanilla: —D Water, Maltodextrin (Corn), Sugar (Sucrose), Calcium Caseinate, High-Oleic Safflower Oil, Canola Oil, Magnesium Chloride, Sodium Citrate, Potassium Citrate, Potassium Phosphate Dibasic, Magnesium Phosphate Dibasic, Natural and Artificial Flavor, Calcium Phosphate Tribasic, Cellulose Gel, Choline Chloride, Soy Lecithin, Carrageenan, Salt (Sodium Chloride), Ascorbic Acid, Cellulose Gum, Ferrous Sulfate, Alpha-Tocopheryl Acetate, Zinc Sulfate, Niacinamide, Manganese Sulfate, Calcium Pantothenate, Cupric Sulfate, Thiamine Chloride Hydrochloride, Vitamin A Palmitate, Pyridoxine Hydrochloride, Riboflavin, Chromium Chloride, Folic Acid, Sodium Molybdate, Biotin, Potassium Iodide, Sodium Selenate, Phylloquinone, Vitamin D3 and Cyanocobalamin.

Protein:
    The protein source is calcium caseinate.

| | |
|---|---|
| Calcium caseinate | 100% |

Fat:
    The fat source is a blend of two oils: high-oleic safflower and canola.

| | |
|---|---|
| High-oleic safflower oil | 70% |
| Canola oil | 30% |

The level of fat in ENSURE LIGHT meets American Heart Association (AHA) guidelines. The 3 grams of fat in ENSURE LIGHT represent 13.5% of the total calories, with 1.4% of the fat being from saturated fatty acids and 2.6% from polyunsaturated fatty acids. These values are within the AHA guidelines of <30% of total calories from fat, <10% of the, calories from saturated fatty acids, and <10% of total calories from polyunsaturated fatty acids.

Carbohydrate:
ENSURE LIGHT contains a combination of maltodextrin and sucrose. The chocolate flavor contains corn syrup as well. The mild sweetness and flavor variety (French vanilla, chocolate supreme, strawberry swirl), plus VARI-FLAVORS® Flavor Pacs in pecan, cherry, strawberry, lemon, and orange, help to prevent flavor fatigue and aid in patient compliance.

Vanilla and other nonchocolate flavors:

| | |
|---|---|
| Sucrose | 51% |
| Maltodextrin | 49% |

Chocolate:

| | |
|---|---|
| Sucrose | 47.0% |
| Corn Syrup | 26.5% |
| Maltodextrin | 26.5% |

Vitamins and Minerals:
An 8 fl-oz serving of ENSURE LIGHT provides at least 25% of the RDIs for 24 key vitamins and minerals.

Caffeine:
Chocolate flavor contains 2.1 mg caffeine/8 fl oz.

E. ENSURE PLUS®
Usage: ENSURE PLUS is a high-calorie, low-residue liquid food for use when extra calories and nutrients, but a normal concentration of protein, are needed. It is designed primarily as an oral nutritional supplement to be used with or between meals or, in appropriate amounts, as a meal replacement. ENSURE PLUS is lactose and gluten-free. Although it is primarily an oral nutritional supplement, it can be fed by tube.

Patient Conditions:
For patients who require extra calories and nutrients, but a normal concentration of protein, in a limited volume
For patients who need to gain or maintain healthy weight Features:
Rich, creamy taste
Good source of essential vitamins and minerals Ingredients:
Vanilla: —D Water, Corn Syrup, Maltodextrin (Corn), Corn Oil, Sodium and Calcium Caseinates, Sugar (Sucrose), Soy Protein Isolate, Magnesium Chloride, Potassium Citrate, Calcium Phosphate Tribasis, Soy Lecithin, Natural and Artificial Flavor, Sodium Citrate, Potassium Chloride, Choline Chloride, Ascorbic Acid, Carrageenan, Zinc Sulfate, Ferrous Sulfate, Alpha-Tocopheryl Acetate, Niacinamide, Calcium Pantothenate, Manganese Sulfate, Cupric Sulfate, Thiamine Chloride Hydrochloride, Pyridoxine Hydrochloride, Riboflavin, Vitamin A Palmitate, Folic Acid, Biotin, Chromium Chloride, Sodium Molybdate, Potassium Iodide, Sodium Selenite, Phylloquinone, Cyanocobalamin and Vitamin D3.

Protein:
The protein source is a blend of two high-biologic-value proteins: casein and soy.

| | |
|---|---|
| Sodium and calcium caseinates | 84% |
| Soy protein isolate | 16% |

Fat:
The fat source is corn oil.
Corn oil

Carbohydrate:
ENSURE PLUS contains a combination of maltodextrin and sucrose. The mild sweetness and flavor variety (vanilla, chocolate, strawberry, coffee, buffer pecan, and eggnog), plus VARI-FLAVORS® Flavor Pacs in pecan, cherry, strawberry, lemon, and orange, help to prevent flavor fatigue and aid in patient compliance.

Vanilla, strawberry, butter pecan, and coffee flavors:

| | |
|---|---|
| Corn Syrup | 39% |
| Maltodextrin | 38% |
| Sucrose | 23% |

Chocolate and eggnog flavors:

| | |
|---|---|
| Corn Syrup | 36% |
| Maltodextrin | 34% |
| Sucrose | 30% |

Vitamins and Minerals:
An 8-fl-oz serving of ENSURE PLUS provides at least 15% of the RDIs for 25 key Vitamins and minerals.

Caffeine:
Chocolate flavor contains 3.1 mg Caffeine/8 fl oz.
Coffee flavor contains a trace amount of caffeine.

F. ENSURE PLUS® HN
Usage: ENSURE PLUS HN is a nutritionally complete high-calorie, high-nitrogen liquid food designed for people with higher calorie and protein needs or limited volume tolerance. It may be used for oral supplementation or for total nutritional support by tube. ENSURE PLUS HN is lactose- and gluten-free.

Patient Conditions:
For patients with increased calorie and protein needs, such as following surgery or injury.
For patients with limited volume tolerance and early satiety.

Features:
- For supplemental or total nutrition
- For oral or tube feeding
- 1.5 Cal/mL,
- High nitrogen
- Calorically dense Ingredients:
- Vanilla: —D Water, Maltodextrin (Corn), Sodium and Calcium Caseinates, Corn Oil, Sugar (Sucrose), Soy Protein Isolate, Magnesium Chloride, Potassium Citrate, Calcium Phosphate Tribasic, Soy Lecithin, Natural and Artificial Flavor, Sodium Citrate, Choline Chloride, Ascorbic Acid, Taurine, L-Carnitine, Zinc Sulfate, Ferrous Sulfate, Alpha-Totopheryl Acetate, Niacinamide, Carrageenan, Calcium Pantethenate, Manganese Sulfate, Cupric Sulfate, Thiamine Chloride Hydrochloride, Pyridoxine Hydrochloride, Riboflavin, Vitamin A Palmitate, Folic Acid, Biotin, Chromium Chloride, Sodium Molybdate, Potassium Iodide, Sodium Selenite, Phylloquinone, Cyanocobalamin and Vitamin D3.

G. ENSURE® POWDER:

Usage: ENSURE POWDER (reconstituted with water) is a low-residue liquid food designed primarily as an oral nutritional supplement to be used with or between meals. ENSURE POWDER is lactose- and gluten-free, and is suitable for use in modified diets, including low-cholesterol diets.

Patient Conditions:
- For patients on modified diets
- For elderly patients at nutrition risk
- For patients recovering from illness/surgery
- For patients who need a low-residue diet Features:
- Convenient, easy to mix
- Low in saturated fat
- Contains 8 g of total fat and <5 mg of cholesterol per serving
- High in vitamins and minerals
- For low-cholesterol diets
- Lactose-free, easily digested Ingredients: —D Corn Syrup, Maltodextrin (Corn), Sugar (Sucrose), Corn Oil, Sodium and Calcium Caseinates, Soy Protein Isolate, Artificial Flavor, Potassium Citrate, Magnesium Chloride, Sodium Citrate, Calcium Phosphate Tribasic, Potassium Chloride, Soy Lecithin, Ascorbic Acid, Choline Chloride, Zinc Sulfate, Ferrous Sulfate, Alpha-Tocopheryl Acetate, Niacinamide, Calcium Pantothenate, Manganese Sulfate, Thiamine Chloride Hydrochloride, Cupric Sulfate, Pyridoxine Hydrochloride, Riboflavin, Vitamin A Palmitate, Folic Acid, Biotin, Sodium Molybdate, Chromium Chloride, Potassium Iodide, Sodium Selenate, Phylloquinone, Vitamin D3 and Cyanocobalamin.

Protein:
The protein source is a blend of two high-biologic-value proteins: casein and soy.

| Sodium and calcium caseinates | 84% |
|---|---|
| Soy protein isolate | 16% |

Fat:
The fat source is corn oil.

| Corn oil | 100% |
|---|---|

Carbohydrate:
ENSURE POWDER contains a combination of corn syrup, maltodextrin, and sucrose. The mild sweetness of ENSURE POWDER, plus VARI-FLAVORS® Flavor Pacs in pecan, cherry, strawberry, lemon, and orange, helps to prevent flavor fatigue and aid in patient compliance.

Vanilla:

| Corn Syrup | 35% |
|---|---|
| Maltodextrin | 35% |
| Sucrose | 30% |

H. ENSURE® PUDDING

Usage: ENSURE PUDDING is a nutrient-dense supplement providing balanced nutrition in a nonliquid form to be used with or between meals. It is appropriate for consistency-modified diets (e.g., soft, pureed, or full liquid) or for people with swallowing impairments. ENSURE PUDDING is gluten-free.

Patient Conditions:
- For patients on consistency-modified diets (e.g., soft, pureed, or full liquid)
- For patients with swallowing impairments Features:
- Rich and creamy, good taste
- Good source of essential vitamins and minerals
- Convenient-needs no refrigeration
- Gluten-free Nutrient Profile per 5 oz: Calories 250, Protein 10.9%, Total Fat 34.9%, Carbohydrate 54.2%

Ingredients:
- Vanilla: —D Nonfat Milk, Water, Sugar (Sucrose), Partially Hydrogenated Soybean Oil, Modified Food Starch, Magnesium Sulfate, Sodium Stearoyl Lactylate, Sodium Phosphate Dibasic, Artificial Flavor, Ascorbic Acid, Zinc Sulfate, Ferrous Sulfate, Alpha-Tocopheryl Acetate, Choline Chloride, Niacinamide, Manganese Sulfate, Calcium Pantothenate, FD&C Yellow #5, Potassium Citrate, Cupric Sulfate, Vitamin A Palmitate, Thiamine Chloride Hydrochloride, Pyridoxine Hydrochloride, Riboflavin, FD&C Yellow #6, Folic Acid, Biotin, Phylioquinone, Vitamin D3 and Cyanocobalamin.

Protein:
The protein source is nonfat milk.

| Nonfat milk | 100% |
|---|---|

Fat:
The fat source is hydrogenated soybean oil.

| | |
|---|---|
| Hydrogenated soybean oil | 100% |

Carbohydrate:
ENSURE PUDDING contains a combination of sucrose and modified food starch. The mild sweetness and flavor variety (vanilla, chocolate, butterscotch, and tapioca) help prevent flavor fatigue. The product contains 9.2 grams of lactose per serving.

Vanilla and other nonchocolate flavors:

| | |
|---|---|
| Sucrose | 56% |
| Lactose | 27% |
| Modified food starch | 17% |

Chocolate:

| | |
|---|---|
| Sucrose | 58% |
| Lactose | 26% |
| Modified food starch | 16% |

I. ENSURE® WITH FIBER:

Usage: ENSURE WITH FIBER is a fiber-containing, nutritionally complete liquid food designed for people who can benefit from increased dietary fiber and nutrients. ENSURE WITH FIBER is suitable for people who do not require a low-residue diet. It can be fed orally or by tube, and can be used as a nutritional supplement to a regular diet or, in appropriate amounts, as a meal replacement. ENSURE WITH FIBER is lactose- and gluten-free, and is suitable for use in modified diets, including low-cholesterol diets.

Patient Conditions:
For patients who can benefit from increased dietary fiber and nutrients Features:
New advanced formula-low in saturated fat, higher in vitamins and minerals
Contains 6 g of total fat and <5 mg of cholesterol per serving
Rich, creamy taste
Good source of fiber
Excellent source of essential vitamins and minerals
For low-cholesterol diets
Lactose- and gluten-free Ingredients:
Vanilla: —D Water; Maltodextrin (Corn), Sugar (Sucrose), Sodium and Calcium Caseinates, Oat Fiber, High-Oleic Safflower Oil, Canola Oil, Soy Protein Isolate, Corn Oil, Soy Fiber, Calcium Phosphate Tribasic, Magnesium Chloride, Potassium Citrate, Cellulose Gel, Soy Lecithin, Potassium Phosphate Dibasic, Sodium Citrate, Natural and Artificial Flavors, Choline Chloride, Magnesium Phosphate, Ascorbic Acid, Cellulose Gum, Potassium Chloride, Carrageenan, Ferrous Sulfate, Alpha-Tocopheryl Acetate, Zinc Sulfate, Niacinamide, Manganese Sulfate, Calcium Pantothenate, Cupric Sulfate, Vitamin A Palmitate, Thiamine Chloride Hydrochloride, Pyridoxine Hydrochloride, Riboflavin, Folic Acid, Chromium Chloride, Biotin, Sodium Molybdate, Potassium Iodide, Sodium Selenate, Phylloquinone, Vitamin D3 and Cyanocobalamin.

Protein:
The protein source is a blend of two high-biologic-value proteins-casein and soy.

| | |
|---|---|
| Sodium and calcium caseinates | 80% |
| Soy protein isolate | 20% |

Fat:
The fat source is a blend of three oils: high-oleic safflower, canola, and corn.

| | |
|---|---|
| High-oleic safflower oil | 40% |
| Canola oil | 40% |
| Corn oil | 20% |

The level of fat in ENSURE WITH FIBER meets American Heart Association (AHA) guidelines. The 6 grams of fat in ENSURE WITH FIBER represent 22% of the total calories, with 2.01% of the fat being from saturated fatty acids and 6.7% from polyunsaturated fatty acids. These values are within the AHA guidelines of ≦30% of total calories from fat, <10% of the calories from saturated fatty acids, and ≦10% of total calories from polyunsaturated fatty acids.

Carbohydrate:
ENSURE WITH FIBER contains a combination of maltodextrin and sucrose. The mild sweetness and flavor variety (vanilla, chocolate, and butter pecan), plus VARI-FLAVORS® Flavor Pacs in pecan, cherry, strawberry, lemon, and orange, help to prevent flavor fatigue and aid in patient compliance.

Vanilla and other nonchocolate flavors:

| | |
|---|---|
| Maltodextrin | 66% |
| Sucrose | 25% |
| Cat Fiber | 7% |
| Soy Fiber | 2% |

Chocolate:

| | |
|---|---|
| Maltodextrin | 55% |
| Sucrose | 36% |
| Cat Fiber | 7% |
| Soy Fiber | 2% |

Fiber:
The fiber blend used in ENSURE WITH FIBER consists of oat fiber and soy polysaccharide. This blend results in approximately 4 grams of total dietary fiber per 8-fl. oz can. The ratio of insoluble to soluble fiber is 95:5.

The various nutritional supplements described above and known to others of skill in the art can be substituted and/or supplemented with the PUFAs produced in accordance with the present invention.

J. Oxepa™ Nutritional Product
Oxepa is a low-carbohydrate, calorically dense, enteral nutritional product designed for the dietary management of patients with or at risk for ARDS. It has a unique combination of ingredients, including a patented oil blend containing eicosapentaenoic acid (EPA from fish oil), γ-linolenic acid (GLA from borage oil), and elevated antioxidant levels.

Caloric Distribution:

Caloric density is high at 1.5 Cal/mL (355 Cal/8 fl oz), to minimize the volume required to meet energy needs. The distribution of Calories in Oxepa is shown in Table IV.

TABLE IV

Caloric Distribution of Oxepa

|  | per 8 fl oz. | per liter | % of Cal |
|---|---|---|---|
| Calories | 355 | 1,500 | — |
| Fat (g) | 23.2 | 93.7 | 55.2 |
| Carbohydrate (g) | 25 | 105.5 | 28.1 |
| Protein (g) | 14.8 | 62.5 | 16.7 |
| Water (g) | 186 | 785 | — |

Fat:

Oxepa contains 22.2 g of fat per 8-fl oz serving (93.7 g/L).

The fat source is an oil blend of 31.8% canola oil, 25% medium-chain triglycerides (MCTs), 20% borage oil, 20% fish oil, and 3.2% soy lecithin. The typical fatty acid profile of Oxepa is shown in Table V.

Oxepa provides a balanced amount of polyunsaturated, monounsaturated, and saturated fatty acids, as shown in Table VI.

Medium-chain trigylcerides (MCTs)—25% of the fat blend—aid gastric emptying because they are absorbed by the intestinal tract without emulsification by bile acids.

The various fatty acid components of Oxepa™ nutritional product can be substituted and/or supplemented with the PUFAs produced in accordance with this invention.

TABLE V

Typical Fatty Acid Profile

|  | % Total Fatty Acids | g/8 fl oz* | 9/L* |
|---|---|---|---|
| Caproic (6:0) | 0.2 | 0.04 | 0.18 |
| Caprylic (8:0) | 14.69 | 3.1 | 13.07 |
| Capric (10:0) | 11.06 | 2.33 | 9.87 |
| Palmitic (16:0) | 5.59 | 1.18 | 4.98 |
| Palmitoleic | 1.82 | 0.38 | 1.62 |
| Stearic | 1.94 | 0.39 | 1.64 |
| Oleic | 24.44 | 5.16 | 21.75 |
| Linoleic | 16.28 | 3.44 | 14.49 |
| α-Linolenic | 3.47 | 0.73 | 3.09 |
| γ- Linolenic | 4.82 | 1.02 | 4.29 |
| Eicosapentaenoic | 5.11 | 1.08 | 4.55 |
| n-3-Docosapent-aenoic | 0.55 | 0.12 | 0.49 |
| Docosahexaenoic | 2.27 | 0.48 | 2.02 |
| Others | 7.55 | 1.52 | 6.72 |

Fatty acids equal approximately 95% of total fat.

TABLE VI

Fat Profile of Oxepa.

| % of total calories from fat | 55.2 |
|---|---|
| Polyunsaturated fatty acids | 31.44 g/L |

TABLE VI-continued

Fat Profile of Oxepa.

| Monounsaturated fatty acids | 25.53 g/L |
|---|---|
| Saturated fatty acids | 32.38 g/L |
| n-6 to n-3 ratio | 1.75:1 |
| Cholesterol | 9.49 mg/8 fl oz |
|  | 40.1 mg/L |

Carbohydrate:

The carbohydrate content is 25.0 g per 8-fl-oz serving (105.5 g/L).

The carbohydrate sources are 45% maltodextrin (a complex carbohydrate) and 55% sucrose (a simple sugar), both of which are readily digested and absorbed.

The high-fat and low-carbohydrate content of Oxepa is designed to minimize carbon dioxide ($CO_2$) production. High $CO_2$ levels can complicate weaning in ventilator-dependent patients. The low level of carbohydrate also may be useful for those patients who have developed stress-induced hyperglycemia.

Oxepa is lactose-free.

Dietary carbohydrate, the amino acids from protein, and the glycerol moiety of fats can be converted to glucose within the body. Throughout this process, the carbohydrate requirements of glucose-dependent tissues (such as the central nervous system and red blood cells) are met. However, a diet free of carbohydrates can lead to ketosis, excessive catabolism of tissue protein, and loss of fluid and electrolytes. These effects can be prevented by daily ingestion of 50 to 100 g of digestible carbohydrate, if caloric intake is adequate. The carbohydrate level in Oxepa is also sufficient to minimize gluconeogenesis, if energy needs are being met.

Protein:

Oxepa contains 14.8 g of protein per 8-fl-oz serving (62.5 g/L).

The total calorie/nitrogen ratio (150:1) meets the need of stressed patients.

Oxepa provides enough protein to promote anabolism and the maintenance of lean body mass without precipitating respiratory problems. High protein intakes are a concern in patients with respiratory insufficiency. Although protein has little effect on $CO_2$ production, a high protein diet will increase ventilatory drive.

The protein sources of Oxepa are 86.8% sodium caseinate and 13.2% calcium caseinate.

The amino acid profile of the protein system in Oxepa meets or surpasses the standard for high quality protein set by the National Academy of Sciences.

*Oxepa is gluten-free.

Default settings for the analysis programs

GCG Programs

FastA Search

Default parameters:

| range of interest | Begin = 1   END = last protein or nucleic acid |
|---|---|
| search set | all of SwissProt (protein) or GenEMBL(nucleic acid) |
| word size | = (2) for protein   = (6) for nucleic acid |

Expected scores lists scores until E( ) value reaches 2.0

| TFastA search | |
|---|---|
| Default parameters: | |
| range of interest | Begin = 1    END = last nucleic acid |
| search set | all of GenEMBL |
| word size | wordsize = (2) |

Expected scores lists scores until E( ) value reaches 2.0

| Pileup | |
|---|---|
| Default parameters: | |
| gap creation penalty | gap weight = 5 |
| gap extension penalty | gap length weight = 12 |
| plot figure | one page plot density = 2.7 |

| Sequencher Program | |
|---|---|
| Default parameters: | |
| Automatic Assembly | Dirty data algorithm = slower contig assembly but more rigorous comparisons between the sequences<br>minimum match = 85%<br>minimum overlap = 20 |

BLAST 2 (blastp, tblastn)

| Default parameters: | V = 50 | Lambda = .329 | W = 3 |
|---|---|---|---|
| | B = 50 | Y = 0.140 | X = 22 |
| | E = 10 | H = 0.427 | | blast n

| Default parameters: | V = 100 | Lambda = 1.37 | W = 11 |
|---|---|---|---|
| | B = 250 | K = 0.171 | X1 = 22 |
| | E = 10 | H = 1.31 | X2 = 25 |

BLAST 2 Command Line Arguments

| -v Hits | number of best scores to show |
|---|---|
| -b Alignments | number of best alignments to show |
| -e Expectation value (E) | [Real] default = 10.0 |
| -m Alignment view options: | 0 = pairwise,<br>1 = master-slave showing identities,<br>2 = master-slave, no identities,<br>3 = flat master-slave, show identities,<br>4 = flat master-slave, no identities,<br>5 = master-slave, no identities and blunt ends,<br>6 = flat master-slave, no identities and blunt ends<br>[Integer]<br>default = 0 |
| -F Filer query seq. (DUST with blastn, SEG with others) [T/F]<br>default = T | |
| -G Cost to open a gap (zero invokes default behavior) [Integer]<br>default = 0 | |
| -E Cost to extend a gap (zero invokes default behavior) [Integer]<br>default = 0 | |
| -X X dropoff value for gapped alignment (in bits) (zero invokes default behavior) [Integer]<br>default = 0 | |
| -I Show GI's in deflines | [T/F]<br>default = F |
| -q Penalty for a nucleotide mismatch | (blastn only) [Integer]<br>default = −3 |
| -r Reward for a nucleotide match | (blastn only) [Integer]<br>default = 1 |
| -t Threshold for extending hits | default if zero [Integer]<br>default = 0 |
| -g Perform gapped alignment (not available with tblastx) [T/F]<br>default = T | |
| -q Query Genetic code to use | [Integer]<br>default = −1 |
| -D DB Genetic code | (for tblast [nx] only) [integer]<br>default = 1 |
| -J Believe the query defline | [T/F]<br>default = F |
| -M Matrix | [String]<br>default = BLOSUM62 |
| -Word size | default it zero [Integer]<br>default = 0 |
| -z Effective length of the database (use zero for the real size) [Integer]<br>default = 0 | |
| -a Number of processors to use | [Integer]<br>default = site configurable (SeqServer.conf) |

Allowed and default values for gap open/gap extension cost (−G/−E) parameters:

| Allowed and default values for gap open/gap extension cost (−G/−E) parameters: | | | | | | | | | | | |
|---|---|---|---|---|---|---|---|---|---|---|---|
| BLOSUM62 | | | | | | | | | | | |
| -G | 9 | 8 | 7 | 12 | 11 | 10 | | | | | |
| -E | 2 | 2 | 2 | 1 | 1 | 1 | | | | | |
| BLOSUM50 | | | | | | | | | | | |
| -G | 12 | 11 | 10 | 9 | 15 | 14 | 13 | 12 | 18 | 17 | 16 | 15 |
| -E | 3 | 3 | 3 | 3 | 2 | 2 | 2 | 2 | 1 | 1 | 1 | 1 |
| PAM250 | | | | | | | | | | | |
| -G | 13 | 12 | 11 | 10 | 15 | 14 | 13 | 12 | 19 | 18 | 17 | 16 |
| -E | 3 | 3 | 3 | 3 | 2 | 2 | 2 | 2 | 1 | 1 | 1 | 1 |
| BLOSUM50 | | | | | | | | | | | |
| -G | 8 | 7 | 6 | 11 | 10 | 9 | | | | | |
| -E | 2 | 2 | 2 | 1 | 1 | 1 | | | | | |
| PAM30 | | | | | | | | | | | |
| -G | 5 | 4 | 3 | 7 | 6 | 5 | 10 | 9 | 8 | | |
| -E | 3 | 3 | 3 | 2 | 2 | 2 | 1 | 1 | 1 | | |
| PAM70 | | | | | | | | | | | |
| -G | 6 | 5 | 4 | 8 | 7 | 6 | 11 | 10 | 9 | | |
| -E | 3 | 3 | 3 | 2 | 2 | 2 | 1 | 1 | 1 | | |

What is claimed is:

1. An isolated nucleic acid selected from the group consisting of: (a) a nucleic acid comprising the polynucleotide of SEQ ID NO:5 and (5) a nucleic acid completely complementary to the polynucleotide of (a).

2. The isolated nucleic acid of claim 1, wherein said isolated nucleic acid encodes a functionally active elongase which utilizes a polyunsaturated fatty acid as a substrate.

3. The isolated nucleic acid of claim 1, wherein said isolated nucleic acid is derived from a mammal.

4. The isolated nucleic acid of claim 3, wherein said isolated nucleic acid is derived from a mouse.

5. A method of producing an elongase enzyme comprising the steps of:
   a) isolating a polynucleotide comprising the nucleotide sequence of SEQ ID NO:5 or SEQ ID NO:6;
   b) constructing a vector comprising said polynucleotide of step (a) operably linked to a promoter; and
   c) introducing said vector into a host cell for a time and under conditions sufficient for expression of said elongase enzyme.

6. The method of claim 5 wherein said host cell is selected from the group consisting of a eukaryotic cell or a prokaryotic cell.

7. The method of claim 6 wherein said prokaryotic cell is selected from the group consisting of *E. coli*, cyanobacteria, and *B. subtilis*.

8. The method of claim 6 wherein said eukaryotic cell is selected from the group consisting of a mammalian cell, an insect cell, a plant cell and a fungal cell.

9. The method of claim 8 wherein said fungal cell is selected from the group consisting of *Saccharomyces* spp., *Candida* spp., *Lipomyces starkey*, *Yarrowia* spp., *Kluyveromyces* spp., *Hansenula* spp., *Aspergillus* spp., *Penicillium* spp., *Neurospora* spp., *Trichoderma* spp. and *Pichia* spp.

10. The method of claim 9 wherein said fungal cell is a yeast cell selected from the group consisting of *Saccharomyces* spp., *Candida* spp., *Hansenula* spp. and *Pichia* spp.

11. The method of claim 10 wherein said yeast cell is *Saccharomyces cerevisiae*.

12. A vector comprising a polynucleotide operably linked to a promoter, wherein said polynucleotide comprises the nucleotide sequence of SEQ ID NO:5.

13. A host cell comprising the vector of claim 12.

14. The host cell of claim 13, wherein said host cell is selected from the group consisting of a eukaryotic cell or a prokaryotic cell.

15. The host cell of claim 14 wherein said prokaryotic cell is selected from the group consisting of *E. coli*, Cyanobacteria, and *B. subtilis*.

16. The host cell of claim 14 wherein said eukaryotic cell is selected from the group consisting of a mammalian cell, an insect cell, a plant cell and a fungal cell.

17. The host cell of claim 16 wherein said fungal cell is selected from the group consisting of *Saccharomyces* spp., *Candida* spp., *Lipomyces starkey*, *Yarrowia* spp., *Kluyveromyces* spp., *Hansenula* spp., *Aspergillus* spp., *Penicillium* spp., *Neurospora* spp., *Trichoderma* spp. and *Pichia* spp.

18. The host cell of claim 17 wherein said fungal cell is a yeast cell selected from the group consisting of *Saccharomyces* spp., *Candida* spp., *Hansenula* spp. and *Pichia* spp.

19. The host cell of claim 18 wherein said host cell is *Saccharomyces cerevisiae*.

20. A plant cell, plant or plant tissue comprising the vector of claim 12, wherein expression of the polynucleotide of said vector results in production of a polyunsaturated fatty acid by said plant cell, plant or plant tissue.

21. The plant cell, plant or plant tissue of claim 20, wherein said polyunsaturated fatty acid is selected from the group consisting of arachidonic acid (AA), adrenic acid (ADA), γ-linoleic acid (GLA) and stearidonic acid (STA).

22. An isolated nucleic acid selected from the group consisting of: (a) a nucleic acid comprising the polynucleotide of SEQ ID NO:6 and (b) a nucleic acid completely complementary to the polynucleotide of (a).

23. An isolated polynucleotide encoding a polypeptide, wherein said polypeptide has elongase activity and comprises an amino acid sequence which is at least 95% identical to the amino acid sequence set forth in SEQ ID NO:63.

24. An isolated polynucleotide encoding a polypeptide, wherein said polypeptide has elongase activity and comprises an amino acid sequence which is at least 95% identical to the amino acid sequence set forth in SEQ ID NO:64.

* * * * *

SEQUENCE LISTING

<160> NUMBER OF SEQ ID NOS: 87

<210> SEQ ID NO 1
<211> LENGTH: 954
<212> TYPE: DNA
<213> ORGANISM: Mortierella alpina

<400> SEQUENCE: 1

```
atggccgccg caatcttgga caaggtcaac ttcggcattg atcagccctt cggaatcaag      60
ctcgacacct actttgctca ggcctatgaa ctcgtcaccg aaagtccat  cgactccttc     120
gtcttccagg agggcgtcac gcctctctcg acccagagag aggtcgccat gtggactatc     180
acttacttcg tcgtcatctt tggtggtcgc cagatcatga gagccagga  cgccttcaag     240
ctcaagcccc tcttcatcct ccacaacttc ctcctgacga tcgcgtccgg atcgctgttg     300
ctcctgttca tcgagaacct ggtccccatc ctcgccagaa acggactttt ctacgccatc     360
tgcgacgacg gtgcctggac ccagcgcctc gagctcctct actacctcaa ctacctggtc     420
aagtactggg agttggccga caccgtcttt ttggtcctca agaagaagcc tcttgagttc     480
ctgcactact ccaccactc  gatgaccatg gttctctgct tgtccagct  tggaggatac     540
acttcagtgt cctgggtccc tattaccctc aacttgactg tccacgtctt catgtactac     600
tactacatgc gctccgctgc cggtgttcgc atctggtgga agcagtactt gaccactctc     660
cagatcgtcc agttcgttct tgacctcgga ttcatctact tctgcgccta cacctacttc     720
gccttcacct acttcccctg ggctcccaac gtcggcaagt gcgccggtac cgagggtgct     780
gctctctttg gctgcggact cctctccagc tatctcttgc tctttatcaa cttctaccgc     840
attacctaca atgccaaggc caaggcagcc aaggagcgtg gaagcaactt taccccccaag    900
actgtcaagt ccggcggatc gcccaagaag ccctccaaga gcaagcacat ctaa           954
```

<210> SEQ ID NO 2
<211> LENGTH: 957
<212> TYPE: DNA
<213> ORGANISM: Mortierella alpina

<400> SEQUENCE: 2

```
atggagtcga ttgcgccatt cctcccatca aagatgccgc aagatctgtt tatggacctt      60
gccaccgcta tcggtgtccg ggccgcgccc tatgtcgatc ctctcgaggc cgcgctggtg     120
gcccaggccg agaagtacat ccccacgatt gtccatcaca cgcgtgggtt cctggtcgcg     180
gtggagtcgc ctttggcccg tgagctgccg ttgatgaacc cgttccacgt gctgttgatc     240
gtgctcgctt atttggtcac ggtctttgtg ggcatgcaga tcatgaagaa ctttgagcgg     300
ttcgaggtca agacgttttc gctcctgcac aacttttgtc tggtctcgat cagcgcctac     360
atgtgcggtg ggatcctgta cgaggcttat caggccaact atggactgtt tgagaacgct     420
gctgatcata ccttcaaggg tcttcctatg gccaagatga tctggctctt ctacttctcc     480
aagatcatgg agtttgtcga caccatgatc atggtcctca agaagaacaa ccgccagatc     540
tccttcttgc acgtttacca ccacagctcc atcttcacca tctggtggtt ggtcacctttt    600
gttgcaccca acggtgaagc ctacttctct gctgcgttga actcgttcat ccatgtgatc     660
atgtacggct actacttctt gtcggccttg gcttcaagc  aggtgtcgtt catcaagttc     720
tacatcacgc gctcgcagat gacacagttc tgcatgatgt cggtccagtc ttcctgggac     780
atgtacgcca tgaaggtcct tggccgcccc ggatacccct tcttcatcac ggctctgctt     840
```

| | |
|---|---|
| tggttctaca tgtggaccat gctcggtctc ttctacaact tttacagaaa gaacgccaag | 900 |
| ttggccaagc aggccaaggc cgacgctgcc aaggagaagg caaggaagtt gcagtaa | 957 |

<210> SEQ ID NO 3
<211> LENGTH: 914
<212> TYPE: DNA
<213> ORGANISM: Homo sapiens

<400> SEQUENCE: 3

| | |
|---|---|
| atggaacatt ttgatgcatc acttagtacc tatttcaagg cattgctagg ccctcgagat | 60 |
| actagagtaa aaggatggtt tcttctggac aattatatac ccacatttat ctgctctgtc | 120 |
| atatatttac taattgtatg gctgggacca aaatacatga ggaataaaca gccattctct | 180 |
| tgccggggga ttttagtggt gtataacctt ggactcacac tgctgtctct gtatatgttc | 240 |
| tgtgagttag taacaggagt atgggaaggc aaatacaact tcttctgtca gggcacacgc | 300 |
| accgcaggag aatcagatat gaagattatc cgtgtcctct ggtggtacta cttctccaaa | 360 |
| ctcatagaat ttatggacac tttcttcttc atcctgcgca agaacaacca ccagatcacg | 420 |
| gtcctgcacg tctaccacca tgcctcgatg ctgaacatct ggtggtttgt gatgaactgg | 480 |
| gtccctgcg gccactctta ttttggtgcc acacttaata gcttcatcca cgtcctcatg | 540 |
| tactcttact atggtttgtc gtcagtccct tccatgcgtc catacctctg gtggaagaag | 600 |
| tacatcactc aggggcagct gcttcagttt gtgctgacaa tcatccagac cagctgcggg | 660 |
| gtcatctggc cgtgcacatt ccctcttggt tggttgtatt ccagattgg atacattatt | 720 |
| tccctgattg ctctcttcac aaacttctac attcagacct acaacaagaa aggggcctcc | 780 |
| cgaaggaaag accacctgaa ggaccaccag aatgggtccg tggctgctgt gaatggacac | 840 |
| accaacagct tttcaccccct ggaaaacaat gtgaagccaa ggaagctgcg gaaggattga | 900 |
| agtcaaagaa ttga | 914 |

<210> SEQ ID NO 4
<211> LENGTH: 867
<212> TYPE: DNA
<213> ORGANISM: Caenorhabditis elegans

<400> SEQUENCE: 4

| | |
|---|---|
| atggctcagc atccgctcgt tcaacggctt ctcgatgtca aattcgacac gaaacgattt | 60 |
| gtggctattg ctactcatgg gccaaagaat ttccctgacg cagaaggtcg caagttcttt | 120 |
| gctgatcact ttgatgttac tattcaggct tcaatcctgt acatggtcgt tgtgttcgga | 180 |
| acaaaatggt tcatgcgtaa tcgtcaacca ttccaattga ctattccact caacatctgg | 240 |
| aatttcatcc tcgccgcatt ttccatcgca ggagctgtca aaatgacccc agagttcttt | 300 |
| ggaaccattg ccaacaaagg aattgtcgca tcctactgca aagtgtttga tttcacgaaa | 360 |
| ggagagaatg gatactgggt gtggctcttc atggcttcca aacttttcga acttgttgac | 420 |
| accatcttct tggttctccg taaacgtcca ctcatgttcc ttcactggta tcaccatatt | 480 |
| ctcaccatga tctacgcctg gtactctcat ccattgaccc caggattcaa cagatacgga | 540 |
| atttatctta actttgtcgt ccacgccttc atgtactctt actacttcct tcgctcgatg | 600 |
| aagattcgcg tgccaggatt catcgcccaa gctatcacat ctcttcaaat cgttcaattc | 660 |
| atcatctctt gcgccgttct tgctcatctt ggttatctca tgcacttcac caatgccaac | 720 |
| tgtgatttcg agccatcagt attcaagctc gcagttttca tggacacaac atacttggct | 780 |

| | |
|---|---|
| cttttcgtca acttcttcct ccaatcatat gttctccgcg gaggaaaaga caagtacaag | 840 |
| gcagtgccaa agaagaagaa caactaa | 867 |

<210> SEQ ID NO 5
<211> LENGTH: 879
<212> TYPE: DNA
<213> ORGANISM: Mus musculus

<400> SEQUENCE: 5

| | |
|---|---|
| atggagcagc tgaaggcctt tgataatgaa gtcaatgctt tcttggacaa catgtttgga | 60 |
| ccacgagatt ctcgagttcg cgggtggttc ctgctggact cttaccttcc cacccttcatc | 120 |
| ctcaccatca cgtacctgct ctcgatatgg ctgggtaaca agtacatgaa gaacaggcct | 180 |
| gctctgtctc tcagggggcat cctcaccttg tataacctcg caatcacact tctttctgcg | 240 |
| tatatgctgg tggagctcat cctctccagc tgggaaggag gttacaactt gcagtgtcag | 300 |
| aatctcgaca gtgcaggaga aggtgatgtc cgggtagcca aggtcttgtg gtggtactac | 360 |
| ttctccaaac tagtggagtt cctggacacg attttctttg ttctacgaaa aaagaccaat | 420 |
| cagatcacct tccttcatgt ctatcaccac gcgtccatgt tcaacatctg gtggtgtgtt | 480 |
| ttgaactgga taccttgtgg tcaaagcttc tttggaccca ccctgaacag ctttatccac | 540 |
| attctcatgt actcctacta cggcctgtct gtgttcccgt ccatgcacaa gtacctttgg | 600 |
| tggaagaagt acctcacaca ggctcagctg gtgcagttcg tactcaccat cacgcacacg | 660 |
| ctgagtgccg tggtgaagcc ctgtggcttc ccctttggct gtctcatctt ccagtcttcc | 720 |
| tatatgatga cgctggtcat cctgttctta aacttctata ttcagacata ccggaaaaag | 780 |
| ccagtgaaga aagagctgca agagaaagaa gtgaagaatg gtttccccaa agcccactta | 840 |
| attgtggcta atggcatgac ggacaagaag gctcaataa | 879 |

<210> SEQ ID NO 6
<211> LENGTH: 900
<212> TYPE: DNA
<213> ORGANISM: Mus musculus

<400> SEQUENCE: 6

| | |
|---|---|
| atggaacatt tcgatgcgtc actcagtacc tatttcaagg ccttcctggg cccccgagat | 60 |
| acaagagtca aggatggtt cctcctggac aattacatcc ctacgtttgt ctgttctgtt | 120 |
| atttacttac tcattgtatg gctgggacca aaatacatga gaaccggca gccgttctct | 180 |
| tgccgaggca tcctgcagtt gtataacctt ggactcaccc tgctgtctct ctacatgttc | 240 |
| tatgagttgg tgacaggtgt gtgggagggc aaatacaact ttttctgcca gggaacacgc | 300 |
| agcgcgggag aatccgatat gaagatcatc cgcgtcctct ggtggtacta cttctccaaa | 360 |
| ctcatcgaat tcatggacac ctttttcttc atccttcgca agaacaacca ccagatcacc | 420 |
| gtgctccatg tctaccacca cgctaccatg ctcaacatct ggtggtttgt gatgaactgg | 480 |
| gttccctgcg gccattcata ttttggtgcg acactcaaca gcttcatcca tgtcctcatg | 540 |
| tactcgtact atggtctgtc ctccatcccg tccatgcgtc cctacctctg gtggaaaaag | 600 |
| tacatcactc aagggcagct ggtccagttt gtgctgacaa tcatccagac gacctgcggg | 660 |
| gtcttctggc catgctcctt ccctctcggg tggctgttct tccagattgg atacatgatt | 720 |
| tccctgattg ctctcttcac aaacttctac attcagactt acaacaagaa aggggcctct | 780 |
| cggaggaaag accactgaa gggccaccag aacgggtctg tggccgccgt caacggacac | 840 |
| accaacagct tcccttccct ggaaaacagc gtgaagccca ggaagcagcg aaaggattga | 900 |

<210> SEQ ID NO 7
<211> LENGTH: 83
<212> TYPE: PRT
<213> ORGANISM: Jojoba KCS

<400> SEQUENCE: 7

```
Ala Thr Leu Pro Asn Phe Lys Ser Ser Ile Asn Leu His His Val Lys
 1               5                  10                  15

Leu Gly Tyr His Tyr Leu Ile Ser Asn Ala Leu Phe Leu Val Phe Ile
             20                  25                  30

Pro Leu Leu Gly Leu Ala Ser Ala His Leu Ser Ser Phe Ser Ala His
         35                  40                  45

Asp Leu Ser Leu Leu Phe Asp Leu Leu Arg Arg Asn Leu Leu Pro Val
     50                  55                  60

Val Val Cys Ser Phe Leu Phe Val Leu Leu Ala Thr Leu His Phe Leu
 65                  70                  75                  80

Thr Arg Pro
```

<210> SEQ ID NO 8
<211> LENGTH: 80
<212> TYPE: PRT
<213> ORGANISM: Saccharomyces cerevisiae

<400> SEQUENCE: 8

```
Ser Thr Leu Pro Pro Val Leu Tyr Ala Ile Thr Ala Tyr Tyr Val Ile
 1               5                  10                  15

Ile Phe Gly Gly Arg Phe Leu Leu Ser Lys Ser Lys Pro Phe Lys Leu
             20                  25                  30

Asn Gly Leu Phe Gln Leu His Asn Leu Val Leu Thr Ser Leu Ser Leu
         35                  40                  45

Thr Leu Leu Leu Met Val Glu Gln Leu Val Pro Ile Ile Val Gln
     50                  55                  60

His Gly Leu Tyr Phe Ala Ile Cys Asn Ile Gly Ala Trp Thr Gln Pro
 65                  70                  75                  80
```

<210> SEQ ID NO 9
<211> LENGTH: 240
<212> TYPE: DNA
<213> ORGANISM: Saccharomyces cerevisiae

<400> SEQUENCE: 9

```
tccaccctcc cccccgtcct ctacgccatc accgcctact acgtcatcat cttcggtggt    60
cgcttcctcc tctccaagtc caagcccttc aagctcaacg gtctcttcca gctccacaac   120
ctcgtcctca cctccctctc cctcaccctc ctcctcctca tggtcgagca gctcgtcccc   180
atcatcgtcc agcacggtct ctacttcgcc atctgcaaca tcggtgcctg gacccagccc   240
```

<210> SEQ ID NO 10
<211> LENGTH: 33
<212> TYPE: DNA
<213> ORGANISM: Mortierella alpina

<400> SEQUENCE: 10

```
gaattcaggc atggccgccg caatcttgga caa                                 33
```

<210> SEQ ID NO 11
<211> LENGTH: 49
<212> TYPE: DNA

-continued

<213> ORGANISM: Mortierella alpina

<400> SEQUENCE: 11
gaattcaggc atctcatgga tccgccatgg ccgccgcaat cttggacaa                49

<210> SEQ ID NO 12
<211> LENGTH: 317
<212> TYPE: PRT
<213> ORGANISM: Mortierella alpina

<400> SEQUENCE: 12

Met Ala Ala Ile Leu Asp Lys Val Asn Phe Gly Ile Asp Gln Pro
1               5                   10                  15

Phe Gly Ile Lys Leu Asp Thr Tyr Phe Ala Gln Ala Tyr Glu Leu Val
                20                  25                  30

Thr Gly Lys Ser Ile Asp Ser Phe Val Phe Gln Glu Gly Val Thr Pro
            35                  40                  45

Leu Ser Thr Gln Arg Glu Val Ala Met Trp Thr Ile Thr Tyr Phe Val
    50                  55                  60

Val Ile Phe Gly Gly Arg Gln Ile Met Lys Ser Gln Asp Ala Phe Lys
65                  70                  75                  80

Leu Lys Pro Leu Phe Ile Leu His Asn Phe Leu Leu Thr Ile Ala Ser
                85                  90                  95

Gly Ser Leu Leu Leu Leu Phe Ile Glu Asn Leu Val Pro Ile Leu Ala
            100                 105                 110

Arg Asn Gly Leu Phe Tyr Ala Ile Cys Asp Asp Gly Ala Trp Thr Gln
        115                 120                 125

Arg Leu Glu Leu Leu Tyr Tyr Leu Asn Tyr Leu Val Lys Tyr Trp Glu
    130                 135                 140

Leu Ala Asp Thr Val Phe Leu Val Leu Lys Lys Pro Leu Glu Phe
145                 150                 155                 160

Leu His Tyr Phe His His Ser Met Thr Met Val Leu Cys Phe Val Gln
                165                 170                 175

Leu Gly Gly Tyr Thr Ser Val Ser Trp Val Pro Ile Thr Leu Asn Leu
            180                 185                 190

Thr Val His Val Phe Met Tyr Tyr Tyr Met Arg Ser Ala Ala Gly
        195                 200                 205

Val Arg Ile Trp Trp Lys Gln Tyr Leu Thr Thr Leu Gln Ile Val Gln
    210                 215                 220

Phe Val Leu Asp Leu Gly Phe Ile Tyr Phe Cys Ala Tyr Thr Tyr Phe
225                 230                 235                 240

Ala Phe Thr Tyr Phe Pro Trp Ala Pro Asn Val Gly Lys Cys Ala Gly
                245                 250                 255

Thr Glu Gly Ala Ala Leu Phe Gly Cys Gly Leu Leu Ser Ser Tyr Leu
            260                 265                 270

Leu Leu Phe Ile Asn Phe Tyr Arg Ile Thr Tyr Asn Ala Lys Ala Lys
        275                 280                 285

Ala Ala Lys Glu Arg Gly Ser Asn Phe Thr Pro Lys Thr Val Lys Ser
    290                 295                 300

Gly Gly Ser Pro Lys Lys Pro Ser Lys Ser Lys His Ile
305                 310                 315

<210> SEQ ID NO 13
<211> LENGTH: 347
<212> TYPE: PRT
<213> ORGANISM: Saccharomyces cerevisiae

<400> SEQUENCE: 13

```
Met Asn Ser Leu Val Thr Gln Tyr Ala Ala Pro Leu Phe Glu Arg Tyr
 1               5                  10                  15

Pro Gln Leu His Asp Tyr Leu Pro Thr Leu Glu Arg Pro Phe Phe Asn
             20                  25                  30

Ile Ser Leu Trp Glu His Phe Asp Asp Val Val Thr Arg Val Thr Asn
         35                  40                  45

Gly Arg Phe Val Pro Ser Glu Phe Gln Phe Ile Ala Gly Glu Leu Pro
     50                  55                  60

Leu Ser Thr Leu Pro Pro Val Leu Tyr Ala Ile Thr Ala Tyr Tyr Val
65                  70                  75                  80

Ile Ile Phe Gly Gly Arg Phe Leu Leu Ser Lys Ser Lys Pro Phe Lys
                 85                  90                  95

Leu Asn Gly Leu Phe Gln Leu His Asn Leu Val Leu Thr Ser Leu Ser
            100                 105                 110

Leu Thr Leu Leu Leu Leu Met Val Glu Gln Leu Val Pro Ile Ile Val
            115                 120                 125

Gln His Gly Leu Tyr Phe Ala Ile Cys Asn Ile Gly Ala Trp Thr Gln
        130                 135                 140

Pro Leu Val Thr Leu Tyr Tyr Met Asn Tyr Ile Val Lys Phe Ile Glu
145                 150                 155                 160

Phe Ile Asp Thr Phe Phe Leu Val Leu Lys His Lys Lys Leu Thr Phe
                165                 170                 175

Leu His Thr Tyr His His Gly Ala Thr Ala Leu Leu Cys Tyr Thr Gln
            180                 185                 190

Leu Met Gly Thr Thr Ser Ile Ser Trp Val Pro Ile Ser Leu Asn Leu
        195                 200                 205

Gly Val His Val Val Met Tyr Trp Tyr Tyr Phe Leu Ala Ala Arg Gly
    210                 215                 220

Ile Arg Val Trp Trp Lys Glu Trp Val Thr Arg Phe Gln Ile Ile Gln
225                 230                 235                 240

Phe Val Leu Asp Ile Gly Phe Ile Tyr Phe Ala Val Tyr Gln Lys Ala
                245                 250                 255

Val His Leu Tyr Phe Pro Ile Leu Pro His Cys Gly Asp Cys Val Gly
            260                 265                 270

Ser Thr Thr Ala Thr Phe Ala Gly Cys Ala Ile Ile Ser Ser Tyr Leu
        275                 280                 285

Val Leu Phe Ile Ser Phe Tyr Ile Asn Val Tyr Lys Arg Lys Gly Thr
    290                 295                 300

Lys Thr Ser Arg Val Val Lys Arg Ala His Gly Gly Val Ala Ala Lys
305                 310                 315                 320

Val Asn Glu Tyr Val Asn Val Asp Leu Lys Asn Val Pro Thr Pro Ser
                325                 330                 335

Pro Ser Pro Lys Pro Gln His Arg Arg Lys Arg
            340                 345
```

<210> SEQ ID NO 14
<211> LENGTH: 345
<212> TYPE: PRT
<213> ORGANISM: Saccharomyces cerevisiae

<400> SEQUENCE: 14

```
Met Asn Thr Thr Thr Ser Thr Val Ile Ala Ala Val Ala Asp Gln Phe
 1               5                  10                  15
```

-continued

```
Gln Ser Leu Asn Ser Ser Ser Ser Cys Phe Leu Lys Val His Val Pro
            20                  25                  30

Ser Ile Glu Asn Pro Phe Gly Ile Glu Leu Trp Pro Ile Phe Ser Lys
        35                  40                  45

Val Phe Glu Tyr Phe Ser Gly Tyr Pro Ala Glu Gln Phe Glu Phe Ile
    50                  55                  60

His Asn Lys Thr Phe Leu Ala Asn Gly Tyr His Ala Val Ser Ile Ile
65                  70                  75                  80

Ile Val Tyr Tyr Ile Ile Ile Phe Gly Gly Gln Ala Ile Leu Arg Ala
                85                  90                  95

Leu Asn Ala Ser Pro Leu Lys Phe Lys Leu Leu Phe Glu Ile His Asn
            100                 105                 110

Leu Phe Leu Thr Ser Ile Ser Leu Val Leu Trp Leu Leu Met Leu Glu
        115                 120                 125

Gln Leu Val Pro Met Val Tyr His Asn Gly Leu Phe Trp Ser Ile Cys
    130                 135                 140

Ser Lys Glu Ala Phe Ala Pro Lys Leu Val Thr Leu Tyr Tyr Leu Asn
145                 150                 155                 160
Tyr Leu Thr Lys Phe Val Glu Leu Ile Asp Thr Val Phe Leu Val Leu
                165                 170                 175

Arg Arg Lys Lys Leu Leu Phe Leu His Thr Tyr His His Gly Ala Thr
            180                 185                 190

Ala Leu Leu Cys Tyr Thr Gln Leu Ile Gly Arg Thr Ser Val Glu Trp
        195                 200                 205

Val Val Ile Leu Leu Asn Leu Gly Val His Val Ile Met Tyr Trp Tyr
    210                 215                 220

Tyr Phe Leu Ser Ser Cys Gly Ile Arg Val Trp Trp Lys Gln Trp Val
225                 230                 235                 240
Thr Arg Phe Gln Ile Ile Gln Phe Leu Ile Asp Leu Val Phe Val Tyr
                245                 250                 255

Phe Ala Thr Tyr Thr Phe Tyr Ala His Lys Tyr Leu Asp Gly Ile Leu
            260                 265                 270

Pro Asn Lys Gly Thr Cys Tyr Gly Thr Gln Ala Ala Ala Ala Tyr Gly
        275                 280                 285

Tyr Leu Ile Leu Thr Ser Tyr Leu Leu Leu Phe Ile Ser Phe Tyr Ile
    290                 295                 300

Gln Ser Tyr Lys Lys Gly Gly Lys Lys Thr Val Lys Lys Glu Ser Glu
305                 310                 315                 320
Val Ser Gly Ser Val Ala Ser Gly Ser Ser Thr Gly Val Lys Thr Ser
                325                 330                 335

Asn Thr Lys Val Ser Ser Arg Lys Ala
            340                 345
```

<210> SEQ ID NO 15
<211> LENGTH: 587
<212> TYPE: DNA
<213> ORGANISM: Mortierella alpina

<400> SEQUENCE: 15

```
tctcgaccca gagagaggtc gccatgtgga ctatcactta cttcgtcgtc atctttggtg     60
gtcgccagat catgaagagc caggacgcct tcaagctcaa gcccctcttc atcctccaca    120
acttcctcct gacgatcgcg tccggatcgc tgttgctcct gttcatcgag aacctggtcc    180
ccatcctcgc cagaaacgga cttttctacg ccatctgcga cgacggtgcc tggacccagc    240
```

```
gcctcgagct cctctactac ctcaactacc tggtcaagta ctgggagttg gccgacaccg    300 tcttttttggt cctcaagaag aagcctcttg agttcctgca ctacttccac cactcgatga    360
ccatggttct ctgctttgtc cagcttggag atacacttc agtgtcctgg gtccctatta    420
ccctcaactt gactgtccac gtcttcatgt actactacta catgcgctcc gctgccggtg    480
ttcgcatctg gtggaagcag tacttgacca ctctccagat cgtccagttc gttcttgacc    540
tcggattcat ctacttctgc gcctacacct acttcgcctt cacctac                  587

<210> SEQ ID NO 16
<211> LENGTH: 590
<212> TYPE: DNA
<213> ORGANISM: Saccharomyces cerevisiae

<400> SEQUENCE: 16
cattaagcac tttgccccct gtgctatacg ccatcactgc ctattacgtt attattttg      60 gtggcaggtt tttgttaagt aagtcgaaac catttaaatt aaatggcctt ttccaattgc    120
ataatttggt tttaacttca ctttcattga cgcttttatt gcttatggtt gaacaattag    180
tgccaattat tgttcagcac gggttatact tcgctatctg taatattggt gcttggactc    240
aaccgctcgt tacattatat tacatgaatt acattgtcaa gtttattgaa tttatagaca    300
cctttttctt ggtgctaaaa cataaaaaat tgacatttt gcatacttat caccatggcg    360
ctactgcctt attatgttac acccaattga tgggcaccac atctatttct tgggtcccta    420
tttcattgaa ccttggtgtt cacgtggtta tgtattggta ctatttcttg ctgccagag    480 gcatcagggt ctggtggaag gaatgggtta ccagatttca aattatccaa tttgttttgg    540
atatcggttt catatatttt gctgtctacc aaaaagcagt tcacttgtat               590

<210> SEQ ID NO 17
<211> LENGTH: 278
<212> TYPE: PRT
<213> ORGANISM: Caenorhabditis elegans

<400> SEQUENCE: 17

Arg Thr Phe Lys Met Met Asp Gln Ile Leu Gly Thr Asn Phe Thr Tyr
 1               5                  10                  15

Glu Gly Ala Lys Glu Val Ala Arg Gly Leu Gly Phe Ser Ala Lys
            20                  25                  30

Leu Ala Val Gly Tyr Ile Ala Thr Ile Phe Gly Leu Lys Tyr Tyr Met
        35                  40                  45

Lys Asp Arg Lys Ala Phe Asp Leu Ser Thr Pro Leu Asn Ile Trp Asn
    50                  55                  60

Gly Ile Leu Ser Thr Phe Ser Leu Leu Gly Phe Leu Phe Thr Phe Pro
65                  70                  75                  80

Thr Leu Leu Ser Val Ile Arg Lys Asp Gly Phe Ser His Thr Tyr Ser
                85                  90                  95

His Val Ser Glu Leu Tyr Thr Asp Ser Thr Ser Gly Tyr Trp Ile Phe
            100                 105                 110

Leu Trp Val Ile Ser Lys Ile Pro Glu Leu Leu Asp Thr Val Phe Ile
        115                 120                 125

Val Leu Arg Lys Arg Pro Leu Ile Phe Met His Trp Tyr His His Ala
    130                 135                 140

Leu Thr Gly Tyr Tyr Ala Leu Val Cys Tyr His Glu Asp Ala Val His
145                 150                 155                 160
```

```
Met Val Trp Val Val Trp Met Asn Tyr Ile Ile His Ala Phe Met Tyr
                165                 170                 175
Gly Tyr Tyr Leu Leu Lys Ser Leu Lys Val Pro Ile Pro Pro Ser Val
            180                 185                 190
Ala Gln Ala Ile Thr Thr Ser Gln Met Val Gln Phe Ala Val Ala Ile
        195                 200                 205
Phe Ala Gln Val His Val Ser Tyr Lys His Tyr Val Glu Gly Val Glu
    210                 215                 220
Gly Leu Ala Tyr Ser Phe Arg Gly Thr Ala Ile Gly Phe Phe Met Leu
225                 230                 235                 240
Thr Thr Tyr Phe Tyr Leu Trp Ile Gln Phe Tyr Lys Glu His Tyr Leu
                245                 250                 255
Lys Asn Gly Gly Lys Lys Tyr Asn Leu Ala Lys Asp Gln Ala Lys Thr
            260                 265                 270
Gln Thr Lys Lys Ala Asn
        275

<210> SEQ ID NO 18
<211> LENGTH: 293
<212> TYPE: PRT
<213> ORGANISM: Mortierella alpina
<220> FEATURE:
<221> NAME/KEY: VARIANT
<222> LOCATION: (293)...(293)
<223> OTHER INFORMATION: Xaa = Unknown or Other at position 293

<400> SEQUENCE: 18

Ala Gln Ala Tyr Glu Leu Val Thr Gly Lys Ser Ile Asp Ser Phe Val
  1               5                  10                  15
Phe Gln Glu Gly Val Thr Pro Leu Ser Thr Gln Arg Glu Val Ala Met
             20                  25                  30
Trp Thr Ile Thr Tyr Phe Val Val Ile Phe Gly Gly Arg Gln Ile Met
         35                  40                  45
Lys Ser Gln Asp Ala Phe Lys Leu Lys Pro Leu Phe Ile Leu His Asn
 50                  55                  60
Phe Leu Leu Thr Ile Ala Ser Gly Ser Leu Leu Leu Leu Phe Ile Glu
 65                  70                  75                  80
Asn Leu Val Pro Ile Leu Ala Arg Asn Gly Leu Phe Tyr Ala Ile Cys
                 85                  90                  95
Asp Asp Gly Ala Trp Thr Gln Arg Leu Glu Leu Leu Tyr Tyr Leu Asn
            100                 105                 110
Tyr Leu Val Lys Tyr Trp Glu Leu Ala Asp Thr Val Phe Leu Val Leu
        115                 120                 125
Lys Lys Lys Pro Leu Glu Phe Leu His Tyr Phe His His Ser Met Thr
    130                 135                 140
Met Val Leu Cys Phe Val Gln Leu Gly Gly Tyr Thr Ser Val Ser Trp
145                 150                 155                 160
Val Pro Ile Thr Leu Asn Leu Thr Val His Val Phe Met Tyr Tyr Tyr
                165                 170                 175
Tyr Met Arg Ser Ala Ala Gly Val Arg Ile Trp Trp Lys Gln Tyr Leu
            180                 185                 190
Thr Thr Leu Gln Ile Val Gln Phe Val Leu Asp Leu Gly Phe Ile Tyr
        195                 200                 205
Phe Cys Ala Tyr Thr Tyr Phe Ala Phe Thr Tyr Phe Pro Trp Ala Pro
    210                 215                 220
Asn Val Gly Lys Cys Ala Gly Thr Glu Gly Ala Ala Leu Phe Gly Cys
```

-continued

```
            225                 230                 235                 240
Gly Leu Leu Ser Ser Tyr Leu Leu Phe Ile Asn Phe Tyr Arg Ile
                245                 250                 255

Thr Tyr Asn Ala Lys Ala Lys Ala Ala Lys Glu Arg Gly Ser Asn Phe
            260                 265                 270

Thr Pro Lys Thr Val Lys Ser Gly Gly Ser Pro Lys Lys Pro Ser Lys
            275                 280                 285

Ser Lys His Ile Xaa
        290
```

<210> SEQ ID NO 19
<211> LENGTH: 238
<212> TYPE: PRT
<213> ORGANISM: Caenorhabditis elegans

<400> SEQUENCE: 19

```
Ser Leu Leu Thr Asn Gln Asp Glu Val Phe Pro His Ile Arg Ala Arg
 1               5                  10                  15

Arg Phe Ile Gln Glu His Phe Gly Leu Phe Val Gln Met Ala Ile Ala
                20                  25                  30

Tyr Val Ile Leu Val Phe Ser Ile Lys Arg Phe Met Arg Asp Arg Glu
            35                  40                  45

Pro Phe Gln Leu Thr Thr Ala Leu Arg Leu Trp Asn Phe Phe Leu Ser
    50                  55                  60

Val Phe Ser Ile Tyr Gly Ser Trp Thr Met Phe Pro Phe Met Val Gln
65                  70                  75                  80

Gln Ile Arg Leu Tyr Gly Leu Tyr Gly Cys Gly Cys Glu Ala Leu Ser
                85                  90                  95

Asn Leu Pro Ser Gln Ala Glu Tyr Trp Leu Phe Leu Thr Ile Leu Ser
            100                 105                 110

Lys Ala Val Glu Phe Val Asp Thr Phe Phe Leu Val Leu Arg Lys Lys
        115                 120                 125

Pro Leu Ile Phe Leu His Trp Tyr His His Met Ala Thr Phe Val Phe
    130                 135                 140

Phe Cys Ser Asn Tyr Pro Thr Pro Ser Ser Gln Ser Arg Val Gly Val
145                 150                 155                 160

Ile Val Asn Leu Phe Val His Ala Phe Met Tyr Pro Tyr Tyr Phe Thr
                165                 170                 175

Arg Ser Met Asn Ile Lys Val Pro Ala Lys Ile Ser Met Ala Val Thr
            180                 185                 190

Val Leu Gln Leu Thr Gln Phe Met Cys Phe Ile Tyr Gly Cys Thr Leu
        195                 200                 205

Met Tyr Tyr Ser Leu Ala Thr Asn Gln Ala Arg Tyr Pro Ser Asn Thr
    210                 215                 220

Pro Ala Thr Leu Gln Cys Leu Ser Tyr Thr Leu His Leu Leu
225                 230                 235
```

<210> SEQ ID NO 20
<211> LENGTH: 289
<212> TYPE: PRT
<213> ORGANISM: Mortierella alpina
<220> FEATURE:
<221> NAME/KEY: VARIANT
<222> LOCATION: (289)...(289)
<223> OTHER INFORMATION: Xaa = Unknown or Other at position 289

<400> SEQUENCE: 20

-continued

```
Glu Leu Val Thr Gly Lys Ser Ile Asp Ser Phe Val Phe Gln Glu Gly
 1               5                  10                  15

Val Thr Pro Leu Ser Thr Gln Arg Glu Val Ala Met Trp Thr Ile Thr
            20                  25                  30

Tyr Phe Val Val Ile Phe Gly Gly Arg Gln Ile Met Lys Ser Gln Asp
        35                  40                  45

Ala Phe Lys Leu Lys Pro Leu Phe Ile Leu His Asn Phe Leu Leu Thr
50                  55                  60

Ile Ala Ser Gly Ser Leu Leu Leu Phe Ile Glu Asn Leu Val Pro
65                  70                  75                  80

Ile Leu Ala Arg Asn Gly Leu Phe Tyr Ala Ile Cys Asp Asp Gly Ala
                85                  90                  95

Trp Thr Gln Arg Leu Glu Leu Leu Tyr Tyr Leu Asn Tyr Leu Val Lys
                100                 105                 110

Tyr Trp Glu Leu Ala Asp Thr Val Phe Leu Val Leu Lys Lys Lys Pro
            115                 120                 125

Leu Glu Phe Leu His Tyr Phe His His Ser Met Thr Met Val Leu Cys
        130                 135                 140

Phe Val Gln Leu Gly Gly Tyr Thr Ser Val Ser Trp Val Pro Ile Thr
145                 150                 155                 160

Leu Asn Leu Thr Val His Val Phe Met Tyr Tyr Tyr Met Arg Ser
                165                 170                 175

Ala Ala Gly Val Arg Ile Trp Trp Lys Gln Tyr Leu Thr Thr Leu Gln
                180                 185                 190

Ile Val Gln Phe Val Leu Asp Leu Gly Phe Ile Tyr Phe Cys Ala Tyr
            195                 200                 205

Thr Tyr Phe Ala Phe Thr Tyr Phe Pro Trp Ala Pro Asn Val Gly Lys
        210                 215                 220

Cys Ala Gly Thr Glu Gly Ala Ala Leu Phe Gly Cys Gly Leu Leu Ser
225                 230                 235                 240

Ser Tyr Leu Leu Leu Phe Ile Asn Phe Tyr Arg Ile Thr Tyr Asn Ala
                245                 250                 255

Lys Ala Lys Ala Ala Lys Glu Arg Gly Ser Asn Phe Thr Pro Lys Thr
                260                 265                 270

Val Lys Ser Gly Gly Ser Pro Lys Lys Pro Ser Lys Ser Lys His Ile
            275                 280                 285

Xaa
```

<210> SEQ ID NO 21
<211> LENGTH: 101
<212> TYPE: PRT
<213> ORGANISM: Caenorhabditis elegans

<400> SEQUENCE: 21

```
Met Leu Tyr Ser Ile Thr Arg Arg Cys Tyr Thr Phe Phe Val Thr Ser
 1               5                  10                  15

Leu His Phe Tyr Gln Leu Tyr Val Thr Glu Cys Leu Glu Asn Val Ile
            20                  25                  30

Phe Asn Val Leu Val Asn Gly Gln Ser Ile Asn Ser Arg Trp Lys Asp
        35                  40                  45

Ala Glu Lys Thr Ile Thr Ser Phe Pro Phe His Phe Pro Gln Thr Phe
    50                  55                  60

Phe Gln Gln Pro His Ile Leu Thr Leu His Phe Leu Phe Val Phe
65                  70                  75                  80
```

```
Val Ser Val Thr Leu Val Thr Val Phe Lys Lys Pro Lys Cys Glu Phe
                85                  90                  95

Pro His Ser Leu Ala
            100

<210> SEQ ID NO 22
<211> LENGTH: 115
<212> TYPE: PRT
<213> ORGANISM: Mortierella alpina

<400> SEQUENCE: 22

Met Ala Ala Ile Leu Asp Lys Val Asn Phe Gly Ile Asp Gln Pro
1               5                   10                  15

Phe Gly Ile Lys Leu Asp Thr Tyr Phe Ala Gln Ala Tyr Glu Leu Val
            20                  25                  30

Thr Gly Lys Ser Ile Asp Ser Phe Val Phe Gln Glu Gly Val Thr Pro
        35                  40                  45

Leu Ser Thr Gln Arg Glu Val Ala Met Trp Thr Ile Thr Tyr Phe Val
    50                  55                  60

Val Ile Phe Gly Gly Arg Gln Ile Met Lys Ser Gln Asp Ala Phe Lys
65                  70                  75                  80

Leu Lys Pro Leu Phe Ile Leu His Asn Phe Leu Thr Ile Ala Ser
                85                  90                  95

Gly Ser Leu Leu Leu Phe Ile Glu Asn Leu Val Pro Ile Leu Ala
                100                 105                 110

Arg Asn Gly
        115

<210> SEQ ID NO 23
<211> LENGTH: 272
<212> TYPE: PRT
<213> ORGANISM: Mus musculus
<220> FEATURE:
<221> NAME/KEY: VARIANT
<222> LOCATION: (272)...(272)
<223> OTHER INFORMATION: Xaa = Unknown or Other at position 272

<400> SEQUENCE: 23

Met Asp Thr Ser Met Asn Phe Ser Arg Gly Leu Lys Met Asp Leu Met
1               5                   10                  15

Gln Pro Tyr Asp Phe Glu Thr Phe Gln Asp Leu Arg Pro Phe Leu Glu
            20                  25                  30

Glu Tyr Trp Val Ser Ser Phe Leu Ile Val Val Tyr Leu Leu Leu
        35                  40                  45

Ile Val Val Gly Gln Thr Tyr Met Arg Thr Arg Lys Ser Phe Ser Leu
    50                  55                  60

Gln Arg Pro Leu Ile Leu Trp Ser Phe Phe Leu Ala Ile Phe Ser Ile
65                  70                  75                  80

Leu Gly Thr Leu Arg Met Trp Lys Phe Met Ala Thr Val Met Phe Thr
                85                  90                  95

Val Gly Leu Lys Gln Thr Val Cys Phe Ala Ile Tyr Thr Asp Asp Ala
                100                 105                 110

Val Val Arg Phe Trp Ser Phe Leu Phe Leu Ser Lys Val Val Glu
            115                 120                 125

Leu Gly Asp Thr Ala Phe Ile Ile Leu Arg Lys Arg Pro Leu Ile Phe
    130                 135                 140

Val His Trp Tyr His His Ser Thr Val Leu Leu Phe Thr Ser Phe Gly
145                 150                 155                 160
```

```
Tyr Lys Asn Lys Val Pro Ser Gly Gly Trp Phe Met Thr Met Asn Phe
            165                 170                 175

Gly Val His Ser Val Met Tyr Thr Tyr Tyr Thr Met Lys Ala Ala Lys
            180                 185                 190

Leu Lys His Pro Asn Leu Leu Pro Met Val Ile Thr Ser Leu Gln Ile
            195                 200                 205

Leu Gln Met Val Leu Gly Thr Ile Phe Gly Ile Leu Asn Tyr Ile Trp
            210                 215                 220

Arg Gln Glu Lys Gly Cys His Thr Thr Thr Glu His Phe Phe Trp Ser
225                 230                 235                 240

Phe Met Leu Tyr Gly Thr Tyr Phe Ile Leu Phe Ala His Phe Phe His
            245                 250                 255

Arg Ala Tyr Leu Arg Pro Lys Gly Lys Val Ala Ser Lys Ser Gln Xaa
            260                 265                 270

<210> SEQ ID NO 24
<211> LENGTH: 318
<212> TYPE: PRT
<213> ORGANISM: Mortierella alpina
<220> FEATURE:
<221> NAME/KEY: VARIANT
<222> LOCATION: (318)...(318)
<223> OTHER INFORMATION: Xaa = Unknown or Other at position 318

<400> SEQUENCE: 24

Met Ala Ala Ile Leu Asp Lys Val Asn Phe Gly Ile Asp Gln Pro
1               5                   10                  15

Phe Gly Ile Lys Leu Asp Thr Tyr Phe Ala Gln Ala Tyr Glu Leu Val
                20                  25                  30

Thr Gly Lys Ser Ile Asp Ser Phe Val Phe Gln Glu Gly Val Thr Pro
            35                  40                  45

Leu Ser Thr Gln Arg Glu Val Ala Met Trp Thr Ile Thr Tyr Phe Val
50                  55                  60

Val Ile Phe Gly Gly Arg Gln Ile Met Lys Ser Gln Asp Ala Phe Lys
65                  70                  75                  80

Leu Lys Pro Leu Phe Ile Leu His Asn Phe Leu Leu Thr Ile Ala Ser
                85                  90                  95

Gly Ser Leu Leu Leu Leu Phe Ile Glu Asn Leu Val Pro Ile Leu Ala
            100                 105                 110

Arg Asn Gly Leu Phe Tyr Ala Ile Cys Asp Asp Gly Ala Trp Thr Gln
            115                 120                 125

Arg Leu Glu Leu Leu Tyr Tyr Leu Asn Tyr Leu Val Lys Tyr Trp Glu
130                 135                 140

Leu Ala Asp Thr Val Phe Leu Val Leu Lys Lys Lys Pro Leu Glu Phe
145                 150                 155                 160

Leu His Tyr Phe His His Ser Met Thr Met Val Leu Cys Phe Val Gln
                165                 170                 175

Leu Gly Gly Tyr Thr Ser Val Ser Trp Val Pro Ile Thr Leu Asn Leu
            180                 185                 190

Thr Val His Val Phe Met Tyr Tyr Tyr Met Arg Ser Ala Ala Gly
            195                 200                 205

Val Arg Ile Trp Trp Lys Gln Tyr Leu Thr Thr Leu Gln Ile Val Gln
            210                 215                 220

Phe Val Leu Asp Leu Gly Phe Ile Tyr Phe Cys Ala Tyr Thr Tyr Phe
225                 230                 235                 240
```

-continued

```
Ala Phe Thr Tyr Phe Pro Trp Ala Pro Asn Val Gly Lys Cys Ala Gly
            245                 250                 255

Thr Glu Gly Ala Ala Leu Phe Gly Cys Gly Leu Leu Ser Ser Tyr Leu
        260                 265                 270

Leu Leu Phe Ile Asn Phe Tyr Arg Ile Thr Tyr Asn Ala Lys Ala Lys
            275                 280                 285

Ala Ala Lys Glu Arg Gly Ser Asn Phe Thr Pro Lys Thr Val Lys Ser
        290                 295                 300

Gly Gly Ser Pro Lys Lys Pro Ser Lys Ser Lys His Ile Xaa
305                 310                 315

<210> SEQ ID NO 25
<211> LENGTH: 178
<212> TYPE: PRT
<213> ORGANISM: Mortierella alpina

<400> SEQUENCE: 25

Asn Leu Val Pro Ile Leu Ala Arg Asn Gly Leu Phe Tyr Ala Ile Cys
1               5                   10                  15

Asp Asp Gly Ala Trp Thr Gln Arg Leu Glu Leu Leu Tyr Tyr Leu Asn
            20                  25                  30

Tyr Leu Val Lys Tyr Trp Glu Leu Ala Asp Thr Val Phe Leu Val Leu
        35                  40                  45

Lys Lys Lys Pro Leu Glu Phe Leu His Tyr Phe His His Ser Met Thr
    50                  55                  60

Met Val Leu Cys Phe Val Gln Leu Gly Gly Tyr Thr Ser Val Ser Trp
65                  70                  75                  80

Val Pro Ile Thr Leu Asn Leu Thr Val His Val Phe Met Tyr Tyr Tyr
                85                  90                  95

Tyr Met Arg Ser Ala Ala Gly Val Arg Ile Trp Trp Lys Gln Tyr Leu
            100                 105                 110

Thr Thr Leu Gln Ile Val Gln Phe Val Leu Asp Leu Gly Phe Ile Tyr
        115                 120                 125

Phe Cys Ala Tyr Thr Tyr Phe Ala Phe Thr Tyr Phe Pro Trp Ala Pro
    130                 135                 140

Asn Val Gly Lys Cys Ala Gly Thr Glu Gly Ala Ala Leu Phe Gly Cys
145                 150                 155                 160

Gly Leu Leu Ser Ser Tyr Leu Leu Phe Ile Asn Phe Tyr Arg Ile
                165                 170                 175

Thr Tyr

<210> SEQ ID NO 26
<211> LENGTH: 147
<212> TYPE: PRT
<213> ORGANISM: Homo sapiens

<400> SEQUENCE: 26

Ser Leu Leu Val Val Lys Asp Leu Thr Tyr Leu Leu Pro Leu Cys Leu
1               5                   10                  15

Pro Gly Asp Thr Ile Phe Ile Ile Leu Arg Lys Gln Lys Leu Ile Phe
            20                  25                  30

Leu His Trp Tyr His His Ile Thr Val Leu Leu Tyr Ser Trp Tyr Ser
        35                  40                  45

Tyr Lys Asp Met Val Ala Gly Gly Trp Phe Met Thr Met Asn Tyr
    50                  55                  60

Gly Val His Ala Val Met Tyr Ser Tyr Tyr Ala Leu Arg Ala Ala Gly
```

```
                    65                  70                  75                  80
Phe Arg Val Ser Arg Lys Phe Ala Met Phe Ile Thr Leu Ser Gln Ile
                85                  90                  95

Thr Gln Met Leu Met Gly Cys Val Val Asn Tyr Leu Val Phe Cys Trp
            100                 105                 110

Met Gln His Asp Gln Cys His Ser His Phe Gln Asn Ile Phe Trp Ser
        115                 120                 125

Ser Leu Met Tyr Leu Ser Tyr Leu Val Leu Phe Cys His Phe Phe Phe
    130                 135                 140

Glu Ala Tyr
145

<210> SEQ ID NO 27
<211> LENGTH: 280
<212> TYPE: PRT
<213> ORGANISM: Mortierella alpina
<220> FEATURE:
<221> NAME/KEY: VARIANT
<222> LOCATION: (280)...(280)
<223> OTHER INFORMATION: Xaa = Unknown or Other at position 280

<400> SEQUENCE: 27

Ser Phe Val Phe Gln Glu Gly Val Thr Pro Leu Ser Thr Gln Arg Glu
1               5                   10                  15

Val Ala Met Trp Thr Ile Thr Tyr Phe Val Ile Phe Gly Gly Arg
                20                  25                  30

Gln Ile Met Lys Ser Gln Asp Ala Phe Lys Leu Lys Pro Leu Phe Ile
            35                  40                  45

Leu His Asn Phe Leu Leu Thr Ile Ala Ser Gly Ser Leu Leu Leu Leu
    50                  55                  60

Phe Ile Glu Asn Leu Val Pro Ile Leu Ala Arg Asn Gly Leu Phe Tyr
65                  70                  75                  80

Ala Ile Cys Asp Asp Gly Ala Trp Thr Gln Arg Leu Glu Leu Leu Tyr
                85                  90                  95

Tyr Leu Asn Tyr Leu Val Lys Tyr Trp Glu Leu Ala Asp Thr Val Phe
            100                 105                 110

Leu Val Leu Lys Lys Lys Pro Leu Glu Phe Leu His Tyr Phe His His
        115                 120                 125

Ser Met Thr Met Val Leu Cys Phe Val Gln Leu Gly Gly Tyr Thr Ser
    130                 135                 140

Val Ser Trp Val Pro Ile Thr Leu Asn Leu Thr Val His Val Phe Met
145                 150                 155                 160

Tyr Tyr Tyr Tyr Met Arg Ser Ala Ala Gly Val Arg Ile Trp Trp Lys
                165                 170                 175

Gln Tyr Leu Thr Thr Leu Gln Ile Val Gln Phe Val Leu Asp Leu Gly
            180                 185                 190

Phe Ile Tyr Phe Cys Ala Tyr Thr Tyr Phe Ala Phe Thr Tyr Phe Pro
        195                 200                 205

Trp Ala Pro Asn Val Gly Lys Cys Ala Gly Thr Glu Gly Ala Ala Leu
    210                 215                 220

Phe Gly Cys Gly Leu Leu Ser Ser Tyr Leu Leu Phe Ile Asn Phe
225                 230                 235                 240

Tyr Arg Ile Thr Tyr Asn Ala Lys Ala Lys Ala Ala Lys Glu Arg Gly
                245                 250                 255

Ser Asn Phe Thr Pro Lys Thr Val Lys Ser Gly Gly Ser Pro Lys Lys
            260                 265                 270
```

```
Pro Ser Lys Ser Lys His Ile Xaa
        275                 280

<210> SEQ ID NO 28
<211> LENGTH: 283
<212> TYPE: PRT
<213> ORGANISM: Unknown
<220> FEATURE:
<223> OTHER INFORMATION: Potential Mammalian Elongase
<221> NAME/KEY: VARIANT
<222> LOCATION: (282)...(282)
<223> OTHER INFORMATION: Xaa = Unknown or Other at position 282

<400> SEQUENCE: 28

Pro Arg Tyr Lys Ser Gln Arg Met Val Pro Pro Gly Gln Leu His Pro
 1               5                  10                  15

Tyr Val Cys Leu Phe Cys Tyr Leu Leu Thr His Cys Met Ala Gly Thr
            20                  25                  30

Lys Ile His Glu Glu Pro Ala Ala Val Leu Leu Pro Ser Ile Leu Gln
        35                  40                  45

Leu Tyr Asn Leu Gly Leu Thr Leu Leu Ser Leu Tyr Met Phe Tyr Glu
     50                  55                  60

Leu Val Thr Gly Val Trp Glu Gly Lys Tyr Asn Phe Phe Cys Gln Gly
65                  70                  75                  80

Thr Arg Ser Ala Gly Glu Ser Asp Met Lys Ile Ile Arg Val Leu Trp
                85                  90                  95

Trp Tyr Tyr Phe Ser Lys Leu Ile Glu Phe Met Asp Thr Phe Phe Phe
            100                 105                 110

Ile Leu Arg Lys Asn Asn His Gln Ile Thr Val Leu His Val Tyr His
        115                 120                 125

His Ala Thr Met Leu Asn Ile Trp Trp Phe Val Met Asn Trp Val Pro
    130                 135                 140

Cys Gly His Ser Tyr Phe Gly Ala Thr Leu Asn Ser Phe Ile His Val
145                 150                 155                 160

Leu Met Tyr Ser Tyr Tyr Gly Leu Ser Ser Ile Pro Ser Met Arg Pro
                165                 170                 175

Tyr Leu Trp Trp Lys Lys Tyr Ile Thr Gln Gly Gln Leu Val Gln Phe
            180                 185                 190

Val Leu Thr Ile Ile Gln Thr Thr Cys Gly Val Phe Trp Pro Cys Ser
        195                 200                 205

Phe Pro Leu Gly Trp Leu Phe Phe Gln Ile Gly Tyr Met Ile Ser Leu
    210                 215                 220

Ile Ala Leu Phe Thr Asn Phe Tyr Ile Gln Thr Tyr Asn Lys Lys Gly
225                 230                 235                 240

Ala Ser Arg Arg Lys Glu His Leu Lys Gly His Gln Asn Gly Ser Val
                245                 250                 255

Ala Ala Val Asn Gly His Thr Asn Ser Phe Pro Ser Leu Glu Asn Ser
            260                 265                 270

Val Lys Pro Arg Lys Gln Arg Lys Asp Xaa Gln
        275                 280

<210> SEQ ID NO 29
<211> LENGTH: 446
<212> TYPE: PRT
<213> ORGANISM: Mortierella alpina

<400> SEQUENCE: 29
```

-continued

```
Met Gly Thr Asp Gln Gly Lys Thr Phe Thr Trp Glu Leu Ala Ala
  1               5                  10                  15

His Asn Thr Lys Asp Asp Leu Leu Leu Ala Ile Arg Gly Arg Val Tyr
             20                  25                  30

Asp Val Thr Lys Phe Leu Ser Arg His Pro Gly Gly Val Asp Thr Leu
             35                  40                  45

Leu Leu Gly Ala Gly Arg Asp Val Thr Pro Val Phe Glu Met Tyr His
 50                  55                  60

Ala Phe Gly Ala Ala Asp Ala Ile Met Lys Lys Tyr Tyr Val Gly Thr
 65                  70                  75                  80

Leu Val Ser Asn Glu Leu Pro Ile Phe Pro Glu Pro Thr Val Phe His
             85                  90                  95

Lys Thr Ile Lys Thr Arg Val Glu Gly Tyr Phe Thr Asp Arg Asn Ile
            100                 105                 110

Asp Pro Lys Asn Arg Pro Glu Ile Trp Gly Arg Tyr Ala Leu Ile Phe
            115                 120                 125

Gly Ser Leu Ile Ala Ser Tyr Tyr Ala Gln Leu Phe Val Pro Phe Val
            130                 135                 140

Val Glu Arg Thr Trp Leu Gln Val Val Phe Ala Ile Ile Met Gly Phe
145                 150                 155                 160

Ala Cys Ala Gln Val Gly Leu Asn Pro Leu His Asp Ala Ser His Phe
            165                 170                 175

Ser Val Thr His Asn Pro Thr Val Trp Lys Ile Leu Gly Ala Thr His
            180                 185                 190

Asp Phe Phe Asn Gly Ala Ser Tyr Leu Val Trp Met Tyr Gln His Met
            195                 200                 205

Leu Gly His His Pro Tyr Thr Asn Ile Ala Gly Ala Asp Pro Asp Val
            210                 215                 220

Ser Thr Ser Glu Pro Asp Val Arg Arg Ile Lys Pro Asn Gln Lys Trp
225                 230                 235                 240

Phe Val Asn His Ile Asn Gln His Met Phe Val Pro Phe Leu Tyr Gly
            245                 250                 255

Leu Leu Ala Phe Lys Val Arg Ile Gln Asp Ile Asn Ile Leu Tyr Phe
            260                 265                 270

Val Lys Thr Asn Asp Ala Ile Arg Val Asn Pro Ile Ser Thr Trp His
            275                 280                 285

Thr Val Met Phe Trp Gly Gly Lys Ala Phe Phe Val Trp Tyr Arg Leu
            290                 295                 300

Ile Val Pro Leu Gln Tyr Leu Pro Leu Gly Lys Val Leu Leu Leu Phe
305                 310                 315                 320

Thr Val Ala Asp Met Val Ser Ser Tyr Trp Leu Ala Leu Thr Phe Gln
            325                 330                 335

Ala Asn His Val Val Glu Glu Val Gln Trp Pro Leu Pro Asp Glu Asn
            340                 345                 350

Gly Ile Ile Gln Lys Asp Trp Ala Ala Met Gln Val Glu Thr Thr Gln
            355                 360                 365

Asp Tyr Ala His Asp Ser His Leu Trp Thr Ser Ile Thr Gly Ser Leu
            370                 375                 380

Asn Tyr Gln Ala Val His His Leu Phe Pro Asn Val Ser Gln His His
385                 390                 395                 400

Tyr Pro Asp Ile Leu Ala Ile Ile Lys Asn Thr Cys Ser Glu Tyr Lys
            405                 410                 415

Val Pro Tyr Leu Val Lys Asp Thr Phe Trp Gln Ala Phe Ala Ser His
```

```
                      420                 425                 430
Leu Glu His Leu Arg Val Leu Gly Leu Arg Pro Lys Glu Glu
            435                 440                 445

<210> SEQ ID NO 30
<211> LENGTH: 318
<212> TYPE: PRT
<213> ORGANISM: Mortierella alpina

<400> SEQUENCE: 30

Met Glu Ser Ile Ala Pro Phe Leu Pro Ser Lys Met Pro Gln Asp Leu
  1               5                  10                  15

Phe Met Asp Leu Ala Thr Ala Ile Gly Val Arg Ala Ala Pro Tyr Val
                 20                  25                  30

Asp Pro Leu Glu Ala Ala Leu Val Ala Gln Ala Glu Lys Tyr Ile Pro
             35                  40                  45

Thr Ile Val His His Thr Arg Gly Phe Leu Val Ala Val Glu Ser Pro
         50                  55                  60

Leu Ala Arg Glu Leu Pro Leu Met Asn Pro Phe His Val Leu Leu Ile
 65                  70                  75                  80

Val Leu Ala Tyr Leu Val Thr Val Phe Val Gly Met Gln Ile Met Lys
                 85                  90                  95

Asn Phe Glu Arg Phe Glu Val Lys Thr Phe Ser Leu Leu His Asn Phe
            100                 105                 110

Cys Leu Val Ser Ile Ser Ala Tyr Met Cys Gly Gly Ile Leu Tyr Glu
        115                 120                 125

Ala Tyr Gln Ala Asn Tyr Gly Leu Phe Glu Asn Ala Ala Asp His Thr
    130                 135                 140

Phe Lys Gly Leu Pro Met Ala Lys Met Ile Trp Leu Phe Tyr Phe Ser
145                 150                 155                 160

Lys Ile Met Glu Phe Val Asp Thr Met Ile Met Val Leu Lys Lys Asn
                165                 170                 175

Asn Arg Gln Ile Ser Phe Leu His Val Tyr His His Ser Ser Ile Phe
            180                 185                 190

Thr Ile Trp Trp Leu Val Thr Phe Val Ala Pro Asn Gly Glu Ala Tyr
        195                 200                 205

Phe Ser Ala Ala Leu Asn Ser Phe Ile His Val Ile Met Tyr Gly Tyr
    210                 215                 220

Tyr Phe Leu Ser Ala Leu Gly Phe Lys Gln Val Ser Phe Ile Lys Phe
225                 230                 235                 240

Tyr Ile Thr Arg Ser Gln Met Thr Gln Phe Cys Met Met Ser Val Gln
                245                 250                 255

Ser Ser Trp Asp Met Tyr Ala Met Lys Val Leu Gly Arg Pro Gly Tyr
            260                 265                 270

Pro Phe Phe Ile Thr Ala Leu Leu Trp Phe Tyr Met Trp Thr Met Leu
        275                 280                 285

Gly Leu Phe Tyr Asn Phe Tyr Arg Lys Asn Ala Lys Leu Ala Lys Gln
    290                 295                 300

Ala Lys Ala Asp Ala Ala Lys Glu Lys Ala Arg Lys Leu Gln
305                 310                 315

<210> SEQ ID NO 31
<211> LENGTH: 279
<212> TYPE: PRT
<213> ORGANISM: Mortierella alpina
```

-continued

```
<400> SEQUENCE: 31

Val Ala Gln Ala Glu Lys Tyr Ile Pro Thr Ile Val His His Thr Arg
  1               5                  10                  15

Gly Phe Leu Val Ala Val Glu Ser Pro Leu Ala Arg Glu Leu Pro Leu
                 20                  25                  30

Met Asn Pro Phe His Val Leu Leu Ile Val Leu Ala Tyr Leu Val Thr
                 35                  40                  45

Val Phe Val Gly Met Gln Ile Met Lys Asn Phe Glu Arg Phe Glu Val
 50                  55                  60

Lys Thr Phe Ser Leu Leu His Asn Phe Cys Leu Val Ser Ile Ser Ala
 65                  70                  75                  80

Tyr Met Cys Gly Gly Ile Leu Tyr Glu Ala Tyr Gln Ala Asn Tyr Gly
                 85                  90                  95

Leu Phe Glu Asn Ala Ala Asp His Thr Phe Lys Gly Leu Pro Met Ala
                100                 105                 110

Lys Met Ile Trp Leu Phe Tyr Phe Ser Lys Ile Met Glu Phe Val Asp
                115                 120                 125

Thr Met Ile Met Val Leu Lys Lys Asn Asn Arg Gln Ile Ser Phe Leu
130                 135                 140

His Val Tyr His His Ser Ser Ile Phe Thr Ile Trp Trp Leu Val Thr
145                 150                 155                 160

Phe Val Ala Pro Asn Gly Glu Ala Tyr Phe Ser Ala Ala Leu Asn Ser
                165                 170                 175

Phe Ile His Val Ile Met Tyr Gly Tyr Tyr Phe Leu Ser Ala Leu Gly
                180                 185                 190

Phe Lys Gln Val Ser Phe Ile Lys Phe Tyr Ile Thr Arg Ser Gln Met
                195                 200                 205

Thr Gln Phe Cys Met Met Ser Val Gln Ser Ser Trp Asp Met Tyr Ala
210                 215                 220

Met Lys Val Leu Gly Arg Pro Gly Tyr Pro Phe Phe Ile Thr Ala Leu
225                 230                 235                 240

Leu Trp Phe Tyr Met Trp Thr Met Leu Gly Leu Phe Tyr Asn Phe Tyr
                245                 250                 255

Arg Lys Asn Ala Lys Leu Ala Lys Gln Ala Lys Ala Asp Ala Ala Lys
                260                 265                 270

Glu Lys Ala Arg Lys Leu Gln
                275

<210> SEQ ID NO 32
<211> LENGTH: 301
<212> TYPE: PRT
<213> ORGANISM: Mortierella alpina
<220> FEATURE:
<221> NAME/KEY: VARIANT
<222> LOCATION: (301)...(301)
<223> OTHER INFORMATION: Xaa = Unknown or Other at position 301

<400> SEQUENCE: 32

Gly Ile Lys Leu Asp Thr Tyr Phe Ala Gln Ala Tyr Glu Leu Val Thr
  1               5                  10                  15

Gly Lys Ser Ile Asp Ser Phe Val Phe Gln Glu Gly Val Thr Pro Leu
                 20                  25                  30

Ser Thr Gln Arg Glu Val Ala Met Trp Thr Ile Thr Tyr Phe Val Val
                 35                  40                  45

Ile Phe Gly Gly Arg Gln Ile Met Lys Ser Gln Asp Ala Phe Lys Leu
 50                  55                  60
```

```
Lys Pro Leu Phe Ile Leu His Asn Phe Leu Leu Thr Ile Ala Ser Gly
 65                  70                  75                  80

Ser Leu Leu Leu Phe Ile Glu Asn Leu Val Pro Ile Leu Ala Arg
             85                  90                  95

Asn Gly Leu Phe Tyr Ala Ile Cys Asp Asp Gly Ala Trp Thr Gln Arg
            100                 105                 110

Leu Glu Leu Leu Tyr Tyr Leu Asn Tyr Leu Val Lys Tyr Trp Glu Leu
            115                 120                 125

Ala Asp Thr Val Phe Leu Val Leu Lys Lys Pro Leu Glu Phe Leu
        130                 135                 140

His Tyr Phe His His Ser Met Thr Met Val Leu Cys Phe Val Gln Leu
145                 150                 155                 160

Gly Gly Tyr Thr Ser Val Ser Trp Val Pro Ile Thr Leu Asn Leu Thr
                165                 170                 175

Val His Val Phe Met Tyr Tyr Tyr Met Arg Ser Ala Ala Gly Val
                180                 185                 190

Arg Ile Trp Trp Lys Gln Tyr Leu Thr Thr Leu Gln Ile Val Gln Phe
            195                 200                 205

Val Leu Asp Leu Gly Phe Ile Tyr Phe Cys Ala Tyr Thr Tyr Phe Ala
210                 215                 220

Phe Thr Tyr Phe Pro Trp Ala Pro Asn Val Gly Lys Cys Ala Gly Thr
225                 230                 235                 240

Glu Gly Ala Ala Leu Phe Gly Cys Gly Leu Leu Ser Ser Tyr Leu Leu
                245                 250                 255

Leu Phe Ile Asn Phe Tyr Arg Ile Thr Tyr Asn Ala Lys Ala Lys Ala
                260                 265                 270

Ala Lys Glu Arg Gly Ser Asn Phe Thr Pro Lys Thr Val Lys Ser Gly
            275                 280                 285

Gly Ser Pro Lys Lys Pro Ser Lys Ser Lys His Ile Xaa
            290                 295                 300

<210> SEQ ID NO 33
<211> LENGTH: 289
<212> TYPE: PRT
<213> ORGANISM: Mortierella alpina

<400> SEQUENCE: 33

Tyr Glu Leu Val Thr Gly Lys Ser Ile Asp Ser Phe Val Phe Gln Glu
  1               5                  10                  15

Gly Val Thr Pro Leu Ser Thr Gln Arg Glu Val Ala Met Trp Thr Ile
             20                  25                  30

Thr Tyr Phe Val Val Ile Phe Gly Gly Arg Gln Ile Met Lys Ser Gln
             35                  40                  45

Asp Ala Phe Lys Leu Lys Pro Leu Phe Ile Leu His Asn Phe Leu Leu
         50                  55                  60

Thr Ile Ala Ser Gly Ser Leu Leu Leu Phe Ile Glu Asn Leu Val
 65                  70                  75                  80

Pro Ile Leu Ala Arg Asn Gly Leu Phe Tyr Ala Ile Cys Asp Asp Gly
             85                  90                  95

Ala Trp Thr Gln Arg Leu Glu Leu Leu Tyr Tyr Leu Asn Tyr Leu Val
            100                 105                 110

Lys Tyr Trp Glu Leu Ala Asp Thr Val Phe Leu Val Leu Lys Lys Lys
            115                 120                 125

Pro Leu Glu Phe Leu His Tyr Phe His His Ser Met Thr Met Val Leu
```

```
            130                 135                 140
Cys Phe Val Gln Leu Gly Gly Tyr Thr Ser Val Ser Trp Val Pro Ile
145                 150                 155                 160

Thr Leu Asn Leu Thr Val His Val Phe Met Tyr Tyr Tyr Met Arg
                165                 170                 175

Ser Ala Ala Gly Val Arg Ile Trp Trp Lys Gln Tyr Leu Thr Thr Leu
                180                 185                 190

Gln Ile Val Gln Phe Val Leu Asp Leu Gly Phe Ile Tyr Phe Cys Ala
                195                 200                 205

Tyr Thr Tyr Phe Ala Phe Thr Tyr Phe Pro Trp Ala Pro Asn Val Gly
210                 215                 220

Lys Cys Ala Gly Thr Glu Gly Ala Ala Leu Phe Gly Cys Gly Leu Leu
225                 230                 235                 240

Ser Ser Tyr Leu Leu Leu Phe Ile Asn Phe Tyr Arg Ile Thr Tyr Asn
                245                 250                 255

Ala Lys Ala Lys Ala Ala Lys Glu Arg Gly Ser Asn Phe Thr Pro Lys
                260                 265                 270

Thr Val Lys Ser Gly Gly Ser Pro Lys Lys Pro Ser Lys Ser Lys His
                275                 280                 285

Ile
```

```
<210> SEQ ID NO 34
<211> LENGTH: 292
<212> TYPE: PRT
<213> ORGANISM: Homo sapiens
<220> FEATURE:
<221> NAME/KEY: VARIANT
<222> LOCATION: (292)...(292)
<223> OTHER INFORMATION: Xaa = Unknown or Other at position 292

<400> SEQUENCE: 34

Ser Thr Tyr Phe Lys Ala Leu Leu Gly Pro Arg Asp Thr Arg Val Lys
1               5                   10                  15

Gly Trp Phe Leu Leu Asp Asn Tyr Ile Pro Thr Phe Ile Cys Ser Val
                20                  25                  30

Ile Tyr Leu Leu Ile Val Trp Leu Gly Pro Lys Tyr Met Arg Asn Lys
                35                  40                  45

Gln Pro Phe Ser Cys Arg Gly Ile Leu Val Val Tyr Asn Leu Gly Leu
        50                  55                  60

Thr Leu Leu Ser Leu Tyr Met Phe Cys Glu Leu Val Thr Gly Val Trp
65                  70                  75                  80

Glu Gly Lys Tyr Asn Phe Phe Cys Gln Gly Thr Arg Thr Ala Gly Glu
                85                  90                  95

Ser Asp Met Lys Ile Ile Arg Val Leu Trp Trp Tyr Tyr Phe Ser Lys
                100                 105                 110

Leu Ile Glu Phe Met Asp Thr Phe Phe Ile Leu Arg Lys Asn Asn
                115                 120                 125

His Gln Ile Thr Val Leu His Val Tyr His Ala Ser Met Leu Asn
130                 135                 140

Ile Trp Trp Phe Val Met Asn Trp Val Pro Cys Gly His Ser Tyr Phe
145                 150                 155                 160

Gly Ala Thr Leu Asn Ser Phe Ile His Val Leu Met Tyr Ser Tyr Tyr
                165                 170                 175

Gly Leu Ser Ser Val Pro Ser Met Arg Pro Tyr Leu Trp Trp Lys Lys
                180                 185                 190
```

```
Tyr Ile Thr Gln Gly Gln Leu Leu Gln Phe Val Leu Thr Ile Ile Gln
            195                 200                 205

Thr Ser Cys Gly Val Ile Trp Pro Cys Thr Phe Pro Leu Gly Trp Leu
    210                 215                 220

Tyr Phe Gln Ile Gly Tyr Met Ile Ser Leu Ile Ala Leu Phe Thr Asn
225                 230                 235                 240

Phe Tyr Ile Gln Thr Tyr Asn Lys Lys Gly Ala Ser Arg Arg Lys Asp
                245                 250                 255

His Leu Lys Asp His Gln Asn Gly Ser Met Ala Ala Val Asn Gly His
                260                 265                 270

Thr Asn Ser Phe Ser Pro Leu Glu Asn Asn Val Lys Pro Arg Lys Leu
            275                 280                 285

Arg Lys Asp Xaa
    290

<210> SEQ ID NO 35
<211> LENGTH: 291
<212> TYPE: PRT
<213> ORGANISM: Mortierella alpina

<400> SEQUENCE: 35

Gln Ala Tyr Glu Leu Val Thr Gly Lys Ser Ile Asp Ser Phe Val Phe
1               5                   10                  15

Gln Glu Gly Val Thr Pro Leu Ser Thr Gln Arg Glu Val Ala Met Trp
            20                  25                  30

Thr Ile Thr Tyr Phe Val Val Ile Phe Gly Gly Arg Gln Ile Met Lys
        35                  40                  45

Ser Gln Asp Ala Phe Lys Leu Lys Pro Leu Phe Ile Leu His Asn Phe
50                  55                  60

Leu Leu Thr Ile Ala Ser Gly Ser Leu Leu Leu Phe Ile Glu Asn
65                  70                  75                  80

Leu Val Pro Ile Leu Ala Arg Asn Gly Leu Phe Tyr Ala Ile Cys Asp
                85                  90                  95

Asp Gly Ala Trp Thr Gln Arg Leu Glu Leu Leu Tyr Tyr Leu Asn Tyr
            100                 105                 110

Leu Val Lys Tyr Trp Glu Leu Ala Asp Thr Val Phe Leu Val Leu Lys
        115                 120                 125

Lys Lys Pro Leu Glu Phe Leu His Tyr Phe His His Ser Met Thr Met
    130                 135                 140

Val Leu Cys Phe Val Gln Leu Gly Gly Tyr Thr Ser Val Ser Trp Val
145                 150                 155                 160

Pro Ile Thr Leu Asn Leu Thr Val His Val Phe Met Tyr Tyr Tyr Tyr
                165                 170                 175

Met Arg Ser Ala Ala Gly Val Arg Ile Trp Trp Lys Gln Tyr Leu Thr
            180                 185                 190

Thr Leu Gln Ile Val Gln Phe Val Leu Asp Leu Gly Phe Ile Tyr Phe
        195                 200                 205

Cys Ala Tyr Thr Tyr Phe Ala Phe Thr Tyr Phe Pro Trp Ala Pro Asn
    210                 215                 220

Val Gly Lys Cys Ala Gly Thr Glu Gly Ala Ala Leu Phe Gly Cys Gly
225                 230                 235                 240

Leu Leu Ser Ser Tyr Leu Leu Phe Ile Asn Phe Tyr Arg Ile Thr
                245                 250                 255

Tyr Asn Ala Lys Ala Lys Ala Ala Lys Glu Arg Gly Ser Asn Phe Thr
            260                 265                 270
```

```
Pro Lys Thr Val Lys Ser Gly Gly Ser Pro Lys Pro Ser Lys Ser
        275                 280                 285

Lys His Ile
    290

<210> SEQ ID NO 36
<211> LENGTH: 276
<212> TYPE: PRT
<213> ORGANISM: Homo sapiens
<220> FEATURE:
<221> NAME/KEY: VARIANT
<222> LOCATION: (276)...(276)
<223> OTHER INFORMATION: Xaa = Unknown or Other at position 276

<400> SEQUENCE: 36

Val Asn Leu Tyr Gln Glu Val Met Lys His Ala Asp Pro Arg Ile Gln
 1               5                  10                  15

Gly Tyr Pro Leu Met Gly Ser Pro Leu Leu Met Thr Ser Ile Leu Leu
            20                  25                  30

Thr Tyr Val Tyr Phe Val Leu Ser Leu Gly Pro Arg Ile Met Ala Asn
        35                  40                  45

Arg Lys Pro Phe Gln Leu Arg Gly Phe Met Ile Val Tyr Asn Phe Ser
    50                  55                  60

Leu Val Ala Leu Ser Leu Tyr Ile Val Tyr Glu Phe Leu Met Ser Gly
65                  70                  75                  80

Trp Leu Ser Thr Tyr Thr Trp Arg Cys Asp Pro Val Asp Tyr Ser Asn
                85                  90                  95

Ser Pro Glu Ala Leu Arg Met Val Arg Val Ala Trp Leu Phe Leu Phe
            100                 105                 110

Ser Lys Phe Ile Glu Leu Met Asp Thr Val Ile Phe Ile Leu Arg Lys
        115                 120                 125

Lys Asp Gly Gln Val Thr Phe Leu His Val Phe His His Ser Val Leu
    130                 135                 140

Pro Trp Ser Trp Trp Trp Gly Val Lys Ile Ala Pro Gly Gly Met Gly
145                 150                 155                 160

Ser Phe His Ala Met Ile Asn Ser Ser Val His Val Ile Met Tyr Leu
                165                 170                 175

Tyr Tyr Gly Leu Ser Ala Phe Gly Pro Val Ala Gln Pro Tyr Leu Trp
            180                 185                 190

Trp Lys Lys His Met Thr Ala Ile Gln Leu Ile Gln Phe Val Leu Val
        195                 200                 205

Ser Leu His Ile Ser Gln Tyr Tyr Phe Met Ser Ser Cys Asn Tyr Gln
    210                 215                 220

Tyr Pro Val Ile Ile His Leu Ile Trp Met Tyr Gly Thr Ile Phe Phe
225                 230                 235                 240

Met Leu Phe Ser Asn Phe Trp Tyr His Ser Tyr Thr Lys Gly Lys Arg
                245                 250                 255

Leu Pro Arg Ala Leu Gln Gln Asn Gly Ala Pro Gly Ile Ala Lys Val
            260                 265                 270

Lys Ala Asn Xaa
        275

<210> SEQ ID NO 37
<211> LENGTH: 219
<212> TYPE: PRT
<213> ORGANISM: Mortierella alpina
```

-continued

```
<400> SEQUENCE: 37

Leu Leu Leu Leu Phe Ile Glu Asn Leu Val Pro Ile Leu Ala Arg Asn
 1               5                  10                  15

Gly Leu Phe Tyr Ala Ile Cys Asp Asp Gly Ala Trp Thr Gln Arg Leu
             20                  25                  30

Glu Leu Leu Tyr Tyr Leu Asn Tyr Leu Val Lys Tyr Trp Glu Leu Ala
             35                  40                  45

Asp Thr Val Phe Leu Val Leu Lys Lys Pro Leu Glu Phe Leu His
         50                  55                  60

Tyr Phe His His Ser Met Thr Met Val Leu Cys Phe Val Gln Leu Gly
 65                  70                  75                  80

Gly Tyr Thr Ser Val Ser Trp Val Pro Ile Thr Leu Asn Leu Thr Val
                 85                  90                  95

His Val Phe Met Tyr Tyr Tyr Met Arg Ser Ala Ala Gly Val Arg
                100                 105                 110

Ile Trp Trp Lys Gln Tyr Leu Thr Thr Leu Gln Ile Val Gln Phe Val
            115                 120                 125

Leu Asp Leu Gly Phe Ile Tyr Phe Cys Ala Tyr Thr Tyr Phe Ala Phe
130                 135                 140

Thr Tyr Phe Pro Trp Ala Pro Asn Val Gly Lys Cys Ala Gly Thr Glu
145                 150                 155                 160

Gly Ala Ala Leu Phe Gly Cys Gly Leu Leu Ser Ser Tyr Leu Leu Leu
                165                 170                 175

Phe Ile Asn Phe Tyr Arg Ile Thr Tyr Asn Ala Lys Ala Lys Ala Ala
            180                 185                 190

Lys Glu Arg Gly Ser Asn Phe Thr Pro Lys Thr Val Lys Ser Gly Gly
            195                 200                 205

Ser Pro Lys Lys Pro Ser Lys Ser Lys His Ile
        210                 215

<210> SEQ ID NO 38
<211> LENGTH: 204
<212> TYPE: PRT
<213> ORGANISM: Mus musculus

<400> SEQUENCE: 38

Ile Val Tyr Glu Phe Leu Met Ser Gly Trp Leu Ser Thr Tyr Thr Trp
 1               5                  10                  15

Arg Cys Asp Pro Ile Asp Phe Ser Asn Ser Pro Glu Ala Leu Arg Met
             20                  25                  30

Val Arg Val Ala Trp Leu Phe Met Leu Ser Lys Val Ile Glu Leu Met
             35                  40                  45

Asp Thr Val Ile Phe Ile Leu Arg Lys Lys Asp Gly Gln Val Thr Phe
         50                  55                  60

Leu His Val Phe His His Ser Val Leu Pro Trp Ser Trp Trp Trp Gly
 65                  70                  75                  80

Ile Lys Ile Ala Pro Gly Gly Met Gly Ser Phe His Ala Met Ile Asn
                 85                  90                  95

Ser Ser Val His Val Val Met Tyr Leu Tyr Tyr Gly Leu Ser Ala Leu
                100                 105                 110

Gly Pro Val Ala Gln Pro Tyr Leu Trp Trp Lys Lys His Met Thr Ala
            115                 120                 125

Ile Gln Leu Ile Gln Phe Val Leu Val Ser Leu His Ile Ser Gln Tyr
130                 135                 140
```

-continued

Tyr Phe Met Pro Ser Cys Asn Tyr Gln Tyr Pro Val Ile Ile His Leu
145                 150                 155                 160

Ile Trp Met Tyr Gly Thr Ile Phe Phe Ile Leu Phe Ser Asn Phe Trp
            165                 170                 175

Tyr His Ser Tyr Thr Lys Gly Lys Arg Leu Pro Arg Ala Val Gln Gln
            180                 185                 190

Asn Gly Ala Pro Ala Thr Thr Lys Val Lys Ala Asn
            195                 200

<210> SEQ ID NO 39
<211> LENGTH: 174
<212> TYPE: PRT
<213> ORGANISM: Mortierella alpina

<400> SEQUENCE: 39

Tyr Glu Leu Val Thr Gly Lys Ser Ile Asp Ser Phe Val Phe Gln Glu
1               5                   10                  15

Gly Val Thr Pro Leu Ser Thr Gln Arg Glu Val Ala Met Trp Thr Ile
            20                  25                  30

Thr Tyr Phe Val Ile Phe Gly Gly Arg Gln Ile Met Lys Ser Gln
            35                  40                  45

Asp Ala Phe Lys Leu Lys Pro Leu Phe Ile Leu His Asn Phe Leu Leu
    50                  55                  60

Thr Ile Ala Ser Gly Ser Leu Leu Leu Phe Ile Glu Asn Leu Val
65                  70                  75                  80

Pro Ile Leu Ala Arg Asn Gly Leu Phe Tyr Ala Ile Cys Asp Asp Gly
                85                  90                  95

Ala Trp Thr Gln Arg Leu Glu Leu Leu Tyr Tyr Leu Asn Tyr Leu Val
                100                 105                 110

Lys Tyr Trp Glu Leu Ala Asp Thr Val Phe Leu Val Leu Lys Lys Lys
            115                 120                 125

Pro Leu Glu Phe Leu His Tyr Phe His His Ser Met Thr Met Val Leu
    130                 135                 140

Cys Phe Val Gln Leu Gly Gly Tyr Thr Ser Val Ser Trp Val Pro Ile
145                 150                 155                 160

Thr Leu Asn Leu Thr Val His Val Phe Met Tyr Tyr Tyr Tyr
                165                 170

<210> SEQ ID NO 40
<211> LENGTH: 145
<212> TYPE: PRT
<213> ORGANISM: Mus musculus

<400> SEQUENCE: 40

Asn Ala Phe Leu Asp Asn Met Phe Gly Pro Arg Asp Ser Arg Val Arg
1               5                   10                  15

Gly Trp Phe Leu Leu Asp Ser Tyr Leu Pro Thr Phe Ile Leu Thr Ile
            20                  25                  30

Thr Tyr Leu Leu Ser Ile Trp Leu Gly Asn Lys Tyr Met Lys Asn Arg
            35                  40                  45

Pro Ala Leu Ser Leu Arg Gly Ile Leu Thr Leu Tyr Asn Leu Ala Ile
    50                  55                  60

Thr Leu Leu Ser Ala Tyr Met Leu Val Glu Leu Ile Leu Ser Ser Trp
65                  70                  75                  80

Glu Gly Gly Tyr Asn Leu Gln Cys Gln Asn Leu Asp Ser Ala Gly Glu
                85                  90                  95

```
Gly Asp Val Arg Val Ala Lys Val Leu Val Trp Tyr Tyr Phe Ser Lys
            100                 105                 110

Leu Val Glu Phe Leu Asp Thr Ile Phe Val Leu Arg Lys Lys Ala
        115                 120                 125

Asn Gln Ile Thr Phe Leu His Val Tyr His Ala Ser Met Phe Asn
    130                 135                 140

Ile
145

<210> SEQ ID NO 41
<211> LENGTH: 238
<212> TYPE: PRT
<213> ORGANISM: Mortierella alpina

<400> SEQUENCE: 41

Leu Ile Val Leu Ala Tyr Leu Val Thr Val Phe Val Gly Met Gln Ile
  1               5                  10                  15

Met Lys Asn Phe Glu Arg Phe Glu Val Lys Thr Phe Ser Leu Leu His
            20                  25                  30

Asn Phe Cys Leu Val Ser Ile Ser Ala Tyr Met Cys Gly Gly Ile Leu
        35                  40                  45

Tyr Glu Ala Tyr Gln Ala Asn Tyr Gly Leu Phe Glu Asn Ala Ala Asp
    50                  55                  60

His Thr Phe Lys Gly Leu Pro Met Ala Lys Met Ile Trp Leu Phe Tyr
65                  70                  75                  80

Phe Ser Lys Ile Met Glu Phe Val Asp Thr Met Ile Met Val Leu Lys
                85                  90                  95

Lys Asn Asn Arg Gln Ile Ser Phe Leu His Val Tyr His His Ser Ser
            100                 105                 110

Ile Phe Thr Ile Trp Trp Leu Val Thr Phe Val Ala Pro Asn Gly Glu
        115                 120                 125

Ala Tyr Phe Ser Ala Ala Leu Asn Ser Phe Ile His Val Ile Met Tyr
    130                 135                 140

Gly Tyr Tyr Phe Leu Ser Ala Leu Gly Phe Lys Gln Val Ser Phe Ile
145                 150                 155                 160

Lys Phe Tyr Ile Thr Arg Ser Gln Met Thr Gln Phe Cys Met Met Ser
                165                 170                 175

Val Gln Ser Ser Trp Asp Met Tyr Ala Met Lys Val Leu Gly Arg Pro
            180                 185                 190

Gly Tyr Pro Phe Phe Ile Thr Ala Leu Leu Trp Phe Tyr Met Trp Thr
        195                 200                 205

Met Leu Gly Leu Phe Tyr Asn Phe Tyr Arg Lys Asn Ala Lys Leu Ala
    210                 215                 220

Lys Gln Ala Lys Ala Asp Ala Ala Lys Glu Lys Ala Arg Lys
225                 230                 235

<210> SEQ ID NO 42
<211> LENGTH: 144
<212> TYPE: PRT
<213> ORGANISM: Homo sapiens

<400> SEQUENCE: 42

Leu Tyr Asn Leu Gly Ile Thr Leu Leu Ser Ala Tyr Met Leu Ala Glu
  1               5                  10                  15

Leu Ile Leu Ser Thr Trp Glu Gly Gly Tyr Asn Leu Gln Cys Gln Asp
            20                  25                  30
```

-continued

```
Leu Thr Ser Ala Gly Glu Ala Asp Ile Arg Val Ala Lys Val Leu Trp
            35                  40                  45

Trp Tyr Tyr Phe Ser Lys Ser Val Glu Phe Leu Asp Thr Ile Phe Phe
    50                  55                  60

Val Leu Arg Lys Lys Thr Ser Gln Ile Thr Phe Leu His Val Tyr His
65                  70                  75                  80

His Ala Ser Met Phe Asn Ile Trp Trp Cys Val Leu Asn Trp Ile Pro
                85                  90                  95

Cys Gly Gln Ser Phe Phe Gly Pro Thr Leu Asn Ser Phe Ile His Ile
                100                 105                 110

Leu Met Tyr Ser Tyr Tyr Gly Leu Ser Val Phe Pro Ser Met His Lys
            115                 120                 125

Tyr Leu Trp Trp Lys Lys Tyr Leu Thr Gln Ala Gln Leu Val Gln Phe
    130                 135                 140

<210> SEQ ID NO 43
<211> LENGTH: 278
<212> TYPE: PRT
<213> ORGANISM: Mortierella alpina

<400> SEQUENCE: 43

Ala Gln Ala Glu Lys Tyr Ile Pro Thr Ile Val His His Thr Arg Gly
1               5                   10                  15

Phe Leu Val Ala Val Glu Ser Pro Leu Ala Arg Glu Leu Pro Leu Met
            20                  25                  30

Asn Pro Phe His Val Leu Leu Ile Val Leu Ala Tyr Leu Val Thr Val
            35                  40                  45

Phe Val Gly Met Gln Ile Met Lys Asn Phe Glu Arg Phe Glu Val Lys
    50                  55                  60

Thr Phe Ser Leu Leu His Asn Phe Cys Leu Val Ser Ile Ser Ala Tyr
65                  70                  75                  80

Met Cys Gly Gly Ile Leu Tyr Glu Ala Tyr Gln Ala Asn Tyr Gly Leu
                85                  90                  95

Phe Glu Asn Ala Ala Asp His Thr Phe Lys Gly Leu Pro Met Ala Lys
                100                 105                 110

Met Ile Trp Leu Phe Tyr Phe Ser Lys Ile Met Glu Phe Val Asp Thr
            115                 120                 125

Met Ile Met Val Leu Lys Lys Asn Asn Arg Gln Ile Ser Phe Leu His
    130                 135                 140

Val Tyr His His Ser Ser Ile Phe Thr Ile Trp Trp Leu Val Thr Phe
145                 150                 155                 160

Val Ala Pro Asn Gly Glu Ala Tyr Phe Ser Ala Ala Leu Asn Ser Phe
                165                 170                 175

Ile His Val Ile Met Tyr Gly Tyr Tyr Phe Leu Ser Ala Leu Gly Phe
                180                 185                 190

Lys Gln Val Ser Phe Ile Lys Phe Tyr Ile Thr Arg Ser Gln Met Thr
            195                 200                 205

Gln Phe Cys Met Met Ser Val Gln Ser Ser Trp Asp Met Tyr Ala Met
    210                 215                 220

Lys Val Leu Gly Arg Pro Gly Tyr Pro Phe Ile Thr Ala Leu Leu
225                 230                 235                 240

Trp Phe Tyr Met Trp Thr Met Leu Gly Leu Phe Tyr Asn Phe Tyr Arg
                245                 250                 255

Lys Asn Ala Lys Leu Ala Lys Gln Ala Lys Ala Asp Ala Ala Lys Glu
                260                 265                 270
```

```
Lys Ala Arg Lys Leu Gln
        275

<210> SEQ ID NO 44
<211> LENGTH: 293
<212> TYPE: PRT
<213> ORGANISM: Homo sapiens

<400> SEQUENCE: 44

Met Glu His Phe Asp Ala Ser Leu Ser Thr Tyr Phe Lys Ala Leu Leu
 1               5                  10                  15

Gly Pro Arg Asp Thr Arg Val Lys Gly Trp Phe Leu Leu Asp Asn Tyr
            20                  25                  30

Ile Pro Thr Phe Ile Cys Ser Val Ile Tyr Leu Leu Ile Val Trp Leu
        35                  40                  45

Gly Pro Lys Tyr Met Arg Asn Lys Gln Pro Phe Ser Cys Arg Gly Ile
50                  55                  60

Leu Val Val Tyr Asn Leu Gly Leu Thr Leu Leu Ser Leu Tyr Met Phe
65                  70                  75                  80

Cys Glu Leu Val Thr Gly Val Trp Glu Gly Lys Tyr Asn Phe Phe Cys
                85                  90                  95

Gln Gly Thr Arg Thr Ala Gly Glu Ser Asp Met Lys Ile Ile Arg Val
            100                 105                 110

Leu Trp Trp Tyr Tyr Phe Ser Lys Leu Ile Glu Phe Met Asp Thr Phe
        115                 120                 125

Phe Phe Ile Leu Arg Lys Asn Asn His Gln Ile Thr Val Leu His Val
130                 135                 140

Tyr His His Ala Ser Met Leu Asn Ile Trp Trp Phe Val Met Asn Trp
145                 150                 155                 160

Val Pro Cys Gly His Ser Tyr Phe Gly Ala Thr Leu Asn Ser Phe Ile
                165                 170                 175

His Val Leu Met Tyr Ser Tyr Tyr Gly Leu Ser Ser Val Pro Ser Met
            180                 185                 190

Arg Pro Tyr Leu Trp Trp Lys Lys Tyr Ile Thr Gln Gly Gln Leu Leu
        195                 200                 205

Gln Phe Val Leu Thr Ile Ile Gln Thr Ser Cys Gly Val Ile Trp Pro
210                 215                 220

Cys Thr Phe Pro Leu Gly Trp Leu Tyr Phe Gln Ile Gly Tyr Met Ile
225                 230                 235                 240

Ser Leu Ile Ala Leu Phe Thr Asn Phe Tyr Ile Gln Thr Tyr Asn Lys
                245                 250                 255

Lys Gly Ala Ser Arg Arg Lys Asp His Leu Lys Asp His Gln Asn Gly
            260                 265                 270

Ser Met Ala Ala Val Asn Gly His Thr Asn Ser Phe Ser Pro Leu Glu
        275                 280                 285

Asn Asn Val Lys Pro
        290

<210> SEQ ID NO 45
<211> LENGTH: 182
<212> TYPE: PRT
<213> ORGANISM: Mortierella alpina

<400> SEQUENCE: 45

Phe Glu Asn Ala Ala Asp His Thr Phe Lys Gly Leu Pro Met Ala Lys
 1               5                  10                  15
```

```
Met Ile Trp Leu Phe Tyr Phe Ser Lys Ile Met Glu Phe Val Asp Thr
             20                  25                  30

Met Ile Met Val Leu Lys Lys Asn Asn Arg Gln Ile Ser Phe Leu His
         35                  40                  45

Val Tyr His His Ser Ser Ile Phe Thr Ile Trp Trp Leu Val Thr Phe
     50                  55                  60

Val Ala Pro Asn Gly Glu Ala Tyr Phe Ser Ala Ala Leu Asn Ser Phe
 65                  70                  75                  80

Ile His Val Ile Met Tyr Gly Tyr Tyr Phe Leu Ser Ala Leu Gly Phe
                 85                  90                  95

Lys Gln Val Ser Phe Ile Lys Phe Tyr Ile Thr Arg Ser Gln Met Thr
            100                 105                 110

Gln Phe Cys Met Met Ser Val Gln Ser Ser Trp Asp Met Tyr Ala Met
            115                 120                 125

Lys Val Leu Gly Arg Pro Gly Tyr Pro Phe Phe Ile Thr Ala Leu Leu
130                 135                 140

Trp Phe Tyr Met Trp Thr Met Leu Gly Leu Phe Tyr Asn Phe Tyr Arg
145                 150                 155                 160

Lys Asn Ala Lys Leu Ala Lys Gln Ala Lys Ala Asp Ala Ala Lys Glu
                165                 170                 175

Lys Ala Arg Lys Leu Gln
            180

<210> SEQ ID NO 46
<211> LENGTH: 141
<212> TYPE: PRT
<213> ORGANISM: Homo sapiens
<220> FEATURE:
<221> NAME/KEY: VARIANT
<222> LOCATION: (141)...(141)
<223> OTHER INFORMATION: Xaa = Unknown or Other at position 141

<400> SEQUENCE: 46

Asp Thr Ile Phe Ile Ile Leu Arg Lys Gln Lys Leu Ile Phe Leu His
 1               5                  10                  15

Trp Tyr His His Ile Thr Val Leu Leu Tyr Ser Trp Tyr Ser Tyr Lys
                 20                  25                  30

Asp Met Val Ala Gly Gly Trp Phe Met Thr Met Asn Tyr Gly Val
             35                  40                  45

His Ala Val Met Tyr Ser Tyr Tyr Ala Leu Arg Ala Ala Gly Phe Arg
         50                  55                  60

Val Ser Arg Lys Phe Ala Met Phe Ile Thr Leu Ser Gln Ile Thr Gln
 65                  70                  75                  80

Met Leu Met Gly Cys Val Val Asn Tyr Leu Val Phe Cys Trp Met Gln
                 85                  90                  95

His Asp Gln Cys His Ser His Phe Gln Asn Ile Phe Trp Ser Ser Leu
            100                 105                 110

Met Tyr Leu Ser Tyr Leu Val Leu Phe Cys His Phe Phe Glu Ala
            115                 120                 125

Tyr Ile Gly Lys Met Arg Lys Thr Thr Lys Ala Glu Xaa
130                 135                 140

<210> SEQ ID NO 47
<211> LENGTH: 241
<212> TYPE: PRT
<213> ORGANISM: Mortierella alpina
```

<400> SEQUENCE: 47

| Leu | Leu | Ile | Val | Leu | Ala | Tyr | Leu | Val | Thr | Val | Phe | Val | Gly | Met | Gln |
|---|---|---|---|---|---|---|---|---|---|---|---|---|---|---|---|
| 1 | | | | 5 | | | | | 10 | | | | | 15 | |

| Ile | Met | Lys | Asn | Phe | Glu | Arg | Phe | Glu | Val | Lys | Thr | Phe | Ser | Leu | Leu |
| | | | 20 | | | | | 25 | | | | | 30 | | |

| His | Asn | Phe | Cys | Leu | Val | Ser | Ile | Ser | Ala | Tyr | Met | Cys | Gly | Gly | Ile |
| | | | 35 | | | | | 40 | | | | | 45 | | |

| Leu | Tyr | Glu | Ala | Tyr | Gln | Ala | Asn | Tyr | Gly | Leu | Phe | Glu | Asn | Ala | Ala |
| | 50 | | | | | 55 | | | | | 60 | | | | |

| Asp | His | Thr | Phe | Lys | Gly | Leu | Pro | Met | Ala | Lys | Met | Ile | Trp | Leu | Phe |
| 65 | | | | | 70 | | | | | 75 | | | | | 80 |

| Tyr | Phe | Ser | Lys | Ile | Met | Glu | Phe | Val | Asp | Thr | Met | Ile | Met | Val | Leu |
| | | | | 85 | | | | | 90 | | | | | 95 | |

| Lys | Lys | Asn | Asn | Arg | Gln | Ile | Ser | Phe | Leu | His | Val | Tyr | His | His | Ser |
| | | | 100 | | | | | 105 | | | | | 110 | | |

| Ser | Ile | Phe | Thr | Ile | Trp | Trp | Leu | Val | Thr | Phe | Val | Ala | Pro | Asn | Gly |
| | | | 115 | | | | | 120 | | | | | 125 | | |

| Glu | Ala | Tyr | Phe | Ser | Ala | Ala | Leu | Asn | Ser | Phe | Ile | His | Val | Ile | Met |
| | | 130 | | | | | 135 | | | | | 140 | | | |

| Tyr | Gly | Tyr | Tyr | Phe | Leu | Ser | Ala | Leu | Gly | Phe | Lys | Gln | Val | Ser | Phe |
| 145 | | | | | 150 | | | | | 155 | | | | | 160 |

| Ile | Lys | Phe | Tyr | Ile | Thr | Arg | Ser | Gln | Met | Thr | Gln | Phe | Cys | Met | Met |
| | | | | 165 | | | | | 170 | | | | | 175 | |

| Ser | Val | Gln | Ser | Ser | Trp | Asp | Met | Tyr | Ala | Met | Lys | Val | Leu | Gly | Arg |
| | | | 180 | | | | | 185 | | | | | 190 | | |

| Pro | Gly | Tyr | Pro | Phe | Phe | Ile | Thr | Ala | Leu | Leu | Trp | Phe | Tyr | Met | Trp |
| | | 195 | | | | | 200 | | | | | 205 | | | |

| Thr | Met | Leu | Gly | Leu | Phe | Tyr | Asn | Phe | Tyr | Arg | Lys | Asn | Ala | Lys | Leu |
| | 210 | | | | | 215 | | | | | 220 | | | | |

| Ala | Lys | Gln | Ala | Lys | Ala | Asp | Ala | Ala | Lys | Glu | Lys | Ala | Arg | Lys | Leu |
| 225 | | | | | 230 | | | | | 235 | | | | | 240 |

Gln

<210> SEQ ID NO 48
<211> LENGTH: 217
<212> TYPE: PRT
<213> ORGANISM: Mus musculus

<400> SEQUENCE: 48

| Ile | Val | Tyr | Asn | Phe | Ser | Leu | Val | Ile | Leu | Ser | Leu | Tyr | Ile | Val | Tyr |
|---|---|---|---|---|---|---|---|---|---|---|---|---|---|---|---|
| 1 | | | | 5 | | | | | 10 | | | | | 15 | |

| Glu | Phe | Leu | Met | Ser | Gly | Trp | Leu | Ser | Thr | Tyr | Thr | Trp | Arg | Cys | Asp |
| | | | 20 | | | | | 25 | | | | | 30 | | |

| Pro | Ile | Asp | Phe | Ser | Asn | Ser | Pro | Glu | Ala | Leu | Arg | Met | Val | Arg | Val |
| | | | 35 | | | | | 40 | | | | | 45 | | |

| Ala | Trp | Leu | Phe | Met | Leu | Ser | Lys | Val | Ile | Glu | Leu | Met | Asp | Thr | Val |
| | 50 | | | | | 55 | | | | | 60 | | | | |

| Ile | Phe | Ile | Leu | Arg | Lys | Lys | Asp | Gly | Gln | Val | Thr | Phe | Leu | His | Val |
| 65 | | | | | 70 | | | | | 75 | | | | | 80 |

| Phe | His | His | Ser | Val | Leu | Pro | Trp | Ser | Trp | Trp | Trp | Gly | Ile | Lys | Ile |
| | | | | 85 | | | | | 90 | | | | | 95 | |

| Ala | Pro | Gly | Gly | Met | Gly | Ser | Phe | His | Ala | Met | Ile | Asn | Ser | Ser | Val |
| | | | 100 | | | | | 105 | | | | | 110 | | |

| His | Val | Val | Met | Tyr | Leu | Tyr | Tyr | Gly | Leu | Ser | Ala | Leu | Gly | Pro | Val |

```
                115                 120                 125
Ala Gln Pro Tyr Leu Trp Trp Lys Lys His Met Thr Ala Ile Gln Leu
        130                 135                 140

Ile Gln Phe Val Leu Val Ser Leu His Ile Ser Gln Tyr Tyr Phe Met
145                 150                 155                 160

Pro Ser Cys Asn Tyr Gln Tyr Pro Val Ile Ile His Leu Ile Trp Met
                165                 170                 175

Tyr Gly Thr Ile Phe Phe Ile Leu Phe Ser Asn Phe Trp Tyr His Ser
                180                 185                 190

Tyr Thr Lys Gly Lys Arg Leu Pro Arg Ala Val Gln Gln Asn Gly Ala
        195                 200                 205

Pro Ala Thr Thr Lys Val Lys Ala Asn
        210                 215

<210> SEQ ID NO 49
<211> LENGTH: 178
<212> TYPE: PRT
<213> ORGANISM: Mortierella alpina

<400> SEQUENCE: 49

Pro Thr Ile Val His His Thr Arg Gly Phe Leu Val Ala Val Glu Ser
1               5                   10                  15

Pro Leu Ala Arg Glu Leu Pro Leu Met Asn Pro Phe His Val Leu Leu
                20                  25                  30

Ile Val Leu Ala Tyr Leu Val Thr Val Phe Val Gly Met Gln Ile Met
                35                  40                  45

Lys Asn Phe Glu Arg Phe Glu Val Lys Thr Phe Ser Leu Leu His Asn
        50                  55                  60

Phe Cys Leu Val Ser Ile Ser Ala Tyr Met Cys Gly Gly Ile Leu Tyr
65                  70                  75                  80

Glu Ala Tyr Gln Ala Asn Tyr Gly Leu Phe Glu Asn Ala Ala Asp His
                85                  90                  95

Thr Phe Lys Gly Leu Pro Met Ala Lys Met Ile Trp Leu Phe Tyr Phe
                100                 105                 110

Ser Lys Ile Met Glu Phe Val Asp Thr Met Ile Met Val Leu Lys Lys
        115                 120                 125

Asn Asn Arg Gln Ile Ser Phe Leu His Val Tyr His His Ser Ser Ile
        130                 135                 140

Phe Thr Ile Trp Trp Leu Val Thr Phe Val Ala Pro Asn Gly Glu Ala
145                 150                 155                 160

Tyr Phe Ser Ala Ala Leu Asn Ser Phe Ile His Val Ile Met Tyr Gly
                165                 170                 175

Tyr Tyr

<210> SEQ ID NO 50
<211> LENGTH: 148
<212> TYPE: PRT
<213> ORGANISM: Mus musculus

<400> SEQUENCE: 50

Asn Glu Val Asn Ala Phe Leu Asp Asn Met Phe Gly Pro Arg Asp Ser
1               5                   10                  15

Arg Val Arg Gly Trp Phe Leu Leu Asp Ser Tyr Leu Pro Thr Phe Ile
                20                  25                  30

Leu Thr Ile Thr Tyr Leu Leu Ser Ile Trp Leu Gly Asn Lys Tyr Met
                35                  40                  45
```

```
Lys Asn Arg Pro Ala Leu Ser Leu Arg Gly Ile Leu Thr Leu Tyr Asn
 50                  55                  60

Leu Ala Ile Thr Leu Leu Ser Ala Tyr Met Leu Val Glu Leu Ile Leu
 65                  70                  75                  80

Ser Ser Trp Glu Gly Gly Tyr Asn Leu Gln Cys Gln Asn Leu Asp Ser
                 85                  90                  95

Ala Gly Glu Gly Asp Val Arg Val Ala Lys Val Leu Val Trp Tyr Tyr
                100                 105                 110

Phe Ser Lys Leu Val Glu Phe Leu Asp Thr Ile Phe Phe Val Leu Arg
                115                 120                 125

Lys Lys Ala Asn Gln Ile Thr Phe Leu His Val Tyr His His Ala Ser
130                 135                 140

Met Phe Asn Ile
145

<210> SEQ ID NO 51
<211> LENGTH: 302
<212> TYPE: PRT
<213> ORGANISM: Mortierella alpina

<400> SEQUENCE: 51

Phe Met Asp Leu Ala Thr Ala Ile Gly Val Arg Ala Ala Pro Tyr Val
  1               5                  10                  15

Asp Pro Leu Glu Ala Ala Leu Val Ala Gln Ala Glu Lys Tyr Ile Pro
                 20                  25                  30

Thr Ile Val His His Thr Arg Gly Phe Leu Val Ala Val Glu Ser Pro
                 35                  40                  45

Leu Ala Arg Glu Leu Pro Leu Met Asn Pro Phe His Val Leu Leu Ile
 50                  55                  60

Val Leu Ala Tyr Leu Val Thr Val Phe Val Gly Met Gln Ile Met Lys
 65                  70                  75                  80

Asn Phe Glu Arg Phe Glu Val Lys Thr Phe Ser Leu Leu His Asn Phe
                 85                  90                  95

Cys Leu Val Ser Ile Ser Ala Tyr Met Cys Gly Gly Ile Leu Tyr Glu
                100                 105                 110

Ala Tyr Gln Ala Asn Tyr Gly Leu Phe Glu Asn Ala Ala Asp His Thr
                115                 120                 125

Phe Lys Gly Leu Pro Met Ala Lys Met Ile Trp Leu Phe Tyr Phe Ser
130                 135                 140

Lys Ile Met Glu Phe Val Asp Thr Met Ile Met Val Leu Lys Lys Asn
145                 150                 155                 160

Asn Arg Gln Ile Ser Phe Leu His Val Tyr His His Ser Ser Ile Phe
                165                 170                 175

Thr Ile Trp Trp Leu Val Thr Phe Val Ala Pro Asn Gly Glu Ala Tyr
                180                 185                 190

Phe Ser Ala Ala Leu Asn Ser Phe Ile His Val Ile Met Tyr Gly Tyr
                195                 200                 205

Tyr Phe Leu Ser Ala Leu Gly Phe Lys Gln Val Ser Phe Ile Lys Phe
                210                 215                 220

Tyr Ile Thr Arg Ser Gln Met Thr Gln Phe Cys Met Met Ser Val Gln
225                 230                 235                 240

Ser Ser Trp Asp Met Tyr Ala Met Lys Val Leu Gly Arg Pro Gly Tyr
                245                 250                 255

Pro Phe Phe Ile Thr Ala Leu Leu Trp Phe Tyr Met Trp Thr Met Leu
```

```
                    260                 265                 270
Gly Leu Phe Tyr Asn Phe Tyr Arg Lys Asn Ala Lys Leu Ala Lys Gln
                275                 280                 285
Ala Lys Ala Asp Ala Ala Lys Glu Lys Ala Arg Lys Leu Gln
    290                 295                 300

<210> SEQ ID NO 52
<211> LENGTH: 271
<212> TYPE: PRT
<213> ORGANISM: Mus musculus

<400> SEQUENCE: 52

Met Asp Thr Ser Met Asn Phe Ser Arg Gly Leu Lys Met Asp Leu Met
  1               5                  10                  15
Gln Pro Tyr Asp Phe Glu Thr Phe Gln Asp Leu Arg Pro Phe Leu Glu
                 20                  25                  30
Glu Tyr Trp Val Ser Ser Phe Leu Ile Val Val Tyr Leu Leu Leu
             35                  40                  45
Ile Val Val Gly Gln Thr Tyr Met Arg Thr Arg Lys Ser Phe Ser Leu
         50                  55                  60
Gln Arg Pro Leu Ile Leu Trp Ser Phe Phe Leu Ala Ile Phe Ser Ile
 65                  70                  75                  80
Leu Gly Thr Leu Arg Met Trp Lys Phe Met Ala Thr Val Met Phe Thr
                 85                  90                  95
Val Gly Leu Lys Gln Thr Val Cys Phe Ala Ile Tyr Thr Asp Asp Ala
                100                 105                 110
Val Val Arg Phe Trp Ser Phe Leu Phe Leu Leu Ser Lys Val Val Glu
            115                 120                 125
Leu Gly Asp Thr Ala Phe Ile Ile Leu Arg Lys Arg Pro Leu Ile Phe
        130                 135                 140
Val His Trp Tyr His His Ser Thr Val Leu Leu Phe Thr Ser Phe Gly
145                 150                 155                 160
Tyr Lys Asn Lys Val Pro Ser Gly Gly Trp Phe Met Thr Met Asn Phe
                165                 170                 175
Gly Val His Ser Val Met Tyr Thr Tyr Tyr Thr Met Lys Ala Ala Lys
            180                 185                 190
Leu Lys His Pro Asn Leu Leu Pro Met Val Ile Thr Ser Leu Gln Ile
        195                 200                 205
Leu Gln Met Val Leu Gly Thr Ile Gly Ile Leu Asn Tyr Ile Trp
    210                 215                 220
Arg Gln Glu Lys Gly Cys His Thr Thr Thr Glu His Phe Phe Trp Ser
225                 230                 235                 240
Phe Met Leu Tyr Gly Thr Tyr Phe Ile Leu Phe Ala His Phe Phe His
                245                 250                 255
Arg Ala Tyr Leu Arg Pro Lys Gly Lys Val Ala Ser Lys Ser Gln
            260                 265                 270

<210> SEQ ID NO 53
<211> LENGTH: 265
<212> TYPE: PRT
<213> ORGANISM: Mortierella alpina

<400> SEQUENCE: 53

Thr Arg Gly Phe Leu Val Ala Val Glu Ser Pro Leu Ala Arg Glu Leu
  1               5                  10                  15
Pro Leu Met Asn Pro Phe His Val Leu Leu Ile Val Leu Ala Tyr Leu
```

-continued

```
                 20                  25                  30
Val Thr Val Phe Val Gly Met Gln Ile Met Lys Asn Phe Glu Arg Phe
            35                  40                  45
Glu Val Lys Thr Phe Ser Leu Leu His Asn Phe Cys Leu Val Ser Ile
        50                  55                  60
Ser Ala Tyr Met Cys Gly Gly Ile Leu Tyr Glu Ala Tyr Gln Ala Asn
65                  70                  75                  80
Tyr Gly Leu Phe Glu Asn Ala Ala Asp His Thr Phe Lys Gly Leu Pro
                85                  90                  95
Met Ala Lys Met Ile Trp Leu Phe Tyr Phe Ser Lys Ile Met Glu Phe
            100                 105                 110
Val Asp Thr Met Ile Met Val Leu Lys Lys Asn Asn Arg Gln Ile Ser
        115                 120                 125
Phe Leu His Val Tyr His His Ser Ser Ile Phe Thr Ile Trp Trp Leu
    130                 135                 140
Val Thr Phe Val Ala Pro Asn Gly Glu Ala Tyr Phe Ser Ala Ala Leu
145                 150                 155                 160
Asn Ser Phe Ile His Val Ile Met Tyr Gly Tyr Tyr Phe Leu Ser Ala
                165                 170                 175
Leu Gly Phe Lys Gln Val Ser Phe Ile Lys Phe Tyr Ile Thr Arg Ser
            180                 185                 190
Gln Met Thr Gln Phe Cys Met Met Ser Val Gln Ser Ser Trp Asp Met
        195                 200                 205
Tyr Ala Met Lys Val Leu Gly Arg Pro Gly Tyr Pro Phe Phe Ile Thr
    210                 215                 220
Ala Leu Leu Trp Phe Tyr Met Trp Thr Met Leu Gly Leu Phe Tyr Asn
225                 230                 235                 240
Phe Tyr Arg Lys Asn Ala Lys Leu Ala Lys Gln Ala Lys Ala Asp Ala
                245                 250                 255
Ala Lys Glu Lys Ala Arg Lys Leu Gln
            260                 265

<210> SEQ ID NO 54
<211> LENGTH: 265
<212> TYPE: PRT
<213> ORGANISM: Caenorhabditis elegans

<400> SEQUENCE: 54

Ala Thr His Gly Pro Lys Asn Phe Pro Asp Ala Glu Gly Arg Lys Phe
1               5                   10                  15
Phe Ala Asp His Phe Asp Val Thr Ile Gln Ala Ser Ile Leu Tyr Met
                20                  25                  30
Val Val Val Phe Gly Thr Lys Trp Phe Met Arg Asn Arg Gln Pro Phe
            35                  40                  45
Gln Leu Thr Ile Pro Leu Asn Ile Trp Asn Phe Ile Leu Ala Ala Phe
        50                  55                  60
Ser Ile Ala Gly Ala Val Lys Met Thr Pro Glu Phe Phe Gly Thr Ile
65                  70                  75                  80
Ala Asn Lys Gly Ile Val Ala Ser Tyr Cys Lys Val Phe Asp Phe Thr
                85                  90                  95
Lys Gly Glu Asn Gly Tyr Trp Val Trp Leu Phe Met Ala Ser Lys Leu
            100                 105                 110
Phe Glu Leu Val Asp Thr Ile Phe Leu Val Leu Arg Lys Arg Pro Leu
        115                 120                 125
```

```
Met Phe Leu His Trp Tyr His His Ile Leu Thr Met Ile Tyr Ala Trp
        130                 135                 140

Tyr Ser His Pro Leu Thr Pro Gly Phe Asn Arg Tyr Gly Ile Tyr Leu
145                 150                 155                 160

Asn Phe Val Val His Ala Phe Met Tyr Ser Tyr Tyr Phe Leu Arg Ser
                165                 170                 175

Met Lys Ile Arg Val Pro Gly Phe Ile Ala Gln Ala Ile Thr Ser Leu
            180                 185                 190

Gln Ile Val Gln Phe Ile Ile Ser Cys Ala Val Leu Ala His Leu Gly
        195                 200                 205

Tyr Leu Met His Phe Thr Asn Ala Asn Cys Asp Phe Glu Pro Ser Val
    210                 215                 220

Phe Lys Leu Ala Val Phe Met Asp Thr Thr Tyr Leu Ala Leu Phe Val
225                 230                 235                 240

Asn Phe Phe Leu Gln Ser Tyr Val Leu Arg Gly Gly Lys Asp Lys Tyr
                245                 250                 255

Lys Ala Val Pro Lys Lys Lys Asn Asn
            260                 265

<210> SEQ ID NO 55
<211> LENGTH: 288
<212> TYPE: PRT
<213> ORGANISM: Caenorhabditis elegans

<400> SEQUENCE: 55

Met Ala Gln His Pro Leu Val Gln Arg Leu Leu Asp Val Lys Phe Asp
 1               5                  10                  15

Thr Lys Arg Phe Val Ala Ile Ala Thr His Gly Pro Lys Asn Phe Pro
            20                  25                  30

Asp Ala Glu Gly Arg Lys Phe Phe Ala Asp His Phe Asp Val Thr Ile
        35                  40                  45

Gln Ala Ser Ile Leu Tyr Met Val Val Phe Gly Thr Lys Trp Phe
    50                  55                  60

Met Arg Asn Arg Gln Pro Phe Gln Leu Thr Ile Pro Leu Asn Ile Trp
65                  70                  75                  80

Asn Phe Ile Leu Ala Ala Phe Ser Ile Ala Gly Ala Val Lys Met Thr
                85                  90                  95

Pro Glu Phe Phe Gly Thr Ile Ala Asn Lys Gly Ile Val Ala Ser Tyr
            100                 105                 110

Cys Lys Val Phe Asp Phe Thr Lys Gly Glu Asn Gly Tyr Trp Val Trp
        115                 120                 125

Leu Phe Met Ala Ser Lys Leu Phe Glu Leu Val Asp Thr Ile Phe Leu
    130                 135                 140

Val Leu Arg Lys Arg Pro Leu Met Phe Leu His Trp Tyr His His Ile
145                 150                 155                 160

Leu Thr Met Ile Tyr Ala Trp Tyr Ser His Pro Leu Thr Pro Gly Phe
                165                 170                 175

Asn Arg Tyr Gly Ile Tyr Leu Asn Phe Val Val His Ala Phe Met Tyr
            180                 185                 190

Ser Tyr Tyr Phe Leu Arg Ser Met Lys Ile Arg Val Pro Gly Phe Ile
        195                 200                 205

Ala Gln Ala Ile Thr Ser Leu Gln Ile Val Gln Phe Ile Ile Ser Cys
    210                 215                 220

Ala Val Leu Ala His Leu Gly Tyr Leu Met His Phe Thr Asn Ala Asn
225                 230                 235                 240
```

```
Cys Asp Phe Glu Pro Ser Val Phe Lys Leu Ala Val Phe Met Asp Thr
                245                 250                 255

Thr Tyr Leu Ala Leu Phe Val Asn Phe Phe Leu Gln Ser Tyr Val Leu
            260                 265                 270

Arg Gly Gly Lys Asp Lys Tyr Lys Ala Val Pro Lys Lys Lys Asn Asn
        275                 280                 285
```

<210> SEQ ID NO 56
<211> LENGTH: 282
<212> TYPE: PRT
<213> ORGANISM: Mortierella alpina

<400> SEQUENCE: 56

```
Ala Ala Leu Val Ala Gln Ala Glu Lys Tyr Ile Pro Thr Ile Val His
  1               5                  10                  15

His Thr Arg Gly Phe Leu Val Ala Val Glu Ser Pro Leu Ala Arg Glu
             20                  25                  30

Leu Pro Leu Met Asn Pro Phe His Val Leu Leu Ile Val Leu Ala Tyr
         35                  40                  45

Leu Val Thr Val Phe Val Gly Met Gln Ile Met Lys Asn Phe Glu Arg
 50                  55                  60

Phe Glu Val Lys Thr Phe Ser Leu Leu His Asn Phe Cys Leu Val Ser
 65                  70                  75                  80

Ile Ser Ala Tyr Met Cys Gly Gly Ile Leu Tyr Glu Ala Tyr Gln Ala
                 85                  90                  95

Asn Tyr Gly Leu Phe Glu Asn Ala Ala Asp His Thr Phe Lys Gly Leu
            100                 105                 110

Pro Met Ala Lys Met Ile Trp Leu Phe Tyr Phe Ser Lys Ile Met Glu
        115                 120                 125

Phe Val Asp Thr Met Ile Met Val Leu Lys Lys Asn Asn Arg Gln Ile
130                 135                 140

Ser Phe Leu His Val Tyr His His Ser Ser Ile Phe Thr Ile Trp Trp
145                 150                 155                 160

Leu Val Thr Phe Val Ala Pro Asn Gly Glu Ala Tyr Phe Ser Ala Ala
                165                 170                 175

Leu Asn Ser Phe Ile His Val Ile Met Tyr Gly Tyr Tyr Phe Leu Ser
            180                 185                 190

Ala Leu Gly Phe Lys Gln Val Ser Phe Ile Lys Phe Tyr Ile Thr Arg
        195                 200                 205

Ser Gln Met Thr Gln Phe Cys Met Met Ser Val Gln Ser Ser Trp Asp
210                 215                 220

Met Tyr Ala Met Lys Val Leu Gly Arg Pro Gly Tyr Pro Phe Phe Ile
225                 230                 235                 240

Thr Ala Leu Leu Trp Phe Tyr Met Trp Thr Met Leu Gly Leu Phe Tyr
                245                 250                 255

Asn Phe Tyr Arg Lys Asn Ala Lys Leu Ala Lys Gln Ala Lys Ala Asp
            260                 265                 270

Ala Ala Lys Glu Lys Ala Arg Lys Leu Gln
        275                 280
```

<210> SEQ ID NO 57
<211> LENGTH: 278
<212> TYPE: PRT
<213> ORGANISM: Drosophila melanogaster
<220> FEATURE:
<221> NAME/KEY: VARIANT -continued

```
<222> LOCATION: (235)...(235)
<223> OTHER INFORMATION: Xaa = Unknown or Other at position 235

<400> SEQUENCE: 57
```

Pro Thr Lys Met Ile Asn Met Asp Ile Ser Val Thr Pro Asn Tyr Ser
 1               5                  10                  15

Tyr Ile Phe Asp Phe Glu Asn Asp Phe Ile His Gln Arg Thr Arg Lys
             20                  25                  30

Trp Met Leu Glu Asn Trp Thr Trp Val Phe Tyr Tyr Cys Gly Ile Tyr
         35                  40                  45

Met Leu Val Ile Phe Gly Gly Gln His Phe Met Gln Asn Arg Pro Arg
 50                  55                  60

Phe Gln Leu Arg Gly Pro Leu Ile Ile Trp Asn Thr Leu Leu Ala Met
65                  70                  75                  80

Phe Ser Ile Met Gly Ala Ala Arg Thr Ala Pro Glu Leu Ile His Val
                 85                  90                  95

Leu Arg His Tyr Gly Leu Phe His Ser Val Cys Val Pro Ser Tyr Ile
             100                 105                 110

Glu Gln Asp Arg Val Cys Gly Phe Trp Thr Trp Leu Phe Val Leu Ser
         115                 120                 125

Lys Leu Pro Glu Leu Gly Asp Thr Ile Phe Ile Val Leu Arg Lys Gln
 130                 135                 140

Pro Leu Ile Phe Leu His Trp Tyr His His Ile Thr Val Leu Ile Tyr
145                 150                 155                 160

Ser Trp Phe Ser Tyr Thr Glu Tyr Thr Ser Ser Ala Arg Trp Phe Ile
                 165                 170                 175

Val Met Asn Tyr Cys Val His Ser Val Met Tyr Ser Tyr Tyr Ala Leu
             180                 185                 190

Lys Ala Ala Arg Phe Asn Pro Pro Arg Phe Ile Ser Met Ile Ile Thr
         195                 200                 205

Ser Leu Gln Leu Ala Gln Met Ile Ile Gly Cys Ala Ile Asn Val Trp
 210                 215                 220

Ala Asn Gly Phe Leu Lys Thr His Gly Thr Xaa Ser Cys His Ile Ser
225                 230                 235                 240

Gln Arg Asn Ile Asn Leu Ser Ile Ala Met Tyr Ser Ser Tyr Phe Val
                 245                 250                 255

Leu Phe Ala Arg Phe Phe Tyr Lys Ala Tyr Leu Ala Pro Gly Gly His
             260                 265                 270

Lys Ser Arg Arg Met Ala
         275

```
<210> SEQ ID NO 58
<211> LENGTH: 286
<212> TYPE: PRT
<213> ORGANISM: Mortierella alpina

<400> SEQUENCE: 58
```

Val Thr Gly Lys Ser Ile Asp Ser Phe Val Phe Gln Glu Gly Val Thr
 1               5                  10                  15

Pro Leu Ser Thr Gln Arg Glu Val Ala Met Trp Thr Ile Thr Tyr Phe
             20                  25                  30

Val Val Ile Phe Gly Gly Arg Gln Ile Met Lys Ser Gln Asp Ala Phe
         35                  40                  45

Lys Leu Lys Pro Leu Phe Ile Leu His Asn Phe Leu Leu Thr Ile Ala
 50                  55                  60

-continued

```
Ser Gly Ser Leu Leu Leu Phe Ile Glu Asn Leu Val Pro Ile Leu
 65                  70                  75                  80

Ala Arg Asn Gly Leu Phe Tyr Ala Ile Cys Asp Asp Gly Ala Trp Thr
                 85                  90                  95

Gln Arg Leu Glu Leu Leu Tyr Tyr Leu Asn Tyr Leu Val Lys Tyr Trp
            100                 105                 110

Glu Leu Ala Asp Thr Val Phe Leu Val Leu Lys Lys Pro Leu Glu
        115                 120                 125

Phe Leu His Tyr Phe His His Ser Met Thr Met Val Leu Cys Phe Val
    130                 135                 140

Gln Leu Gly Gly Tyr Thr Ser Val Ser Trp Val Pro Ile Thr Leu Asn
145                 150                 155                 160

Leu Thr Val His Val Phe Met Tyr Tyr Tyr Met Arg Ser Ala Ala
                165                 170                 175

Gly Val Arg Ile Trp Trp Lys Gln Tyr Leu Thr Thr Leu Gln Ile Val
                180                 185                 190

Gln Phe Val Leu Asp Leu Gly Phe Ile Tyr Phe Cys Ala Tyr Thr Tyr
            195                 200                 205

Phe Ala Phe Thr Tyr Phe Pro Trp Ala Pro Asn Val Gly Lys Cys Ala
    210                 215                 220

Gly Thr Glu Gly Ala Ala Leu Phe Gly Cys Gly Leu Leu Ser Ser Tyr
225                 230                 235                 240

Leu Leu Leu Phe Ile Asn Phe Tyr Arg Ile Thr Tyr Asn Ala Lys Ala
                245                 250                 255

Lys Ala Ala Lys Glu Arg Gly Ser Asn Phe Thr Pro Lys Thr Val Lys
                260                 265                 270

Ser Gly Gly Ser Pro Lys Lys Pro Ser Lys Ser Lys His Ile
                275                 280                 285
```

<210> SEQ ID NO 59
<211> LENGTH: 261
<212> TYPE: PRT
<213> ORGANISM: Drosophila melanogaster
<220> FEATURE:
<221> NAME/KEY: VARIANT
<222> LOCATION: (218)...(218)
<223> OTHER INFORMATION: Xaa = Unknown or Other at position 218

<400> SEQUENCE: 59

```
Ile Phe Asp Phe Glu Asn Asp Phe Ile His Gln Arg Thr Arg Lys Trp
  1               5                  10                  15

Met Leu Glu Asn Trp Thr Trp Val Phe Tyr Tyr Cys Gly Ile Tyr Met
                 20                  25                  30

Leu Val Ile Phe Gly Gly Gln His Phe Met Gln Asn Arg Pro Arg Phe
             35                  40                  45

Gln Leu Arg Gly Pro Leu Ile Ile Trp Asn Thr Leu Leu Ala Met Phe
         50                  55                  60

Ser Ile Met Gly Ala Ala Arg Thr Ala Pro Glu Leu Ile His Val Leu
 65                  70                  75                  80

Arg His Tyr Gly Leu Phe His Ser Val Cys Val Pro Ser Tyr Ile Glu
                 85                  90                  95

Gln Asp Arg Val Cys Gly Phe Trp Thr Trp Leu Phe Val Leu Ser Lys
            100                 105                 110

Leu Pro Glu Leu Gly Asp Thr Ile Phe Ile Val Leu Arg Lys Gln Pro
        115                 120                 125

Leu Ile Phe Leu His Trp Tyr His His Ile Thr Val Leu Ile Tyr Ser
```

```
                130                 135                 140
Trp Phe Ser Tyr Thr Glu Tyr Thr Ser Ser Ala Arg Trp Phe Ile Val
145                 150                 155                 160

Met Asn Tyr Cys Val His Ser Val Met Tyr Ser Tyr Tyr Ala Leu Lys
                165                 170                 175

Ala Ala Arg Phe Asn Pro Pro Arg Phe Ile Ser Met Ile Ile Thr Ser
            180                 185                 190

Leu Gln Leu Ala Gln Met Ile Ile Gly Cys Ala Ile Asn Val Trp Ala
        195                 200                 205

Asn Gly Phe Leu Lys Thr His Gly Thr Xaa Ser Cys His Ile Ser Gln
210                 215                 220

Arg Asn Ile Asn Leu Ser Ile Ala Met Tyr Ser Ser Tyr Phe Val Leu
225                 230                 235                 240

Phe Ala Arg Phe Phe Tyr Lys Ala Tyr Leu Ala Pro Gly Gly His Lys
                245                 250                 255

Ser Arg Arg Met Ala
            260

<210> SEQ ID NO 60
<211> LENGTH: 299
<212> TYPE: PRT
<213> ORGANISM: Homo sapiens

<400> SEQUENCE: 60

Met Glu His Phe Asp Ala Ser Leu Ser Thr Tyr Phe Lys Ala Leu Leu
1               5                   10                  15

Gly Pro Arg Asp Thr Arg Val Lys Gly Trp Phe Leu Leu Asp Asn Tyr
            20                  25                  30

Ile Pro Thr Phe Ile Cys Ser Val Ile Tyr Leu Leu Ile Val Trp Leu
        35                  40                  45

Gly Pro Lys Tyr Met Arg Asn Lys Gln Pro Phe Ser Cys Arg Gly Ile
    50                  55                  60

Leu Val Val Tyr Asn Leu Gly Leu Thr Leu Leu Ser Leu Tyr Met Phe
65                  70                  75                  80

Cys Glu Leu Val Thr Gly Val Trp Glu Gly Lys Tyr Asn Phe Phe Cys
                85                  90                  95

Gln Gly Thr Arg Thr Ala Gly Glu Ser Asp Met Lys Ile Ile Arg Val
            100                 105                 110

Leu Trp Trp Tyr Tyr Phe Ser Lys Leu Ile Glu Phe Met Asp Thr Phe
        115                 120                 125

Phe Phe Ile Leu Arg Lys Asn Asn His Gln Ile Thr Val Leu His Val
    130                 135                 140

Tyr His His Ala Ser Met Leu Asn Ile Trp Trp Phe Val Met Asn Trp
145                 150                 155                 160

Val Pro Cys Gly His Ser Tyr Phe Gly Ala Thr Leu Asn Ser Phe Ile
                165                 170                 175

His Val Leu Met Tyr Ser Tyr Tyr Gly Leu Ser Ser Val Pro Ser Met
            180                 185                 190

Arg Pro Tyr Leu Trp Trp Lys Lys Tyr Ile Thr Gln Gly Gln Leu Leu
        195                 200                 205

Gln Phe Val Leu Thr Ile Ile Gln Thr Ser Cys Gly Val Ile Trp Pro
    210                 215                 220

Cys Thr Phe Pro Leu Gly Trp Leu Tyr Phe Gln Ile Gly Tyr Ile Ile
225                 230                 235                 240
```

```
Ser Leu Ile Ala Leu Phe Thr Asn Phe Tyr Ile Gln Thr Tyr Asn Lys
            245                 250                 255

Lys Gly Ala Ser Arg Arg Lys Asp His Leu Lys Asp His Gln Asn Gly
        260                 265                 270

Ser Val Ala Ala Val Asn Gly His Thr Asn Ser Phe Ser Pro Leu Glu
    275                 280                 285

Asn Asn Val Lys Pro Arg Lys Leu Arg Lys Asp
290                 295
```

<210> SEQ ID NO 61
<211> LENGTH: 798
<212> TYPE: DNA
<213> ORGANISM: Homo sapiens

<400> SEQUENCE: 61

```
atgaacatgt cagtgttgac tttacaagaa tatgaattcg aaaagcagtt caacgagaat      60
gaagccatcc aatggatgca ggaaaactgg aagaaatctt tcctgttttc tgctctgtat     120
gctgccttta tattcggtgg tcggcaccta atgaataaac gagcaaagtt tgaactgagg     180
aagccattag tgctctggtc tctgacccct gcagtcttca gtatattcgg tgctcttcga     240
actggtgctt atatggtgta cattttgatg accaaaggcc tgaagcagtc agtttgtgac     300
cagggttttt acaatggacc tgtcagcaaa ttctgggctt atgcatttgt gctaagcaaa     360
gcacccgaac taggagatac aatattcatt attctgagga agcagaagct gatcttcctg     420
cactggtatc accacatcac tgtgctcctg tactcttggt actcctacaa agacatggtt     480
gccgggggag gttggttcat gactatgaac atggcgtgc acgccgtgat gtactcttac      540
tatgccttgc gggcggcagg tttccgagtc tcccggaagt tgccatgtt catcaccttg       600
tcccagatca ctcagatgct gatgggctgt gtggttaact acctggtctt ctgctggatg     660
cagcatgacc agtgtcactc tcactttcag aacatcttct ggtcctcact catgtacctc     720
agctaccttg tgctcttctg ccatttcttc tttgaggcct acatcggcaa aatgaggaaa     780
acaacgaaag ctgaatag                                                    798
```

<210> SEQ ID NO 62
<211> LENGTH: 265
<212> TYPE: PRT
<213> ORGANISM: Homo sapiens

<400> SEQUENCE: 62

```
Met Asn Met Ser Val Leu Thr Leu Gln Glu Tyr Glu Phe Glu Lys Gln
1               5                   10                  15

Phe Asn Glu Asn Glu Ala Ile Gln Trp Met Gln Glu Asn Trp Lys Lys
            20                  25                  30

Ser Phe Leu Phe Ser Ala Leu Tyr Ala Ala Phe Ile Phe Gly Gly Arg
        35                  40                  45

His Leu Met Asn Lys Arg Ala Lys Phe Glu Leu Arg Lys Pro Leu Val
    50                  55                  60

Leu Trp Ser Leu Thr Leu Ala Val Phe Ser Ile Phe Gly Ala Leu Arg
65                  70                  75                  80

Thr Gly Ala Tyr Met Val Tyr Ile Leu Met Thr Lys Gly Leu Lys Gln
                85                  90                  95

Ser Val Cys Asp Gln Gly Phe Tyr Asn Gly Pro Val Ser Lys Phe Trp
            100                 105                 110

Ala Tyr Ala Phe Val Leu Ser Lys Ala Pro Glu Leu Gly Asp Thr Ile
        115                 120                 125
```

-continued

```
Phe Ile Ile Leu Arg Lys Gln Lys Leu Ile Phe Leu His Trp Tyr His
            130                 135                 140
His Ile Thr Val Leu Leu Tyr Ser Trp Tyr Ser Tyr Lys Asp Met Val
145                 150                 155                 160
Ala Gly Gly Gly Trp Phe Met Thr Met Asn Tyr Gly Val His Ala Val
                    165                 170                 175
Met Tyr Ser Tyr Tyr Ala Leu Arg Ala Ala Gly Phe Arg Val Ser Arg
            180                 185                 190
Lys Phe Ala Met Phe Ile Thr Leu Ser Gln Ile Thr Gln Met Leu Met
        195                 200                 205
Gly Cys Val Val Asn Tyr Leu Val Phe Cys Trp Met Gln His Asp Gln
    210                 215                 220
Cys His Ser His Phe Gln Asn Ile Phe Trp Ser Ser Leu Met Tyr Leu
225                 230                 235                 240
Ser Tyr Leu Val Leu Phe Cys His Phe Phe Glu Ala Tyr Ile Gly
            245                 250                 255
Lys Met Arg Lys Thr Thr Lys Ala Glu
            260                 265
```

<210> SEQ ID NO 63
<211> LENGTH: 292
<212> TYPE: PRT
<213> ORGANISM: Mus musculus

<400> SEQUENCE: 63

```
Met Glu Gln Leu Lys Ala Phe Asp Asn Glu Val Asn Ala Phe Leu Asp
1               5                   10                  15
Asn Met Phe Gly Pro Arg Asp Ser Arg Val Arg Gly Trp Phe Leu Leu
            20                  25                  30
Asp Ser Tyr Leu Pro Thr Phe Ile Leu Thr Ile Thr Tyr Leu Leu Ser
        35                  40                  45
Ile Trp Leu Gly Asn Lys Tyr Met Lys Asn Arg Pro Ala Leu Ser Leu
    50                  55                  60
Arg Gly Ile Leu Thr Leu Tyr Asn Leu Ala Ile Thr Leu Leu Ser Ala
65                  70                  75                  80
Tyr Met Leu Val Glu Leu Ile Leu Ser Ser Trp Glu Gly Gly Tyr Asn
                85                  90                  95
Leu Gln Cys Gln Asn Leu Asp Ser Ala Gly Glu Gly Asp Val Arg Val
            100                 105                 110
Ala Lys Val Leu Trp Trp Tyr Tyr Phe Ser Lys Leu Val Glu Phe Leu
        115                 120                 125
Asp Thr Ile Phe Phe Val Leu Arg Lys Lys Thr Asn Gln Ile Thr Phe
    130                 135                 140
Leu His Val Tyr His His Ala Ser Met Phe Asn Ile Trp Trp Cys Val
145                 150                 155                 160
Leu Asn Trp Ile Pro Cys Gly Gln Ser Phe Phe Gly Pro Thr Leu Asn
                165                 170                 175
Ser Phe Ile His Ile Leu Met Tyr Ser Tyr Tyr Gly Leu Ser Val Phe
            180                 185                 190
Pro Ser Met His Lys Tyr Leu Trp Trp Lys Lys Tyr Leu Thr Gln Ala
        195                 200                 205
Gln Leu Val Gln Phe Val Leu Thr Ile Thr His Thr Leu Ser Ala Val
    210                 215                 220
Val Lys Pro Cys Gly Phe Pro Phe Gly Cys Leu Ile Phe Gln Ser Ser
```

-continued

```
            225                 230                 235                 240
Tyr Met Met Thr Leu Val Ile Leu Phe Leu Asn Phe Tyr Ile Gln Thr
                245                 250                 255
Tyr Arg Lys Lys Pro Val Lys Lys Glu Leu Gln Glu Lys Glu Val Lys
            260                 265                 270
Asn Gly Phe Pro Lys Ala His Leu Ile Val Ala Asn Gly Met Thr Asp
        275                 280                 285
Lys Lys Ala Gln
    290

<210> SEQ ID NO 64
<211> LENGTH: 299
<212> TYPE: PRT
<213> ORGANISM: Mus musculus

<400> SEQUENCE: 64

Met Glu His Phe Asp Ala Ser Leu Ser Thr Tyr Phe Lys Ala Phe Leu
1               5                   10                  15
Gly Pro Arg Asp Thr Arg Val Lys Gly Trp Phe Leu Leu Asp Asn Tyr
            20                  25                  30
Ile Pro Thr Phe Val Cys Ser Val Ile Tyr Leu Leu Ile Val Trp Leu
        35                  40                  45
Gly Pro Lys Tyr Met Lys Asn Arg Gln Pro Phe Ser Cys Arg Gly Ile
    50                  55                  60
Leu Gln Leu Tyr Asn Leu Gly Leu Thr Leu Leu Ser Leu Tyr Met Phe
65                  70                  75                  80
Tyr Glu Leu Val Thr Gly Val Trp Glu Gly Lys Tyr Asn Phe Phe Cys
                85                  90                  95
Gln Gly Thr Arg Ser Ala Gly Glu Ser Asp Met Lys Ile Ile Arg Val
            100                 105                 110
Leu Trp Trp Tyr Tyr Phe Ser Lys Leu Ile Glu Phe Met Asp Thr Phe
        115                 120                 125
Phe Phe Ile Leu Arg Lys Asn Asn His Gln Ile Thr Val Leu His Val
    130                 135                 140
Tyr His His Ala Thr Met Leu Asn Ile Trp Trp Phe Val Met Asn Trp
145                 150                 155                 160
Val Pro Cys Gly His Ser Tyr Phe Gly Ala Thr Leu Asn Ser Phe Ile
                165                 170                 175
His Val Leu Met Tyr Ser Tyr Tyr Gly Leu Ser Ser Ile Pro Ser Met
            180                 185                 190
Arg Pro Tyr Leu Trp Trp Lys Lys Tyr Ile Thr Gln Gly Gln Leu Val
        195                 200                 205
Gln Phe Val Leu Thr Ile Ile Gln Thr Thr Cys Gly Val Phe Trp Pro
    210                 215                 220
Cys Ser Phe Pro Leu Gly Trp Leu Phe Gln Ile Gly Tyr Met Ile
225                 230                 235                 240
Ser Leu Ile Ala Leu Phe Thr Asn Phe Tyr Ile Gln Thr Tyr Asn Lys
                245                 250                 255
Lys Gly Ala Ser Arg Arg Lys Asp His Leu Lys Gly His Gln Asn Gly
            260                 265                 270
Ser Val Ala Ala Val Asn Gly His Thr Asn Ser Phe Pro Ser Leu Glu
        275                 280                 285
Asn Ser Val Lys Pro Arg Lys Gln Arg Lys Asp
    290                 295
```

<210> SEQ ID NO 65
<211> LENGTH: 33
<212> TYPE: DNA
<213> ORGANISM: Artificial Sequence
<220> FEATURE:
<223> OTHER INFORMATION: Internal Primer RO339

<400> SEQUENCE: 65
ttggagagga ggaagcgacc accgaagatg atg       33

<210> SEQ ID NO 66
<211> LENGTH: 31
<212> TYPE: DNA
<213> ORGANISM: Artificial Sequence
<220> FEATURE:
<223> OTHER INFORMATION: Forward Primer RO317

<400> SEQUENCE: 66
cacacaggaa acagctatga ccatgattac g       31

<210> SEQ ID NO 67
<211> LENGTH: 35
<212> TYPE: DNA
<213> ORGANISM: Artificial Sequence
<220> FEATURE:
<223> OTHER INFORMATION: Primer RO350

<400> SEQUENCE: 67
catctcatgg atccgccatg gccgccgcaa tcttg       35

<210> SEQ ID NO 68
<211> LENGTH: 18
<212> TYPE: DNA
<213> ORGANISM: Artificial Sequence
<220> FEATURE:
<223> OTHER INFORMATION: Reverse Primer RO352

<400> SEQUENCE: 68
acgcgtacgt aaagcttg       18

<210> SEQ ID NO 69
<211> LENGTH: 37
<212> TYPE: DNA
<213> ORGANISM: Artificial Sequence
<220> FEATURE:
<223> OTHER INFORMATION: Primer RO514

<400> SEQUENCE: 69
ggctatggat ccatgaattc actcgttact caatatg       37

<210> SEQ ID NO 70
<211> LENGTH: 35
<212> TYPE: DNA
<213> ORGANISM: Artificial Sequence
<220> FEATURE:
<223> OTHER INFORMATION: Primer RO515

<400> SEQUENCE: 70
cctgccaagc ttttaccttt tcttctgtg ttgag       35

<210> SEQ ID NO 71
<211> LENGTH: 21
<212> TYPE: DNA
<213> ORGANISM: Artificial Sequence
<220> FEATURE:
<223> OTHER INFORMATION: Forward Primer RO541

```
<400> SEQUENCE: 71
gattactagc agctgtaata c                                         21

<210> SEQ ID NO 72
<211> LENGTH: 21
<212> TYPE: DNA
<213> ORGANISM: Artificial Sequence
<220> FEATURE:
<223> OTHER INFORMATION: Reverse Primer RO540

<400> SEQUENCE: 72
gtgaatgtaa gcgtgacata a                                         21

<210> SEQ ID NO 73
<211> LENGTH: 18
<212> TYPE: DNA
<213> ORGANISM: Artificial Sequence
<220> FEATURE:
<223> OTHER INFORMATION: Internal Forward Primer RO728

<400> SEQUENCE: 73
gagactttga gcggttcg                                             18

<210> SEQ ID NO 74
<211> LENGTH: 20
<212> TYPE: DNA
<213> ORGANISM: Artificial Sequence
<220> FEATURE:
<223> OTHER INFORMATION: Internal Forward Primer RO730

<400> SEQUENCE: 74
tctctgctgc gttgaactcg                                           20

<210> SEQ ID NO 75
<211> LENGTH: 19
<212> TYPE: DNA
<213> ORGANISM: Artificial Sequence
<220> FEATURE:
<223> OTHER INFORMATION: Reverse Primer RO729

<400> SEQUENCE: 75
aaagctcttg acctcgaac                                            19

<210> SEQ ID NO 76
<211> LENGTH: 20
<212> TYPE: DNA
<213> ORGANISM: Artificial Sequence
<220> FEATURE:
<223> OTHER INFORMATION: Reverse Primer RO731

<400> SEQUENCE: 76
aacttgatga acgacacgtg                                           20

<210> SEQ ID NO 77
<211> LENGTH: 29
<212> TYPE: DNA
<213> ORGANISM: Artificial Sequence
<220> FEATURE:
<223> OTHER INFORMATION: Primer RO719

<400> SEQUENCE: 77
ggttctccca tggaacattt tgatgcatc                                 29

<210> SEQ ID NO 78
```

```
<211> LENGTH: 30
<212> TYPE: DNA
<213> ORGANISM: Artificial Sequence
<220> FEATURE:
<223> OTHER INFORMATION: Primer RO720

<400> SEQUENCE: 78
ggtttcaaag ctttgacttc aatccttccg                              30

<210> SEQ ID NO 79
<211> LENGTH: 37
<212> TYPE: DNA
<213> ORGANISM: Artificial Sequence
<220> FEATURE:
<223> OTHER INFORMATION: Primer RO738

<400> SEQUENCE: 79
aatcaggaat tcatggctca gcatccgctc gttcaac                      37

<210> SEQ ID NO 80
<211> LENGTH: 36
<212> TYPE: DNA
<213> ORGANISM: Artificial Sequence
<220> FEATURE:
<223> OTHER INFORMATION: Primer RO739

<400> SEQUENCE: 80
ccgcttgtcg acttagttgt tcttcttctt tggcac                       36

<210> SEQ ID NO 81
<211> LENGTH: 30
<212> TYPE: DNA
<213> ORGANISM: Artificial Sequence
<220> FEATURE:
<223> OTHER INFORMATION: Primer RP735

<400> SEQUENCE: 81
cctcctgaat tccaacacta ttcagctttc                              30

<210> SEQ ID NO 82
<211> LENGTH: 20
<212> TYPE: DNA
<213> ORGANISM: Artificial Sequence
<220> FEATURE:
<223> OTHER INFORMATION: Primer RO73

<400> SEQUENCE: 82
taatacgact cactataggg                                         20

<210> SEQ ID NO 83
<211> LENGTH: 30
<212> TYPE: DNA
<213> ORGANISM: Artificial Sequence
<220> FEATURE:
<223> OTHER INFORMATION: Primer RO819

<400> SEQUENCE: 83
atgatgccat ggagcagctg aaggcctttg                              30

<210> SEQ ID NO 84
<211> LENGTH: 27
<212> TYPE: DNA
<213> ORGANISM: Artificial Sequence
<220> FEATURE:
<223> OTHER INFORMATION: Primer RO820

<400> SEQUENCE: 84
```

```
cagtctctgc tttaaaacaa gctcgtc                                        27

<210> SEQ ID NO 85
<211> LENGTH: 31
<212> TYPE: DNA
<213> ORGANISM: Artificial Sequence
<220> FEATURE:
<223> OTHER INFORMATION: Primer RO833

<400> SEQUENCE: 85
ggttttacca tggaacattt cgatgcgtca c                                   31

<210> SEQ ID NO 86
<211> LENGTH: 20
<212> TYPE: DNA
<213> ORGANISM: Artificial Sequence
<220> FEATURE:
<223> OTHER INFORMATION: Primer RO832

<400> SEQUENCE: 86
cgacctgcag ctcgagcaca                                                20

<210> SEQ ID NO 87
<211> LENGTH: 28
<212> TYPE: PRT
<213> ORGANISM: Homo sapiens

<400> SEQUENCE: 87

Asp Thr Ile Phe Ile Ile Leu Arg Lys Gln Lys Leu Ile Phe Leu His
 1               5                  10                  15

Trp Tyr His His Ile Thr Val Leu Leu Tyr Ser Trp
            20                  25
```